US007968103B2

(12) United States Patent
Westphal et al.

(10) Patent No.: US 7,968,103 B2
(45) Date of Patent: Jun. 28, 2011

(54) COMPOSITIONS COMPRISING FETAL HEMOGLOBIN AND BACTERIAL ENDOTOXIN AND OPTIONALLY ADDITIONAL FETAL LIVER COMPONENTS

(76) Inventors: Otto Westphal, Montreux (CH); Josette Westphal, legal representative, Montreux (CH); Alexander Westphal, legal representative, Montreux (CH); Thierry Walli, Clarens-Montreaux (CH); Reginald Gorczynski, Toronto (CA); Silke Muller, Schonborn (DE); Jean-Pierre Mach, Lausanne (CH); Alfred Hartman, Erlenbach (CH); Wolfgang Bessler, Freiburg (DE); Petra Hofmann, Regensburg (DE); Ulrich Zahringer, Borstel (DE); Christian Alexander, Borstel (DE); Ulrich vor dem Esche, Freiburg (DE); Artur J. Ulmer, Borstel (DE); Antonio Verdini, Castrocarro Terme (IT)

( * ) Notice: Subject to any disclaimer, the term of this patent is extended or adjusted under 35 U.S.C. 154(b) by 869 days.

(21) Appl. No.: 10/545,500

(22) PCT Filed: Feb. 18, 2004

(86) PCT No.: PCT/EP2004/001553
§ 371 (c)(1),
(2), (4) Date: Jan. 30, 2007

(87) PCT Pub. No.: WO2004/073728
PCT Pub. Date: Sep. 2, 2004

(65) Prior Publication Data
US 2008/0075742 A1  Mar. 27, 2008

(30) Foreign Application Priority Data
Feb. 18, 2003 (EP) .................................. 03003687

(51) Int. Cl.
*A61K 39/02* (2006.01)
*A61K 38/17* (2006.01)
*A61P 31/00* (2006.01)
(52) U.S. Cl. ............. 424/236.1; 424/94.5; 514/2; 514/6
(58) Field of Classification Search ............... 424/236.1, 424/94.5; 514/2, 6
See application file for complete search history.

(56) References Cited

U.S. PATENT DOCUMENTS
| | | | |
|---|---|---|---|
| 4,473,647 A | | 9/1984 | Carpenter et al. |
| 4,987,237 A | | 1/1991 | Myers et al. |
| 5,543,300 A | * | 8/1996 | Inglot et al. ..................... 435/29 |
| 6,670,323 B1 | * | 12/2003 | Looker et al. ..................... 514/6 |
| 2001/0034037 A1 | * | 10/2001 | Patel et al. ..................... 435/7.21 |
| 2002/0065211 A1 | * | 5/2002 | Jacobs et al. ..................... 514/1 |

FOREIGN PATENT DOCUMENTS
| | | |
|---|---|---|
| DE | 101 03 211 | 7/2002 |
| EP | 0 405 315 B1 | 1/1991 |
| EP | 0 472 467 | 2/1992 |
| EP | 0 477 050 | 3/1992 |
| EP | 1 316 315 | 6/2003 |
| JP | 04-187640 | 7/1992 |
| JP | 06-157333 | 6/1994 |
| WO | WO 87/06830 | 11/1987 |
| WO | WO 95/13829 | 5/1995 |
| WO | WO 95/23156 | 8/1995 |
| WO | WO 95/26507 | 10/1995 |
| WO | WO 97/12855 | 4/1997 |
| WO | WO 97/25061 | 7/1997 |
| WO | WO 98/33948 | 8/1998 |
| WO | WO 01/34648 | 5/2001 |
| WO | WO 01/51008 | 7/2001 |

OTHER PUBLICATIONS

Anspach et al., "Endotoxin removal by affinity sorbents," J. Biochem. Biophys. Methods 49, 2001, pp. 665-681.*
Setlow et al., J. of Bacteriology vol. 89, No. 5, 1237-1243 (1965).*
D'Agnillo, F. et al., "Synergistic Toxicity of Acellular Hemoglobin and Lipopolysaccharide in Cultured Endothelial Cells Under Oxidative Conditions," Blood, 98:53B (2001) (Abstract).
Simsa, J. et al., "Changes in the Contents of Some Rat Serum Proteins Under Pathologic Conditions, Part 2 the Influence of Some Further Noxious Factors in Comparison with the Effect of Ionizing Radiation," *Radiobiologia Radiotherapia*, 15:509-519 (1974).

(Continued)

*Primary Examiner* — Chih-Min Kam
(74) *Attorney, Agent, or Firm* — Ropes & Gray LLP; Barbara A. Ruskin; Wyan-Ching M. Lee

(57) ABSTRACT

The present invention relates to a pharmaceutical composition representing a novel immunomodulating principle comprising bacterial endotoxin, fetal hemoglobin or more particularly a heme-free derivative or the γ-chain thereof, and optionally, components which are present in the fetal liver in addition to HbF. The composition is delivered to humans in a pharmaceutically acceptable carrier and/or diluent. In accordance with the present invention it was surprisingly found that endotoxin and fetal hemoglobin partial structures display a pronounced synergistic biomedical activity. The biomedical effect of fetal hemoglobin and its partial structures is surprisingly not based on a classical hemoglobin function as an oxygen transporter but related to a modulation of endotoxin-mediated bioactivity. This biomedical activity is surprisingly also observed after oral application of the composition. The composition of the invention finds a variety of applications which have in common the stimulation of the immune system and the reversion in polarization of cytokines and chemokines from a Th2-directed response to a Th1-type response. The proposed applications would therefore include the treatment of allergic conditions, malignancies, chronic infections, autoimmune phenomena and age-related imbalances.

17 Claims, 65 Drawing Sheets

OTHER PUBLICATIONS

Westerwoudt, R.J. et al., "The Growth Promoting Activity of Lipopolysaccharide, Dextran Sulfate, and Red Cell Lysate Added to Hy-Clone Calf Serum," *Cellular Immunology*, 81:268-275 (1983).

Alexander, C. and Rietschel, E., "Bacterial lipopolysaccharides and innate immunity." *Journal of Endotoxin Research*, vol. 7, No. 3, pp. 167-202 (2001).

Bacher, M. et al., "An essential regulatory role for macrophage migration inhibitory factor in T-cell activation," *Proc. Natl. Acad. Sci. USA*, vol. 93, pp. 7849-7854 (1996).

Bacher, M. et al., "Migration Inhibitory Factor Expression in Experimentally Induced Endotoxemia," *American Journal of Pathology*, vol. 150, No. 1, pp. 235-246 (1997).

Bernhagen, J. et al., "Regulation of the immune response by macrophage migration inhibitory factor: biological and structural features," *J. Mol. Med*, vol. 76, pp. 151-161 (1998).

Bertok, L., "Role of Bile in Detoxification of Lipopolysaccharide," *American Society of Microbiology*—1980 (D. Schlesinger, edition), pp. 91-93 (1980).

Bernier, I. et al., "Ligand-binding studies with a 23 kDa protein purified from bovine brain cytosol," *Biochimica et Biophysica Acta*, vol. 871, pp. 19-23 (1986).

Bertini, R. et al., "Thioredoxin, a Redox Enzyme Released in Infection and Inflammation, Is a Unique Chemoatractant for Neutrophils, Monocytes, and T Cells," *The Journal of Experimental Medicine*, vol. 189, No. 11, pp. 1783-1789 (1999).

Brabetz, W. et al., "Bacterial Lipopolysaccharides: Chemical Constitution, Endotoxic Activity, and Biological Neutralization," *Symposium in Immunology*, vol. VIII, pp. 89-121 (M. Eibl et al. edit), Springer Berlin, Heidelberg (1999).

Bradenburg, K. et al., "Confirmation of lipid a, the endotoxic center of bacterial lipopolysaccharide," *Journal of Endotoxin Research*, vol. 3, pp. 173-178 (1996).

Calandra, T. et al., "The Macrophage Is an Important and Previously Unrecognized Source of Macrophage Migration Inhibitory Factor," *J. Exp. Med.*, vol. 179, pp. 1895-1902 (1994).

Carrillo, E.H. et al., "Free Hemoglobin Enhances Tumor Necrosis Factor-α Production in Isolated Human Monocytes," *The Journal of Trauma*, vol. 52, No. 3, pp. 449-452 (2002).

David, S.A, "The Interaction of Lipid A and Lipopolysaccharide with Human Serum Albumin," *Endotoxin in Health and Disease*, (H. Brade edit), pp. 413-422 (1999).

Dunn, D.L. et al., "Mechanisms of the adjuvant effect of hemoglobin in experimental peritonitis. VI. Effects of stroma-free hemoglobin and red blood cell stroma on mortality and neutrophil function," *Surgery*, vol. 93, No. 5, pp. 653-659 (1983).

Freudenberg, M.A. and Galanos, C., "Bacterial Lipopolysaccharides: Structure, Metabolism and Mechanisms of Action," *Intern. Rev. Immunol.*, vol. 6, pp. 207-221 (1990).

Gorczynski, R.M. et al., "A fetal sheep liver extract reverses age-related increments in spontaneous and induced cytokine production by indirect environmental effects," *Immunology Letters*, vol. 60, pp. 157-164 (1998).

Gorczynski, R.M, et al., "An antibody specific for interleukin-6 reverses age-associated changes in spontaneous and induced cytokine production in mice," *Immunology*, vol. 92, pp. 20-25 (1997).

Goto, S. et al., "Intradermal administration of lipopolysaccharide in treatment of human cancer," *Cancer Immunol. Immunotherapy*, vol. 42, pp. 255-261 (1996).

Inagawa, H. et al., "Anti-tumor Effect of Lipopolysaccharide by Intradermal Administration as a Novel Drug Delivery System," *Anticancer Research*, vol. 17, pp. 2153-2158 (1997).

Kaca, W. et al., "Hemoglobin, a Newly Recognized Lipopolysaccharide (LPS)-binding Protein That Enhances LPS Biological Activity," *The Journal of Biological Chemistry*, Vo. 269, No. 40, pp. 25078-25084 (1994).

Kaca, W. and Roth, R., "Activation of complement by human hemoglobin and by mixtures of hemoglobin and bacterial endotoxin," *Biochimica and Biophysica Acta*, vol. 1245, pp. 49-56 (1995).

Katayama, Y. et al., "Scrutiny Of The Endotoxin-Like Substance in Human Placenta," *Japanese Journal of Medical Science & Biology*, vol. 28, pp. 304-307 (1975).

Lotan, R., "Retinoids in cancer chemoprevention," *The FASEB Journal*, vol. 10, pp. 1031-1039 (1996).

Luderitz, O. et al., "Fixation of P32-labeled lipopolysaccharides (endotoxin) from *Escherichia coli* to human erythrocytes," (article in German, no abstract available), Biochem. Z., vol. 30, No. 1, pp. 34-46 (1958).

Metz, C.N. and Bucala, R., "MIF," *Academic Press*, Cytokine Reference (J. Oppenheim et al., edition), pp. 703-716 (2001).

Miller, R.A., "The Aging Immune System: Primer and Prospectus," *Science*, vol. 273, pp. 70-74 (1996).

Munford, R.S. and Hall, C.L., "Detoxification of Bacterial Lipopolysaccharides (Endotoxins) by a Human Neutrophil Enzyme," *Science*, vol. 234, pp. 203-205 (1986).

Nabika, T. et al., "Synergistic effect of ubiquitin on lipopolysaccharide-induced TNF-α production in murine macrophage cell line RAW 264.7 cells," *Biochimica and Biophysica Acta*, vol. 1450, pp. 25-34 (1999).

Neter, E. et al., "The Effects of Protamine and Histone on Enterobacterial Lipopolysaccharides and Hemolysis," *Canadian Journal of Microbiology*, vol. 4, pp. 371-383 (1958).

Nishizawa, T. et al., "Hoeostasis as Regulated by Activated Macrophage. I. Lipopolysaccharide (LPS) from Wheat Flour: Isolation, Purification and Some Biological Activities," *Chemical and Pharmaceutical Bulletin*, vol. 40, No. 2, pp. 479-483 (1992).

Opal, S.M. and Yu, Jr., R.L., "Antiendotoxin Strategies for the Prevention and Treatment of Septic Shock," *Drugs*, vol. 55, No. 4, pp. 497-508 (1998).

Poelstra, K. et al., "Dephosphorylation of Endotoxin by Alkaline Phosphatase in Vivo," *American Journal of Pathology*, vol. 151, No. 4, pp. 1163-1169 (1997).

Poltorak, A. et al., "Defective LPS Signaling in C3H/HeJ and C57BL/10ScCr Mice: Mutations in *Tlr4* Gene," *Science*, vol. 282, pp. 2085-2088 (1998).

Porro, M., "LPS/Lipid A-Binding Synthetic Peptides," *Endotoxin in Health and Disease*, (H. Brade edit), pp. 403-411 (1999).

Rietschel, E. et al., "Bacterial endotoxin: molecular relationships of structure to activity and function," *The FASEB Journal*, vol. 8, pp. 217-225 (1994).

Roger, T. et al., "MIF regulates innate immune responses through modulation of Toll-like receptor4," *Nature*, vol. 414, Issue No. 6866, pp. 920-924 (2001).

Roth, R.I. et al., "Hemoglobin: A Newly Recognized Binding Protein for Bacterial Endotoxins (LPS)," *Bacterial Endotoxins: Basic Science to Anti-Sepsis Strategies*, pp. 161-172 (1994).

Roth, R.I. and Levin, J., "Effects of Human Hemoglobin on Bacterial Endotoxin in Vitro and in Vivo," *Endotoxin in Health and Disease*, (H. Brade edit), pp. 389-401 (1999).

Su, D. et al., "Hemoglobin Increases Mortality from Bacterial Endotoxin," *Infection and Immunity*, vol. 65, No. 4, pp. 1258-1266 (1997).

Rifkind, David, "Prevention by Polymyxin B of Endotoxin Lethality in Mice," Journal of Bacteriology, vol. 93, No. 4, pp. 1463-1464 (1967).

Ulrich, J.T. and Kent R.M., "Monophosphoryl Lipid as an Adjuvant," *Pharm. Biotechnol.*, vol. 6, pp. 495-524 (1995).

Van Bossuyt, H. et al. "Cellular and subcellular distribution of injected lipopolysaccharide in rat liver and its inactivation by bile salts," *Journal of Hepatology*, vol. 7, pp. 325-337 (1988).

Waeber, G. et al., "Insulin secretion is regulated by the glucose-dependent production of islet β cell macrophage migration inhibitory factor," *Proc. Natl. Acad. Sci. USA*, vol. 94, pp. 4782-4787 (1997).

Weksler, M.E. and Schwab, R., "The Immunogenetics of Immune Senescence," *Exp. Clin. Immunogenet.*, vol. 9, pp. 182-187 (1992).

White, C.T. et al., "Synergistic toxicity of endotoxin and hemoglobin," *The Journal of Laboratory and Clinical Medicine*, vol. 108, No. 2, pp. 132-137 (1986).

Zahringer, U. et al., "Molecular Structure of Lipid A, The Endotoxic Center of Bacterial Lipopolysaccharides," *Advances in Carbohydrate Chemistry and Biochemistry*, vol. 50, pp. 211-277 (2001).

Zhang, M. And K.J. Tracey, "Endotoxin and Cancer," *Endotoxin in Health and Disease (Marcel Dekker, Inc.)*, pp. 915-926 (1999).

Zuckerman, S.H. et al., "Endotoxin Tolerance: Independent Regulation of Interleukin-1 and Tumor Necrosis Factor Expression," *Infection and Immunity*, vol. 59, No. 8, pp. 2774-2780 (1991).

Jurgens et al., "Interaction of hemoglobin with enterobacterial lipopolysaccharide and lipid A. Physicochemical characterization and biological activity," European Journal of Biochemistry, 268(15):4233-4242 (2001).

* cited by examiner

Bacterial Lipopolysaccharides: Chemical Constitution

Fig. 10
Induction of nitric oxide release in BMDM from LPS responder and LPS non-responder mice
Comparison of LPS and CLP pools as stimulators
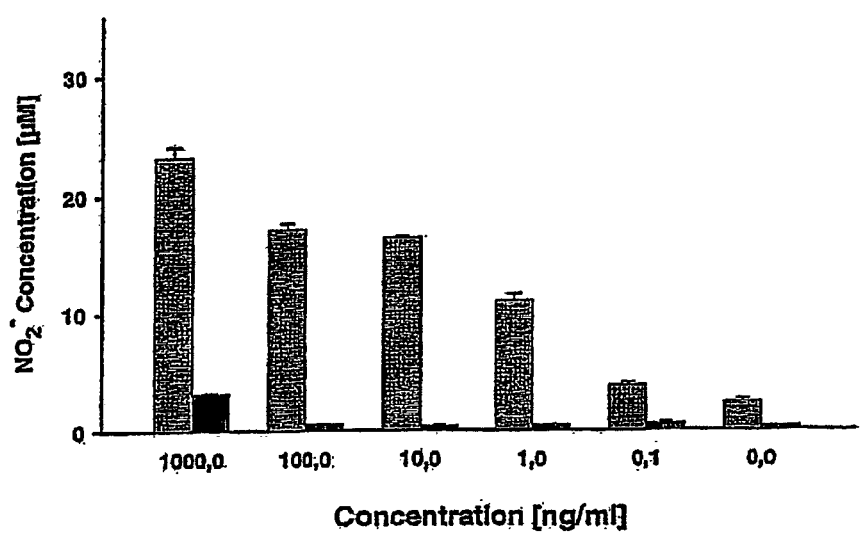
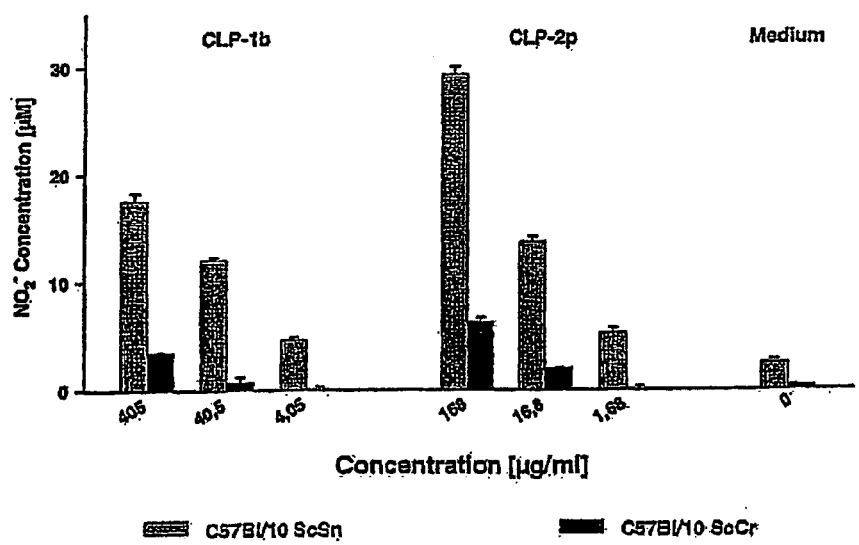

Fig. 20

Tryptic Peptide 1: VGGNAGAYGAEAER
Tryptic Peptide 2: TYFPHEDLSHGSAQVK

```
HBA_HUMAN    VLSPADKTNVKAAWGKVGAHAGEYGAEALERMFLSFPTTKTYFPHFDLSHGSAQVKGHGK   60
HBA_CAPHI    VLSAADKSNVKAAWGKVGGNAGAYGAEALERMFLSFPTTKTYFPHFDLSHGSAQVKGHGE   60
HBA_BOVIN    VLSAADKGNVKAAWGKVGGHAAEYGAEALERMFLSFPTTKTYFPHFDLSHGSAQVKGHGA   60
HBA_MOUSE    VLSGEDKSNIKAAWGKIGGHGAEYGAEALERMEASFPTTKTYFPHFDVSHGSAQVKGHGK   60
HBA_RAT      VLSADDKTNIKNCWGKIGGHGGEYGEEALQRMFAAFPTTKTYFSHIDVSPGSAQVKAHGK   60
HBA_RABIT    VLSPADKTNIKTAWEKIGSHGGEYGAEAVERMFLGFPTTKTYFPHFDFTHGSEQIKAHGK   60
             **: * **.:* . **::*.:.*.** ** ** : ********.* *: .****::.*:

HBA_HUMAN    KVADALTNAVAHVDDMPNALSALSDLHAHKLRVDPVNFKLLSHCLLVTLAAHLPAEFTPA  120
HBA_CAPHI    KVAAALTKAVGHLDDLPGTLSDLSDLHAHKLRVDPVNFKLLSHSLLVTLACHLPNDFTPA  120
HBA_BOVIN    KVAAALTKAVEHLDDLPGALSELSDLHAHKLRVDPVNFKLLSHSLLVTLASHLPSDFTPA  120
HBA_MOUSE    KVADALASAAGHLDDLPGALSALSDLHAHKLRVDPVNFKLLSHCLLVTLASHHPADFTPA  120
HBA_RAT      KVADALAKAADHVEDLPGALSTLSDLHAHKLRVDPVNFKLSHCLLVTLACHHPGDFTPA  120
HBA_RABIT    KVSEALTKAVGHLDDLPGALSTLSDLHAHKLRVDPVNFKLLSHCLLVTLANHHPSEFTPA  120
             **: ** .*. *::**  :* :*****************::*. ****** * . ****

HBA_HUMAN    VHASLDKFLASVSTVLTSKYR  141
HBA_CAPHI    VHASLDKFLANVSTVLTSKYR  141
HBA_BOVIN    VHASLDKFLANVSTVLTSKYR  141
HBA_MOUSE    VHASLDKFLASVSTVLTSKYR  141
HBA_RAT      MHASLDKFLANVSTVLTSKYR  141
HBA_RABIT    VHASLDKFLANVSTVLTSKYR  141
             :*********::*********
```

|     | 1 | 2 | 3 | 4 | 5 | 6 | 7 | 8 | 9 | 10 | 11 | 12 | 13 | 14 | 15 |     |
|-----|---|---|---|---|---|---|---|---|---|----|----|----|----|----|----|-----|
| 1   | Val | Leu | Ser | Ala | Ala | Asp | Lys | Ser | Asn | Val | Lys | Ala | Ala | Trp | Gly | 15  |
| 16  | Lys | Val | Gly | Gly | Asn | Ala | Gly | Ala | Tyr | Gly | Ala | Glu | Ala | Leu | Glu | 30  |
| 31  | Arg | Met | Phe | Leu | Ser | Phe | Pro | Thr | Thr | Lys | Thr | Tyr | Phe | Pro | His | 45  |
| 46  | Phe | Asp | Leu | Ser | His | Gly | Ser | Ala | Gln | Val | Lys | Gly | His | Gly | Glu | 60  |
| 61  | Lys | Val | Ala | Ala | Ala | Leu | Thr | Lys | Ala | Val | Gly | His | Leu | Asp | Asp | 75  |
| 76  | Leu | Pro | Gly | Thr | Leu | Ser | Asp | Leu | Ser | Asp | Leu | His | Ala | His | Lys | 90  |
| 91  | Leu | Arg | Val | Asp | Pro | Val | Asn | Phe | Lys | Leu | Leu | Ser | His | Ser | Leu | 105 |
| 106 | Leu | Val | Thr | Leu | Ala | Cys | His | Leu | Pro | Asn | Asp | Phe | Thr | Pro | Ala | 120 |
| 121 | Val | His | Ala | Ser | Leu | Asp | Lys | Phe | Leu | Ala | Asn | Val | Ser | Thr | Val | 135 |
| 136 | Leu | Thr | Ser | Lys | Tyr | Arg |   |   |   |    |    |    |    |    |    |     |

B

|     | 1 | 2 | 3 | 4 | 5 | 6 | 7 | 8 | 9 | 10 | 11 | 12 | 13 | 14 | 15 |     |
|-----|---|---|---|---|---|---|---|---|---|----|----|----|----|----|----|-----|
| 1   | Met | Leu | Thr | Ala | Glu | Glu | Lys | Ala | Ser | Val | Ile | Ser | Leu | Phe | Ala | 15  |
| 16  | Lys | Val | Asn | Val | Glu | Glu | Val | Gly | Gly | Glu | Ala | Leu | Gly | Arg | Leu | 30  |
| 31  | Leu | Val | Val | Tyr | Pro | Trp | Thr | Gln | Arg | Phe | Phe | Glu | His | Phe | Gly | 45  |
| 46  | Asp | Leu | Ser | Ser | Ala | Asp | Ala | Ile | Leu | Gly | Asn | Pro | Lys | Val | Lys | 60  |
| 61  | Gly | His | Gly | Lys | Lys | Val | Leu | Asn | Ser | Phe | Ser | Glu | Gly | Leu | Lys | 75  |
| 76  | Gln | Leu | Asp | Asp | Leu | Lys | Gly | Ala | Phe | Ala | Ser | Leu | Ser | Glu | Leu | 90  |
| 91  | His | Cys | Asp | Lys | Leu | His | Val | Asp | Pro | Glu | Asn | Phe | Arg | Leu | Leu | 105 |
| 106 | Gly | Asn | Val | Leu | Val | Val | Val | Leu | Ala | Arg | Arg | Phe | Gly | Gly | Glu | 120 |
| 121 | Phe | Thr | Pro | Glu | Leu | Gln | Ala | Asn | Phe | Gln | Lys | Val | Val | Thr | Gly | 135 |
| 136 | Val | Ala | Asn | Ala | Leu | Ala | His | Arg | Tyr | His |    |    |    |    |    |     |

Fig. 34
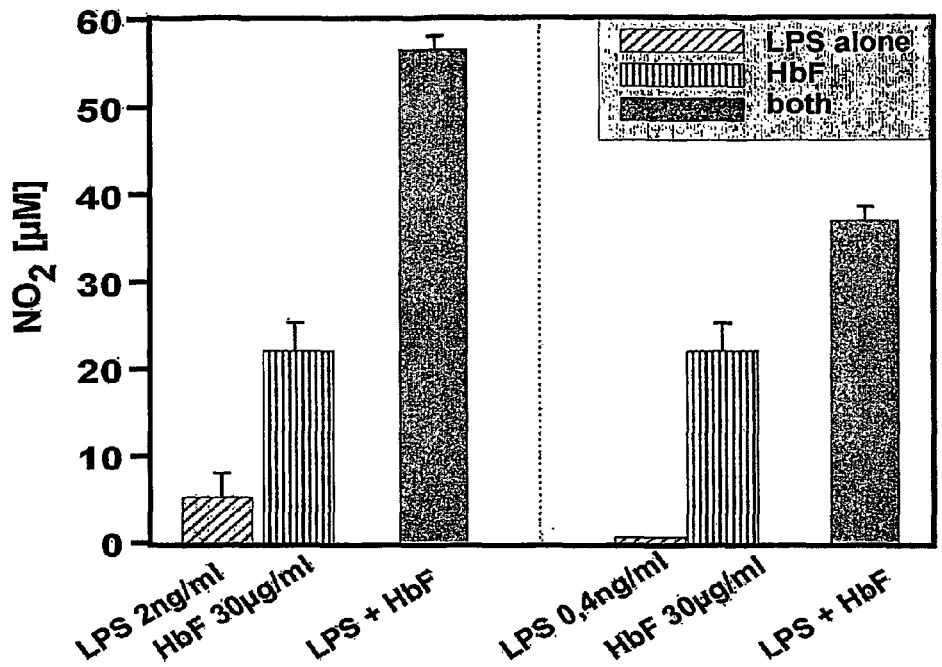
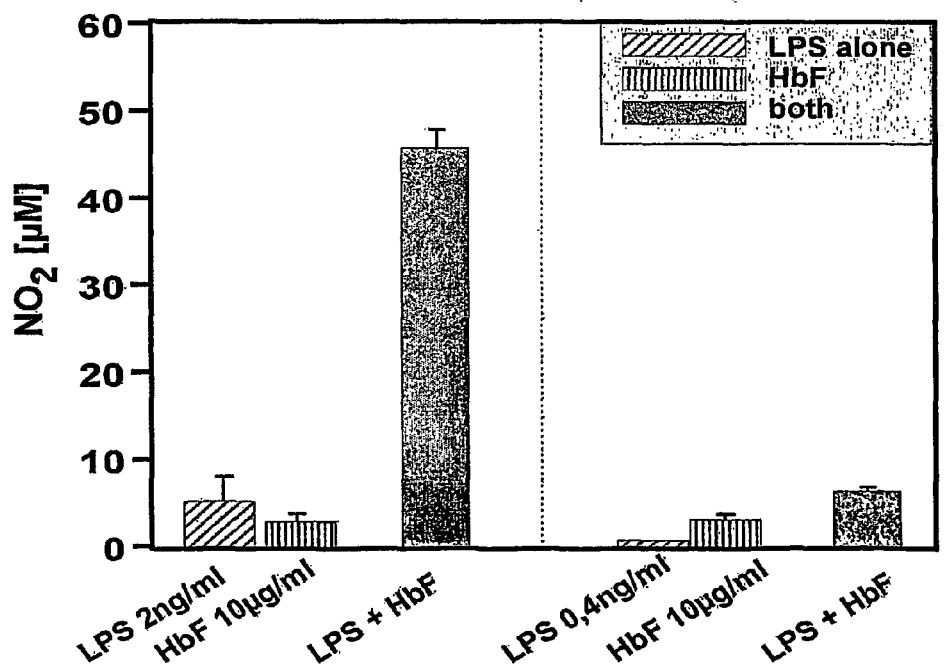

Fig. 35
Synergistic effect of Re-LPS
and HbF without heme [30μg/ml]
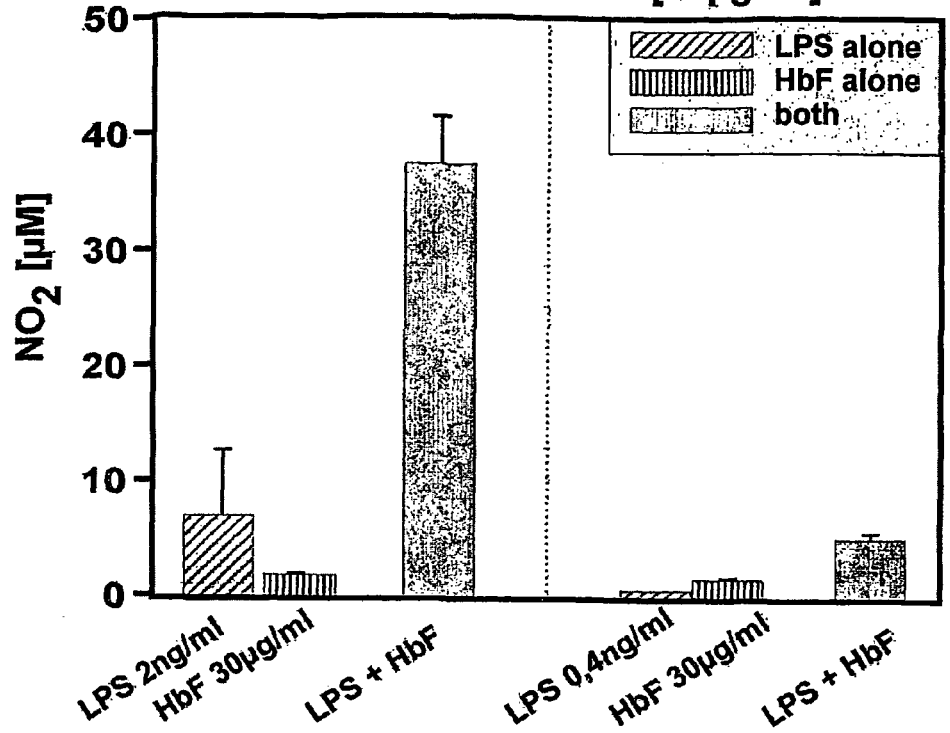
a
Synergistic effect of Re-LPS
and HbF without heme [10μg/ml]
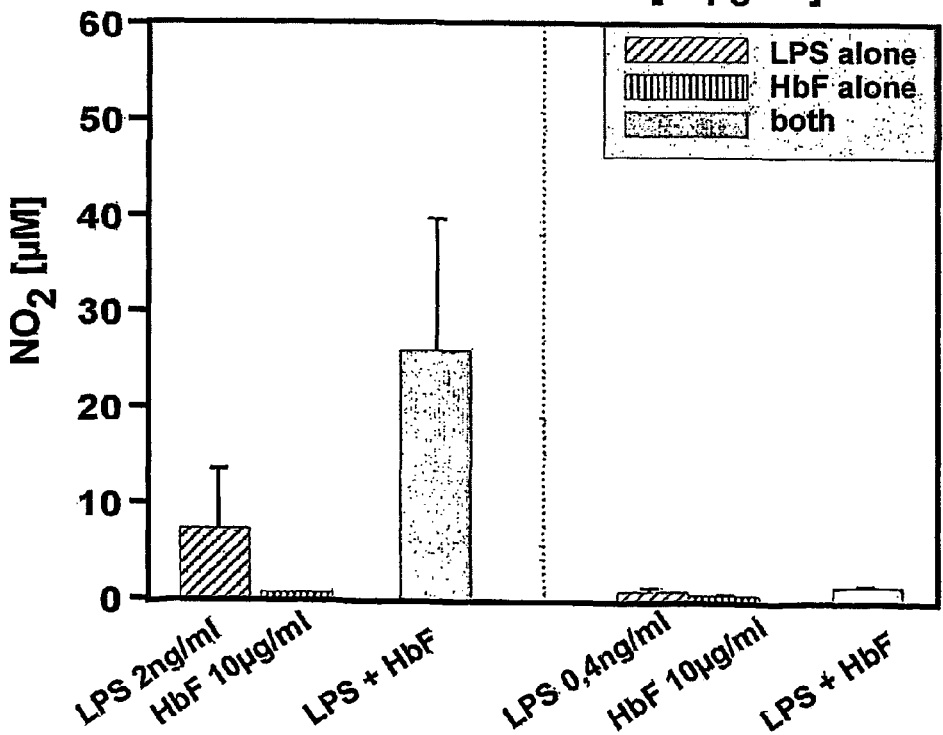
b Fig. 36
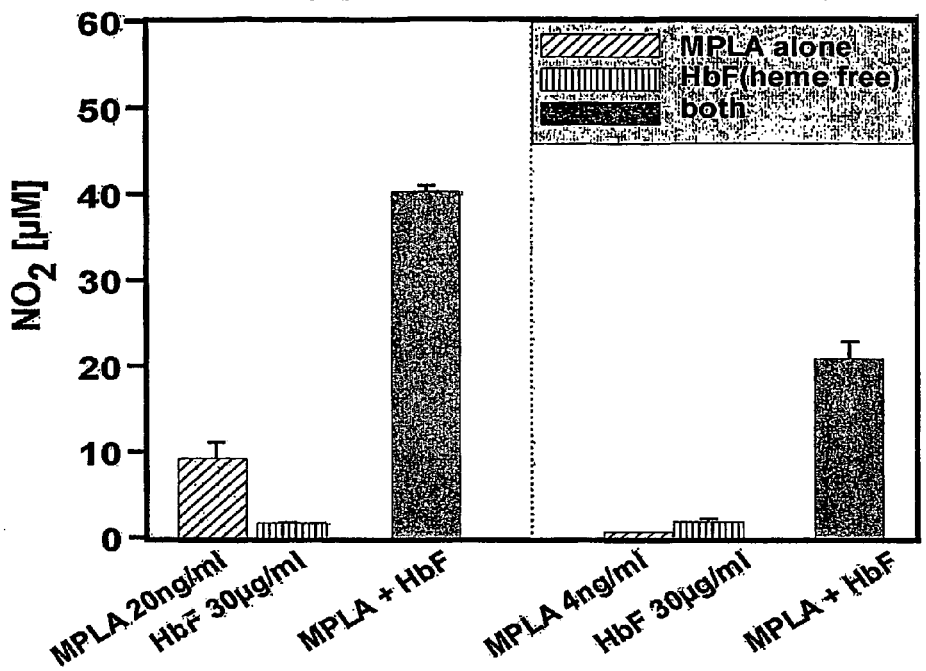
a
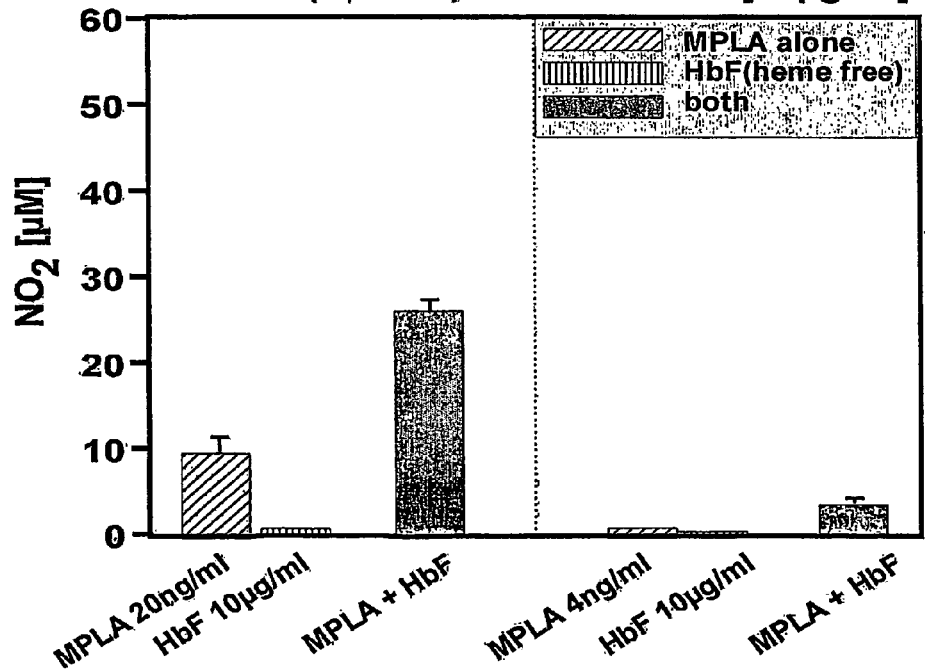
b Fig. 40
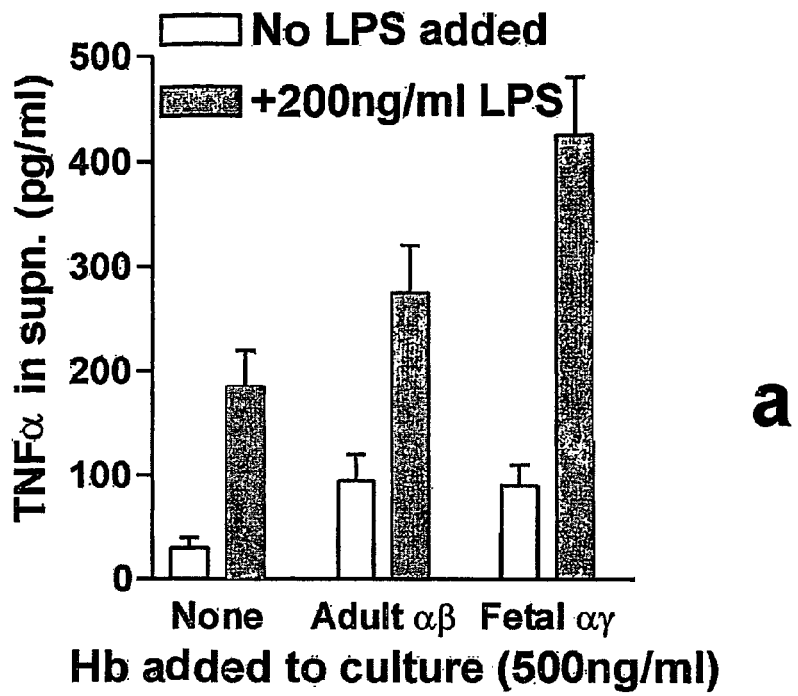
a
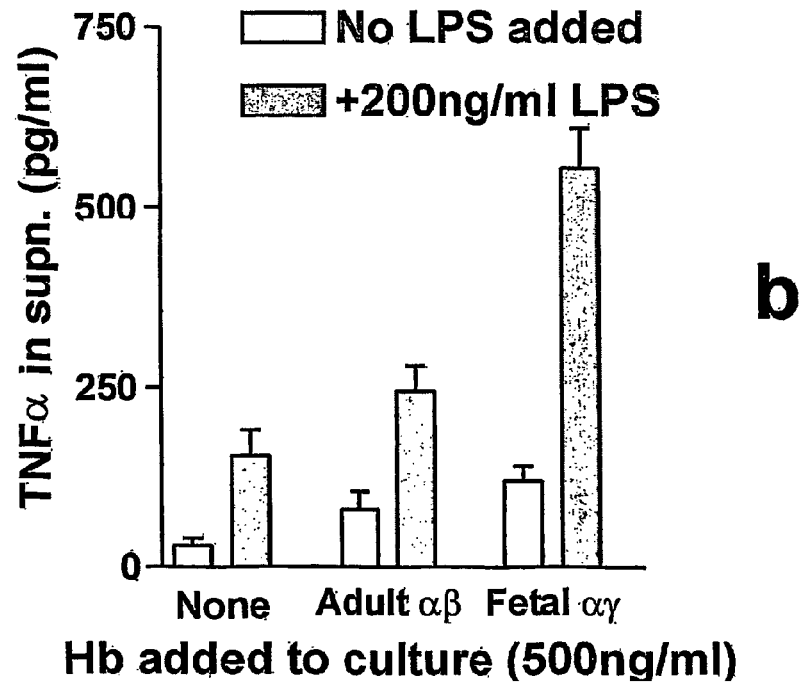
b LPS used in vitro at 100ng/ml; all CHO extracts used at 20μg/ml; TNFα assayed at 24hrs by ELISA.

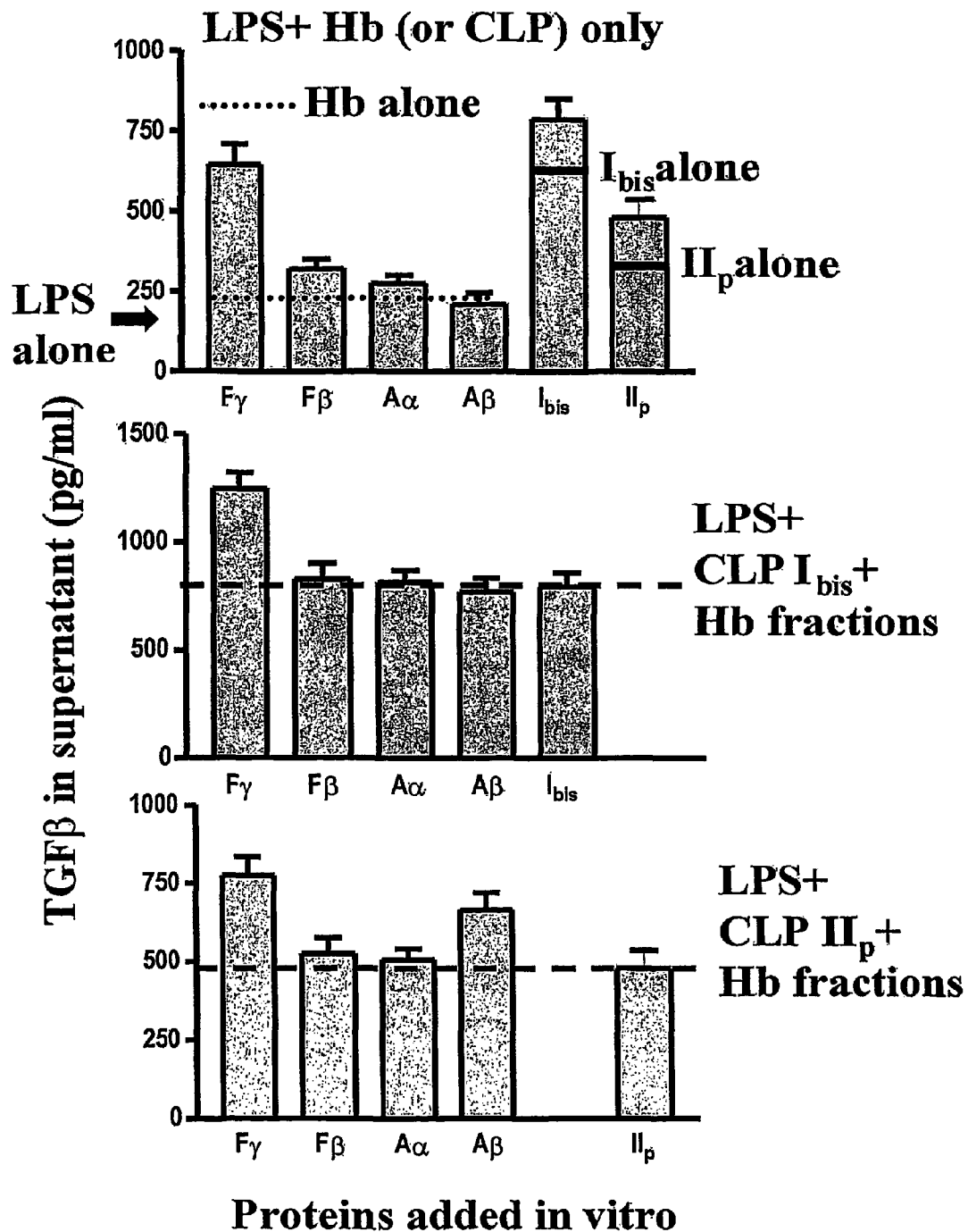

Fig. 46
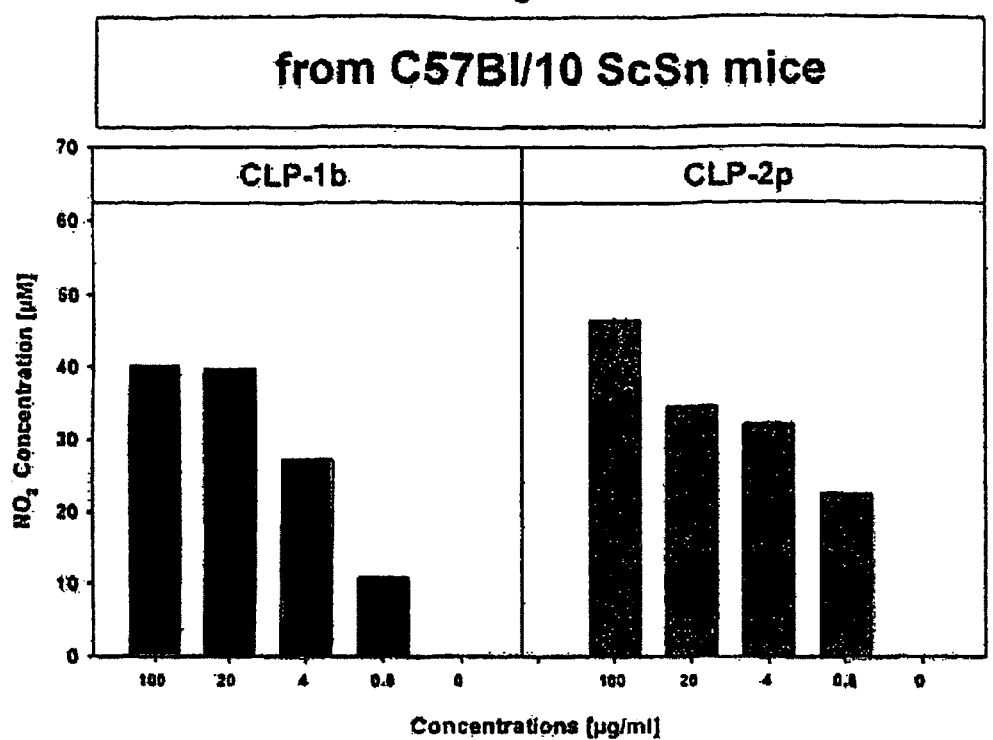
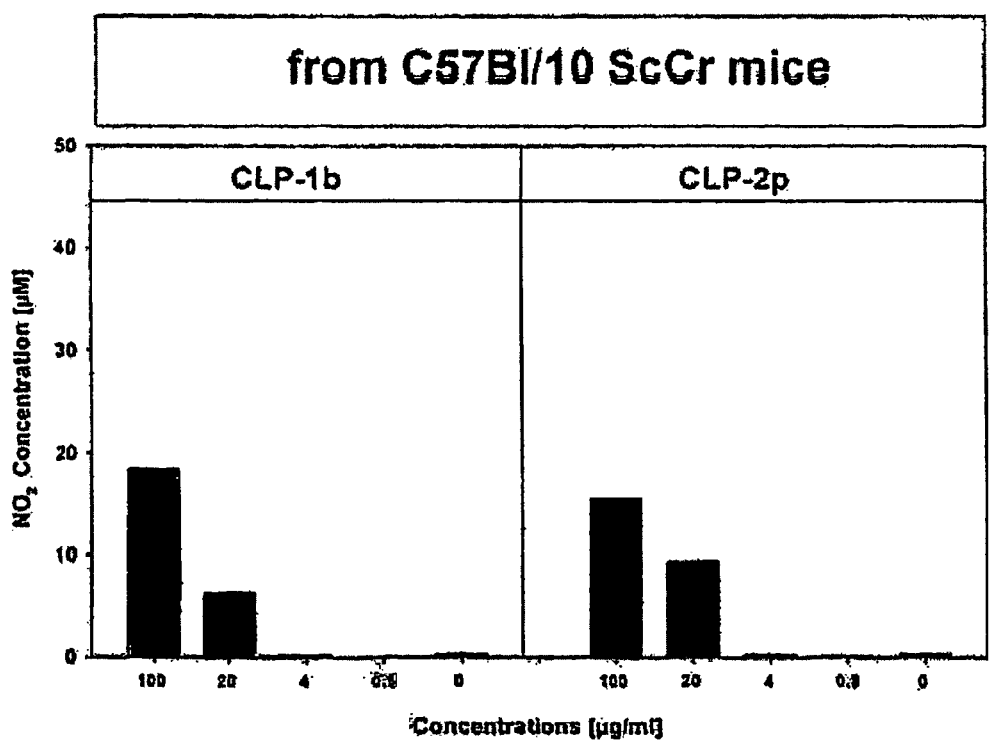

Fig. 60
Cytokine production by human monocytes
Stimulation In vitro with CLP pools
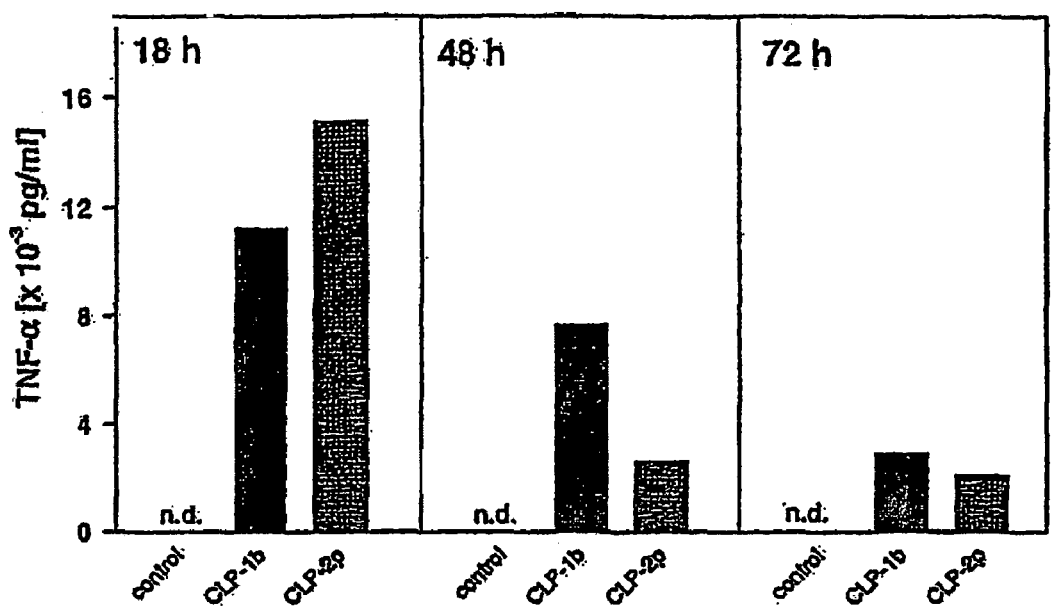
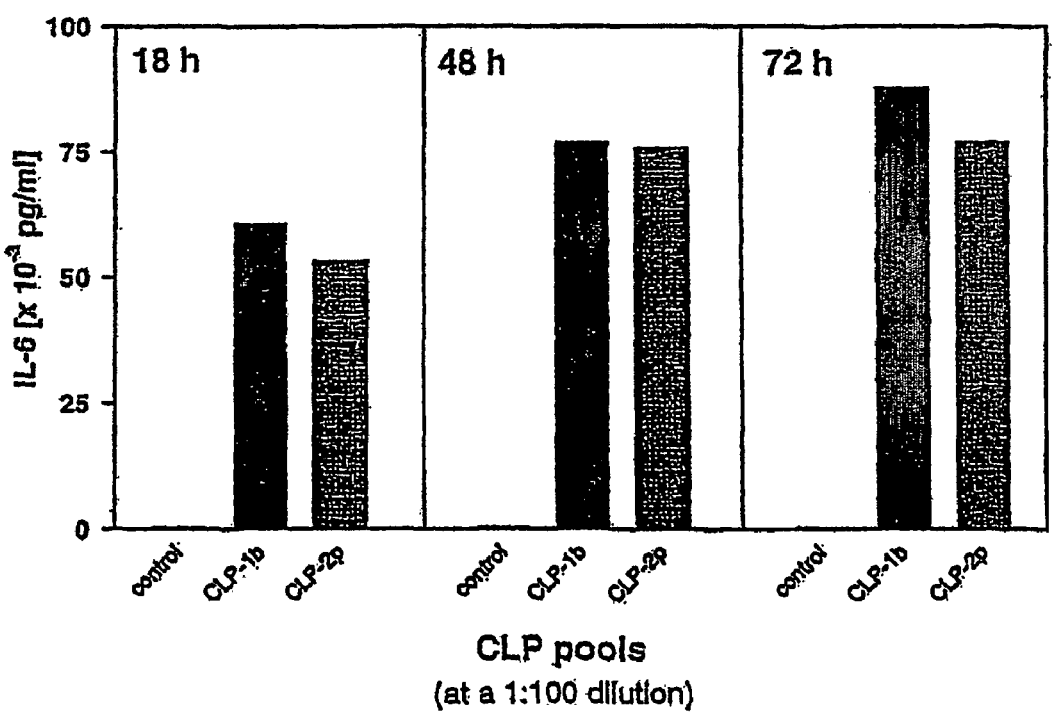
CLP pools
(at a 1:100 dilution)

```
SEQUENCE LISTING

<160> NUMBER OF SEQ ID NOS: 32

<210> SEQ ID NO 1
<211> LENGTH: 16
<212> TYPE: PRT
<213> ORGANISM: Ovis aries

<400> SEQUENCE: 1

Val Leu Ser Ala Ala Asp Lys Ser Asn Val Lys Ala Ala Trp Gly Lys
1               5                   10                  15

<210> SEQ ID NO 2
<211> LENGTH: 16
<212> TYPE: PRT
<213> ORGANISM: Ovis aries

<400> SEQUENCE: 2

Val Leu Ser Ala Ala Asp Lys Ser Asn Val Lys Ala Ala Trp Gly Lys
1               5                   10                  15

<210> SEQ ID NO 3
<211> LENGTH: 16
<212> TYPE: PRT
<213> ORGANISM: Ovis aries

<400> SEQUENCE: 3

Met Leu Thr Ala Glu Glu Lys Ala Ser Val Ile Ser Leu Phe Ala Lys
1               5                   10                  15

<210> SEQ ID NO 4
<211> LENGTH: 16
<212> TYPE: PRT
<213> ORGANISM: Ovis aries

<400> SEQUENCE: 4

Met Leu Thr Ala Glu Glu Lys Ala Ala Val Thr Gly Phe Trp Gly Lys
1               5                   10                  15

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atggagacag acacactcct gctatgggta ctgctgctct gggttccagg ttccactggt    60
```

```
<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taaatgctag cgccaccatg gagacagac                                         29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attataccgg tgtcaccagt ggaacctgg                                         29

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taataaccgg tatggtgcac ctgactcctg agga                                   34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atttaaccgg tagcttagtg atacttgtgg gcca                                   34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taataaccgg tatggtgcac ctgactcctg agga                                   34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atttaaccgg tagcttagtg atacttgtgg gcca                                   34
```

(gac 63 continued from previous page)

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taataaccgg tatgggtcat ttcacagagg ag                                32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atttaaccgg tctcagtggt atctggagga ca                                32

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taataaccgg tatgctgact gctgaggaga a                                 31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atttaaccgg tggaagggga gcttagtgat a                                 31

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
1               5

<210> SEQ ID NO 17
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agcaccggtc atcatcatca tcatcatgat ctgtacgacg atgacgataa gatggtgcac    60
ctgactcctg agga                                                     74

```
<210> SEQ ID NO 18
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcaccggtc atcatcatca tcatcatgat ctgtacgacg atgacgataa gatgggtcat      60
ttcacagagg aggac                                                       75

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agcaccggtc atcatcatca tcatcatgat ctgtacgacg atgacgataa gatgctgact      60
gctgaggaga aggc                                                        74

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccgaattcg aatccggaga c                                                21

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ala Ile Met Gly Asn Pro Lys Val Lys Ala His Gly Lys Lys Val
 1               5                  10                  15

Leu Thr Ser Leu Gly Asp Ala Ile
            20

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Ala Ile Leu Gly Asn Pro Lys Val Lys Gly His Gly Lys Lys Val
 1               5                  10                  15

Leu Asn Ser Phe Ser Glu Gly Leu Lys
            20                  25

<210> SEQ ID NO 23
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Gly Gly Asn Ala Gly Ala Tyr Gly Ala Glu Ala Leu Glu Arg
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Tyr Phe Pro His Phe Asp Leu Ser His Gly Ser Ala Gln Val Lys
1               5                   10                  15

<210> SEQ ID NO 25
<211> LENGTH: 141
<212> TYPE: PRT
<213> ORGANISM: Homo sapiens

<400> SEQUENCE: 25

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
        50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 26
<211> LENGTH: 141
<212> TYPE: PRT
<213> ORGANISM: Capra hircus

<400> SEQUENCE: 26

Val Leu Ser Ala Ala Asp Lys Ser Asn Val Lys Ala Ala Trp Gly Lys
1               5                   10                  15

Val Gly Gly Asn Ala Gly Ala Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Glu Lys Val Ala Ala
        50                  55                  60
```

```
Ala Leu Thr Lys Ala Val Gly His Leu Asp Asp Leu Pro Gly Thr Leu
 65                  70                  75                  80

Ser Asp Leu Ser Asp Leu His Ala His Lys Leu Arg Val Asp Pro Val
                 85                  90                  95

Asn Phe Lys Leu Leu Ser His Ser Leu Leu Val Thr Leu Ala Cys His
            100                 105                 110

Leu Pro Asn Asp Phe Thr Pro Ala Val His Ala Ser Leu Asp Lys Phe
        115                 120                 125

Leu Ala Asn Val Ser Thr Val Leu Thr Ser Lys Tyr Arg
    130                 135                 140
```

<210> SEQ ID NO 27
<211> LENGTH: 141
<212> TYPE: PRT
<213> ORGANISM: Bos taurus

<400> SEQUENCE: 27

```
Val Leu Ser Ala Ala Asp Lys Gly Asn Val Lys Ala Ala Trp Gly Lys
  1               5                  10                  15

Val Gly Gly His Ala Ala Glu Tyr Gly Ala Glu Ala Leu Glu Arg Met
             20                  25                  30

Phe Leu Ser Phe Pro Thr Thr Lys Thr Tyr Phe Pro His Phe Asp Leu
         35                  40                  45

Ser His Gly Ser Ala Gln Val Lys Gly His Gly Ala Lys Val Ala Ala
     50                  55                  60

Ala Leu Thr Lys Ala Val Glu His Leu Asp Asp Leu Pro Gly Ala Leu
 65                  70                  75                  80

Ser Glu Leu Ser Asp Leu His Ala His Lys Leu Arg Val Asp Pro Val
                 85                  90                  95

Asn Phe Lys Leu Leu Ser His Ser Leu Leu Val Thr Leu Ala Ser His
            100                 105                 110

Leu Pro Ser Asp Phe Thr Pro Ala Val His Ala Ser Leu Asp Lys Phe
        115                 120                 125

Leu Ala Asn Val Ser Thr Val Leu Thr Ser Lys Tyr Arg
    130                 135                 140
```

<210> SEQ ID NO 28
<211> LENGTH: 141
<212> TYPE: PRT
<213> ORGANISM: Mus musculus

<400> SEQUENCE: 28

```
Val Leu Ser Gly Glu Asp Lys Ser Asn Ile Lys Ala Ala Trp Gly Lys
  1               5                  10                  15

Ile Gly Gly His Gly Ala Glu Tyr Gly Ala Glu Ala Leu Glu Arg Met
             20                  25                  30

Phe Ala Ser Phe Pro Thr Thr Lys Thr Tyr Phe Pro His Phe Asp Val
         35                  40                  45

Ser His Gly Ser Ala Gln Val Lys Gly His Gly Lys Lys Val Ala Asp
     50                  55                  60

Ala Leu Ala Ser Ala Ala Gly His Leu Asp Asp Leu Pro Gly Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ser His
            100                 105                 110
```

His Pro Ala Asp Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 29
<211> LENGTH: 141
<212> TYPE: PRT
<213> ORGANISM: Rattus norvegicus

<400> SEQUENCE: 29

Val Leu Ser Ala Asp Asp Lys Thr Asn Ile Lys Asn Cys Trp Gly Lys
1               5                   10                  15

Ile Gly Gly His Gly Gly Glu Tyr Gly Glu Ala Leu Gln Arg Met
            20                  25                  30

Phe Ala Ala Phe Pro Thr Thr Lys Thr Tyr Phe Ser His Ile Asp Val
        35                  40                  45

Ser Pro Gly Ser Ala Gln Val Lys Ala His Gly Lys Lys Val Ala Asp
    50                  55                  60

Ala Leu Ala Lys Ala Ala Asp His Val Glu Asp Leu Pro Gly Ala Leu
65                  70                  75                  80

Ser Thr Leu Ser Asp Leu His Ala His Lys Leu Arg Val Asp Pro Val
                85                  90                  95

Asn Phe Lys Phe Leu Ser His Cys Leu Leu Val Thr Leu Ala Cys His
            100                 105                 110

His Pro Gly Asp Phe Thr Pro Ala Met His Ala Ser Leu Asp Lys Phe
        115                 120                 125

Leu Ala Ser Val Ser Thr Val Leu Thr Ser Lys Tyr Arg
    130                 135                 140

<210> SEQ ID NO 30
<211> LENGTH: 141
<212> TYPE: PRT
<213> ORGANISM: Oryctolagus cuniculus

<400> SEQUENCE: 30

Val Leu Ser Pro Ala Asp Lys Thr Asn Ile Lys Thr Ala Trp Glu Lys
1               5                   10                  15

Ile Gly Ser His Gly Gly Glu Tyr Gly Ala Glu Ala Val Glu Arg Met
            20                  25                  30

Phe Leu Gly Phe Pro Thr Thr Lys Thr Tyr Phe Pro His Phe Asp Phe
        35                  40                  45

Thr His Gly Ser Glu Gln Ile Lys Ala His Gly Lys Lys Val Ser Glu
    50                  55                  60

Ala Leu Thr Lys Ala Val Gly His Leu Asp Asp Leu Pro Gly Ala Leu
65                  70                  75                  80

Ser Thr Leu Ser Asp Leu His Ala His Lys Leu Arg Val Asp Pro Val
                85                  90                  95

Asn Phe Lys Leu Leu Ser His Cys Leu Leu Val Thr Leu Ala Asn His
            100                 105                 110

His Pro Ser Glu Phe Thr Pro Ala Val His Ala Ser Leu Asp Lys Phe
        115                 120                 125

Leu Ala Asn Val Ser Thr Val Leu Thr Ser Lys Tyr Arg
    130                 135                 140

<210> SEQ ID NO 31
<211> LENGTH: 141
<212> TYPE: PRT

```
<213> ORGANISM: Ovis aries

<400> SEQUENCE: 31

Val Leu Ser Ala Ala Asp Lys Ser Asn Val Lys Ala Ala Trp Gly Lys
1               5                   10                  15

Val Gly Gly Asn Ala Gly Ala Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Glu Lys Val Ala Ala
        50                  55                  60

Ala Leu Thr Lys Ala Val Gly His Leu Asp Asp Leu Pro Gly Thr Leu
65                  70                  75                  80

Ser Asp Leu Ser Asp Leu His Ala His Lys Leu Arg Val Asp Pro Val
                85                  90                  95

Asn Phe Lys Leu Leu Ser His Ser Leu Leu Val Thr Leu Ala Cys His
                100                 105                 110

Leu Pro Asn Asp Phe Thr Pro Ala Val His Ala Ser Leu Asp Lys Phe
            115                 120                 125

Leu Ala Asn Val Ser Thr Val Leu Thr Ser Lys Tyr Arg
        130                 135                 140

<210> SEQ ID NO 32
<211> LENGTH: 145
<212> TYPE: PRT
<213> ORGANISM: Capra hircus

<400> SEQUENCE: 32

Met Leu Thr Ala Glu Glu Lys Ala Ser Val Ile Ser Leu Phe Ala Lys
1               5                   10                  15

Val Asn Val Glu Glu Val Gly Gly Glu Ala Leu Gly Arg Leu Leu Val
                20                  25                  30

Val Tyr Pro Trp Thr Gln Arg Phe Phe Glu His Phe Gly Asp Leu Ser
            35                  40                  45

Ser Ala Asp Ala Ile Leu Gly Asn Pro Lys Val Lys Gly His Gly Lys
        50                  55                  60

Lys Val Leu Asn Ser Phe Ser Glu Gly Leu Lys Gln Leu Asp Asp Leu
65                  70                  75                  80

Lys Gly Ala Phe Ala Ser Leu Ser Glu Leu His Cys Asp Lys Leu His
                85                  90                  95

Val Asp Pro Glu Asn Phe Arg Leu Leu Gly Asn Val Leu Val Val Val
                100                 105                 110

Leu Ala Arg Arg Phe Gly Gly Glu Phe Thr Pro Glu Leu Gln Ala Asn
            115                 120                 125

Phe Gln Lys Val Val Thr Gly Val Ala Asn Ala Leu Ala His Arg Tyr
        130                 135                 140

His
145
```

COMPOSITIONS COMPRISING FETAL HEMOGLOBIN AND BACTERIAL ENDOTOXIN AND OPTIONALLY ADDITIONAL FETAL LIVER COMPONENTS

This application is a 371 of PCT/EP04/01553, filed Feb. 18, 2004, which claims the benefit of European Patent Office application EPO 03003687.5, filed Feb. 18, 2003.

Sequence Listing

The instant application contains a Sequence Listing which has been submitted via EFS-Web and is hereby incorporated by reference in its entirety. Said ASCII text file, created on Mar. 30, 2010, is named Sequence Listing.txt, and is 16,850 bytes in size.

In the specification, a number of prior art documents is cited. The contents of these documents including manufacturers' manuals is herewith incorporated by reference into the specification.

The present invention relates to a composition preferably a pharmaceutical composition comprising endotoxin, preferably bacterial endotoxin, fetal hemoglobin and, optionally, additional components such as additional fetal liver components and a pharmaceutically acceptable carrier and/or diluent. In accordance with the present invention it was surprisingly found that bacterial endotoxin and fetal hemoglobin display a pronounced synergistic biomedical activity. The composition of the invention finds a variety of applications including the stimulation of the immune system, the prevention and/or treatment of cancer, infections such as viral infections and/or allergy and the reversion of age-related immune imbalances.

In the fight of mankind against diseases such as cancer or severe infections—and also against the process of aging—the transfer of fetal organs, tissues, or cells has been propagated over many decades as a preventive or therapeutic measure. The history of fetal "cellular therapy" is rich in anecdotes describing restoration of health and reporting on rejuvenating effects [Lambert, G., 1959; Schmid, F., 1963]. The medical effects, although often striking, were for many years judged only by subjective criteria and the factors responsible for bioactivity of fetal tissue remained undefined. Medical activity of components derived from fetal tissue was postulated to be due to the immunogenic properties of onco-fetal antigens cross-reacting with certain membrane structures [H. Röhrer, 1987], thus underlining the xenogenicity of the injected material (sheep vs. man) [Coggin, J. H. et al., 1971; Renner, H. 1977]. Extracts of fetal tissue thus appeared to have a beneficial medical effect and at times were recommended particularly in the treatment or prevention of cancer and certain infections. The medically active principles in these fetal tissue extracts have so far been elusive, despite considerable interest in the field. Problems with the registration of such compositions are self-evident. Since more than a century the treatment of cancer by injections of viable and/or heat-killed bacteria was propagated [Coley, W. 1893]. About 50 years ago it was shown that the tumor-necrotizing effect of such treatment is due to bacterial endotoxin. On a weight basis, bacterial endotoxin (lipopolysaccharide, LPS) is the most active antitumoral agent, a fact which prompted, repeatedly, experimental research along these lines. However, unwanted side effects due to endotoxin did not allow a wider, more general application of that therapy. As is well known, numerous further approaches have been taken to conquer these diseases or to successfully antagonize the phenomenon of aging. Yet, cancer—like infectious as well as allergic diseases and/or aging—remain serious problems for mankind today, since many of these approaches have failed or have not brought about the results man had hoped for. Thus, the technical problem underlying the present invention was to find a means that may favorably be engaged in the fight against said diseases or against aging. The solution to said technical problem is achieved by providing the embodiments characterized in the claims.

Accordingly, the present invention relates to a composition, preferably a pharmaceutical composition comprising or consisting of endotoxin, preferably bacterial endotoxin, more preferably enterobacterial endotoxin or an endotoxically active portion thereof, and fetal hemoglobin, such as heme-free hemoglobin or (a) single chain(s) thereof or (a) combination(s) of chains thereof, and optionally (an) additional compound(s) such as fetal liver (glyco)peptides and, optionally, a pharmaceutically acceptable carrier and/or diluent and/or an excipient.

Specifically, the invention relates to a pharmaceutical composition (or "medicinal product") consisting of endotoxin or an endotoxically active portion thereof, fetal hemoglobin or (a) single chain(s) thereof or (a) combination(s) of chains thereof, and, optionally, (an) additional compound(s) and optionally an excipient; or
comprising endotoxin or an endotoxically active portion thereof, fetal hemoglobin or (a) single chain(s) thereof or (a) combination(s) of chains thereof, optionally (an) additional compound(s) and a pharmaceutically acceptable carrier and/or diluent and/or excipient.

The term "pharmaceutical composition" (which is used interchangeably with the term "medicinal product") as used in the present invention generally has the broadest meaning as employed in the art. Preferably, it means any substance or combination of substances (as above), optionally in combination with pharmaceutically acceptable carriers, diluents and/or excipients, presented for treating or preventing diseases in human beings or animals. In other words, this term denotes any substance or combination of substances (as above) which may be administered to human beings or animals with a view to making a medical diagnosis or to restoring, correcting or modifying physiological functions in human beings or in animals. It is preferred, but not necessary in accordance with the invention that the pharmaceutical composition is sold/requires a market authorization. In other terms, compositions sold OTC with the design to restoring, correcting or modifying physiological functions in human beings or in animals or preventing, treating or modulating any disease such as recited herein or enhancing the overall well-being or counterbalancing phenomena/causes of aging (see also below) are also comprised by the invention.

The term "endotoxin" (lipopolysaccharide, LPS) refers to bioactive compounds produced, in general, by Gram-negative bacteria, and constituting a major component of the bacterial outer membrane from which they may be released biologically or chemically. The structure of endotoxins follows a general scheme which is shown in FIG. 1 for *Salmonella enterica*, as an example. Endotoxins are amphiphilic molecules consisting of a lipid component, termed Lipid A, and a covalently bound polysaccharide. Because of genetic, biosynthetic, biological, and structural characteristics, the carbohydrate portion can be further divided into a Lipid A-proximal core region and an O-specific side chain. It is understood in accordance with the invention that endotoxin employed in the composition of the invention may be of any Gram-negative, endotoxin carrying bacterium. It is in one embodiment preferred that said endotoxin is derived from *Escherichia coli*. In general, O-specific chains are heteropolymers, made up of repeating oligosaccharide units (in enterobacteria up to 50) which consist of between two and eight monomers. The core region of LPS consists of a complex oligosaccharide and, as regards its structure, shows less variability in comparison to the O-specific chain [Zähringer, U. et al. 1994]. In enterobacteria and some other families, one can differentiate between an outer core region with predominantly pyranosidic hexoses, such as D-glucose, D-galactose, 2-amino-2-deoxy-D-glucose or 2-amino-2-deoxy- D-galactose, and an inner core region. In all gram-negative bacteria, the latter contains 3-deoxy- D-manno-oct-2-ulosonic acid (2-keto-3-deoxy-D-manno-octonic acid, Kdo) and often L-glycero- D-manno-heptose (Hep).

Structurally, the Lipid A component forms the most uniform part of LPS. It can be separated from the carbohydrate portion by mild acid hydrolysis leading to the cleavage of the glycosidic bond between Kdo and Lipid A, and, hence, becomes accessible to a detailed structural elucidation. Lipid A samples prepared from *E. coli* turned out to be as endotoxically active in vitro and in animal models as LPS, showing that Lipid A represents the endotoxically active principle of LPS. This was unequivocally proven by chemical synthesis of Lipid A from *E. coli* and the demonstration of full biological activity of the synthetic product. FIG. 2 shows the chemical structure of Lipid A of *Escherichia coli* LPS in the form of the monophosphoryl partial structure (MPLA). Mature Lipid A contains a further phosphoryl group at the glycosidic position of the reducing glucosamine residue. The term LPS comprises S-form and R-form LPS and substructures such as Lipid A and partial structures thereof.

The term "endotoxically active portion" of endotoxin refers to portions that display at least 50%, preferably at least 75%, more preferred at least 90% such as at least 95% and most preferred at least 100% of the endotoxic activity of naturally occurring endotoxin. It is preferred that said endotoxically active portion is the Lipid A component. Most preferred is that the endotoxically active portion is monophosphorylated lipid A (MPLA) further described herein below and in the appended examples.

Hemoglobin (Hb) refers in the art to a hemeprotein of about 64,500 Da molecular weight, the main biological function of which is the transport of oxygen ($O_2$). Adult Hb (HbA) consists of 4 polypeptides (two α- and two β-chains) and one heme group. Fetal Hb (HbF) contains two α-chains and two γ-chains. HbA is synthesized in the bone marrow whereas HbF is primarily produced in the liver (and spleen) of the fetus. In the present invention, the term fetal hemoglobin denotes the tetrameric forms of HbF as well as heme-free HbF. Combinations of chains include the α-, γ-dimers. Monomers include α- and γ-monomers.

When starting experiments that led to the present invention, it was surprisingly found that the biological activity of fractions derived from fetal (sheep) liver extract (FSLE)—for nomenclature see Example 1—is associated with the presence of small amounts of bacterial endotoxin in the order of 10 ng/g (100 EU/g) of FSLE. If fetal sheep liver extract is fractionated on Sephadex G100, as described in Example 2, the small amounts of endotoxin accumulate in two fractions, called CLP1b and CLP2p, which are the most active preparations in the biological assay applied.

Comparative biological analyses employing purified endotoxin suggested the presence in CLP1b and CLP2p of a factor capable of modifying endotoxin activity. Such factor was here identified as fetal hemoglobin and, in particular, its γ-chain constituent. It was further found that endotoxin and fetal hemoglobin interact to exert synergistic, i.e. maximal bioactivity. In comparative studies it was found that fetal hemoglobin and subunits containing the γ-chain are biologically significantly more active than adult hemoglobin and substructures containing the β-chain (see Examples 8 and 9). It was also found that fetal liver extract, in addition, acts favourably on endotoxin and hemoglobin—possibly with regard to their pharmacological tolerability, or the duration of their in vivo activity i.e. their biological dynamics. Consequently, extract from fetal tissue (liver) was extensively analyzed for such additional bioactive factors, probably of polypeptide nature (see protein analysis of fetal liver extract in Examples 3.3.2 and Table 4).

Various combinations of endotoxin, hemoglobin, and FSLE were analyzed for biomedical activities, such as the activation of macrophages, tumor cytostasis and tumor cytotoxicity, dynamics of cytokine production, antiaging phenomena etc., also in various human systems (see Examples 8, 12, 13, 15)

These FSLE-derived compounds were further found to express bioactivity (in mice) also when administered orally. Thus, the oral use of a suitable combination of these so different bioactive principles, like endotoxin, hemoglobin, and FSLE (polypeptides) may open the door to wider, more efficient medical application, for example in the field of cancer, infections, allergy and age-related immune imbalances.

The components of the (pharmaceutical) composition of this invention can be obtained by different methods of manufacture, wherein the following options are not exclusive of other processes but refer to preferred embodiments: either by extraction from fetal liver, the active components then being present as they are biologically accumulated in the fetal liver tissue; or by chemical preparation from available sources, such as endotoxin from cultures of gram-negative bacteria or hemoglobin from umbilical cord blood; single chains such as its γ-chain as well as the combinations of chains can also be produced by gene technological procedures. Thus, components of the preparation contained in the composition of the invention may be obtained from natural sources, by recombinant DNA technology/biochemical synthesis or by chemical synthesis as well as any combinations thereof. Interaction of the components of the preparation may take place after synthesis.

As regards the recombinant production, nucleic acid encoding said (poly)peptide may be used in a conventional expression process using a variety of host cells and expression vectors (see, e.g., Sambrook et al., "Molecular Cloning, A Laboratory Manual", CSH Press, Cold Spring Harbor, 1989, "Current Protocols in Molecular Biology, John Wiley & Sons, New York, 2001).

Generally and for all embodiments of the invention, said host cell used for the recombinant production may be a prokaryotic or a eukaryotic cell. The polynucleotide or vector which is present in the host cell may either be integrated into the genome of the host cell or it may be maintained extrachromosomally.

The term "prokaryotic" is meant to include all bacteria which can be transformed or transfected with the nucleic acid molecule or vector referred to above. Prokaryotic hosts may include Gram-negative as well as Gram-positive bacteria such as, for example, *Escherichia coli, Salmonella typhimurium, Serratia marcescens* and *Bacillus subtilis*. The term "eukaryotic" is meant to include yeast those of the genus *Saccharomyces*, in particular those of the species *S. cerevisiae*, higher plant, fungal, insect and preferably mammalian such as human cells. Furthermore, transgenic animals, preferably mammals, comprising said host cells may be used for the large scale production of the proteinaceous compounds contained in the composition of the invention.

The vectors may be particularly plasmids, cosmids, viruses and bacteriophages used conventionally in genetic engineering that comprise the polynucleotide of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector into targeted cell population. Methods which are well known to those skilled in the art can be used to construct recombinant viral vectors; see, for example, the techniques described in Sambrook et al., Molecular Cloning A Laboratory Manual, Cold Spring Harbor Laboratory (1989) N.Y. and Ausubel et al., Current Protocols in Molecular Biology, Green Publishing Associates and Wiley Interscience, N.Y. (1989). Alternatively, the polynucleotides and vectors can be reconstituted into liposomes for delivery to target cells. The vectors containing the polynucleotides encoding said polypeptides can be transferred into the host cell by well-known methods, which vary depending on the type of cellular host. For example, calcium chloride transfection is commonly utilized for prokaryotic cells, whereas, e.g., calcium phosphate or DEAE-Dextran mediated transfection or electroporation may be used for other cellular hosts; see Sambrook, supra.

Such vectors may comprise further genes such as marker genes which allow for the selection of said vector in a suitable host cell and under suitable conditions. Preferably, the sequence encoding said polypeptide is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and, optionally, a poly-A signal ensuring termination of transcription and stabilization of the transcript, and/or an intron further enhancing expression of said polynucleotide. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used, leader sequences capable of directing the polypeptide to a cellular compartment or secreting it into the medium may be added to the coding sequence of the polynucleotide encoding the polypeptide comprised in the pharmaceutical composition of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3, the Echo™ Cloning System (Invitrogen), pSPORT1 (GIBCO BRL) or pRevTet-On/pRevTet-Off or pCI (Promega). Preferably, the expression control sequences will be eukaryotic promoter systems in vectors capable of transforming or transfecting eukaryotic host cells, but control sequences for prokaryotic hosts may also be used.

The hemoglobin component (including single chain(s) or combination(s) of chains) of the invention may be produced by a method comprising culturing said host cell under suitable conditions that allow the synthesis of said (poly)peptide (i.e. peptide up to 30 amino acids or polypeptide of more than 30 amino acids) and recovery and/or isolation of the said (poly)peptide, either from the supernatant or from the cell body.

Specifically, the transformed/transfected hosts can be grown in fermentors and cultured according to techniques known in the art to achieve optimal cell growth. The hemoglobin component and optionally further proteins can then be isolated from the growth medium, cellular lysates, or cellular membrane fractions. Once expressed, said protein can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure polypeptides of at least about 90 to 95% homogeneity are preferred, and 98% to 99% or more homogeneity are most preferred, for pharmaceutical uses.

The (partially) purified components can be mixed in any desired proportion (weight). Pure endotoxin and pure fetal hemoglobin could also be added in defined amounts to a given amount of fetal liver extract (FSLE) to arrive at compositions in accordance with the invention.

A starting dose for the i.m. injection of the pharmaceutical composition, as exemplified by the FSLE, can be 680 mg (defined as one unit) of which approximately 300 mg are protein, approximately 320 mg are non-proteinaceous material and 60 mg represent sodium chloride. Of this material one unit contains approximately 6 ng of LPS equivalents. From 680 mg of FSLE, upon Sephadex G-100 fractionation, approximately 20 mg of CLP1b/2p (~3%) are obtained. In the *Limulus*-Test (LAL) assay this material gave a content of approximately 2 µg ($2 \times 10^4$ EU) of LPS-equivalents for the 20 mg which are part of the standard i.m. injection.

The maximal tolerable dose (MTD) of isolated LPS (i.v.) in humans is in the order of 0.05 to 0.1 µg totally (approximately 1 ng/kg body weight). The respective unit of FSLE with 620 mg of organic matter, accordingly, contains an average of 20-40 MTD (i.v.) of LPS which are injected (i.m.) without subjective side effects.

Thus, depending on the route of administration a unit injection may contain
10-100 ng (i.v.) or 0.2-2 µg (i.m., s.c. or i.d.) or up to 1 mg (oral) LPS equivalents,
0.001-10 mg (or more) fetal hemoglobin or partial structures such as preferably containing the γ-chain and
~0.1-500 mg (or more) of fetal liver (glyco)-protein (polypeptides).

The composition of the present invention may further comprise a pharmaceutically acceptable carrier and/or diluent and/or excipient. Examples of suitable pharmaceutical carriers are well known in the art and include isotonic solutions of phosphate buffered saline solutions, water, emulsions, such as oil/water emulsions, various types of wetting agents, sterile solutions etc. Compositions comprising such carriers can be formulated by well known conventional methods. The formulations may be as liquids, gels, syrups, suspensions, tablets, pills, capsules or dragees, depending on the route of administration. These compositions can be administered to the subject at a suitable dose. Administration of the suitable compositions may be effected by different ways, e.g., by intravenous, subcutaneous, intramuscular, topical, intradermal, intranasal or oral administration. The dosage regimen will be determined by the attending physician and clinical factors. As is well known in the medical arts, dosages for any one patient depends upon many factors, including the particular compound to be administered: the patient's general health, size, body surface area, age, sex, time and route of administration, and other drugs being administered concurrently. As outlined above, related to the route of administration a typical dose for the human can, for example, correspond to 0.01 to 1000 µg of LPS equivalents. However, doses below or above this exemplary range are envisioned, especially considering the aforementioned factors also with regard to oral application. The pharmaceutical composition of the invention is formulated in accordance with national laws and regulatory requirements according to GMP standards. Examples of excipients are also well-known in the art and relate to any more or less inert substance which is added to a prescription in order to confer a suitable consistency or form to the drug. Examples of the excipient include, but are not limited to, lactose, sucrose, sorbitol, manitol, starch, amylopektin, cellulose and sugar components.

As outlined above and in accordance with the present invention, it was surprisingly realized that a preparation comprising endotoxin, fetal hemoglobin or (a) single chain(s) thereof or (a) combination(s) of chains thereof such as heme-free hemoglobin and optionally further components of a fetal liver extract may exert beneficial biological effects, in particular in the fight against cancer, infections by pathogens and in particular viruses, allergies and the process of aging. The present invention thus provides a new concept that a physiological and in vivo interaction between endotoxin, hemoglobin as present in ovine fetal liver leads to a preparation expressing beneficial effects including inhibition of tumor growth and activation of the immune system. As a consequence it was found in accordance with the invention that such preparations, after their isolation from preferably fetal liver tissue or manufacture preferably by the techniques of chemistry or molecular biology, also exert therapeutically useful effects if applied to adult mammalians including man (see Examples 8, 12, 13, 15). As described in the Example Section below, it was possible to enrich such preparations from extracts of fetal liver homogenates and to show that they strongly activate macrophages, induce tumor cytotoxicity also in human cellular systems, inhibit tumor growth, and reverse an aged-associated immune status to that of young individuals. These preparations appear to be responsible for many of the beneficial medical effects exerted by fetal liver tissue as applied in the so-called "cellular therapy". In addition, the composition of the invention can be used as a means to block adverse reactions of irradiation, for example, as an adjuvans to avoid or reduce adverse side effects in the treatment of tumors by irradiation. In all the above applications, it is of note that the composition of the invention has been demonstrated or is expected to be well tolerated by the respective patients. As can be taken from the above description, the composition of the present invention may beneficially be employed in the treatment or prevention of a wide variety of different diseases as well as an anti-aging drug. Whereas the different medical applications were certainly surprising, it is even more astounding that the composition of the invention displays this heterogeneous pattern of beneficial activities. These findings are surprising in spite of the fact that the biological activity of adult hemoglobin or derivatives thereof has been studied previously. Adult hemoglobin was shown to represent a bacterial growth adjuvant [Dunn et al. 1983], to activate complement [Kaca, W 1995], and to induce TNFα in monocytes [Carillo, E., 2002]. Adult hemoglobin was also found to interact with endotoxin [Roth R J and Levin J, 1999]. In particular, enhanced toxicity was seen when endotoxin and hemoglobin were applied simultaneously. This effect was explained as an endotoxin-mediated enhancement of hemoglobin bioactivity [White C. T., 1986] or alternatively, as an hemoglobin-mediated enhancement of endotoxin activity [Su, D. et al 1999]. In these studies LPS and hemoglobin were analyzed in various in vitro assays employing, in general, mononuclear cells or were administered to mice or rabbits by the intravenous or intraperitoneal route. The hemoglobin preparations used in these previous studies comprise human and bovine impure and stroma-free hemoglobin (SFH), human cross-linked α,α-Hb, polymerized bovine hemoglobin (Biopure 2) and a chemical modification thereof. No studies have been performed so far with fetal hemoglobin or the α,γ-chain dimer or purified α- and γ-chains nor were such studies, to the best of the application's knowledge ever suggested. In accordance with the present invention it was surprisingly found that fetal hemoglobin or the α,γ-chain dimer or the γ-chain monomer exerted a significantly more pronounced synergistic effect with endotoxin than HbA or its substructures. It was a further surprising finding that synergy was also expressed by heme-deprived-hemoglobin (globin). This is in contrast to what could have been assumed, namely that negatively charged LPS interacts with the $Fe^{2+}$-ions present in heme. A further surprising finding was that for the interaction with endotoxin the complete globin structure was not required but that rather the α,γ-chain or the γ-chain alone was sufficient. As the α,β-chain dimers showed a very moderate synergistic activity with LPS it is evident that this biological effect is optimally mediated by the γ-chain. The bioenhancing effect of fetal hemoglobin or partial structures is not observed with heme-containing myoglobin (data not shown). The intravenous application of HbA and LPS leads to the expression of acute biological effects. In contrast, the preparations of the present invention are being applied intramusculary or orally expressing no toxic but only favourable effects.

The endotoxin present in fetal extracts may derive from the bacterial flora of the maternal organism, however, in a biologically cryptic form although the applicant does not wish to be bound by any theory in this regard. This is supported by the observation that keeping at 37° C. for 0.5 to 2 h, the bioactive fractions (in the Examples identified as CLP1b and 2p) are 30-40 fold more active in antitumoral activity. Concomitant with these changes, a parallel increase (up to 75 fold) of the concentration of free endotoxin, i.e. endotoxin detectable by the *Limulus*-Amoebocyte-Lysate-Test (LAL-Test) is observed. It, thus, appears that additional LPS bioactivity can be set free by a short-term incubation of the liver homogenate at physiological temperature. Again, although the applicant does not wish to be bound by any theory, the following is envisaged: Fetal sheep liver apparently contains small (picogram per milligram) amounts of endotoxin in a physical state of aggregation in which it is hardly reactive in the LAL assay i.e. in which it is largely inactive biologically. By interaction of the aggregated endotoxin with fetal hemoglobin—as it may occur after intramuscular or oral application—endotoxin will be transformed into a bioactive form exerting also the beneficial medical effects as described for the composition of the present invention. The composition may act as a depot from which bioactive endotoxin is being dynamically released. In this way endotoxin will act less acutely and, consequently, in a manner being better tolerable.

The composition of the invention contains for medical use, preferably a minimal amount of 0.001-10 mg of fetal hemoglobin or single chains or combination of chains thereof and of 0.01-1000 µg of endotoxin or the endotoxically active portion thereof.

The composition of the invention may comprise one or more endotoxin types (such as bacterial S- and R-form LPS or substructures) and one or more fetal hemoglobin (substructures) or additional (poly)peptides. Thus, the composition may be homogenous or heterogenous.

In a preferred embodiment of the composition of the present invention said fetal hemoglobin or single chain(s) or combination(s) of chains thereof is/are derived from non-human fetal tissue.

In connection with the present invention, the term "said fetal hemoglobin or single chain(s) thereof or combination(s) of chains thereof is/are derived from non-human fetal tissue" preferably means that said preparation is directly obtained from said tissue by means of purification. Alternatively, said term means that said preparation is identical or essentially identical to a preparation directly obtained from said tissue but produced by recombinant or (semi)synthetic means.

In a particularly preferred embodiment of the composition of the present invention said non-human fetal tissue is derived from sheep, goat, horse or beef.

Although in the appended examples (showing a preferred way of obtaining the ingredients of the composition), extracts from sheep fetal tissue were used for the further analysis of the active principle(s) contained in the composition of the invention, fetal liver tissue from other mammals is expected to serve the same purpose, in particular, other ruminants because of an expected similar microbial intestinal flora. In addition to liver or as an alternative to liver, placenta from these animals may be used as a source of the above recited ingredients of the (pharmaceutical) composition of the invention. These sources are therefore also included as preferred sources in accordance with the invention.

The here described preparations are either very weakly immunogenic or nonimmunogenic if administered to a xenogenic organism such as man due to the conserved primary structure of the fetal proteins (see Example 3) and the small amounts of LPS present in the preparations. This, together with the lack of antibody formation provides an explanation for the clinically observed good long-term tolerability of extracts obtainable as recited above and demonstrated in the appended examples and subfractions even to repeated applications.

In a particularly preferred embodiment of the composition of the present invention said non-human fetal tissue is obtained from pregnant sheep between about four weeks before birth and birth.

If fetal tissue such as sheep liver of different developmental states are being extracted and the relevant fractions (designated in the appended examples CLP1b and CLP2p) are comparatively tested for antitumoral macrophage-activation, it is apparent that during the fetal state the biological activity, especially that of CLP2p, is increasing to a maximum at birth. Afterwards, activity decreases significantly to much lower levels in the order of 0.1 to 1% of the concentration shortly before and at birth. This indicates that fetal principle(s) change after birth, or that in fetal life considerably higher concentrations of active compounds are being produced as compared to adult life and at aging. This observation is consistent with the kinetics of hemoglobin biosynthesis. Thus, it is well known that the formation of fetal hemoglobin (HbF) consisting of $\alpha,\gamma$-dimers diminishes around birth in favor of the synthesis $\alpha,\beta$-dimers present in adult hemoglobin (HbA). In fact, the synthesis of human $\beta$-chains starts several weeks before birth. In sheep, however, the synthesis of $\beta$-chain starts a short period before birth, so that in the fetus from approximately 100 days before birth to approximately a week before delivery, exclusively the $\alpha_2\gamma_2$-form of Hb is present [Hammerberg, B. et al. 1974].

In another particularly preferred embodiment of the composition of the present invention said non-human fetal tissue is liver.

Most advantageously and equally preferred as recombinant or chemical production, the active principle(s) contained in the composition of the invention is/are obtained from liver. In particular, the protocol for obtaining said active principle described for sheep in the appended Examples can be adapted by the skilled artisan to fetal-liver tissue from other non-human mammals.

As demonstrated in the appended Examples and in order to characterize further the bioactive principles, the lyophilized fetal liver extract (FSLE) may be subjected to extraction with water or saline, ultracentrifugation and fractionation by Sephadex G100 chromatography or subfractionation yielding two pools which contained the bulk of bioactivity and which are termed CLP-Ibis or CLP1b and CLP-IIprime or CLP2p. Biochemical analysis of CLP1b and CLP2p revealed the presence of endotoxin and of a total of 576 proteins of which 25 have so far been identified (see Example 3.3.2). It is envisaged that besides fetal hemoglobin some of these further proteins, in particular those specified further below may modify the beneficial effect(s) of the composition of the invention. The above protocol can be further refined by reverting to the teachings contained in the appended Examples (see, in particular, Examples 2 and 3).

In a further preferred embodiment of the (pharmaceutical) composition of the invention, said additional compound(s) is/are (a) fetal liver (glyco)peptide(s). In accordance with the present invention it has been found that additional components derived from fetal liver and of proteinaceous nature, preferably glycoproteins (used here to describe the same subject-matter as glycopeptides), may enhance the therapeutically active principle provided by hemoglobin or single chain(s) or combination(s) of chains thereof and endotoxin or and endotoxically active fragment or derivative thereof (see Examples 8 and 9).

It is further preferred in accordance with the invention that the combination of chains is the $\alpha$-, $\gamma$-dimer of fetal hemoglobin. As was already pointed out above, it was surprisingly found that the $\alpha$-, $\gamma$-dimer and even the $\gamma$-monomeric chain alone of fetal hemoglobin acts in an unexpectedly pronounced synergistic way with endotoxin. Beneficial effect combined with the good tolerability of these ingredients of the composition of the invention could not be derived without inventive step from the prior art.

Also preferred in accordance with the present invention is that the single chain is the $\gamma$-chain of fetal hemoglobin.

It was further surprising to find in accordance with the invention that the heme portion of hemoglobin is not needed to find these beneficial effects. Therefore, in a further preferred embodiment of the composition of the invention, the combination(s) of chains is/are free of heme, the iron containing fraction of hemoglobin.

In another preferred embodiment of the composition of the present invention said endotoxin is bacterial lipopolysaccharide (LPS) and preferably bacterial S- or R-form lipopolysaccharide or a biologically active fragment or derivative thereof.

In an additional preferred embodiment of the composition of the present invention, said endotoxin is bacterial LPS from an enterobacterium.

In an additional more preferred embodiment of the composition of the present invention, said enterobacterium is selected from the species or genera *Escherichia coli, Salmonella, Yersinia, Klebsiella, Citrobacter, Enterobacter* and/or *Shigella*.

The term "biologically active fragment or derivative" of LPS refers to compounds that are derived either by chemical or enzymatic fragmentation of LPS or by (bio)chemical modification of LPS whereby the pharmaceutically beneficial activities are (essentially) maintained or improved. These components include fragments produced by partial enzymatic/hydrolytic deglycosylation, desphosphorylation and deacylation, or derivatives generated by the action of glycosyl, phosphoryl or acyltransferases or by other enzymatic modification steps known to take place in mammalian tissue, in particular in the liver.

Bacterial endotoxin or LPS, a macromolecular amphiphile, exhibits in higher animals and man, depending on the route of application, a great variety of biological activities of pharmacological interest, already in doses as small as 0.01-0.1 ng/kg body weight [Alexander, Ch., 2001]. LPS-effects are mediated by immune cells and factors released thereof including cytokines, reactive oxygen species and Lipid mediators [Brabetz, W., 1999]. LPS-bioactivity is based on its Lipid A component, the primary structure of which is known for many bacterial genera [Zähringer, U., 1994]. The expression of Lipid A (or LPS) bioactivity is dependent on its molecular conformation, degree of aggregation, and three-dimensional organization [Brandenburg, K., 1996], these factors being determined by the degree of acylation and phosphorylation. Thus, full endotoxicity is expressed by hexaacyl bisphosphoryl Lipid A whereas the pentaacyl bisphosphoryl or the hexaacyl monophosphoryl partial structures are approximately 10-100 fold less active [Rietschel, E. Th. 1994]. In particular, monophosphoryl (hexaacyl) Lipid A (MPLA) has been analyzed in various systems and was shown to express significantly (about 10-100 fold) reduced toxicity as compared to Lipid A or LPS [Ulrich, J. T. et al. 1995].

Medical application of LPS including treatment of tumors and prevention of infections was propagated since more than a century ago, but often hampered by untoward side effects accompanying pharmacologically effective doses [Zhang, M., 1999]. Thus, impressive results of LPS-mediated regression of tumors have been reported [Zhang, M., 1999], but side reactions such as fever and hypotension have prohibited widespread acceptance of endotoxin in medical practice. In order to control acute toxicity it was propagated to apply LPS intracutaneously instead of the generally used intravenous injections. Thus, Nishizawa et al. [1992] isolated LPS from *Pantoea agglomerans*, a microorganism growing on wheat, which they recommend to apply by intracutaneous injections and which is believed to restore homeostasis (i.e. health) in patients suffering from various diseases [Goto, S., 1996]. From the toxicologic point of view, the authors suggest a much better tolerability under these conditions [Inagawa, H., 1997]. Little is known about those mechanisms and molecules which control LPS-bioactivity in higher organisms including man, in particular, and the pharmacokinetics of LPS in vivo. Studies on the fate of LPS, either injected or set free from Gram-negative bacteria under physiological or pathophysiological conditions showed that among all organs the liver plays a primary and central role [Freudenberg, M. A., 1990]. The liver was shown to eliminate LPS from the circulation in a noninflammatory fashion and to store it in a non-toxic or less toxic form [Freudenberg, M. A., 1990]. Thus, the main route of endotoxins that enter the blood from the gut leads through the portal vein to the liver where they may be taken up by Kupffer cells, again released into the blood stream, and subsequently redistributed into hepatocytes which finally secrete them together with bile [Bertok, L. 1980; Van Bossuyt, H., 1988]. Enzymatic degradation of endotoxins leading to less or non-toxic Lipid A partial structures has been shown to occur by macrophage- and neutrophil-derived enzymes. Dephosphorylation of the Lipid A backbone in eukaryotic cells and serum has been reported [Poelstra, K., 1997]. This phosphatase activity was identified in cell lysates and intact cells of peritoneal macrophages where it was localized in lysosomes. In addition, the neutrophil-derived acyloxyacyl hydrolase [Munford, S., 1986] cleaves secondary ester-bound fatty acids of Lipid A. The fate of endotoxins is as well determined by serum factors such as HDL, LDL and Complement factors which form in the circulatory system complexes with LPS. Further, complexation with BPI leads to transport to the liver and uptake by hepatocytes. In pregnant mammals, also the placenta may enrich LPS. Thus, Y. Katayama et al. (1975) described an "LPS (endotoxin)-like substance in human placenta". The authors relate to the Shwartzman sensitivity of the pregnant mother and fetus and show that Shwartzman-active material accumulates in the placenta, from which it can be extracted in small quantities by known extraction procedures for LPS. Activity of the extract was about one thousands of that of pure *E. coli* LPS. The authors announced further characterization of the active principle in future reports, which, however, did not appear so far. The bulk of studies shows that the liver represents the main organ to which the body targets circulating LPS.

In a further preferred embodiment the endotoxically active portion of endotoxin is the LPS derived polysaccharide-free Lipid A component.

In the art, synthetic efforts were undertaken by preparing structural analogues of the Lipid A region of LPS [Jeanin, J. F., 1991; Kusawa, T., 1991] with the aim to favorably dissociate endotoxicity and antitumoral activity. Numerous attempts have been made to chemically alter isolated LPS in such a way that its unwanted side effects are eliminated, whereas its therapeutically useful properties, such as tumor necrotic activity are retained [Zhang, M., 1999 and U.S. Pat. No. 4,185,090, GB2147806 and WO0026384]. These irreversible chemical or enzymatic modifications included dephosphorylation and saponification of Lipid A-bound acyl residues as well as derivatisation i.e. by phthalic acid [Elin, R. J., 1981].

The chemical structure of Lipid A, the bioactive center of LPS, harbours a hydrophilic and a lipophilic region which are both required for the expression of LPS bioactivity. Accordingly, Lipid A is a preferred example of a biologically active fragment of LPS. Natural compounds are known which associate with either region of Lipid A, thereby physically and reversibly complexing to LPS and reducing its bioactivity [David, S. A., 1999; Porro, M., 1999]. Molecules binding to both the hydrophilic and hydrophobic region of Lipid A and suppressing its biological effects include bactericidal/permeability-increasing protein (BPI), endotoxin-neutralizing protein (ENP), the antibiotic polymyxin B [Rifkind, D., 1967] and the cationic peptide 18 (CAP 18) [Opal, S. M., 1998], whereas lipopolysaccharide binding protein (LBP), adult hemoglobin (Hb) and soluble CD14 enhance endotoxin activity [Roth, R. J., 1999, Kitchens et al., 2000]. Compounds associating primarily with the lipophilic region of Lipid A, and thereby inhibiting its bioactivity, comprise surfactants such as sodium dodecylsulfate and certain bile acids [Bertok, L. 1980; Van Bossuyt, H., 1988]. The capacity of LPS to associate with cationic or hydrophobic molecules far beyond stoichiometric proportions is known since some time [Lüderitz, O., 1958]. In such complexes protein can no longer be precipitated by protein denaturing chemicals such as trichloroacetic acid, or Lipids by Lipid precipitating reagents as, for example, cholesterol by digitonin [Lüderitz, O., 1958; Neter, E., 1958]. According to present knowledge, complexing molecules may cover particular sites of those Lipid A regions which are required for its interaction with humoral (e.g. LBP) or cellular (e.g. CD14/TLR4) host receptors [Poltorak, 1998]. The suppression of the interaction of complexes of LPS with its host receptors inhibits the initiation and manifestation of LPS-effects [Opal, S. M., 1998]. All of these previous investigations on the formation of complexes of LPS with other compounds exclusively aimed at the detoxification of LPS [Opal, S. M., 1998]. Although one approach aimed at the use of LPS as a stimulant of phagocytosis (EP-A 0 405 315) the potentially beneficial properties of preparations resulting from the interaction between LPS and other compounds such as hemoglobin have not been systematically explored so far [see Brade, H., 1999].

It is further preferred in accordance with the invention that said endotoxin is natural or synthetic penta- and/or hexaacyl-Lipid A.

In an additional further embodiment of the invention said endotoxin comprised in said composition is natural or synthetic penta- and/or hexaacyl-Lipid A monophosphate (MPLA).

The advantage of using these endotoxins relates to the fact that their acute toxicity is significantly lower (about 100 fold) as compared to the toxicity of hexaacyl bisphosphoryl Lipid A or LPS (see also page 15).

It is further preferred in one embodiment in accordance with the invention that in the composition the weight relation of the components is about 1000:1 or in the range of 1:1 to 1000:1 of fetal hemoglobin or single chains thereof or combinations of chains thereof to endotoxin or the endotoxically active portion thereof. Other embodiments encompass different relations.

In a further preferred embodiment, the composition of the present invention further comprises a liver (glyco)peptide which is thioredoxin, phosphatidylethanolamine-binding protein (PBP), peptidyl-prolyl-cis-trans-isomerase A (PPIase A), macrophage-migration inhibition factor (MIF) or ubiquitin (Ub) or any other of the proteins listed in Table 4.

Ubiquitin and thioredoxin may act as chemokines and MIF may upregulate TLR-4 receptors, thereby generating a favourable cellular environment for LPS activation [Roger et al. 2001].

It is also preferred that said composition is or comprises a food additive (food supplement). This holds also true for other (preferred) embodiments discussed in accordance with this invention.

The term "food additive" in connection with the present invention has the broadest meaning as employed in the art. Typically, a food additive is or comprises substances added to food to preserve it, or to improve its flavour and appearance. Said food additives comprise, but are not limited to acids, acidity regulators, anticaking agents, antifoaming agents, antioxidants, bulking agents, colours, colour retention agents, emulsifiers, flavours, flavour enhancers, flour treatment agents, humectants, preservatives, propellants, stabilizers and/or sweeteners. All these components may also be added to the composition of the invention. It is crucial in connection with the invention, however, that the food additive consists of or comprises the above recited endotoxin or an endotoxically active portion thereof, and fetal hemoglobin, such as heme-free hemoglobin or (a) single chain(s) thereof or (a) combination(s) of chains thereof, and optionally (an) additional compound(s) such as fetal liver (glyco)peptides. These ingredients representing or contained in the food additive of the invention may contribute to the overall well-being of the food customer. For example, they are expected to counterbalance phenomena/causes observed in connection with aging as explained elsewhere in this specification.

In a further preferred embodiment, the pharmaceutical composition of the present invention is confectioned for oral administration. Examples of such a confection include but are not limited to tablets (coated or uncoated), soft gelatin capsules, hard gelatin capsules, lozenges, troches, solutions, emulsions, suspensions, syrups, elixirs, powders/granules for reconstitution, dispersible powders/granules, medicated gums, chewing tablets and effervescent tablets.

Oral administration has a number of advantages, in particular the considerable application comfort for the patient.

Surprisingly, the pharmaceutical composition of the invention was found to be also biologically active in mice if given orally in doses of 0.5 µg to 50 µg. Previous studies have regularly shown that LPS expresses bioactivity in higher animals including humans only if applied by non-oral routes such as the intravenous, intraperitoneal, subcutaneous or intramuscular route. Thus, Ch. Galanos (Max-Planck-Institute for Immunobiology Freiburg, Germany; personal communication) has shown that oral doses as high as 5 mg per animal did not kill D-galactosamine—sensitized mice which are susceptible to 1 to 5 ng/mouse if LPS is applied intravenously. Thus, the here observed bioactivity of the endotoxin/hemoglobin composition has not been described before. It could further be demonstrated in accordance with the present invention that LPS after interaction with fetal hemoglobin is significantly more active than equal amounts of free LPS. The bioactive components derived from fetal tissue which have been described in the literature so far have been claimed to be heatlabile and sensitive to proteolysis, whereas the here described LPS preparations, in contrast, are rather heatstabile and resistant towards proteolytic enzymes. The person skilled in the art would readily extend the data obtained with mice to other mammals including humans (see Examples 8, 12, 13 and 15).

In an additional preferred embodiment, said composition comprises between 0.001 and 10 mg of fetal hemoglobin or single chains thereof or combinations of chains thereof and between 0.01 and 1000 µg of endotoxin or an endotoxically active portion thereof.

The present invention also relates to the use of endotoxin or an endotoxically active portion thereof, fetal hemoglobin or (a) single chain(s) thereof or combination(s) of chains thereof and optionally (an) additional compound for the preparation of a composition for stimulating the innate and adaptive immune system.

Also, the present invention relates to the use of endotoxin or an endotoxically active portion thereof, fetal hemoglobin or (a) single chain(s) thereof or combination(s) of chains thereof and optionally (an) additional compound for the preparation of a composition for treating cancer.

Cancerous tumors that can be treated or prevented by administration of the composition of the invention include, but are not limited to prostate cancer such as adenocarcinoma of the prostate, breast cancer, squamous cell carcinoma of the cervix and adenocarcinoma of the pancreas. Infections by pathogens include infections by viruses, bacteria, and eukaryotic organisms, either of single-cell or of multi-cell structure such as yeast cells, fungi, helminths etc.

The present invention also relates to the use of endotoxin or an endotoxically active portion thereof, fetal hemoglobin or (a) single chain(s) thereof or combination(s) of chains thereof and optionally (an) additional compound(s) for the preparation of a composition for preventing or treating infections.

In addition, the present invention relates to the use of endotoxin or an endotoxically active portion thereof, fetal hemoglobin or (a) single chain(s) thereof or combination(s) of chains thereof and optionally (an) additional compound for the preparation of a composition for preventing or treating allergic conditions. Said allergic conditions include in preferred embodiments all type-1 allergies, hayfever and allergic asthma.

In another preferred embodiment, the present invention relates to the use of endotoxin or an endotoxically active portion thereof, fetal hemoglobin or (a) single chain(s) thereof or (an) combination(s) of chains thereof and optionally (an) additional compound for the preparation of a composition for reverting changes of cytokine/chemokine production which occurs in a age-related manner. In a further preferred embodiment, the present invention relates to a method for reverting age-related immune imbalances comprising administering endotoxin or an endotoxically active portion thereof, fetal hemoglobin or (a) single chain(s) thereof or (an) combination(s) of chains thereof and optionally (an) additional compound(s) to a human. Aging, in its broadest sense in accordance with the invention, relates to the usually irreversible generation of immune-imbalances over time.

In a further preferred embodiment of the use of the present invention said age-related immune imbalances comprise abnormal cytokine production. In a further preferred embodiment of the composition of the present invention said age-related abnormal cytokine production is an increased TNFα, IL-1, IL-4, IL-6, IL-8 and/or IL-10 production and/or a decreased IL-2 production.

A further surprising finding of the present invention is that by administering the composition of the invention, age-related immune imbalances are reverted. Since these immune imbalances may be regarded as one critical factor in the aging phenomenon, the present invention provides an important step in the attempt of mankind to influence aging and the associated increased susceptibility to diseases such as cancer, allergy and infections. Optionally, the composition of the invention may be administered together with further pharmaceutically active compounds developed to halt or retard the physiological or pathophysiological consequences of aging including increased susceptibility to cancer, infection and allergy. Further age-related diseases include, but are not limited to Alzheimer disease, Parkinson disease, osteoporosis and acratia.

The present invention also relates to the use of endotoxin or an endotoxically active portion thereof, fetal hemoglobin or (a) single chain(s) thereof or (an) combination(s) of chains thereof and optionally (an) additional compound for the preparation of a composition for alleviating the adverse side effects of irradiation. Diseases related with the adverse side effects of irradiation comprise but are not limited to any pathophysiological condition correlated with immune suppression. This includes, for example, diseases related with a reduced number of leucocytes.

In a most preferred embodiment of the use of the present invention said cancer is prostate carcinoma such as adenocarcinoma of the prostrate, breast cancer, squamous cell carcinoma of the cervix or adenocarcinoma of the pancreas. Also particularly preferred in accordance with the invention is that said infections are viral infections, preferably chronic viral infections, more preferred herpes, hepatitis B or hepatitis C infections.

It is further preferred in accordance with the use of the invention that the reverting of said age-related cytokine/chemokine production is related to an activation of macrophages.

In a preferred embodiment of the use of the present invention said preparation is for oral application.

In another preferred embodiment of the composition or the use of the present invention said preparation is present in an amount equivalent to 0.01 to 2 µg of LPS (and Lipid A partial structures). Depending on the route of administration, for oral application up to 1 mg of LPS as present in the preparation can be applied.

In a further preferred embodiment of the composition or the use of the present invention said endotoxin is biochemically or chemically produced. In an additional preferred embodiment of the composition or the use of the present invention said hemoglobin and/or said further (poly)peptide is biochemically or chemically or recombinantly produced. Biochemical, chemical and recombinant means and methods of production have been referred to herein above.

Patients treated in accordance with this invention as described herein below all gave their informed consent.

According to chemical, biosynthetic, biological and genetic criteria, LPS can be divided into three regions: O-specific chain, core oligosaccharide, and Lipid A. The O-specific chain represents a polymer of repeating oligosaccharide units characteristic of each bacterial strain. The terms Ra—Re refer to structures of LPS from rough (R) mutants which, due to genetic defects, synthesize a truncated core oligosaccharide and, therefore, lack an O-specific chain. The smallest LPS structure which can be found in still viable *Salmonella enterica* strains consists of Lipid A and two Kdo-residues (Re-mutant). Saccharide groups are depicted by hexagons, and dotted lines represent non-stoichiometric substitutions. GlcN, D-glucosamine; Kdo, 3-deoxy- D-manno-oct-2-ulosonic acid (2-Keto-3-deoxy- D-manno-octonic acid); Hep, L-glycero- D-manno-heptose; Glc, D-glucose; Gal, D-galactose; GlcNAc, N-acetyl- D-glucosamine; P, phosphate.

Figure 1:
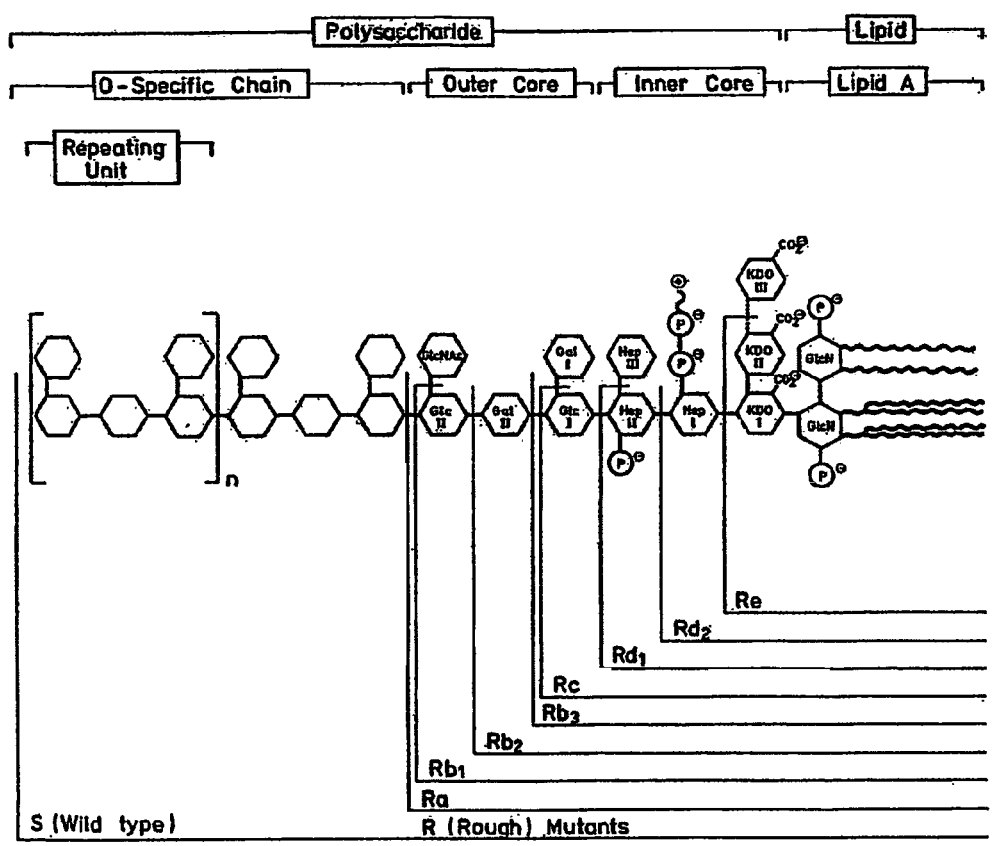
FIG. 1: Schematic representation of the structure of *Salmonella enterica* wild type and rough mutant lipopolysaccharides (LPS)
Figure 2:
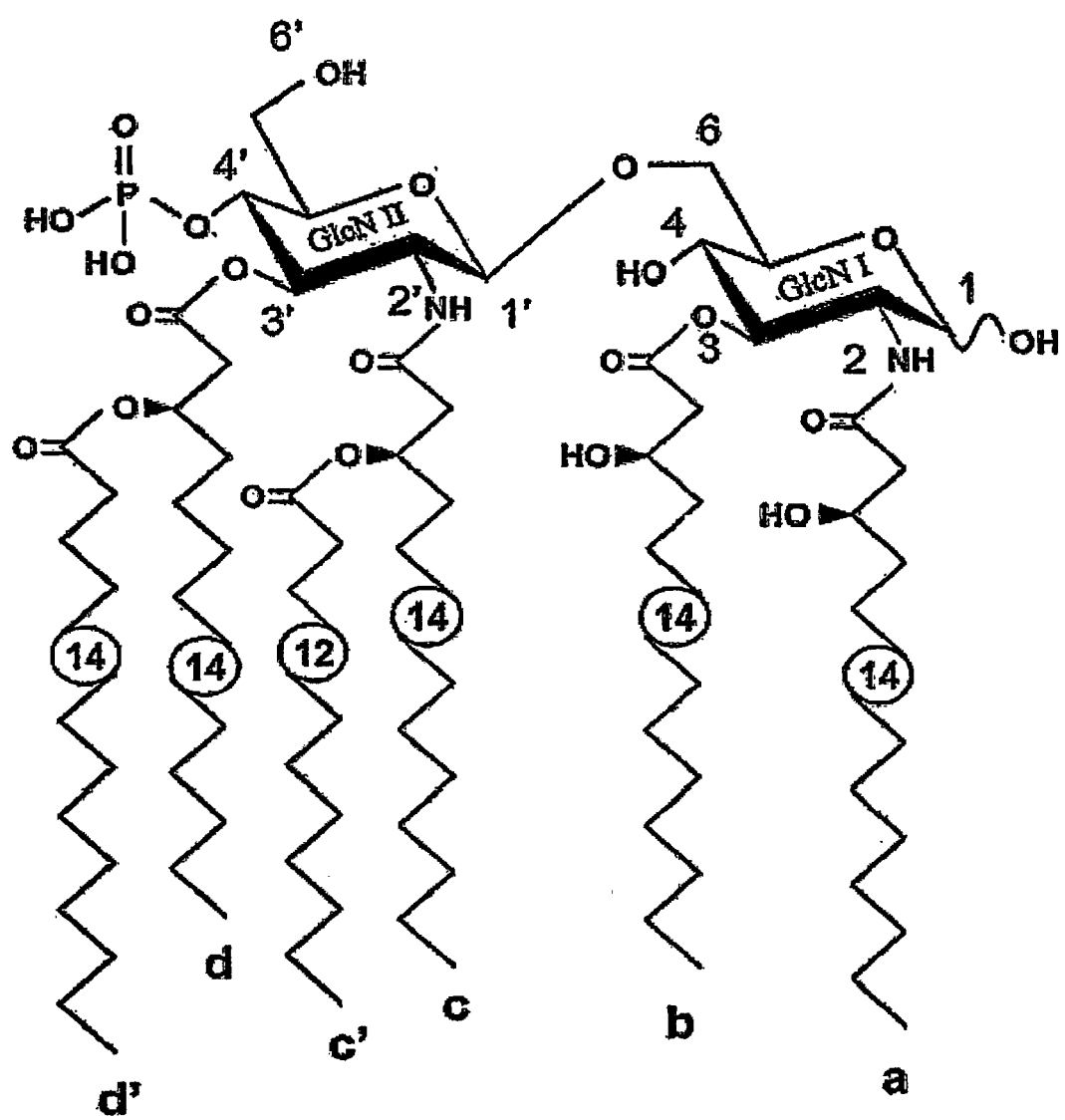

FIG. 2: Structure of hexa-acyl monophosphoryl Lipid A (MPLA$_{hexa}$) isolated from LPS of the *E. coli* Re mutant (strain F515)

Letters a-d indicate primary [14:0(3-OH)] and c'-d' secondary fatty acids (12:0 and 14:0). Shown is the fully protonated form of the monophosphoryl hexa-acyl Lipid A structure.

Figure 3:
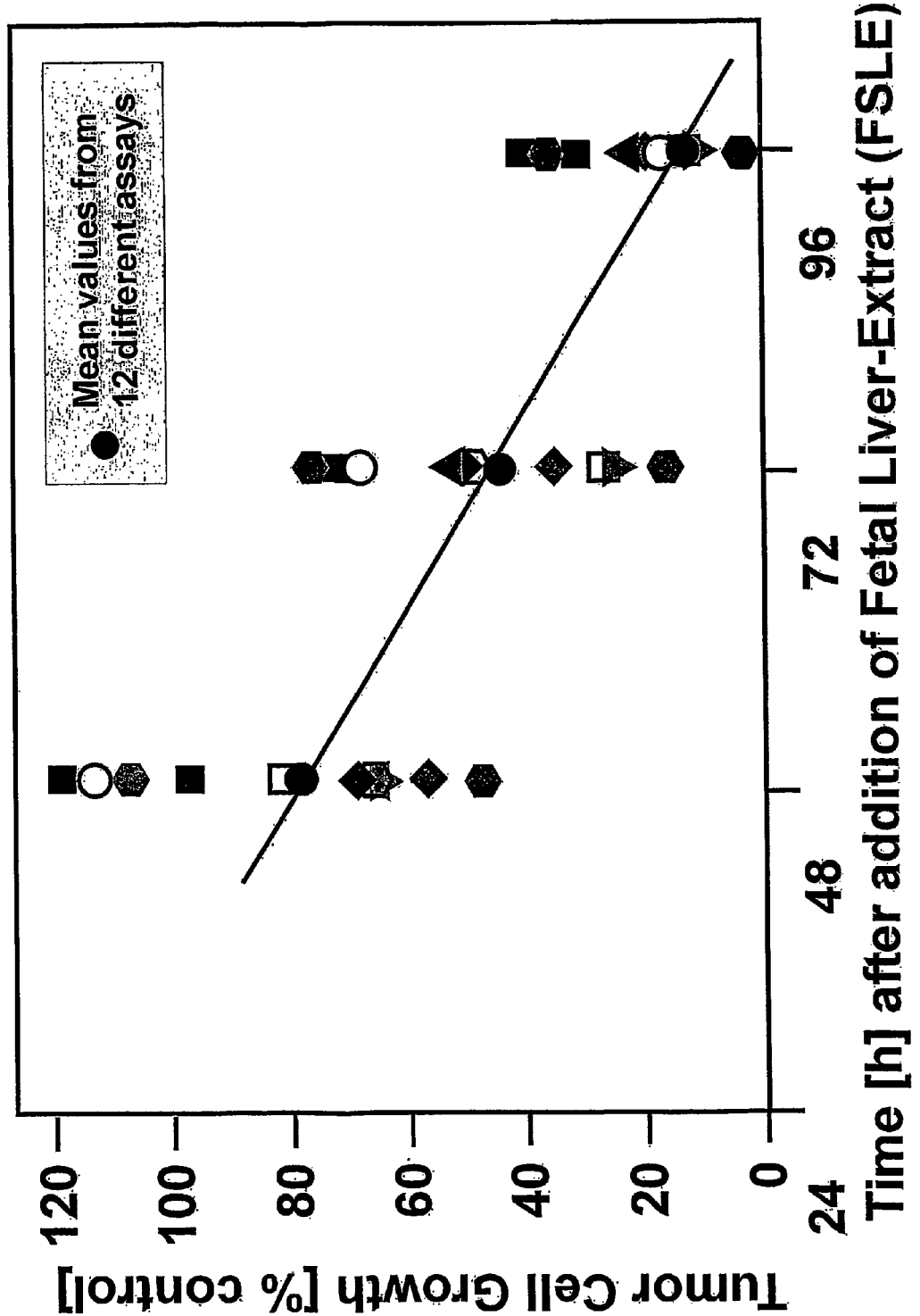

FIG. 3: In vivo activation of mouse spleen cells with different batches of FSLE for the induction of macrophage-mediated tumor cell growth inhibition.

Figure 4:
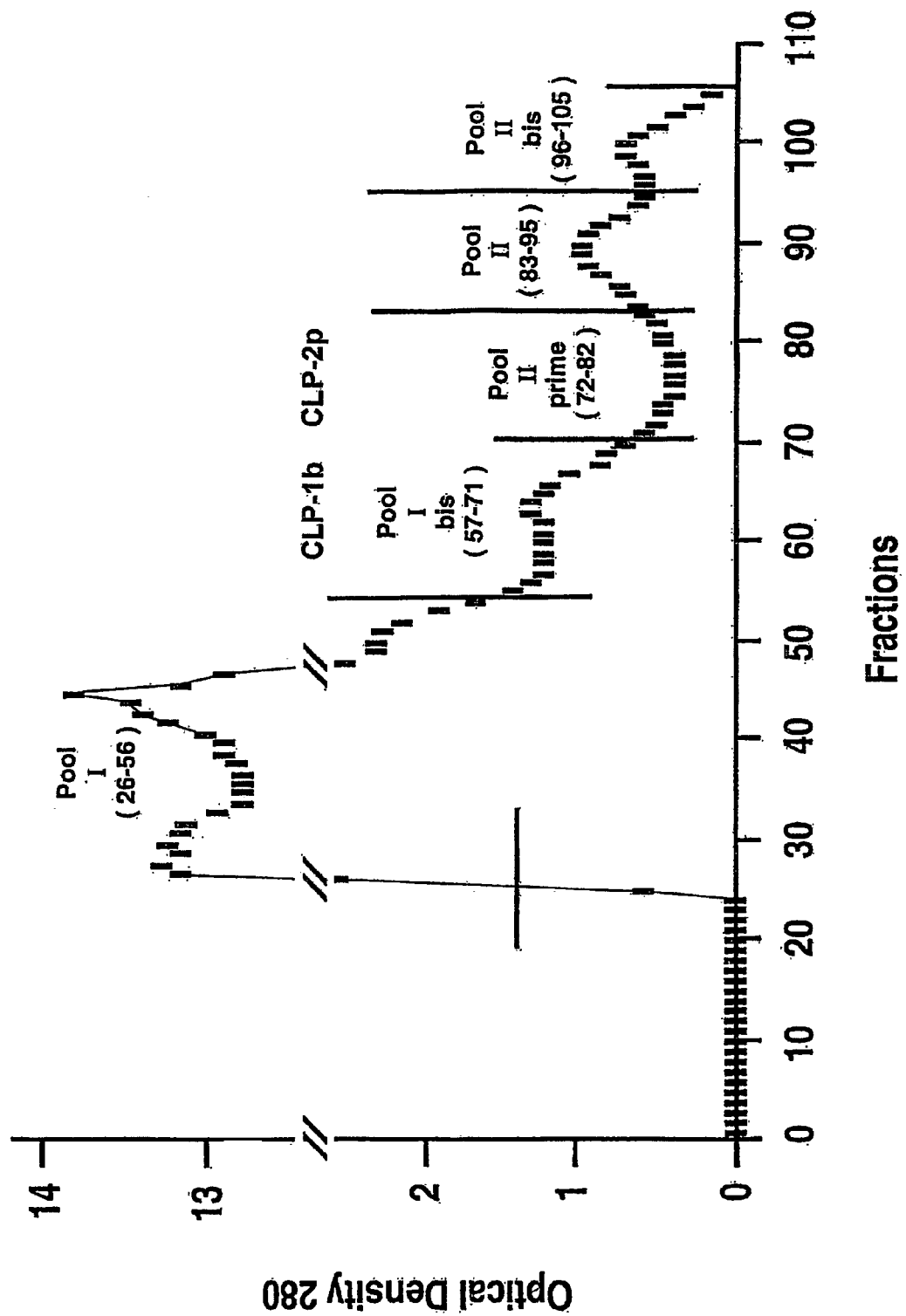

FIG. 4: Fractionation of FSLE by Sephadex G-100® chromatography after dialysis.

Figure 5:
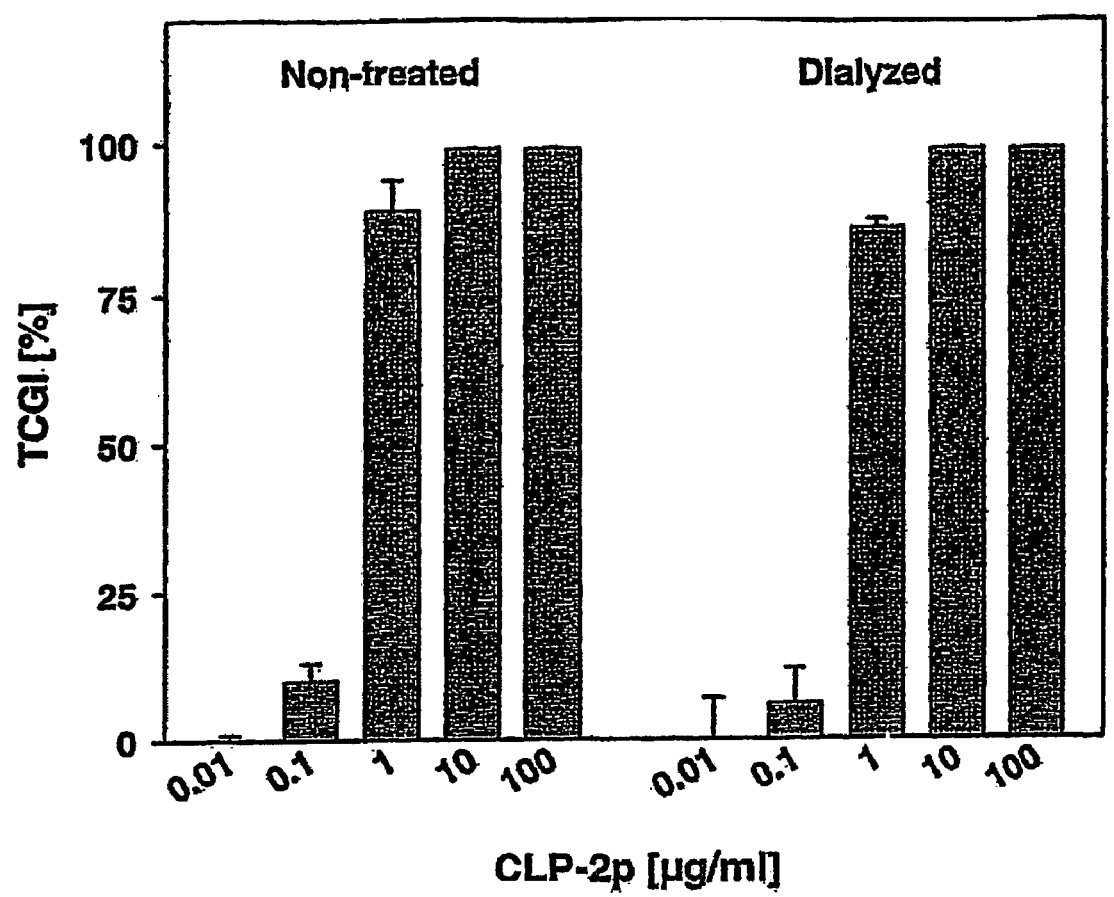

FIG. 5: Bioactivity (tumor cell growth inhibition) of CLP2p before and after dialysis with a cut off of 35 kDa.

Murine BMDM were stimulated with CLP2p prepared from dialyzed and non-dialyzed material and tested for TCGI-activity on Abelson 8-1 tumor cells.

Figure 6:
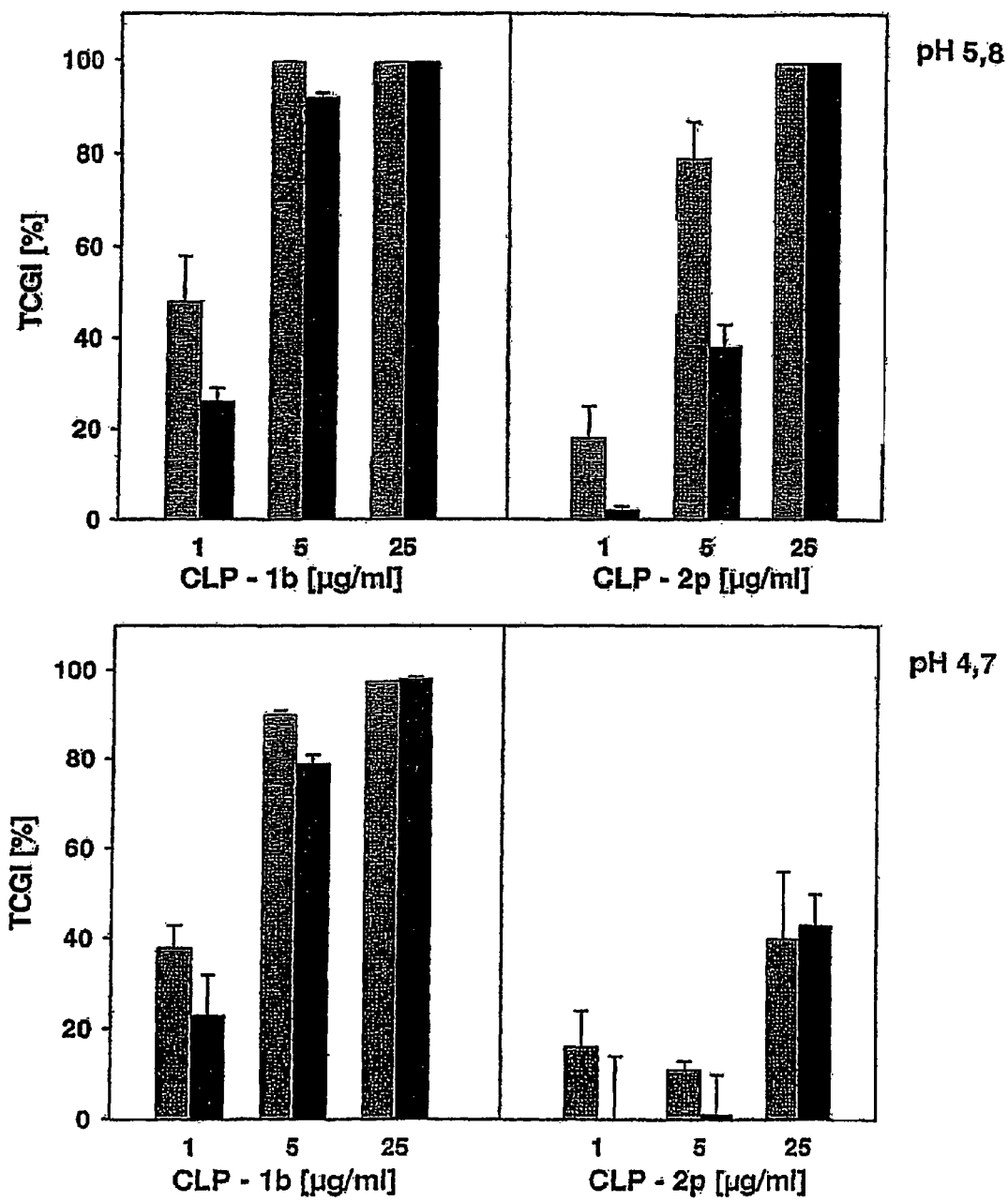

FIG. 6: Heat stability of the antitumoral macrophage activator present in CLP1b and CLP2p at different pH values.

Lyophilized preparations (0.25 mg) of CLP1b and CLP2p were solubilized in pyrogen-free water at pH 5.8 (upper panels) or in 20 mM sodium acetate buffer, pH 4.7 (lower panels), respectively. The samples were incubated at 4° C. (controls, gray bars) or at 100° C (black bars) for 60 min. Antitumoral activation of murine BMDM by heat-treated and control samples was determined at the indicated final concentrations in the TCGI-assay.

FIG. 7: Protease resistance of the TCGI-inducing activity present in CLP1b and CLP2p.

CLP1b (FIG. 7A) and CLP2p (FIG. 7B) were subjected to treatment with the indicated proteases at an enzyme to total protein ratio of 1:10 (w/w) at 37° C. for 21 h followed by an additional incubation at 100 ° C. for 30 min for heat inactivation of the proteases. Macrophage-mediated antitumoral activities of protease-treated samples and corresponding controls of CLP1b (FIG. 7A) and CLP2p (FIG. 7B) were then tested in the TCGI assay at the final concentrations indicated.

Figure 8:
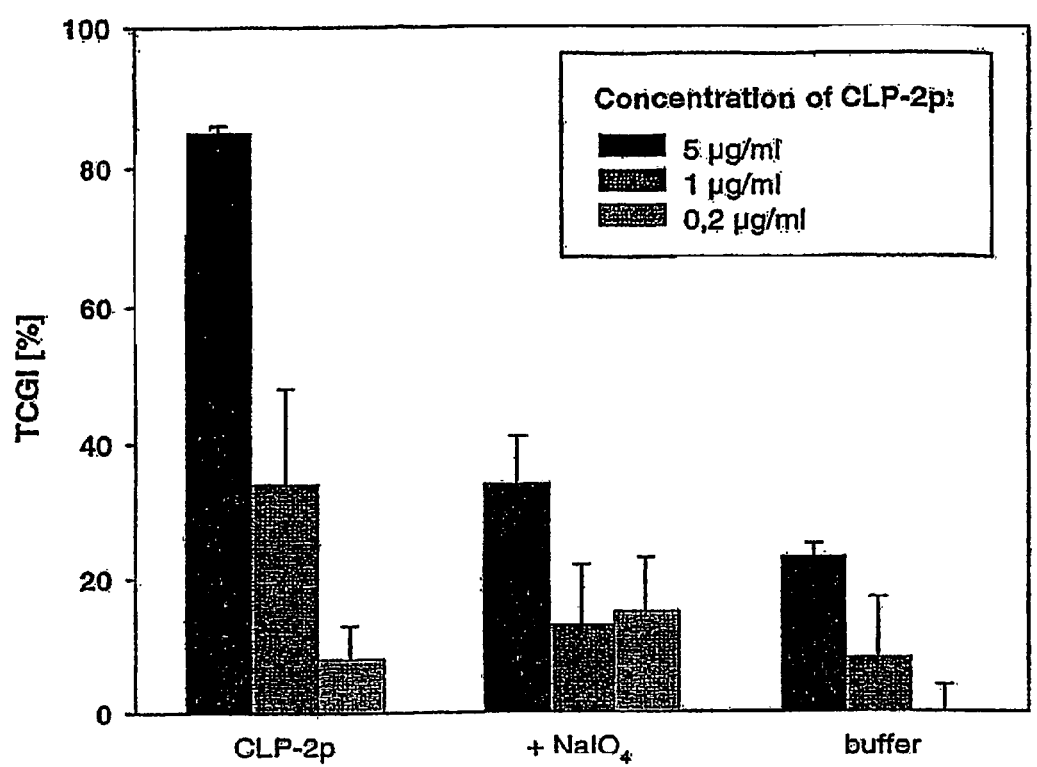

FIG. 8: Sensitivity of the macrophage activating principle present in CLP2p to mild sodium periodate treatment FIG. 9: Adsorption of the antitumoral macrophage activator by Affi-Prep® Polymyxin.

CLP2p was preincubated in the absence (gray bars) or presence (black bars) of Affi-Prep® Polymyxin at 4° C. for 14 h. After removal of the affinity resin the samples were analyzed in the TCGI assay at the concentrations indicated.

FIG. 10: Induction of nitric oxide release in BMDM from LPS responder (C57Bl/10 ScSn) and LPS non-responder (C57Bl/10 ScCr) mice by LPS or CLP pools.

BMDM from LPS responder (C57Bl/10 ScSn, gray bars) or LPS non-responder (C57Bl/10 ScCr, black bars) mice were stimulated with LPS or one of the CLP-pools at the concentrations indicated. Nitric oxide released by the cells was determined after 48 h as nitrate in the culture supernatants.

Figure 11:
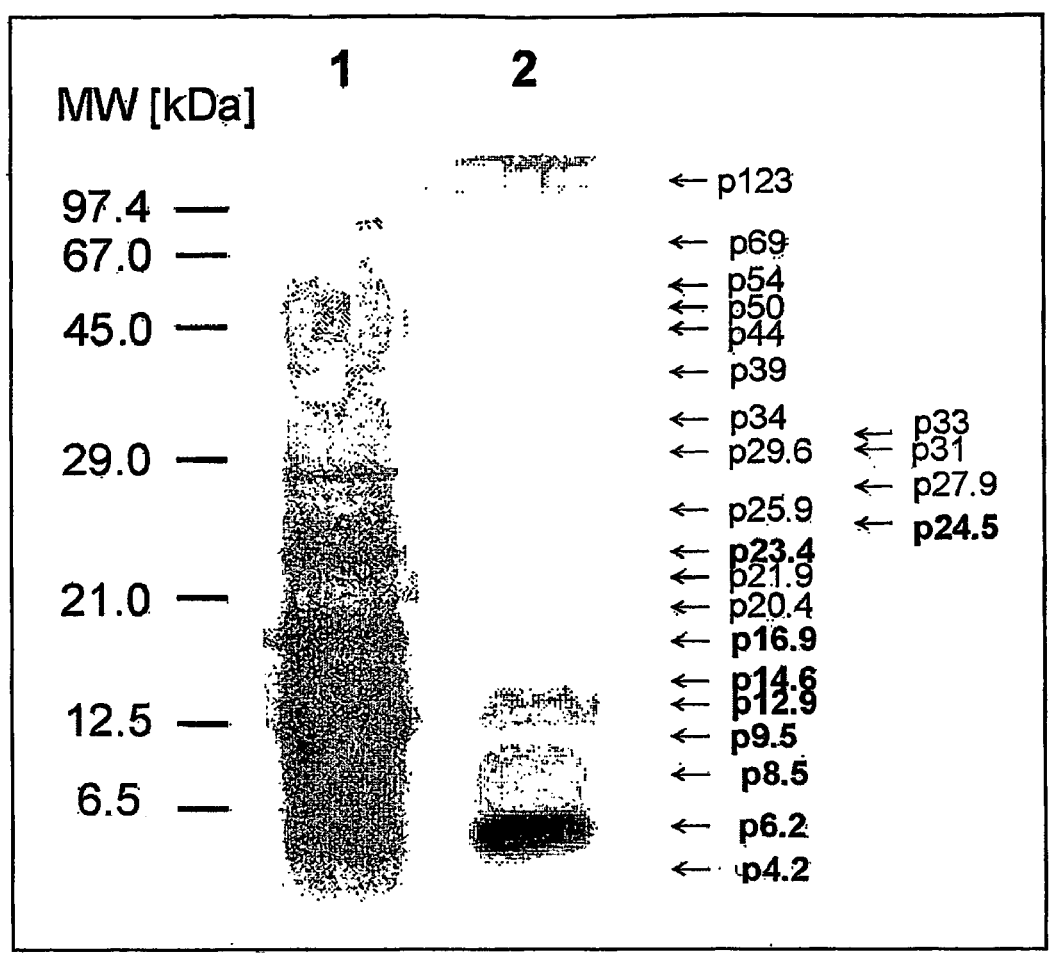

FIG. 11: SDS-PAGE analysis of CLP1b and CLP2p.

An amount of 0.02 mg of CLP1b (lane 1) and CLP2p (lane 2) were analyzed by SDS-PAGE and subsequent silver staining. The positions of individual protein bands designated according to the corresponding apparent molecular weights are indicated.

Figure 12:
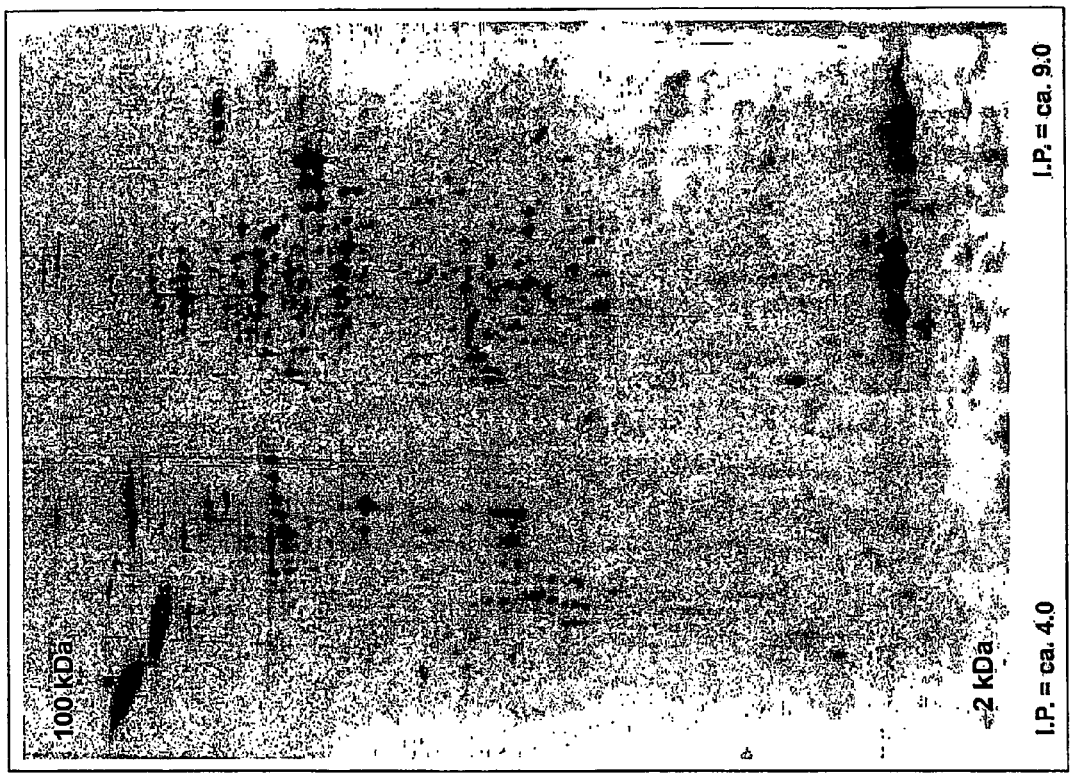

FIG. 12: 2-DE analysis of FSLE

The total protein composition of fetal sheep liver extract was analyzed by high resolution two-dimensional electrophoresis (2-DE) and silver staining as described in the material and methods section.

Figure 13:
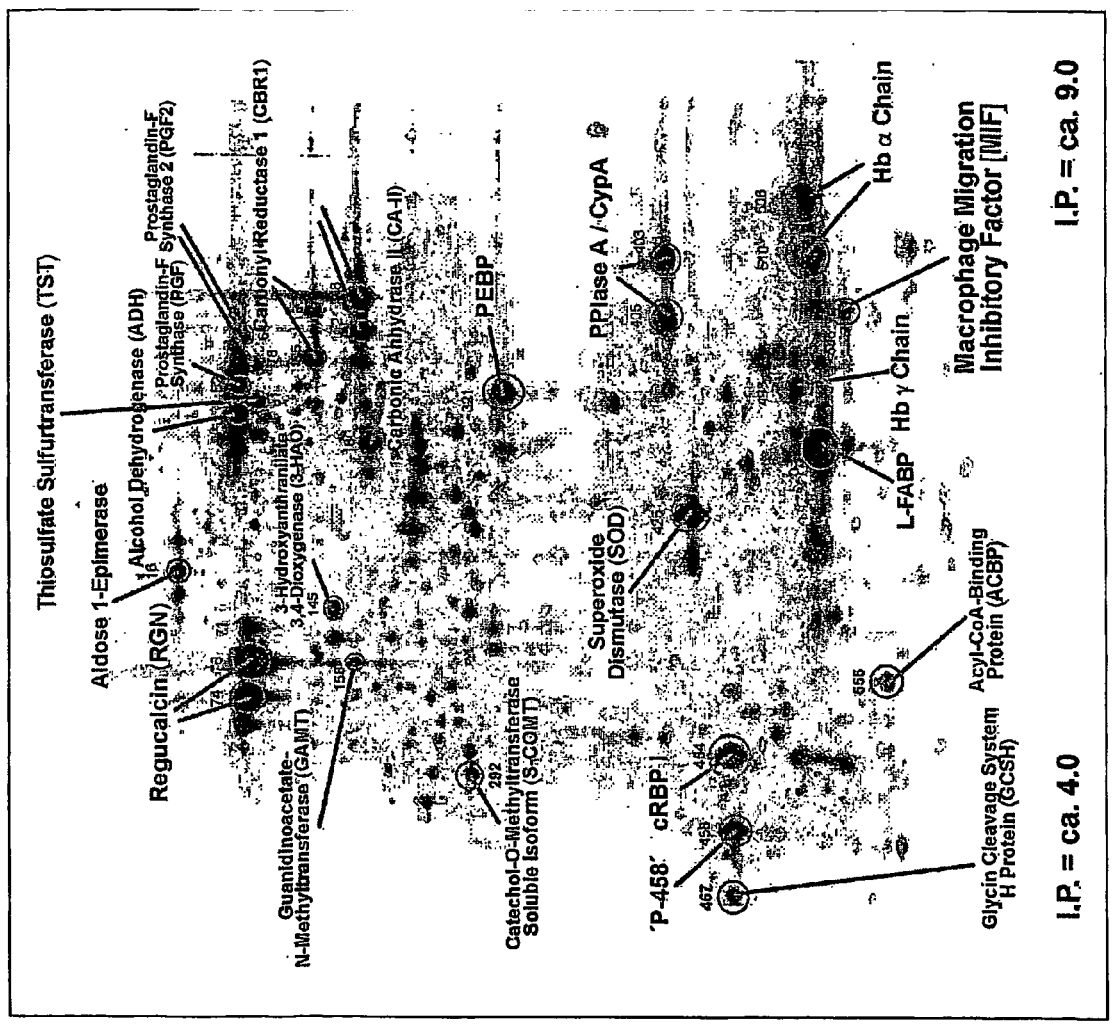

FIG. 13: 2-DE-analysis of CLP1b from fetal sheep liver extract

The protein composition of CLP1b derived from fetal sheep liver extract was analyzed by high resolution two-dimensional electrophoresis (2-DE) and silver staining as described in the material and methods section. Selected proteins in the 2-DE-gels were identified by tryptic in gel-digestion of corresponding spots in the silver stained gels and subsequent mass spectrometric analysis of the peptide mixture. In addition, electrotransfer onto Immobilon PVDF membranes and N-terminal Edman sequencing of Coomassie Brilliant Blue stained spots was employed for the identification of proteins in CLP1b. The overall 2DE pattern of proteins in CLP1b and the systematic numbering for the identified single spots is given. In panel B the corresponding assignment of the identified proteins as described in more detail in Table 2 is additionally displayed.

Figure 14:
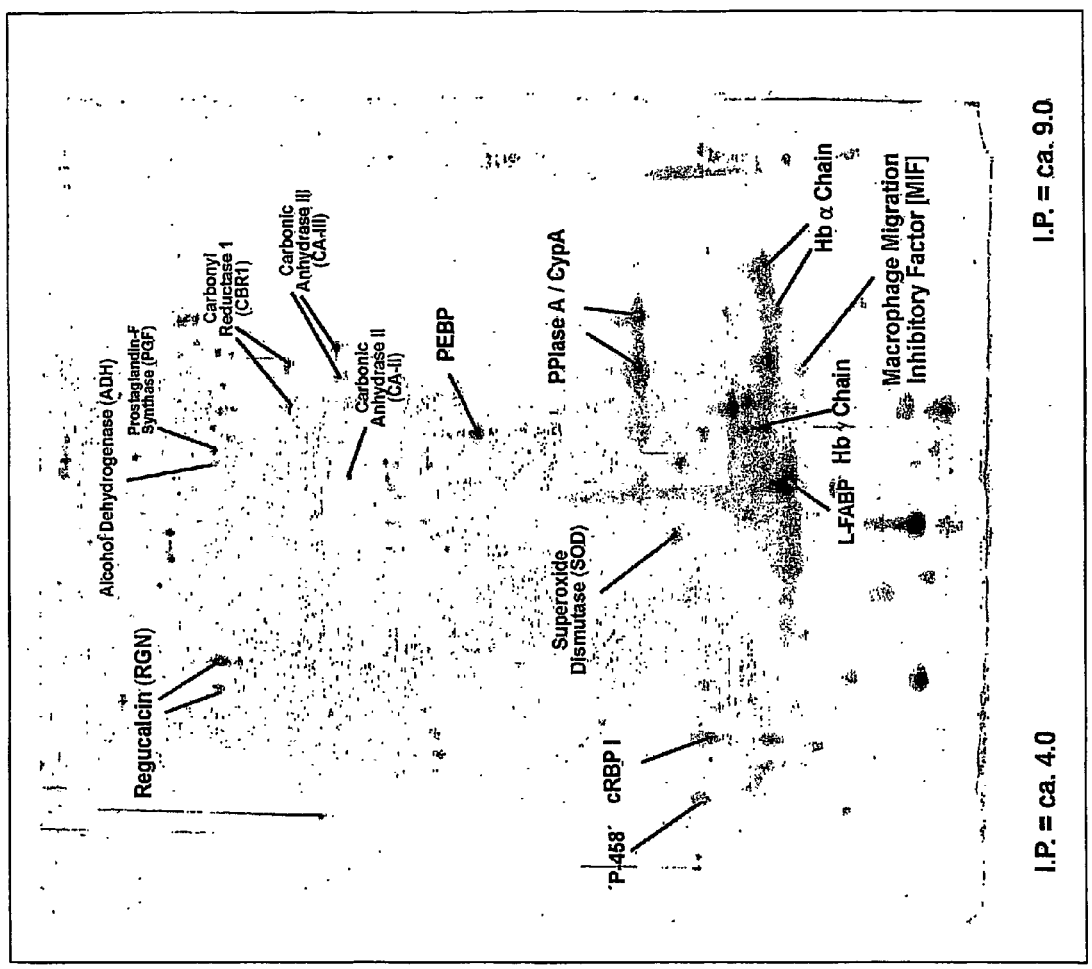

FIG. 14: 2-DE-analysis of CLP2p from fetal sheep liver extract

The protein composition of CLP2p was analyzed in an analogous manner as CLP1b (FIG. 13) by high resolution two-dimensional electrophoresis (2-DE) and silver staining. Individual spots in the silver stained 2-DE gels of CLP2p were assigned according to identified proteins in CLP1b by application of the software package Delta2D (DECODON GmbH; Greifswald).

Figure 15:
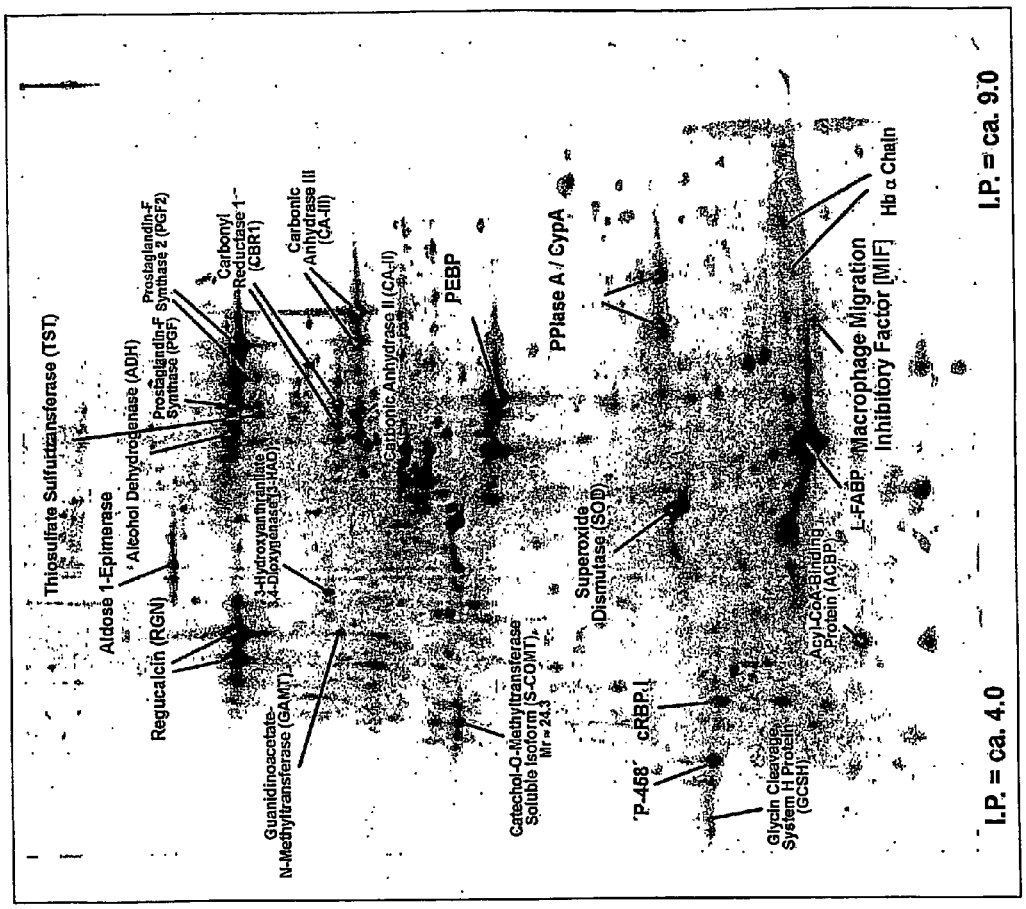

FIG. 15: 2-DE-analysis of CLP1b from adult sheep liver extract

The protein composition of a CLP1b preparation from adult sheep liver was analyzed analogous to the fetal CLP1b and CLP2p preparations (FIGS. 13 and 14) by high resolution two-dimensional electrophoresis (2-DE) and silver staining.

Individual spots in the silver stained 2-DE gels of the adult CLP1b sample could be assigned according to identified proteins in fetal CLP1b by application of the software package Delta2D (DECODON GmbH; Greifswald). The corresponding software-calculated overlay of the 2-DE protein patterns of the fetal and adult CLP1b preparations is shown in FIG. 13.

Figure 16:
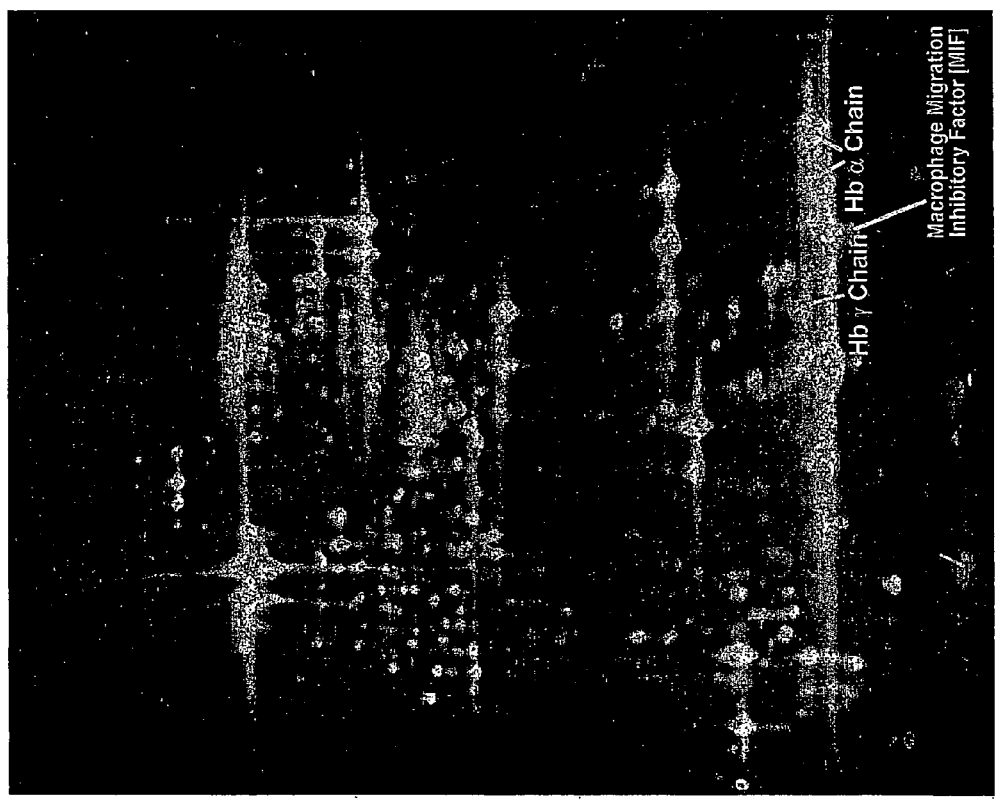

FIG. 16: Overlay analysis of 2-DE-patterns of CLP1b from fetal and adult sheep liver Major differences in the 2-DE protein patterns of fetal versus adult CLP1b preparations were detected by a software-optimized overlay of silver stained 2-DE gels applying the software package Delta2D (DECODON GmbH; Greifswald). Protein spots that are specific for the fetal and ovine CLP1b preparations are depicted in green and red colouring, respectively, whereas spot signals common to the fetal and adult samples are shown in yellow.

Figure 17:
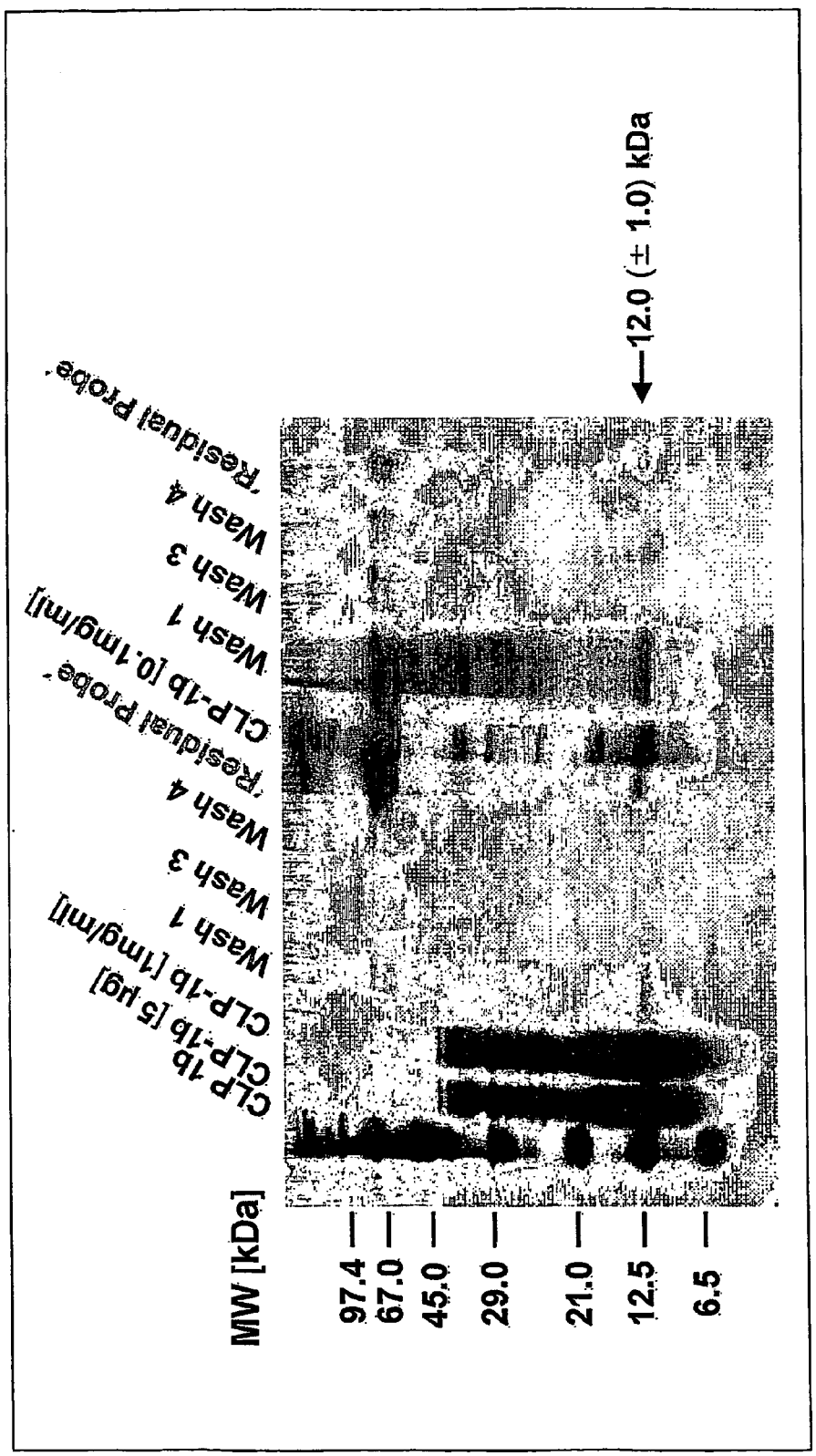

FIG. 17: Selective adsorption of a 12 kDa protein of CLP1b to S-Form LPS

For screening of CLP1b derived from fetal sheep liver for LPS and Lipid A-binding proteins an adsorption assay based on the initial coating of polyvinylchloride 96-well microtiter plates with S-form LPS from *Salmonella enterica* sv. Minnesota 188233 (see methods) was performed (see methods). Final analysis of wash supernatants and residual adsorbed proteins by SDS PAGE revealed the S-type LPS-dependent enrichment of a single protein band displaying an apparent molecular weight of about 12 (±1) kDa.

Figure 18:
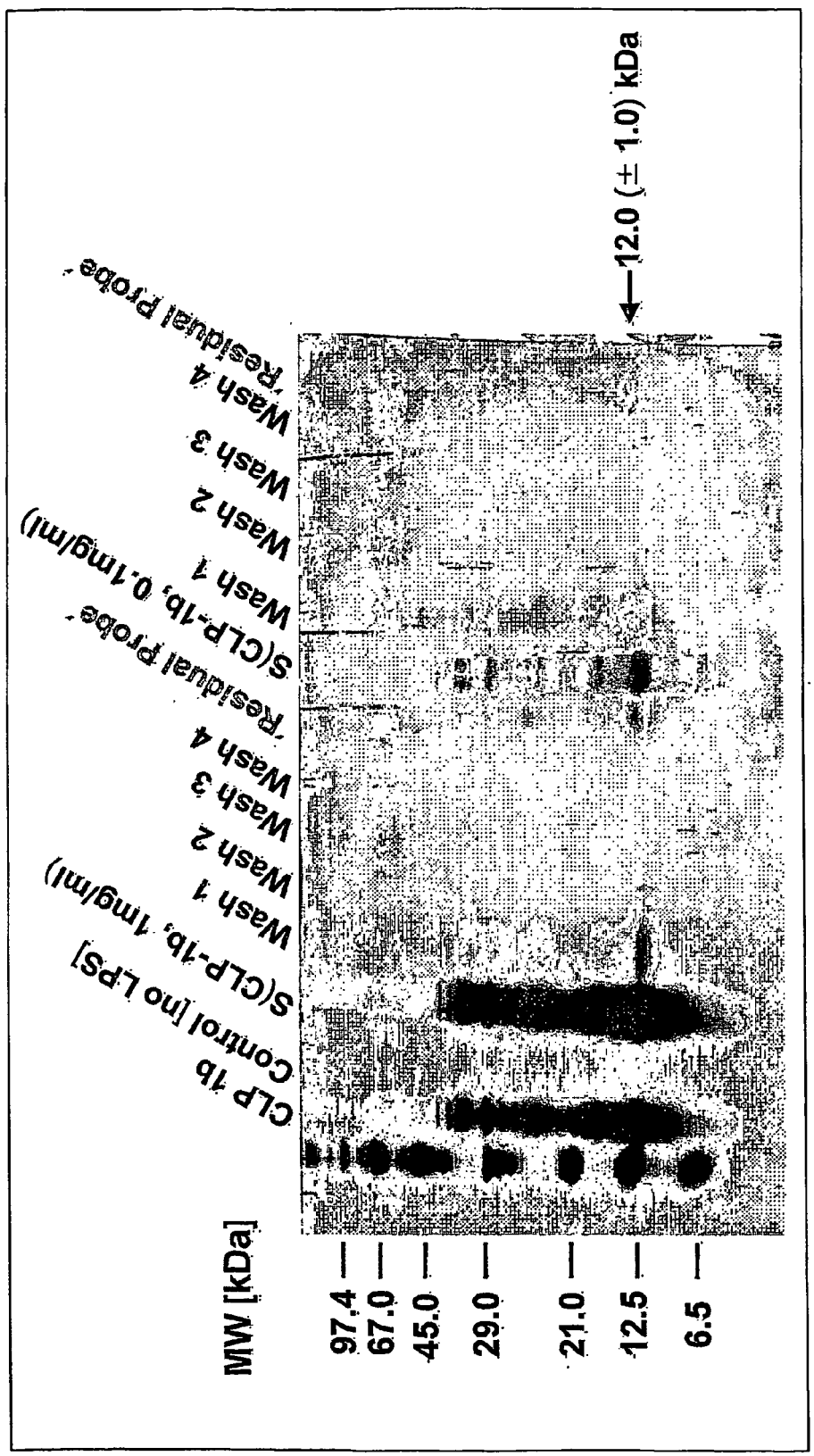

FIG. 18: Selective adsorption of a 12 kDa protein of CLP1b to Re-LPS

In the adsorption assay performed with Re-LPS from *E. coli* strain F515 as the coating material (see methods) a LPS-dependent enrichment of a single 12 (±1) kDa protein band from CLP1b was obtained.

Figure 19:
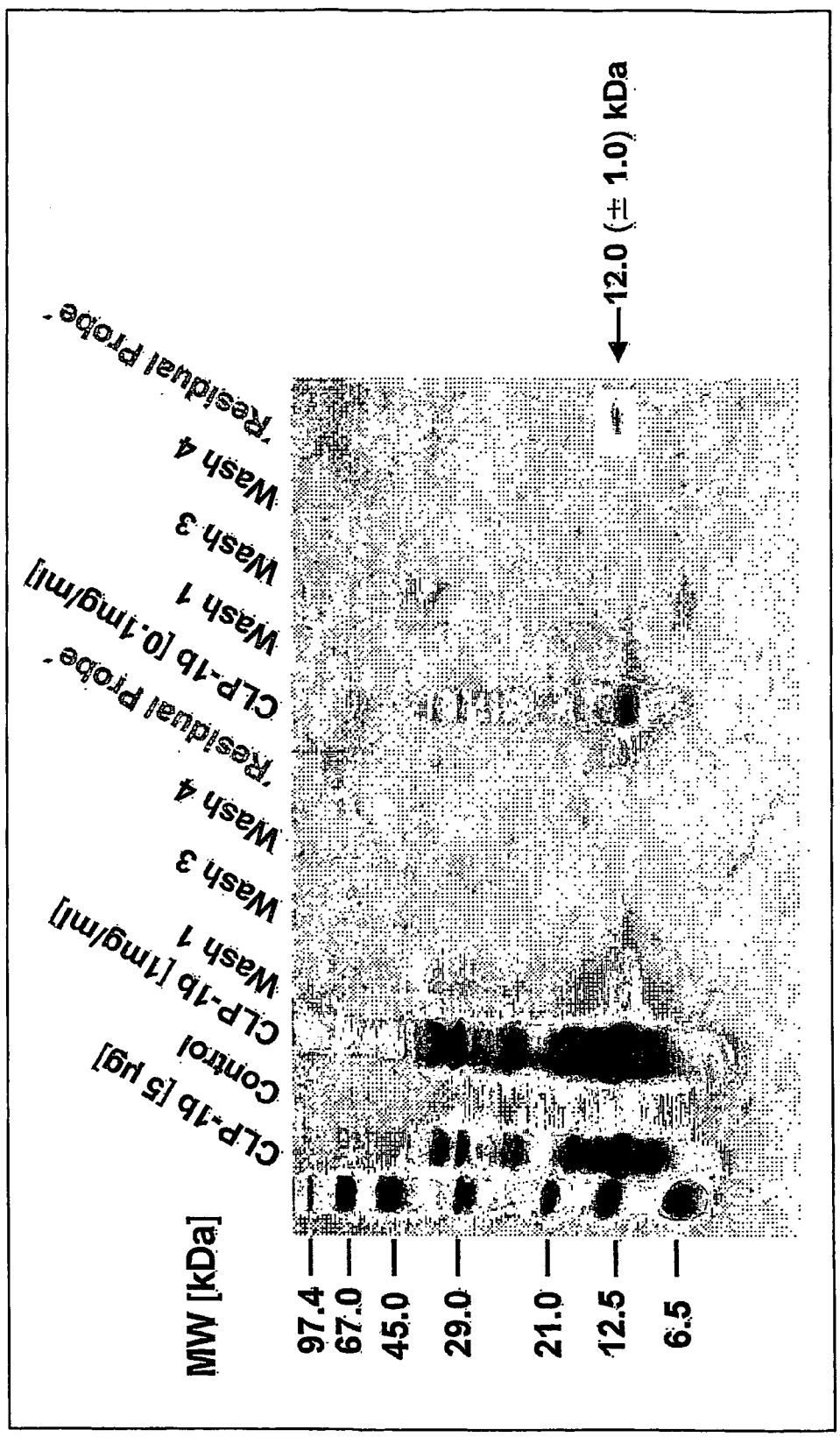

FIG. 19: Selective adsorption of a 12 kDa protein of CLP1b to Lipid A

Utilization of free Lipid A derived from *E. coli* Re LPS as the coating material in the adsorption assay (see methods) revealed the Lipid A-dependent enrichment of a single 12 (±1) kDa protein band from CLP1b.

FIG. 20: Identification of the major LPS/Lipid A-binding 12 kDa protein in CLP1b By performance of the adsorption assay for CLP1b in a preparative scale employing Re-LPS as the coating material, followed by in-gel tryptic digestion of the 12 kDa protein band and tandem mass spectrometry the major component of this LPS/Lipid A-specific protein band was identified as the ovine hemoglobin alpha chain (Hb-alpha). Shown are two tryptic peptides (SEQ ID NOS: 23 and 24, respectively, in order of appearance) and Hb alpha-chain amino acid sequences of various animal species ISEQ ID NOS: 25-30, respectively, in order of appearance).

Figure 21:
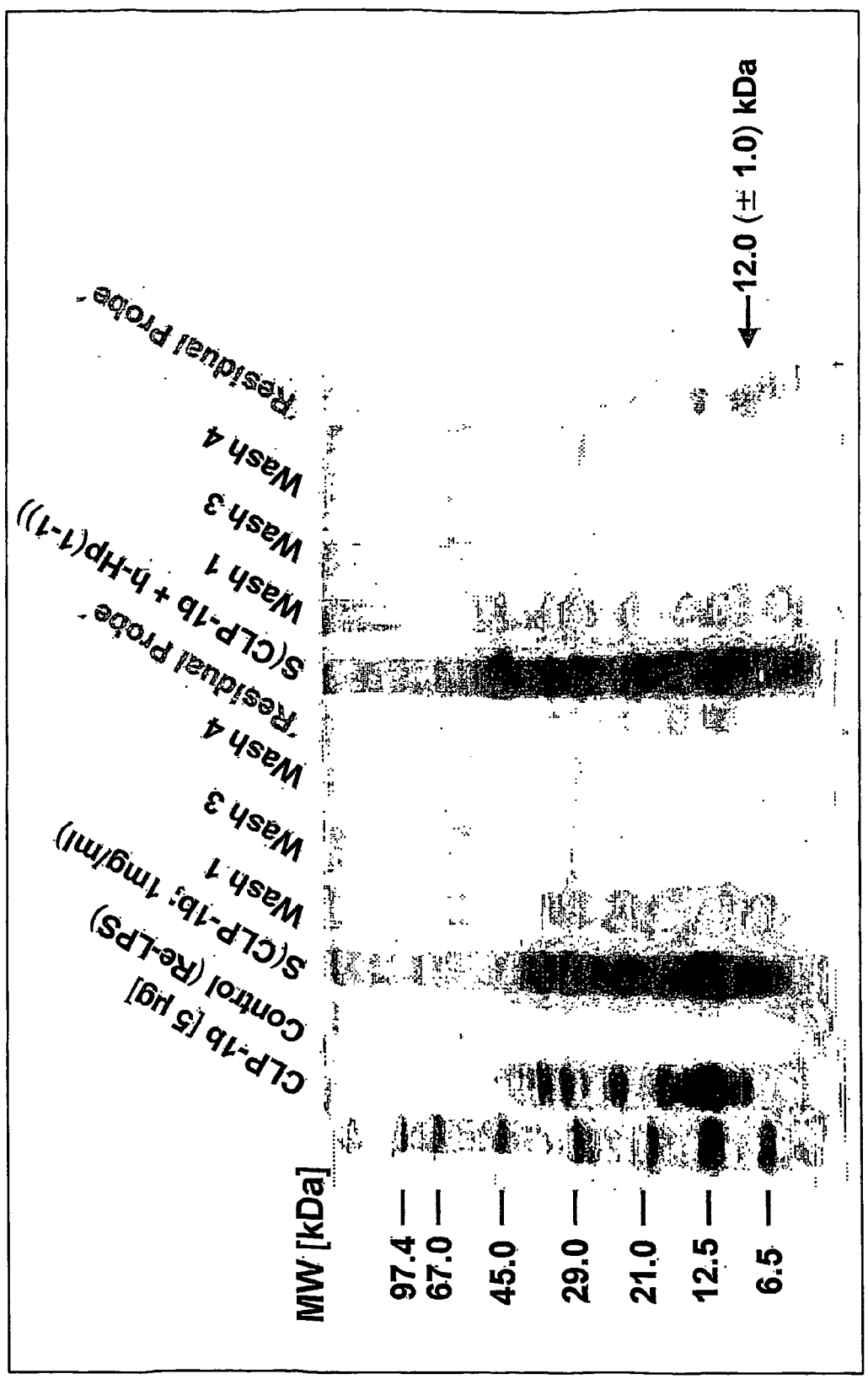

FIG. 21: Reduction of the LPS-specific adsorption of fetal ovine hemoglobin by pretreatment of CLP1b with human haptoglobin The assignment of the major LPS/Lipid A binding protein in CLP1b as the fetal ovine form of hemoglobin was further verified by preincubation of the CLP preparation with human haptoglobin (phenotype 1-1)—representing an evolutionary well conserved high affinity hemoglobin-binding reagent—prior to performance of the adsorption test. Shown is the inhibition by haptoglobin of Hb association to coated LPS.

FIG. 22: Primary structures of ovine Hemoglobin alpha and gamma chains

The amino acid sequences of ovine hemoglobin alpha (A) (SEQ ID NO: 31) and gamma (B)(SEQ ID NO: 32) chains have been retrieved from the SWISS-PROT database and represent the entries HBBF_SHEEP and HBA_CAPHI, respectively. In the upper panel (A) the sequence of the ovine Hb alpha1 variant is given. Single residue differences found in additional isoforms of the ovine hemoglobin alpha chain are indicated in bold. In the Hb-alpha1 variant Asp-75 is substituted by a Tyr residue, whereas in the Hb-alpha2 variant Gly-19, Leu-113 and Asn-115 are replaced by Ser, His and Ser, respectively. The sheep alpha-D allele in addition differs from the alpha-A allele in the displacement of Gly-15 by an Asp residue.

Figure 23:
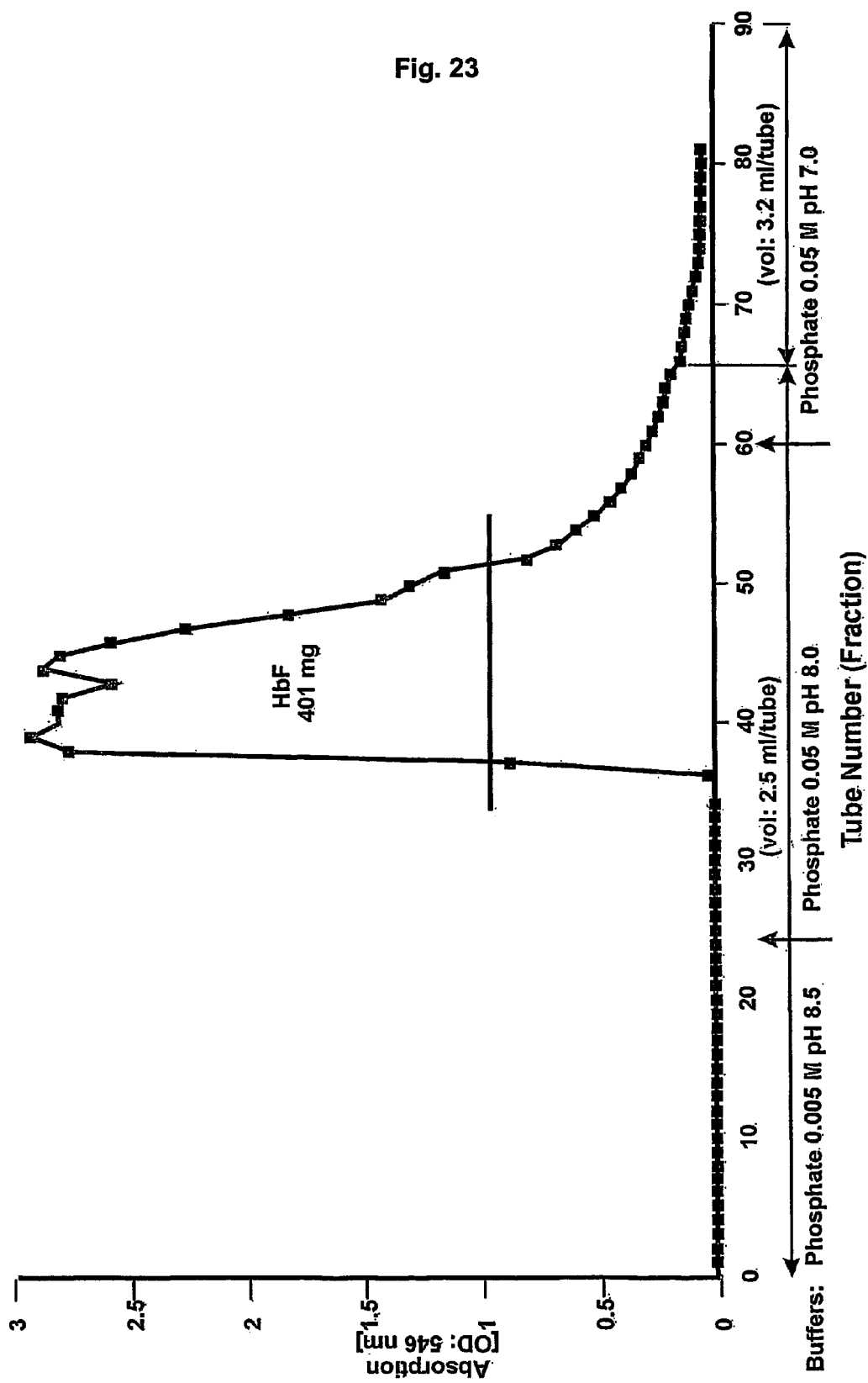

FIG. 23: DE52 Ion exchange chromatography of fetal sheep hemoglobin

The material of 70 KDa obtained after Sephadex G100 chromatography was applied.

Figure 24:
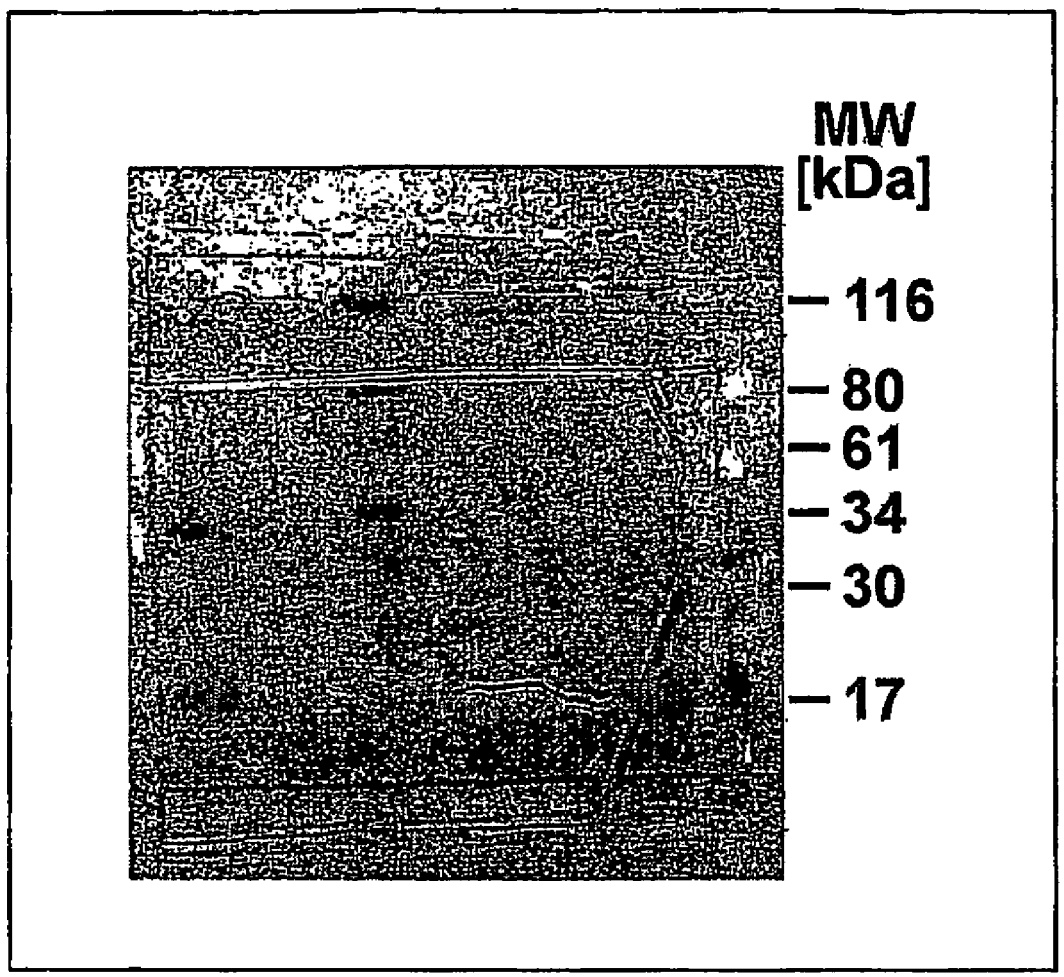

FIG. 24: SDS-PAGE of the material obtained by DE52-chromatography (see. FIG. 23)

Left lane, purified fetal ovine hemoglobin (10 microgrammes/ml), under non-reducing conditions; right lane, same hemoglobin sample after reduction (20 mM DL-dithiothreitol). Central lane molecular weight markers.

Figure 25:
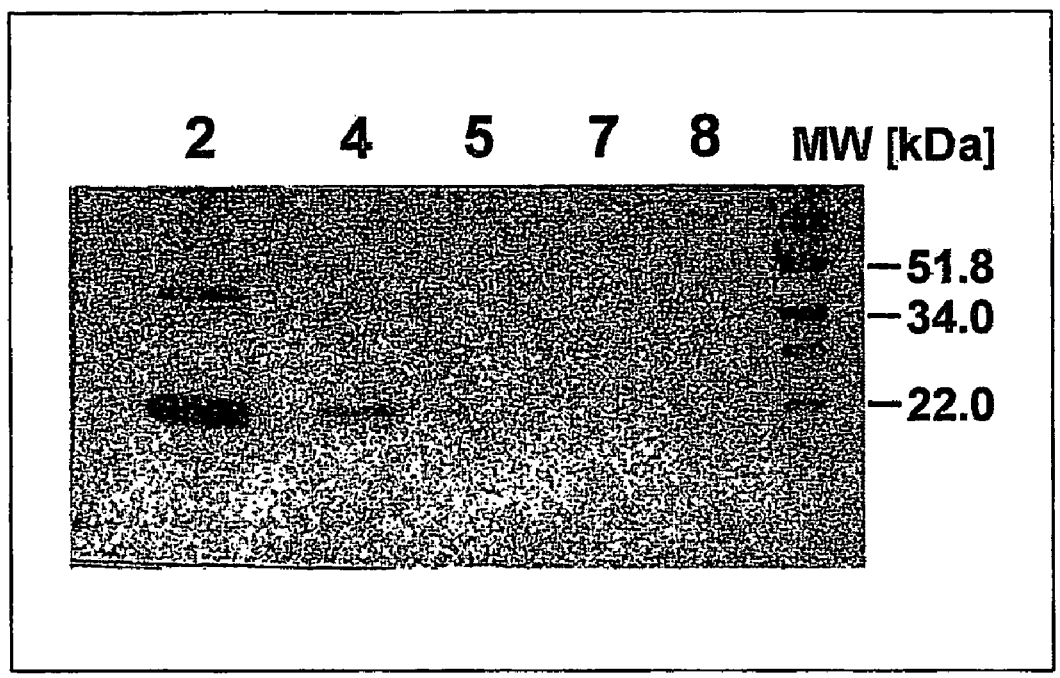

FIG. 25: SDS-PAGE of heme-free Hb

Lane 2, purified heme-free globin (10 microgrammes/ml) under non-reducing conditions; lanes 4 and 5, same globin sample after reduction (20 mM DL-dithiothreitol) (10 and 5 microgrammes/ml, respectively); lanes 7 and 8, two fractions of heme-free globin after separation on cation exchange chromatography (faint bands due to low solubility of the protein); right lane, molecular weight markers.

Figure 26:
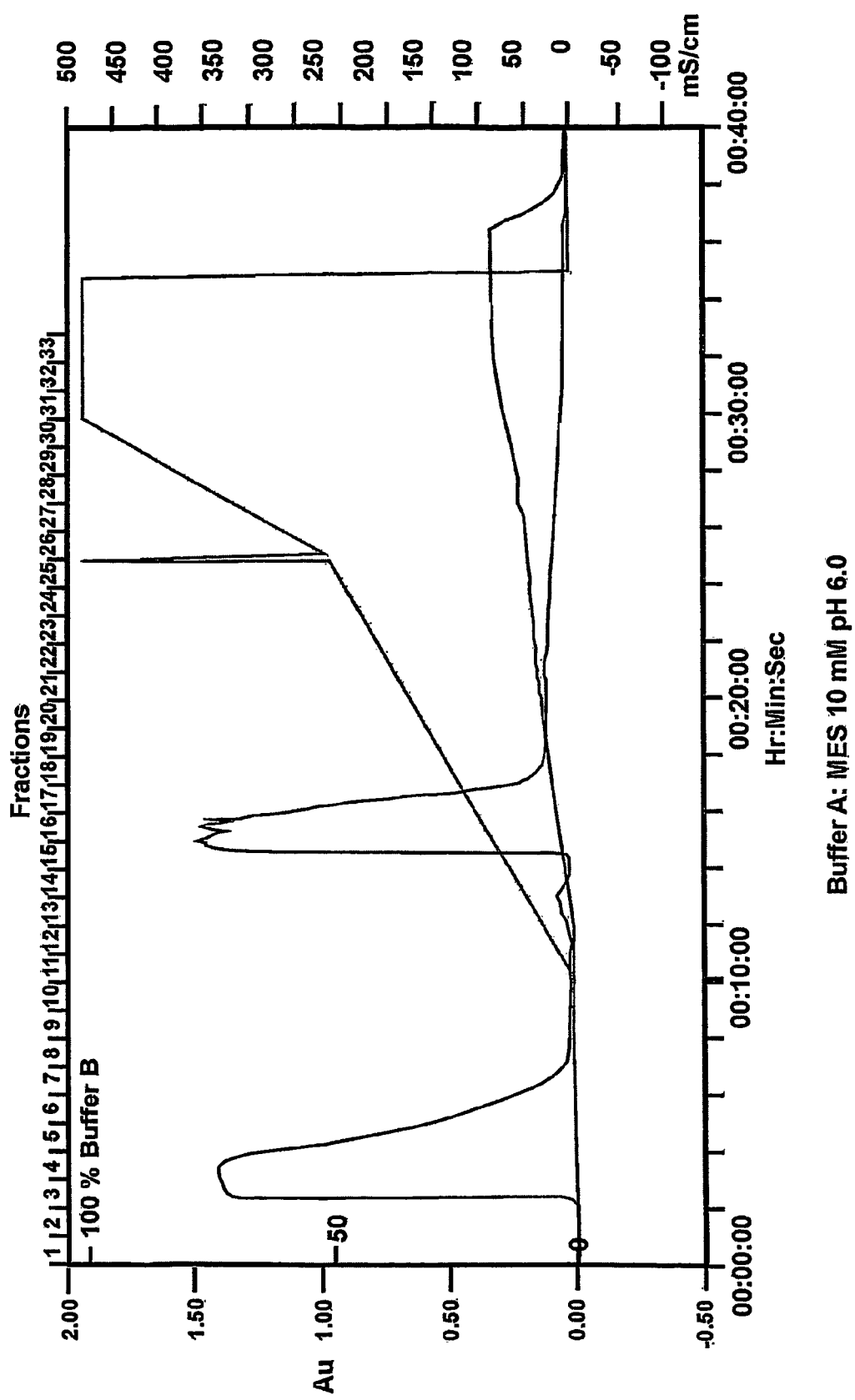

FIG. 26: UNO-S® Cation exchange chromatography of Hb treated with HMB.

Peak 1 contains intact (tetrameric) Hb, peak 2 contains monomeric Hb chains (Mw=17 KDa)

Figure 27:
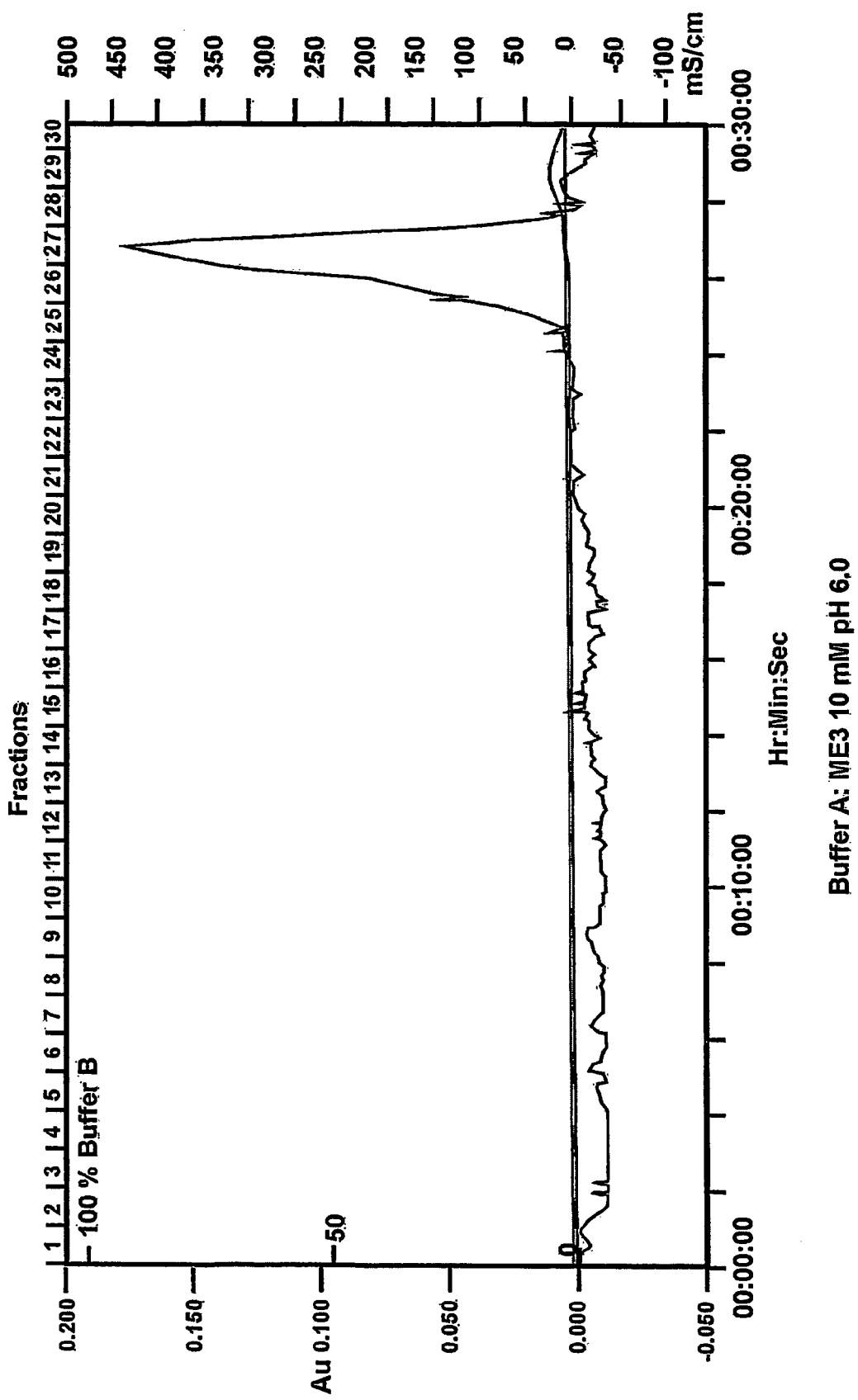

FIG. 27: Superdex S75® chromatography of monomeric Hb chains (peak 2 of FIG. 26)

Figure 28:
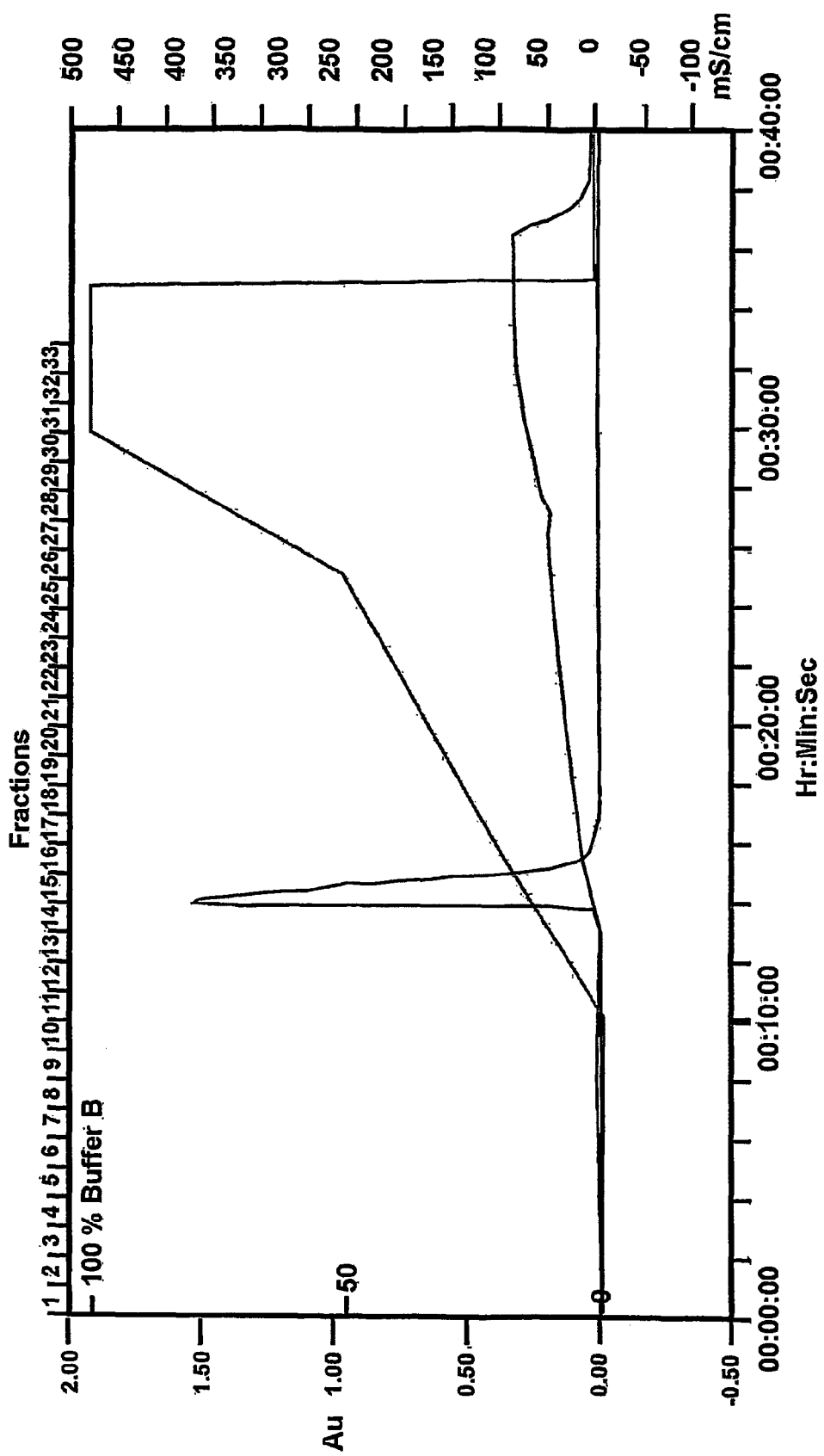

FIG. 28: Purification of monomeric Hb chains (see FIG. 27) by anion exchange chromatography (UNO-Q)

Figure 29:
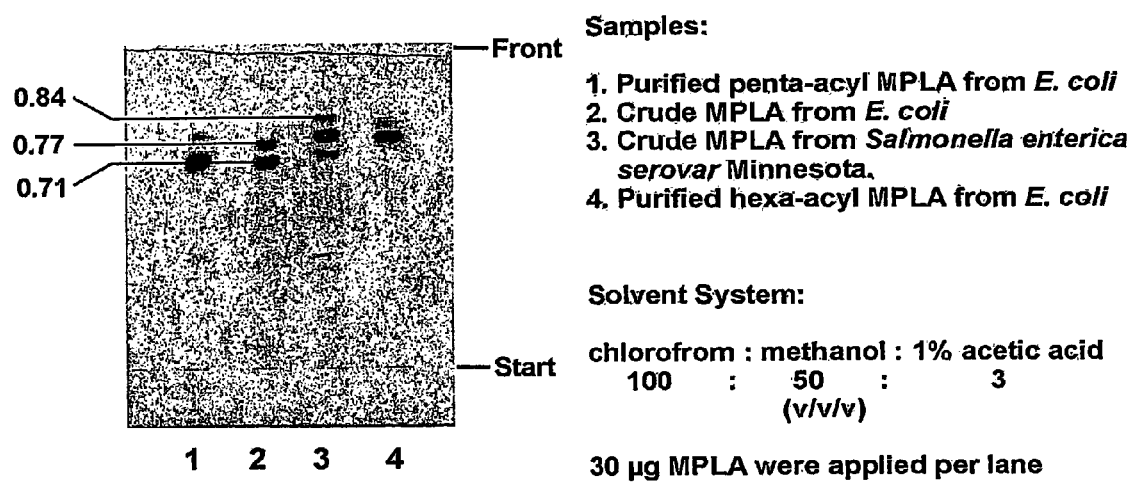

FIG. 29: TLC-analysis of crude Monophosphoryl Lipid A (MPLA, lane 2) isolated from Re-LPS of *E. coli* strain F515

The reference purified penta-acyl MPLA ($R_f$=0.71, lane 1) also contains a minor amount of hexa-acyl MPLA ($R_f$=0.77). The reference hexa-acyl MPLA (lane 4) contains traces of contaminating 14:0(3-OH) ($R_f$=0.82).

Figure 30:
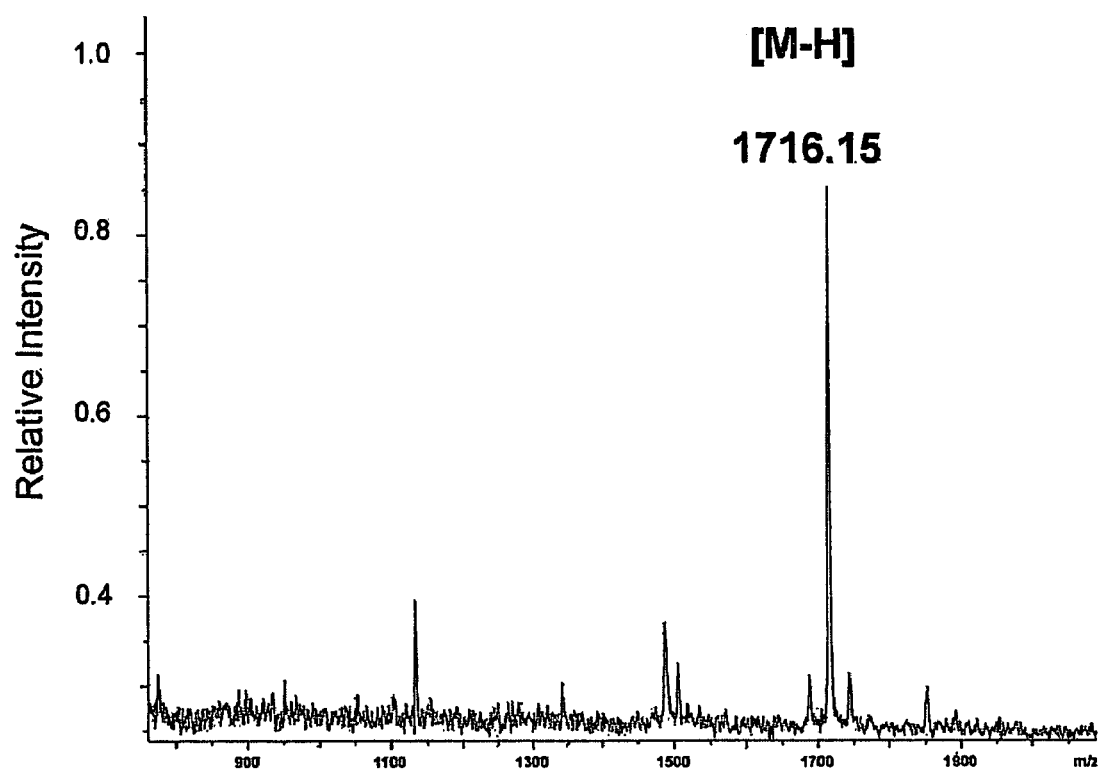

FIG. 30: Negative-ion mode MALDI-TOF mass spectrum of Monophosphoryl Lipid A ($MPLA_{hexa}$) (calculated molecular mass m/z 17617.21)

Minor peaks belong to $MPLA_{hexa}$ fragments with M-(14:0) and M-[14:0(3-OH)] and M-[14:0-14:0(3-OH)].

Figure 31:
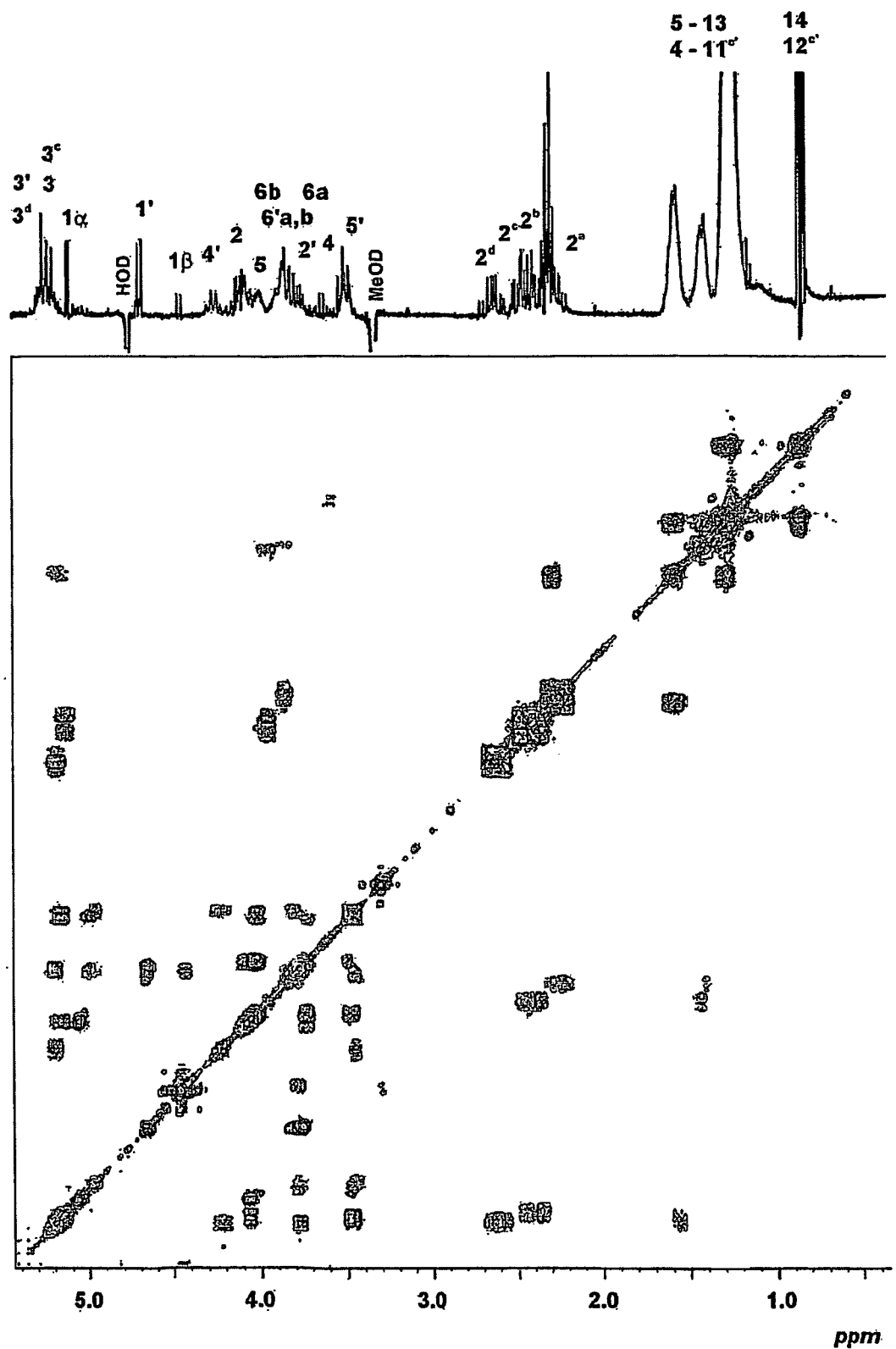

FIG. 31: Contour plot of a $^1H,^1H$—COSY spectrum of $MPLA_{hexa}$ (600 MHz, chloroform-d: methanol-$d_4$, 300 K)

Protons assigned to GlcN I (H-1 to H-6a,b) and GlcN II (H-1' to H-6a,b') and fatty acids $2^a$, $2^b$, $2^c$, $2^d$, $2^{c'}$, $2^{d'}$ etc. are indicated at the top $F_2$-projection of a 1D $^1H$-NMR spectrum.

Figure 32:
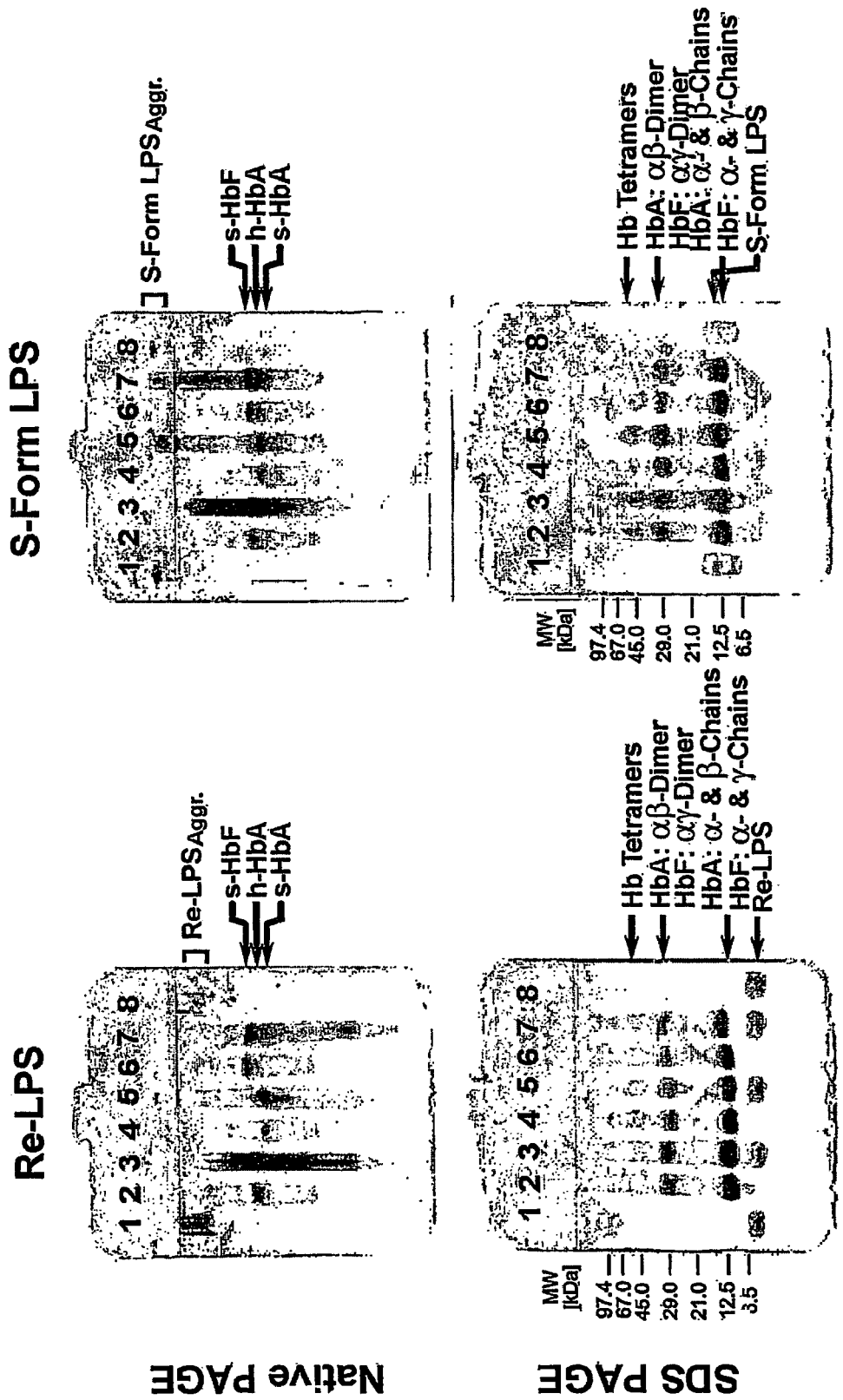

FIG. 32: Induction of LPS disaggregation by fetal ovine hemoglobin

The modulation of native high molecular weight aggregate ultrastructures of Re-LPS from *E. coli* F515 (left panels) and S-form LPS from *Salmonella enterica* sv. Minnesota 188233 (right panels) by purified fetal ovine hemoglobin (s-HbF) was analyzed by an automated native PAGE assay employing the PhastSystem™ apparatus (Amersham Pharmacia Biotech). Prior to nondenaturing electrophoresis the samples were incubated at 37° C. for 30 min. For comparison adult human and ovine hemoglobin preparations (h-HbA and s-HbA) were tested and the integrity of the hemoglobin preparations was additionally verified by subsequent SDS PAGE (lower panels). The following samples were applied to the native (upper panels) and SDS Phast™ gels (lower panels): lanes 1 and 8: LPS (Re-LPS or S-form LPS); lane 2: human HbA; lane 3: LPS plus human HbA; lane 4: ovine HbA; lane 5: LPS plus ovine HbA; lane 6: ovine HbF; lane 7: LPS plus ovine HbF.

Figure 33:
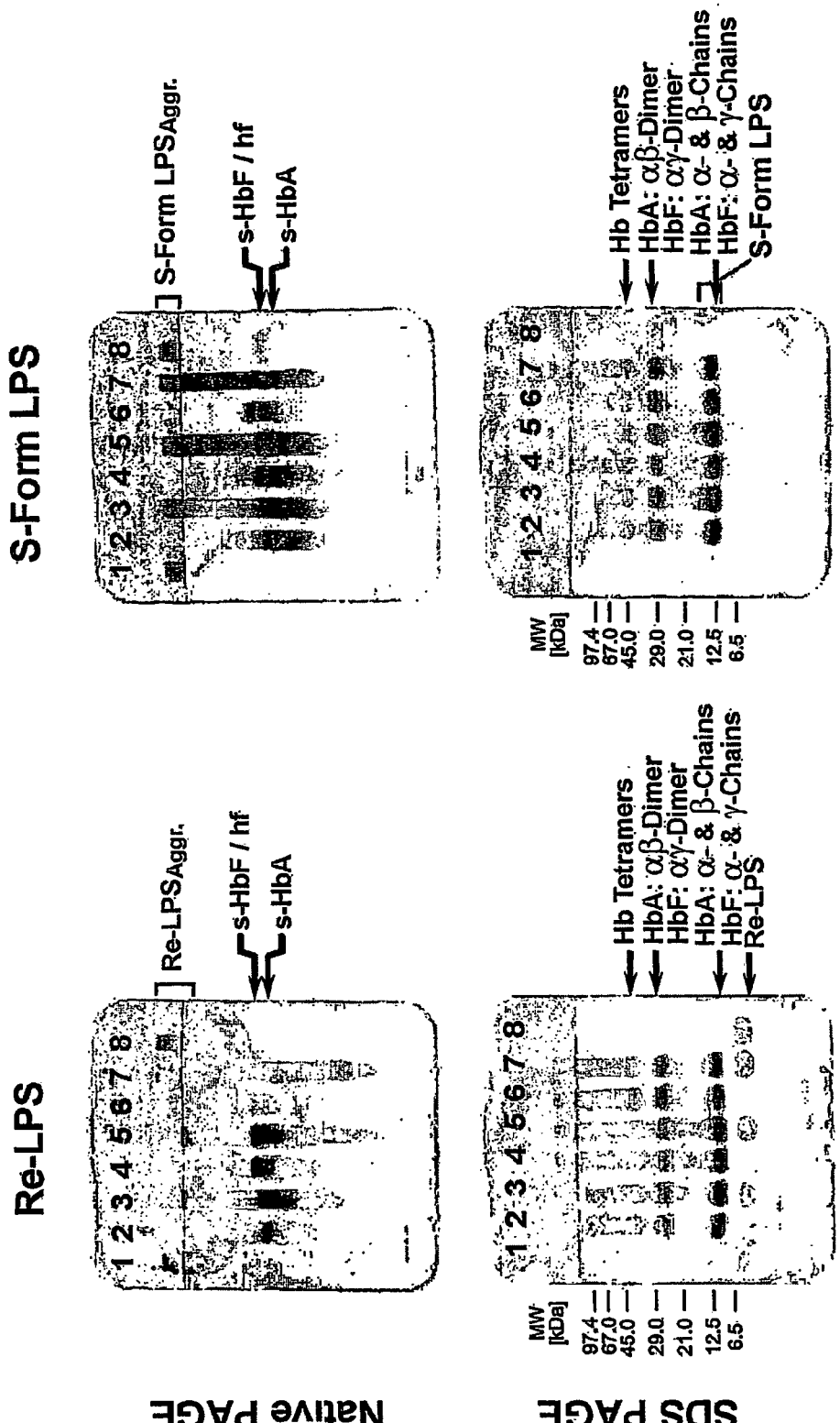

FIG. 33: Induction of LPS disaggregation by heme-free fetal ovine hemoglobin A heme-free preparation of fetal ovine hemoglobin (s-HbF/heme-free) was analysed in comparison to adult s-HbA and the original heme-iron containing s-HbF preparation for LPS disaggregation activities in the automated native Phast™ PAGE assay. The integrity of the hemoglobin preparations was verified by subsequent SDS PAGE (lower panels). The following samples were applied to the native (upper panels) and SDS Phast™ gels (lower panels): lanes 1 and 8: LPS (Re-LPS or S-form LPS); lane 2: ovine HbA; lane 3: LPS plus ovine HbA; lane 4: ovine HbF; lane 5: LPS plus ovine HbF; lane 6: ovine heme-free HbF; lane 7: LPS plus ovine heme-free HbF.

FIG. 34: Synergistic effect (NO production) of Re-LPS and ovine HbF (a:30 μg/ml; b: 10 μg/ml)

FIG. 35: Synergistic effect (NO production) of Re-LPS and heme-depleted ovine HbF (a:30 μg/ml; b: 10 μg/ml)

FIG. 36: Synergistic effect of MonophosphorylLipidA and heme-depleted ovine HbF (a:30 μg/ml; b: 10 μg/ml)

Figure 37:
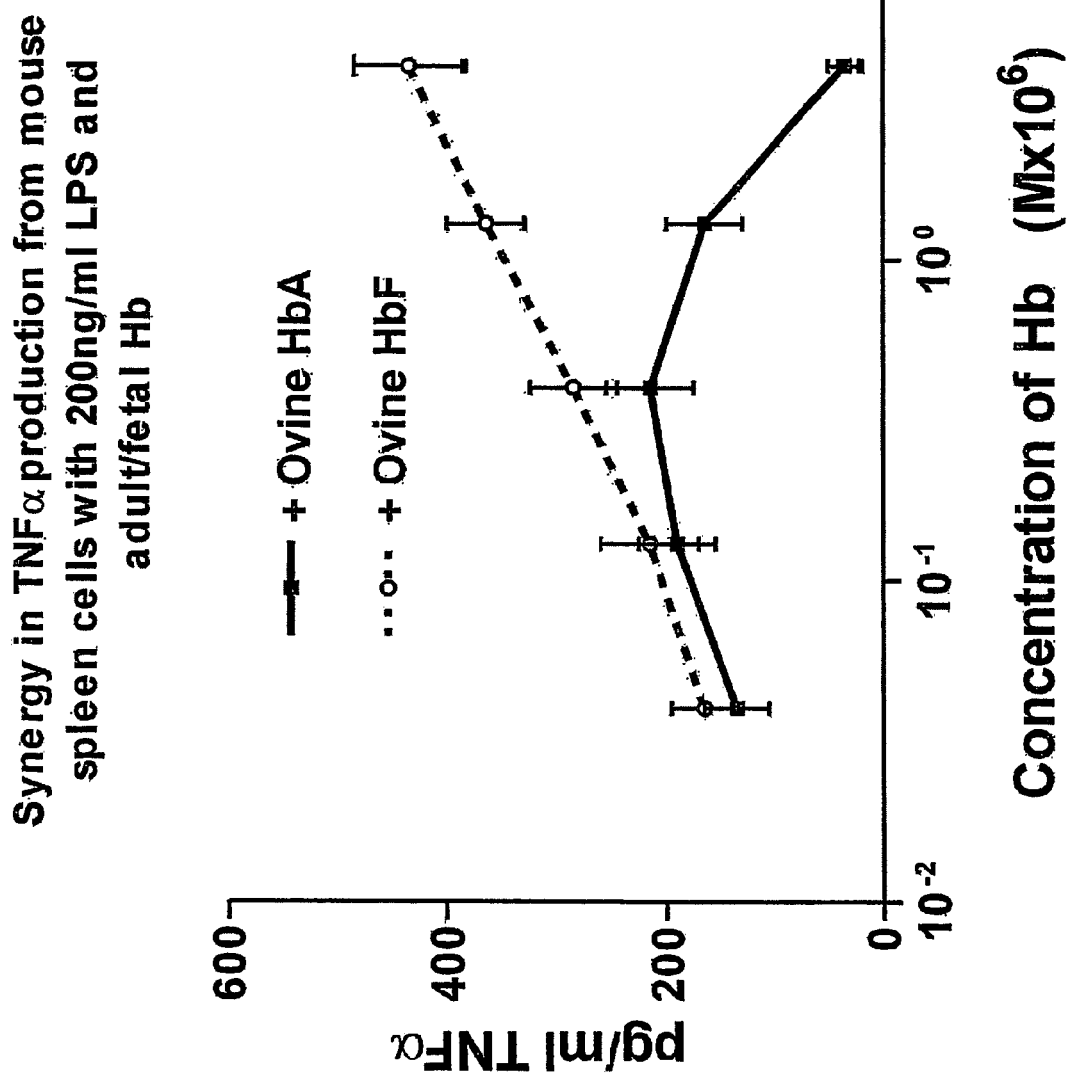

FIG. 37: Synergy in TNFα production by mouse spleen cells with LPS and adult or fetal Hb Spleen cells were pooled from 3 C57BL/6 donors (8-week male). Cells were incubated in triplicate in 2 ml medium (with 10% fetal calf serum and 200 ng/ml LPS) at a concentration of $1 \times 10^6$/ml. Medium contained in addition adult or fetal (sheep) hemoglobin at the various concentrations shown. Supernatants were harvested 24 hrs later to assay in triplicate for TNFα by ELISA. Data show arithmetic means (±SD). Control cultures (no LPS, LPS only, or fetal/adult Hb only) produced levels <50 ng/ml, <70 ng/ml or <50 ng/ml respectively.

Figure 38:
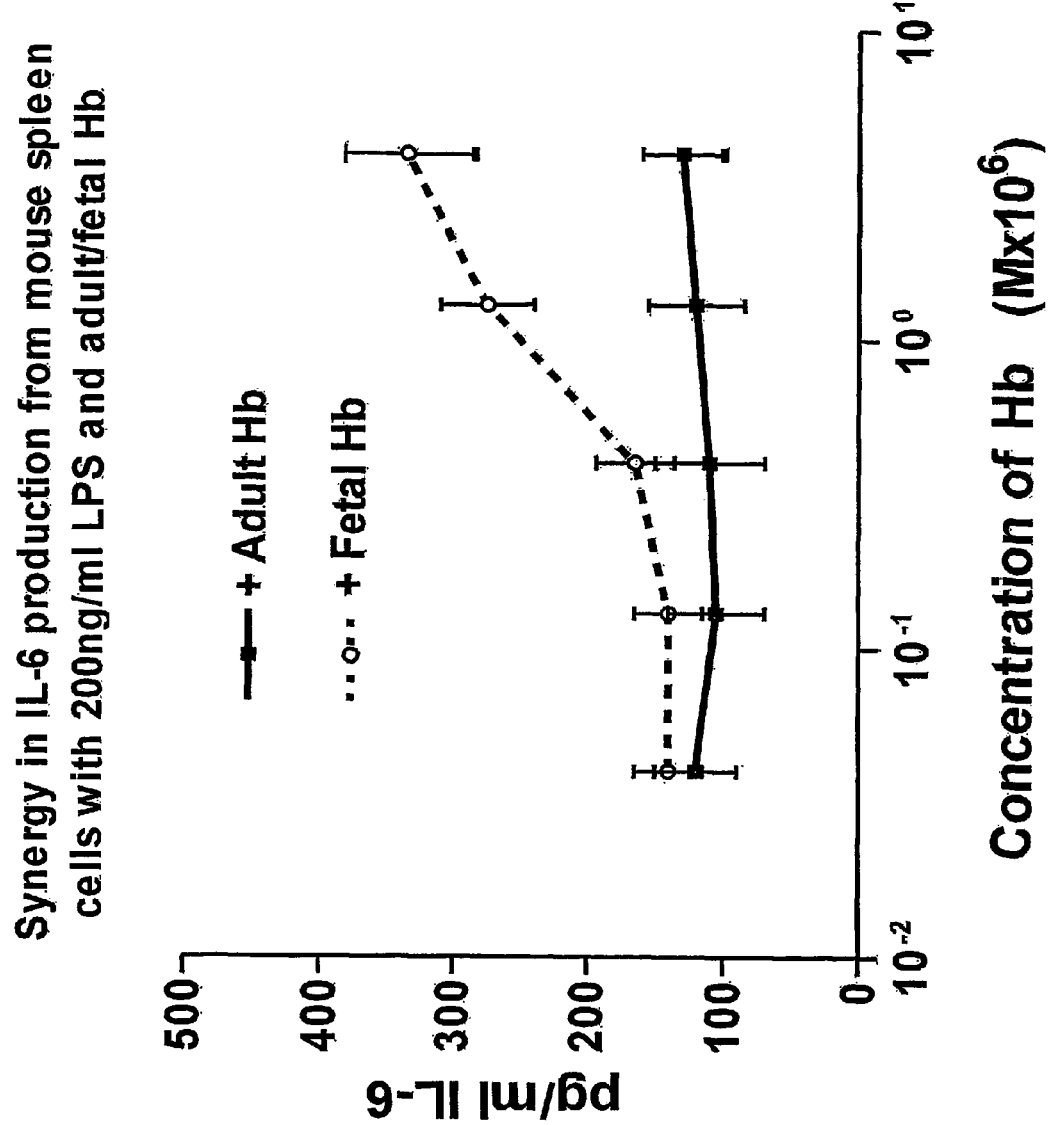

FIG. 38: Synergy in IL-6 production by mouse spleen cells with LPS and adult/fetal Hb Spleen cells were pooled from 3 C57BL/6 donors (8-week male). Cells were incubated in triplicate in 2 ml medium (with 10% fetal calf serum and 200 ng/ml LPS) at a concentration of $1 \times 10^6$/ml. Medium contained in addition adult or fetal (sheep) hemoglobin at the various concentrations shown. Supernatants were harvested 24 hrs later to assay for IL-6 in triplicate by ELISA. Data show arithmetic means (±SD). Control cultures (no LPS, LPS only, or fetal/adult Hb only) produced levels <100 ng/ml, <120 ng/ml or <100 ng/ml respectively.

Figure 39:
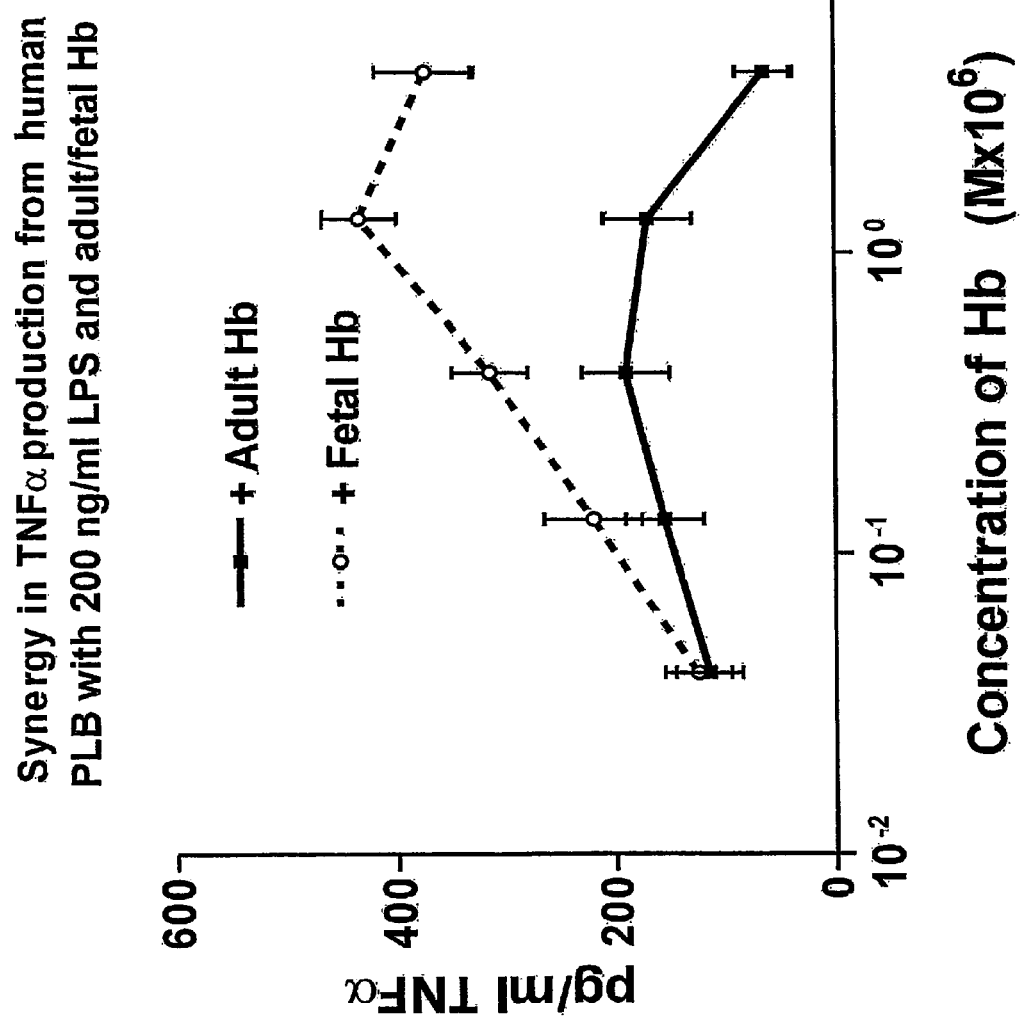

FIG. 39: Synergy in TNFα production by human PBL with LPS and adult or fetal Hb PBL were obtained by Ficoll-hypaque purification from volunteers. Cells were incubated in triplicate in 2 ml medium (with 10% commercial human AB serum and 200 ng/ml LPS) at a concentration of $1 \times 10^6$/ml. Medium contained in addition adult or fetal (sheep) hemoglobin at the various concentrations shown. Supernatants were harvested 24 hrs later to assay in triplicate for TNFα by ELISA. Data show arithmetic means ±SD. Control cultures (no LPS, LPS only, or fetal/adult Hb only) produced levels <50 ng/ml, <100 ng/ml or <65 ng/ml respectively.

FIG. 40: Synergy in TNFα production by human PBL in vitro with LPS and fetal or adult ovine Hb PBL were obtained by Ficoll-hypaque purification from volunteers. Cells were incubated in 2 ml medium (with 10% commercial human AB serum). Cells were incubated in the presence/absence of 500 ng/ml adult or fetal sheep hemoglobin α- or γ-chain. Control cells were incubated in the absence of hemoglobin protein (far left of Figure). In addition, each group was further subdivided into triplicates which received no additional materials (open bars), or 200 ng/ml LPS (closed bars). Supernatants were harvested 24 hrs later to assay (in triplicate) for TNFα by ELISA. Data in panels A and B are independent studies using different volunteer donors (mean ±SD). Panels a and b show data obtained with two different human PBL donors.

Figure 40A:
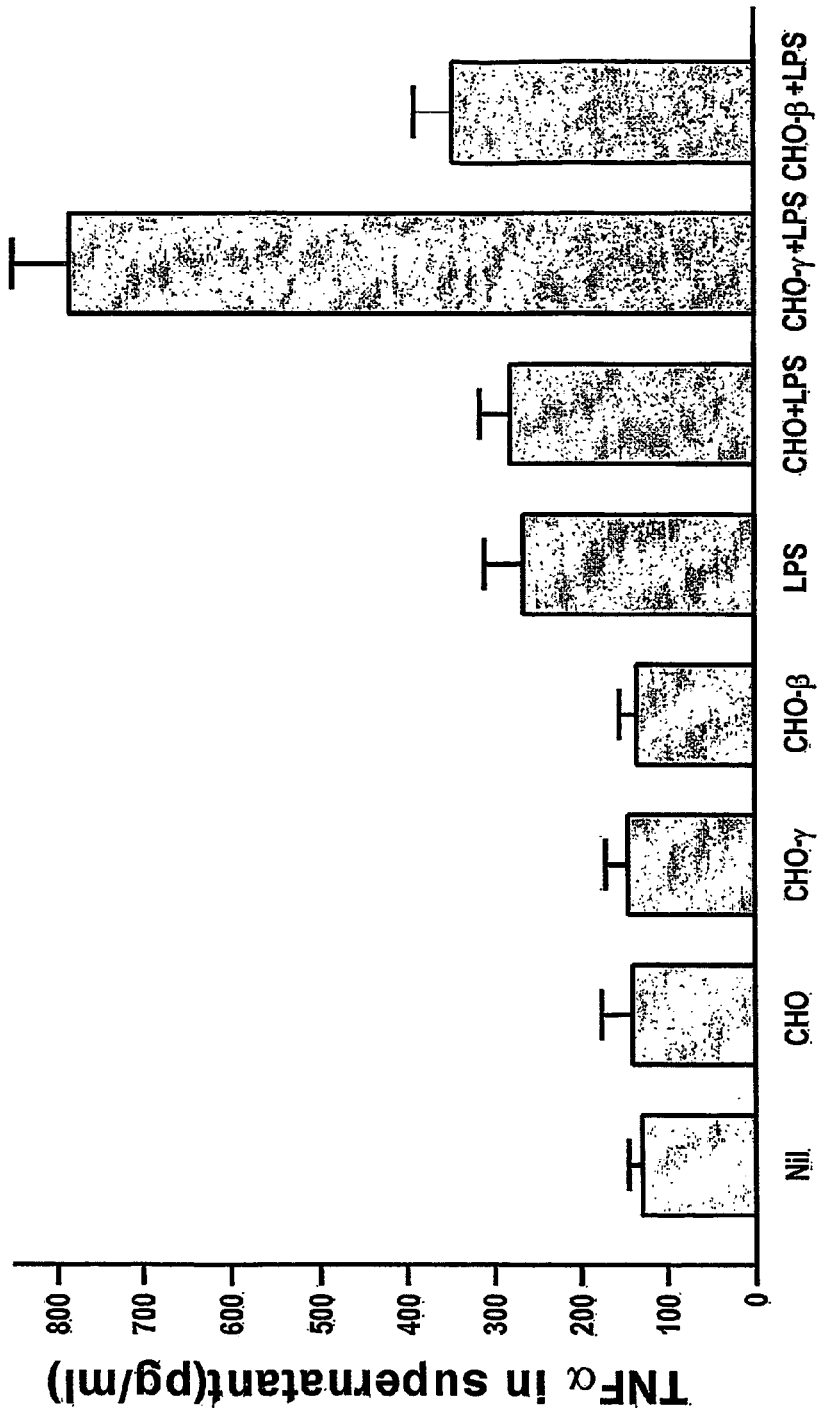

FIG. 40A: Synergy between Hb and LPS is mediated by the Hbγ-chain

In this experiment the cloned γ- and β-chain of sheep Hb were assayed as CHO extracts (20 µg/ml) together with LPS (100 ng/ml) to stimulate murine spleen cells in vitro for the production of TNFα (detection at 24 hr by ELISA)

Figure 40B:
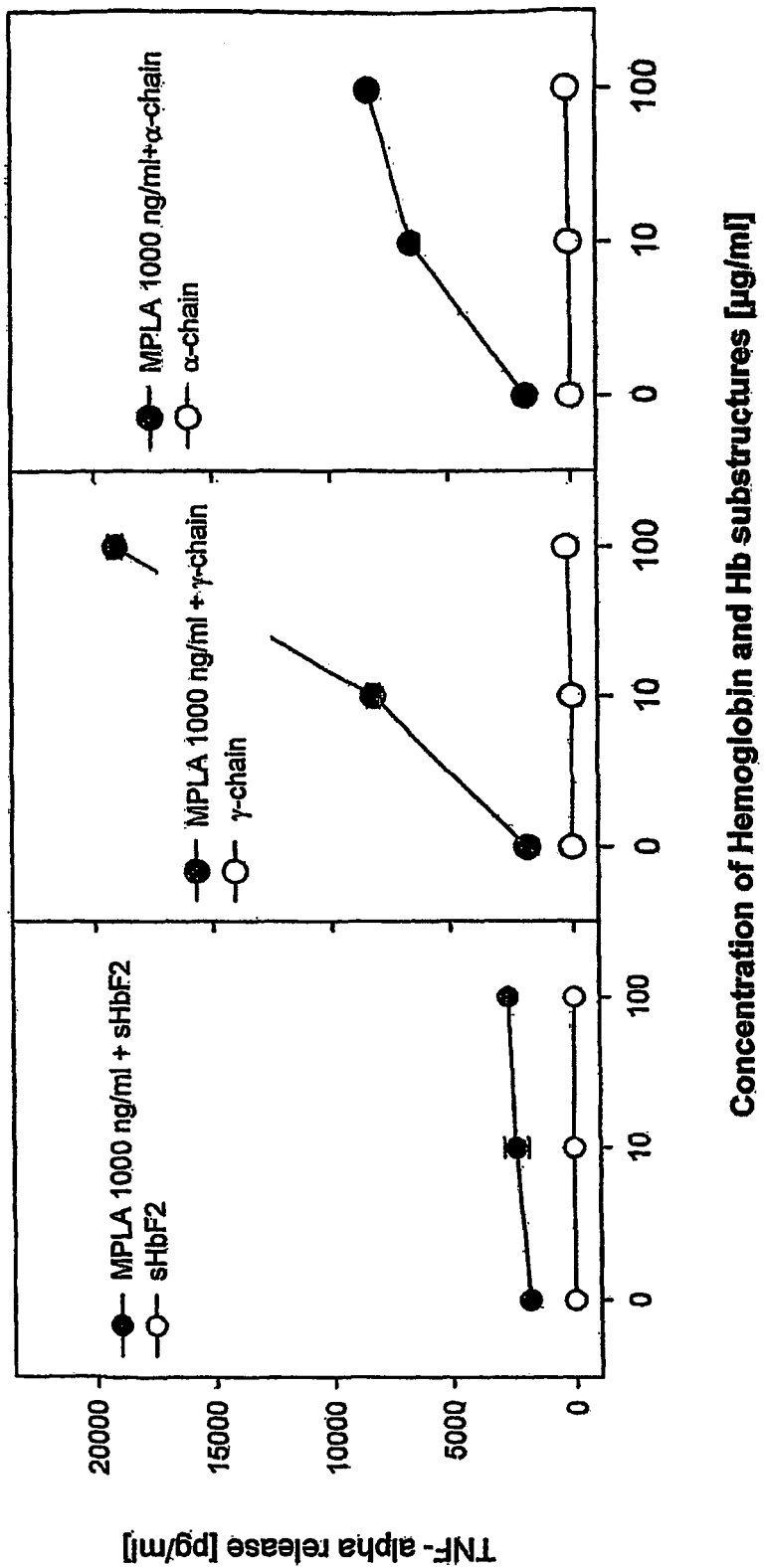

FIG. 40B: Synergism between MPLA and the biochemically purified γ-chain of fetal sheep Hb as determined by TNFα production of human peripheral monocytes FIG. 40C: Enhancing effect of CLP1b and CLP2p on the synergism between fetal ovine hemoglobin (sHbF) and its substructures (isolated chains) with LPS as determined by TGFβ-release of murine spleen cells. For details see section 8.4.2

The lower panels (broken lane) show cytokine production from LPS with CLP. Production above this line indicates further synergy with Hb fractions and indicates clearly that there is evidence of a "three-way" synergy between LPS, Hb fraction and CLP pools.

Figure 40D:
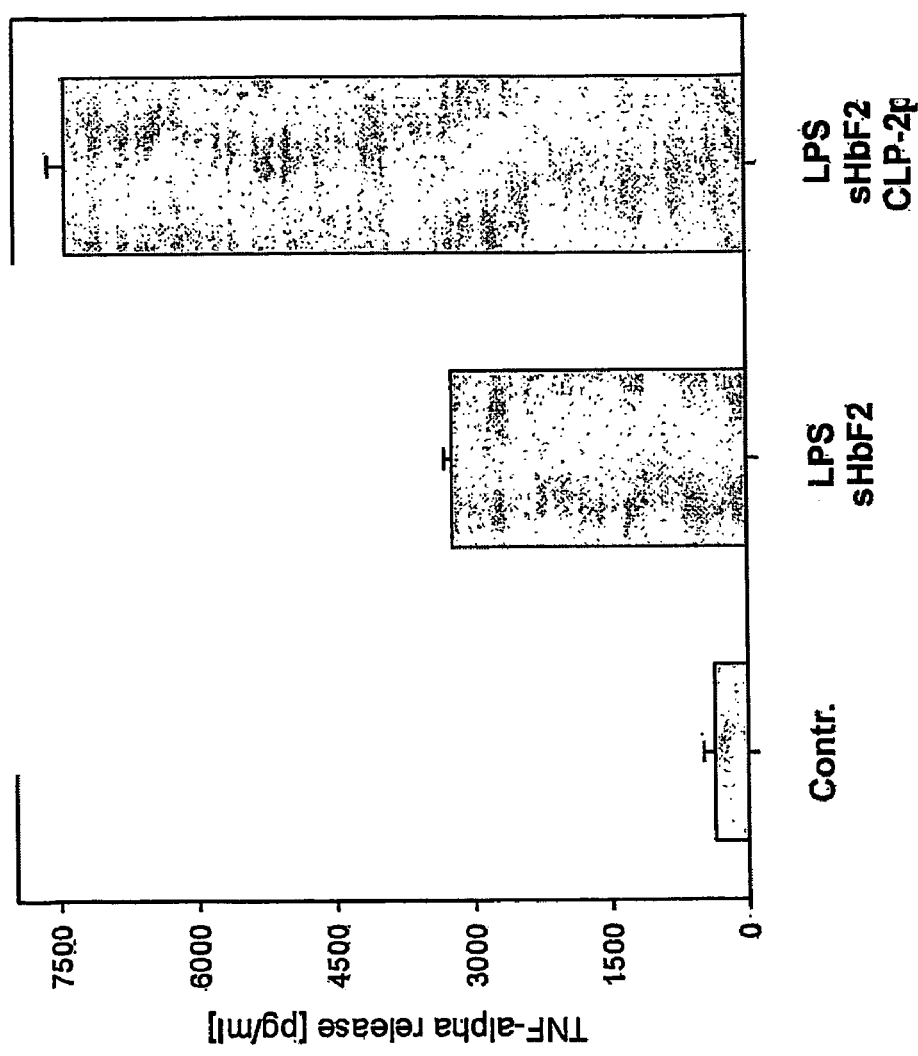
Figure 41:
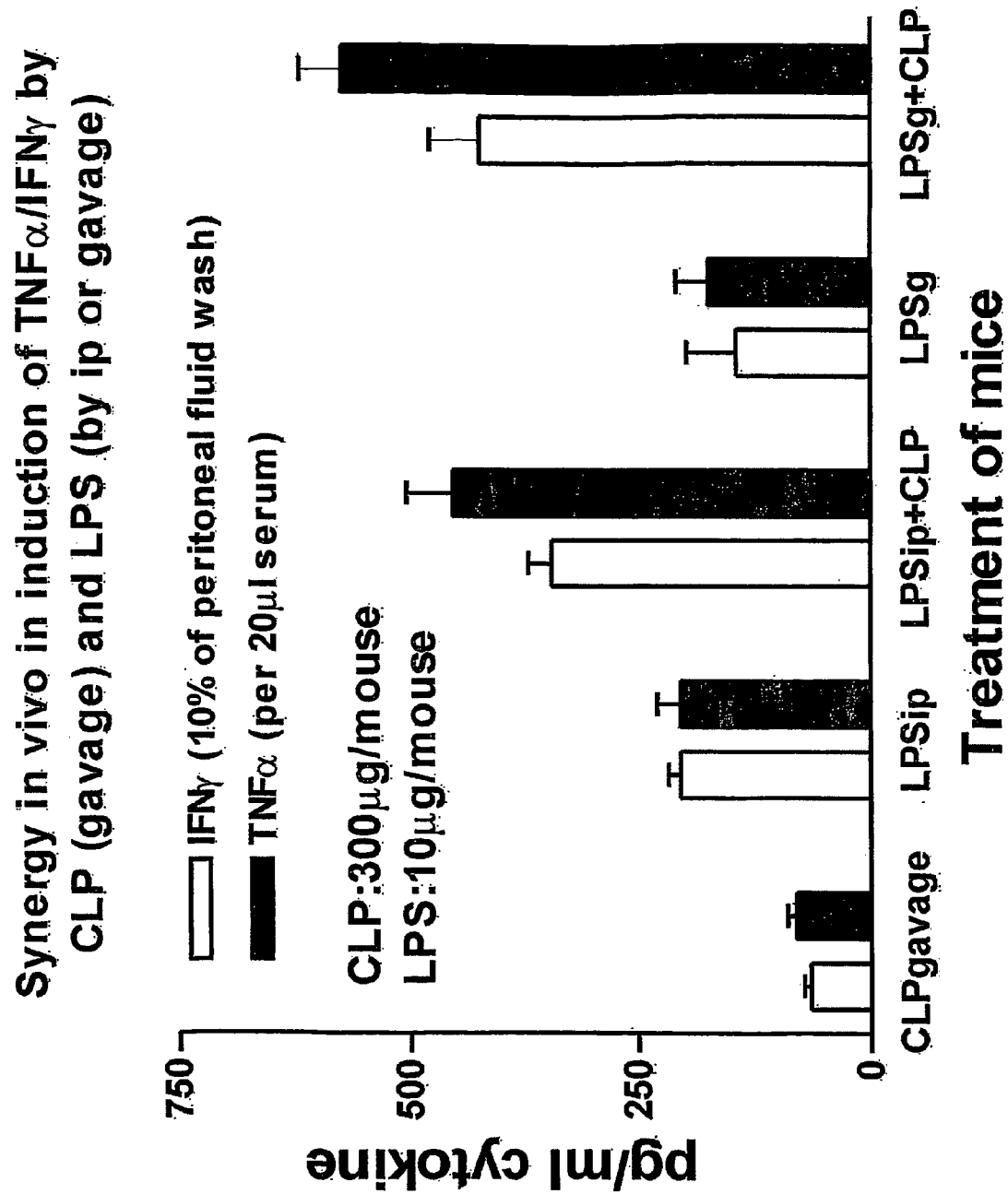

FIG. 40D: Enhancing effect of CLP2p on sHbF/LPS induced TNFα-release of human peripheral monocytes FIG. 41: Synergy in serum TNFα/IFNγ production following gavage of FSLE and LPS alone or together Groups of 5 mice received either 100 µl saline alone or 100 µl saline containing 300 µg of FSLE by gavage, or LPS (10 µg/mouse), given intraperitoneally or by gavage. Two separate groups received FSLE by gavage as well as LPS, either by gavage or ip. All mice were sacrificed at 24 hrs, and blood collected by cardiac puncture. Blood was stored at 4° C. for 4 hrs, and serum collected following high speed centrifugation (10,000 rpm for 20 minutes). Peritoneal wash fluid was harvested from individual mice by flushing with 2 mls warm medium with 10% fetal calf serum-cells were removed by centrifugation (1500 rpm for 10 minutes at 4° C.) and the medium used for cytokine assays. TNFα and IFNγ was assayed in triplicate for each sample by ELISA and bioassay (see Gorczynski et al, 2001 for ELISA assays); Bioassays measured inhibition of proliferation of Wehi 279 cells (IFNγ) or Wehi 1640 cells (TNFα)-equivalent data were seen using each assay). Data show means (±SD).for the 5 mice/group, using 200 µL medium (10% of peritoneal wash fluid) or 20 µl serum.

Figure 42:
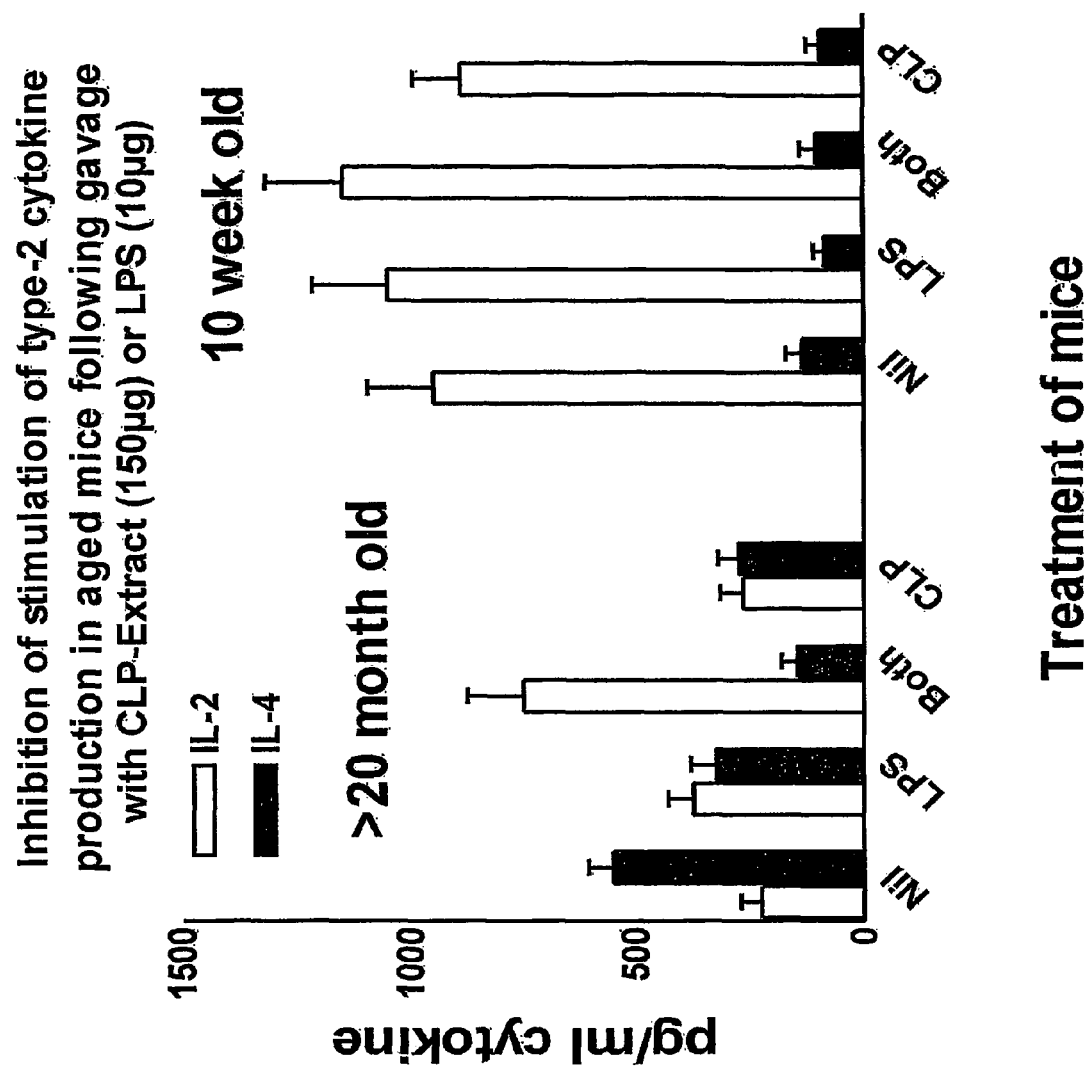

FIG. 42: Inhibition of stimulation of type-2 cytokine production in aged mice following gavage with FSLE or LPS Groups of 5 C57BL/6 mice aged >20 months or 10-weeks of age received either 100 µl saline alone or 100 µl saline containing 150 µg of FSLE or LPS (10 µg/mouse), alone or in combination, on days 0 and 10. All mice were sacrificed at 20 days, spleen cells collected, and cells stimulated in vitro in 2 mls medium with 10% fetal calf serum, at a concentration of $1\times10^6$ cells/ml and Concanavalin A (ConA) at a concentration of 5 µg/ml. Supernatants were harvested at 40 hrs and cytokines (IL-2 (open bars)/IL-4 (closed bars)) measured by ELISA [Gorczynski et al. 2001]. Data show arithmetic means (±SD). Control cultures (no Con A stimulation) produced IL-2 and IL-4 levels <50 pg/ml for all groups (data not shown). Data show means (±SD) for the 5 mice/group.

Figure 43:
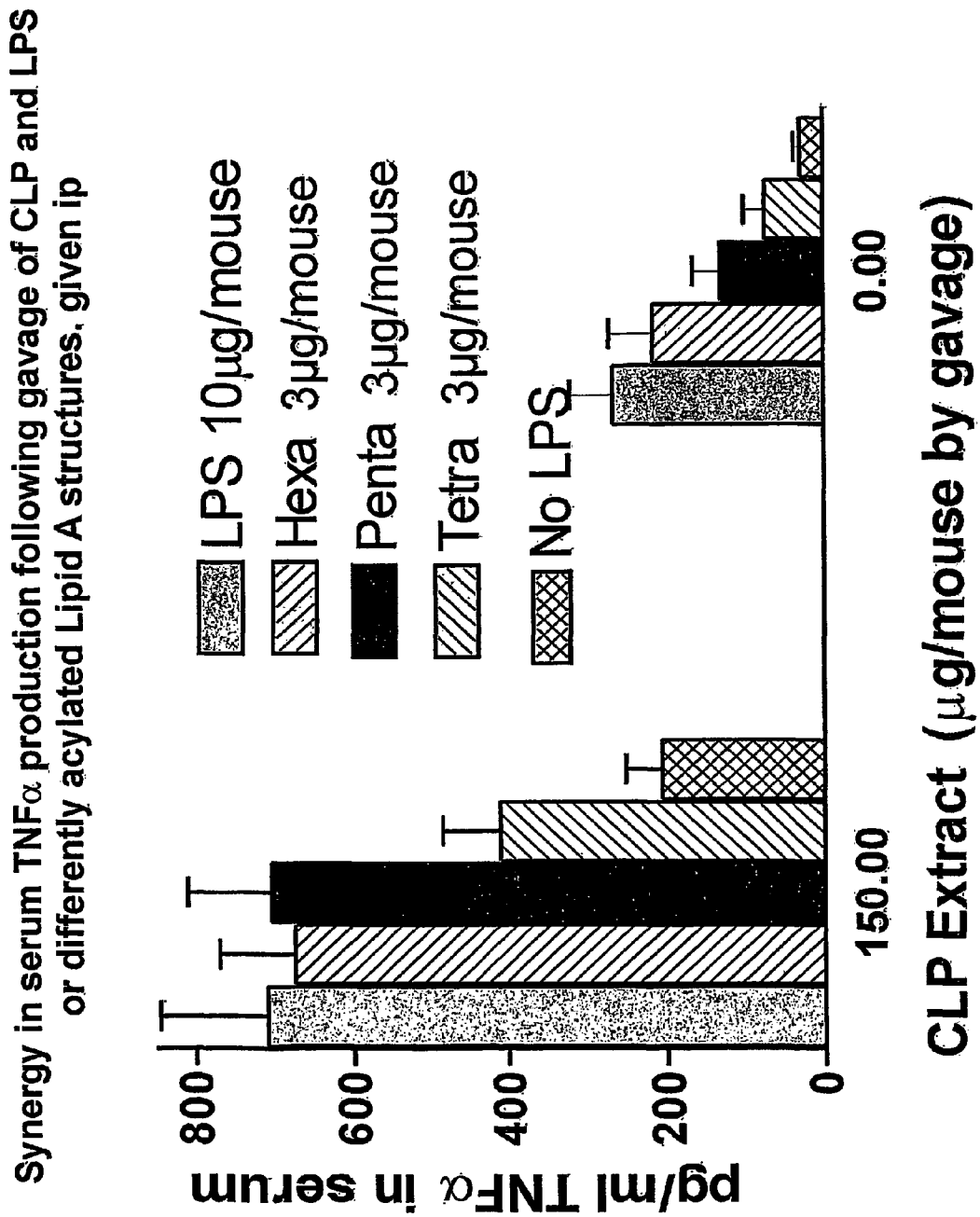

FIG. 43: Synergy in serum TNFα production following gavage of FSLE and LPS or Monophosphoryl Lipid A preparations given i.p.

Groups of 5 mice received either 100 µl saline (bars to far right of Figure) or 150 µg CLP lot 072 (bars to far left of Figure) by gavage. Within 15 minutes mice in the different groups shown received in addition 100 µl of saline with no additives, or 100 µg/ml LPS or 30 µg/ml of the different Lipid A partial structures (hexa, penta and tetraacyl) shown. All mice were sacrificed at 24 hrs, and blood collected by cardiac puncture. Blood was stored at 4° C. for 4 hrs, and serum collected following high speed centrifugation (10,000 rpm for 20 minutes). TNFα was assayed in triplicate for each sample by ELISA [Gorczynski et al, 2001). Data show means (±SD) for the 5 mice/group.

Figure 44:
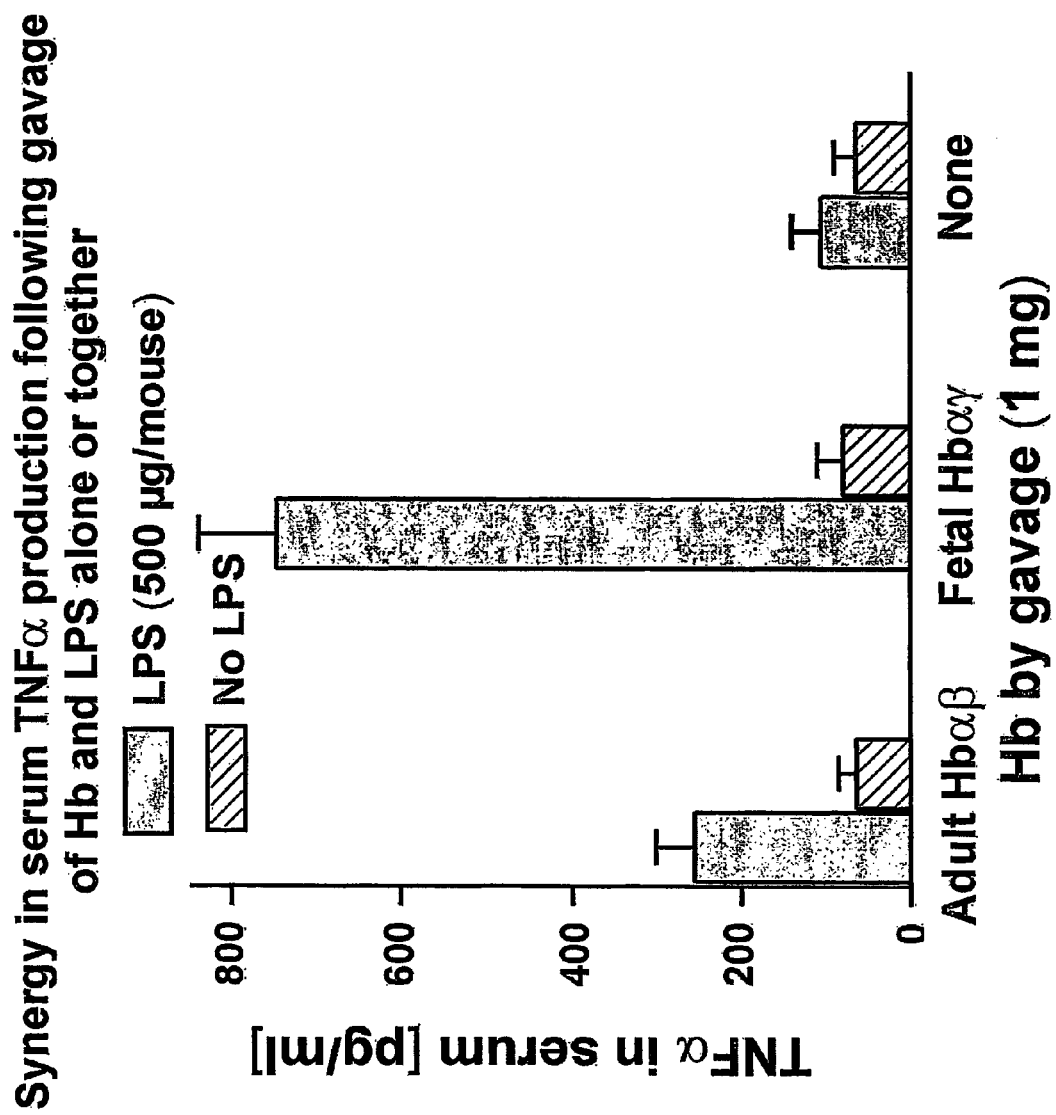

FIG. 44: Synergy in serum TNFα production following gavage of Hb and LPS alone or together Groups of 10 mice received either 100 µl saline alone or 100 µl saline containing 1 mg of purified adult (or fetal) hemoglobin protein chains (αβ or αγ) by gavage. For 5 mice within each group the 100 µl volume also contained LPS (500 µg). All mice were sacrificed at 24 hrs, and blood collected by cardiac puncture. Blood was stored at 4° C. for 4 hrs, and serum collected following high speed centrifugation (10,000 rpm for 20 minutes). TNFα was assayed in triplicate for each sample by ELISA [Gorczynski et al, 2001). Data show means (±SD) for the 5 mice/group.

Figure 45:
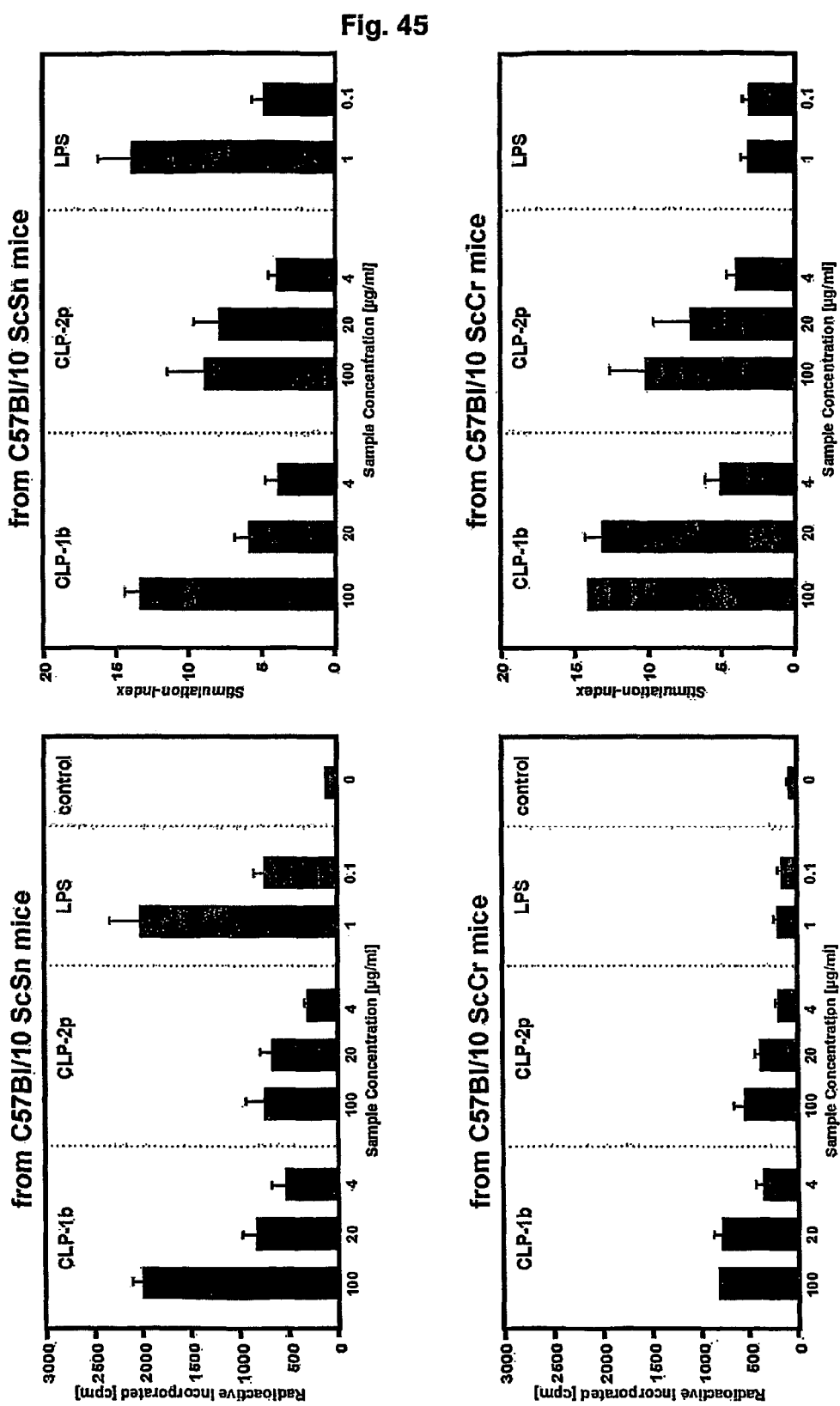

FIG. 45: Proliferation of murine splenocytes after stimulation with CLP1b, CLP2p and LPS in LPS responder (C57 BR/10 ScSn) and LPS-nonresponder mice (C57 Bl/10 ScSr)

Figure 47:
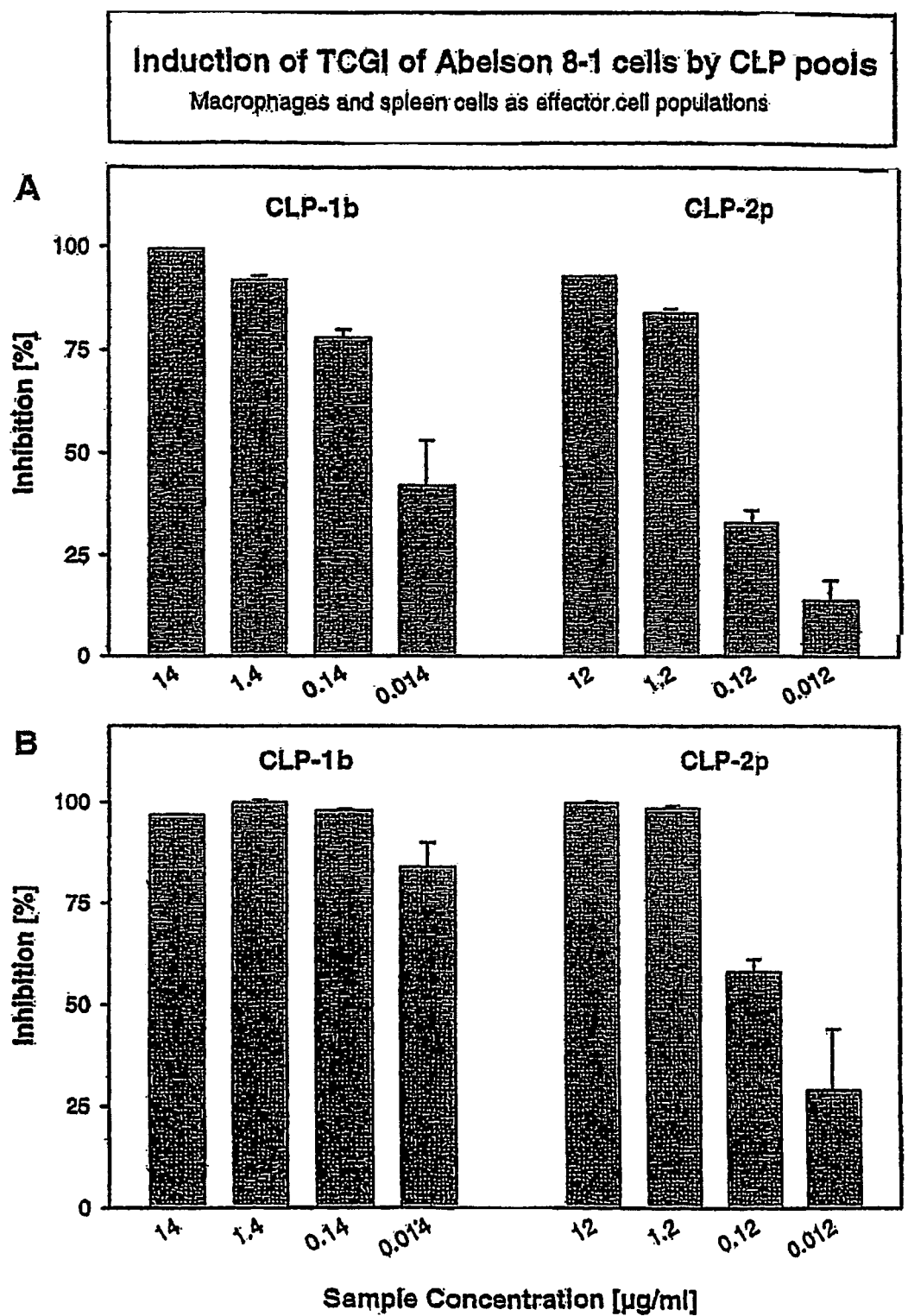

FIG. 46: NO-inducing activity of CLP1b and CLP2p in LPS responder (a) and non-responder (b) mice FIG. 47: Induction of TCGI activity in murine BMDM by CLP1b and CLP2p.

Murine BMDM were stimulated in the absence (A) or presence (B) of syngeneic spleen cells with CLP1b or CLP2p at the concentrations indicated and tested for their TCGI activity on Abelson 8-1 tumor cells as described in Example 12.

Figure 48:
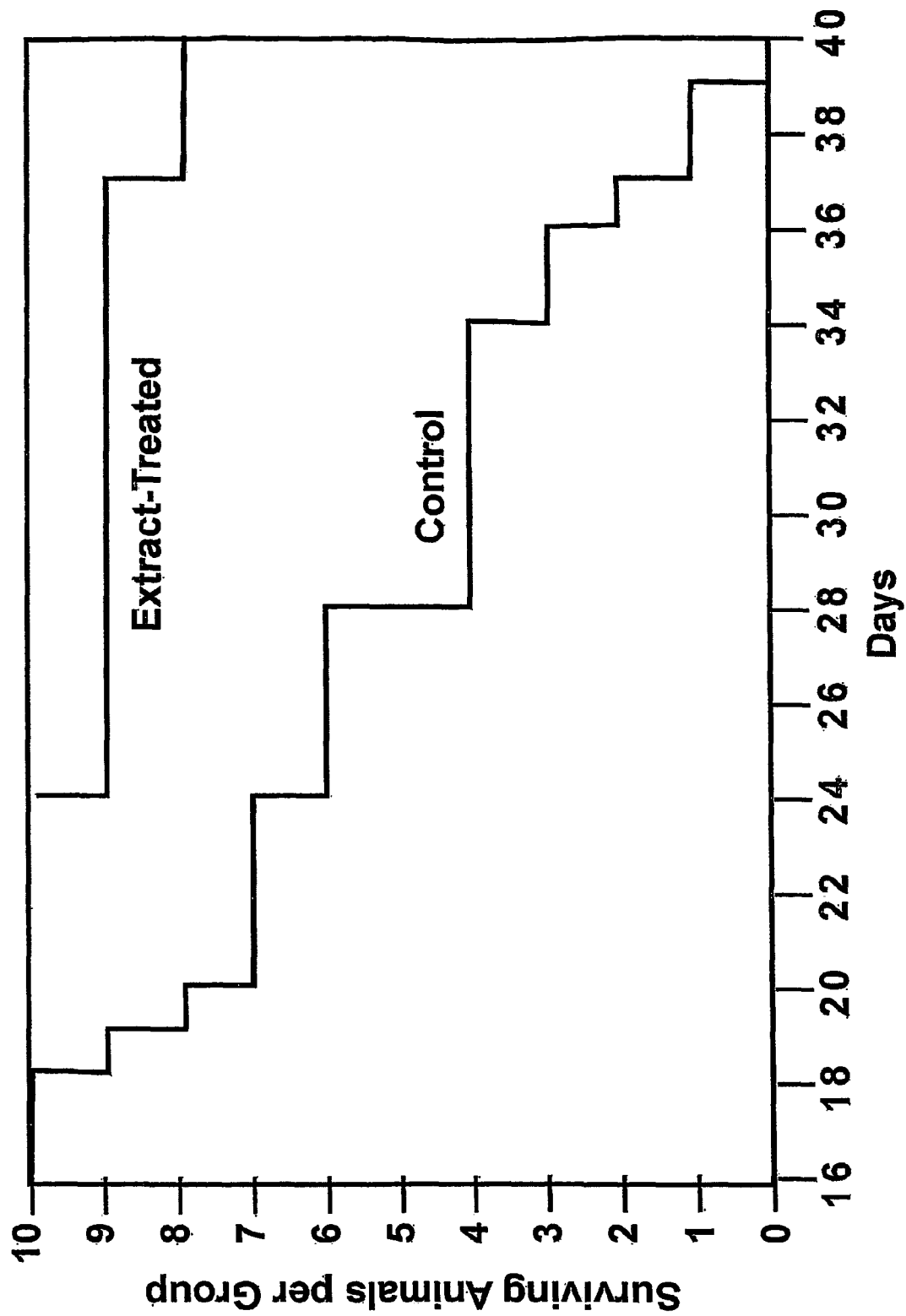

FIG. 48: Effect of FSLE on metastasis of 3-Lewis lung carcinoma in mice.

Figure 49:
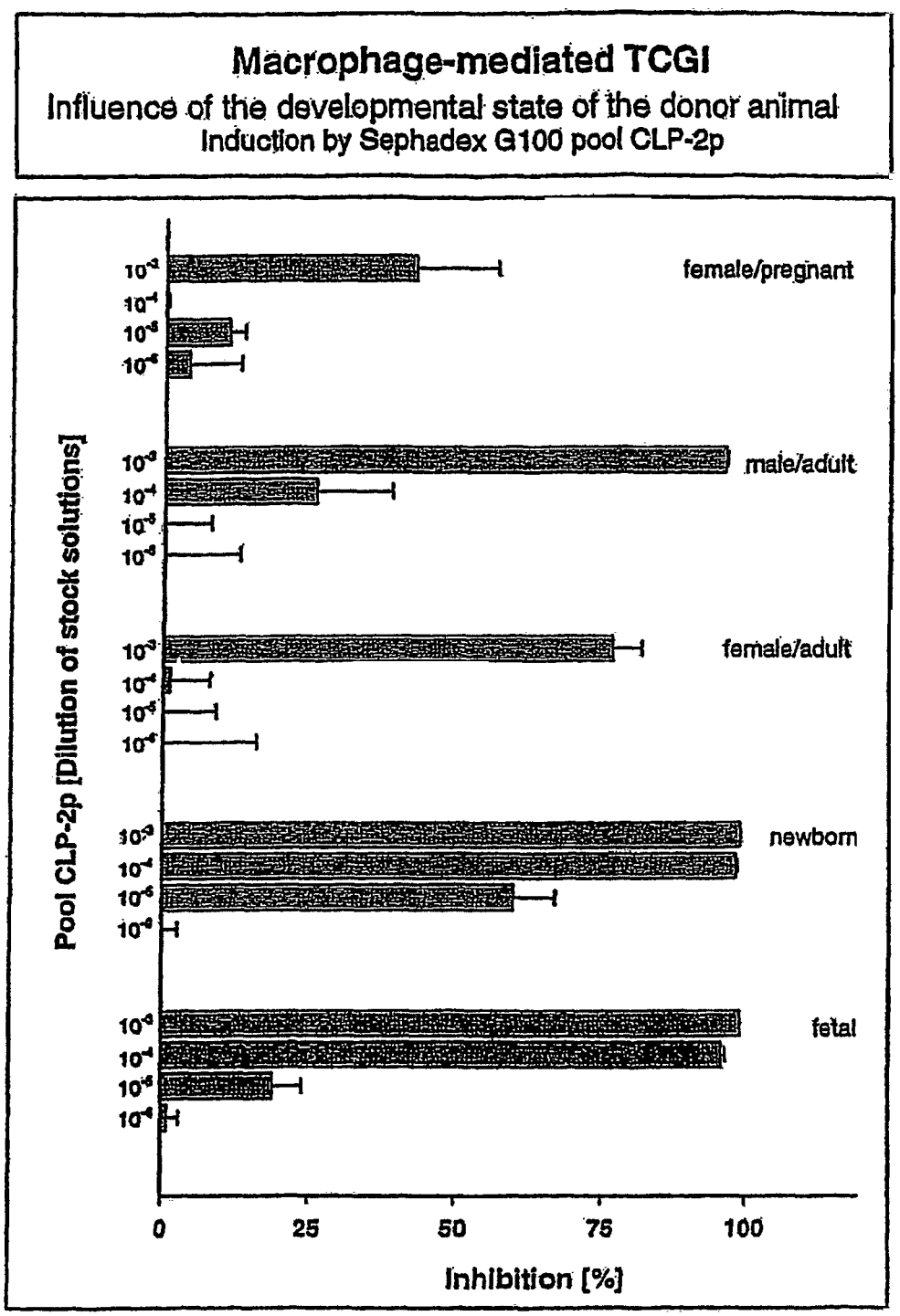

FIG. 49: Macrophage-mediated antitumoral activity of CLP2p derived from animals at different developmental stages.

CLP2p pools were prepared from liver extracts derived from animals at different developmental stages and tested for their TCGI inducing activity in murine BMDM as described in Example 12.

Figure 50:
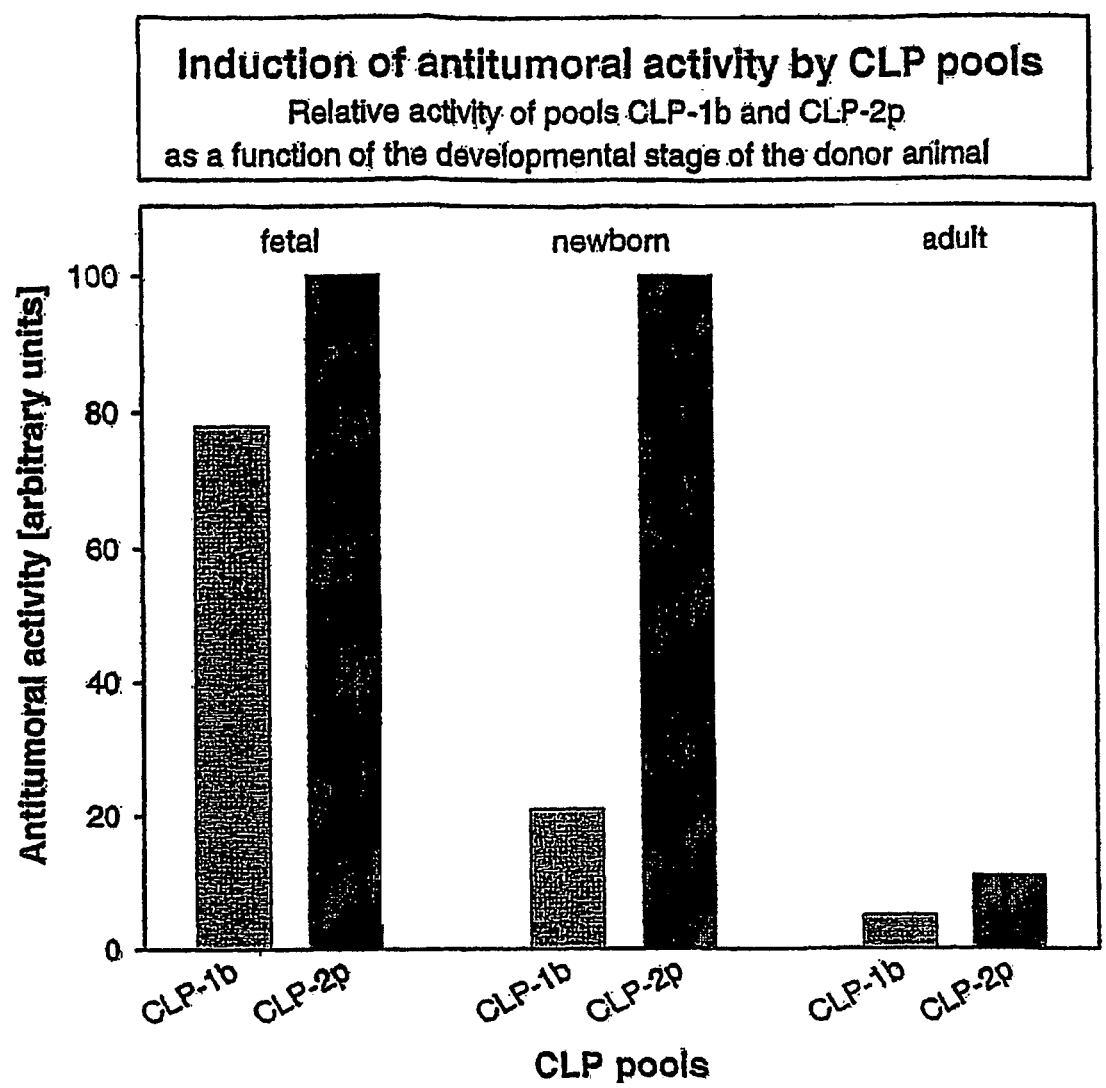

FIG. 50: Relative activity of CLP1b and CLP2p as a function of the developmental stage.

Liver extracts derived from animals at different developmental stages were separated on Sephadex G-100® to yield the five pools shown in FIG. 3. They were tested for their TCGI inducing activity in murine BMDM as described in Example 3.1.1.3. The activity of the most active pool of each separation was arbitrarily set to 100 and the activities of CLP1b and CLP2p set in relation to it.

Figure 51:
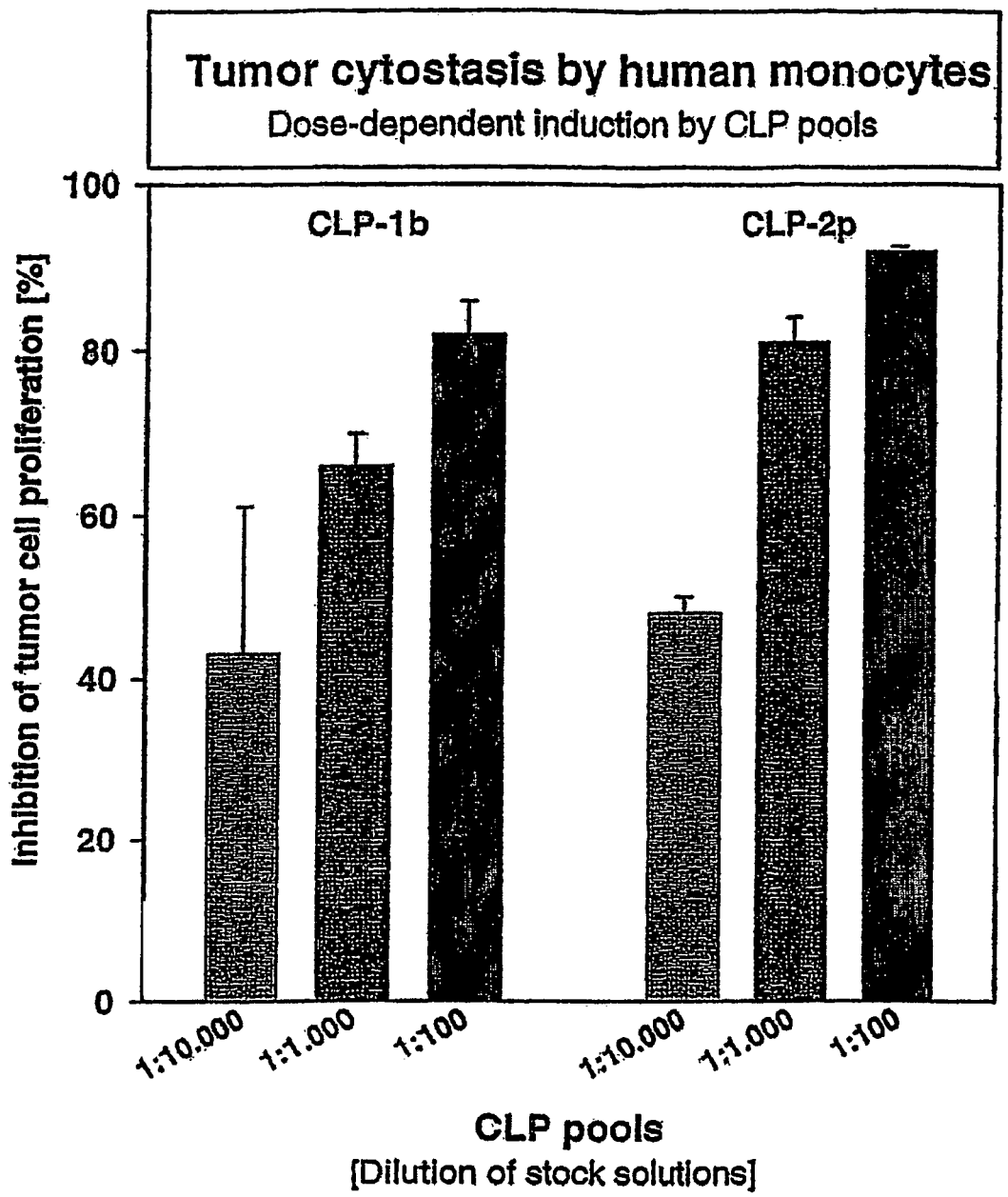

FIG. 51: Tumor cytostasis induced by human monocytes stimulated with CLP1b or CLP2p.

Human peripheral blood monocytes were stimulated with CLP1b or CLP2p and tested for their tumor cytostatic activity at a ratio of 10:1 on U 937 tumor cells. The concentrations of the stock solutions were 20 mg/ml and 10 mg/ml for CLP1b and CLP2p, respectively.

Figure 52:
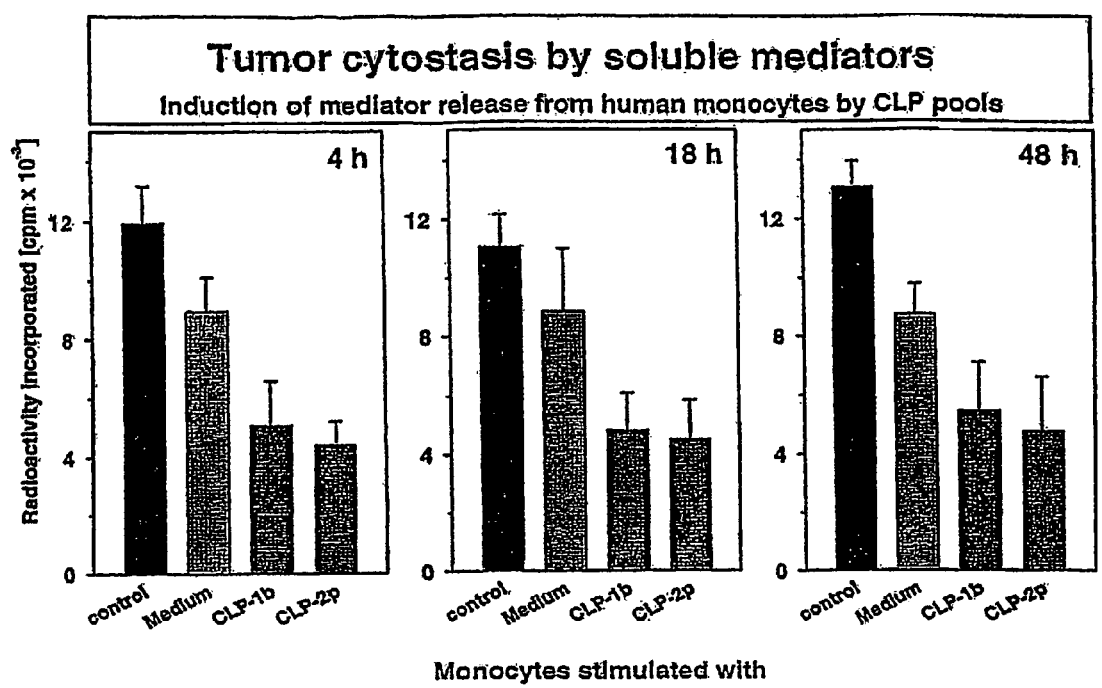

FIG. 52: Tumor cytostatic mediators released from human monocytes stimulated with CLP1b or CLP2p.

Human peripheral blood monocytes were stimulated with CLP1b [200 µg/ml] or CLP2p [100 µg/ml] or incubated in medium for the times indicated and supernatants were tested for their tumor cytostatic activity on U 937 tumor cells. Proliferation of untreated tumor cells (control) is shown as reference.

Figure 53:
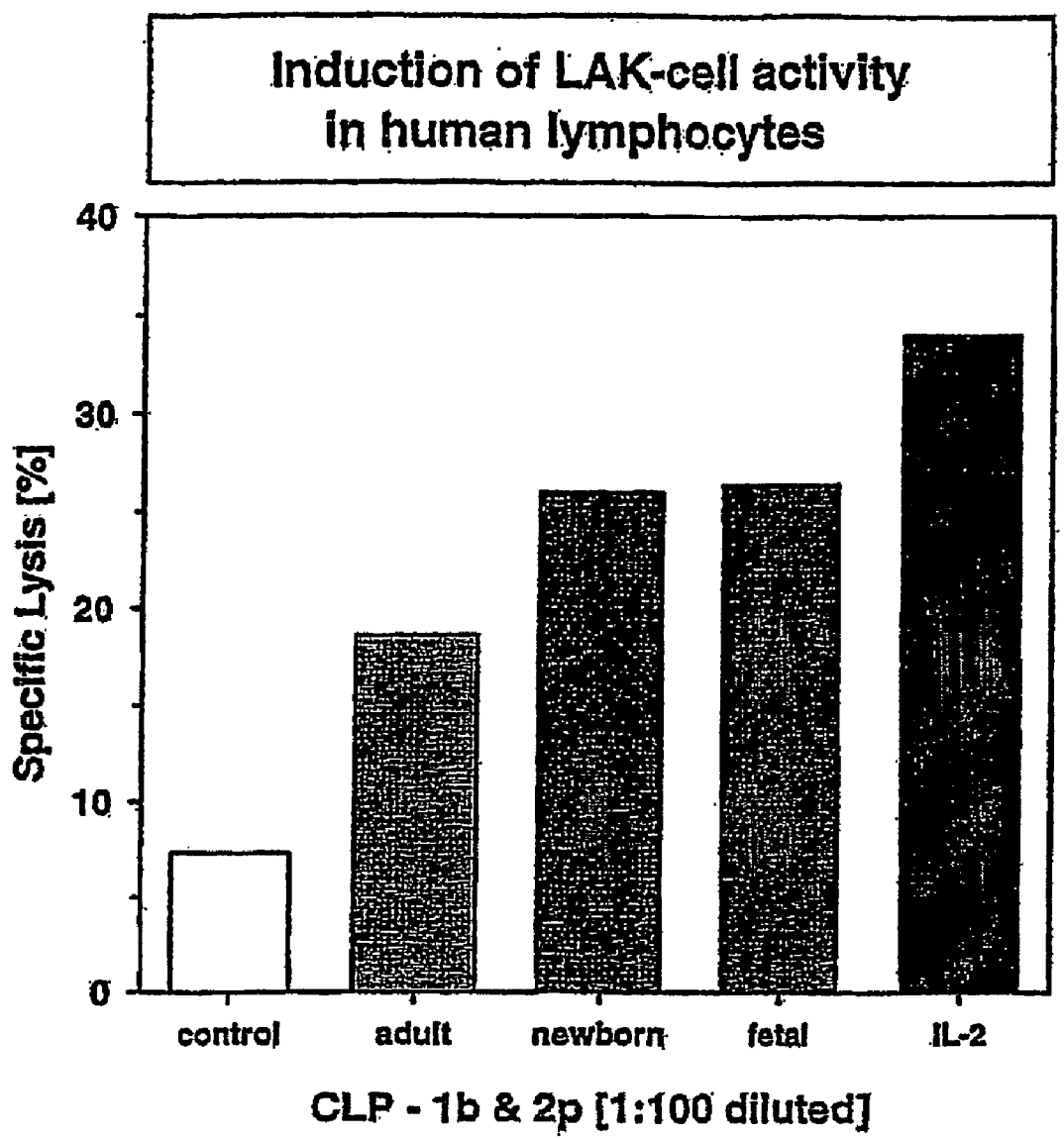

FIG. 53: Induction of LAK-cell activity in human lymphocytes by CLP pools derived from animals at different developmental stages.

Human lymphocytes isolated from peripheral blood were stimulated with a 1:1 mixture of CLP1b and CLP2p derived from fetal, newborn or adult animals [5080 µg/ml] or IL-2 [100 U/ml] for 3 days and tested for LAK-cell activity on Raji tumor cells.

Figure 54:
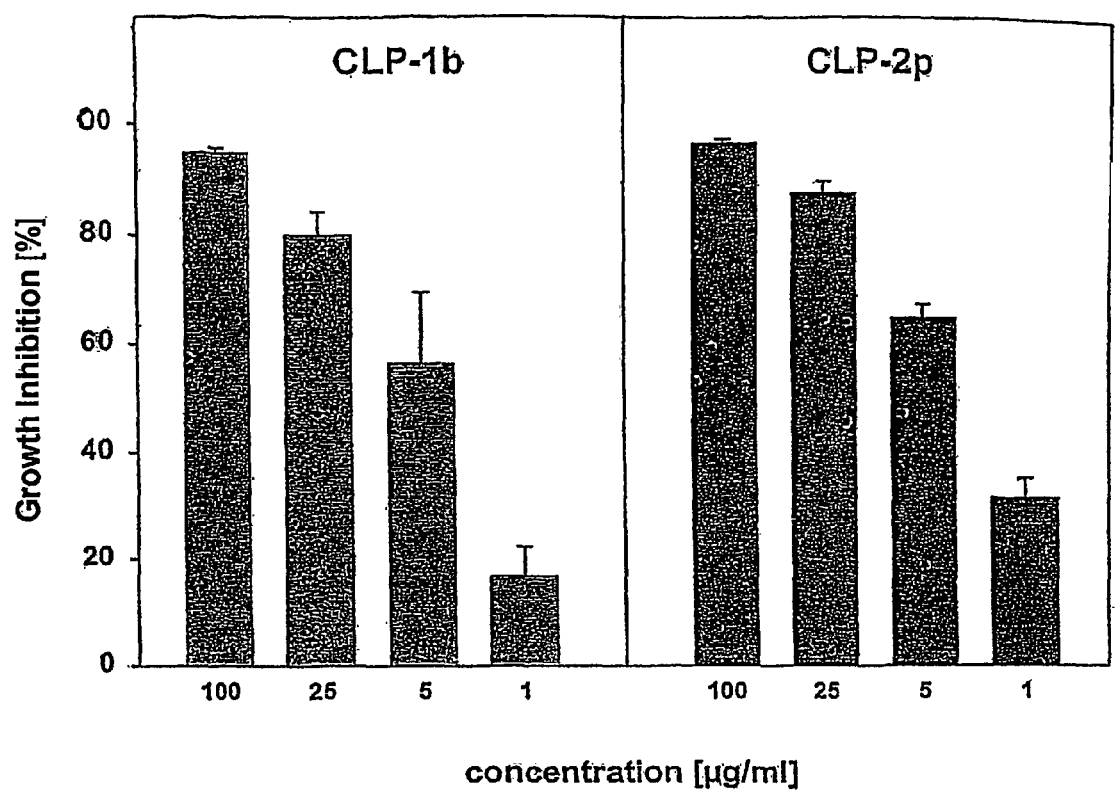

FIG. 54: Cytostatic activity of human monocytes activated by CLP1b/CLP2p against the tumor cell line LNCaP (E:T=Effector:Target Cell Count.=1:2)

Figure 55:
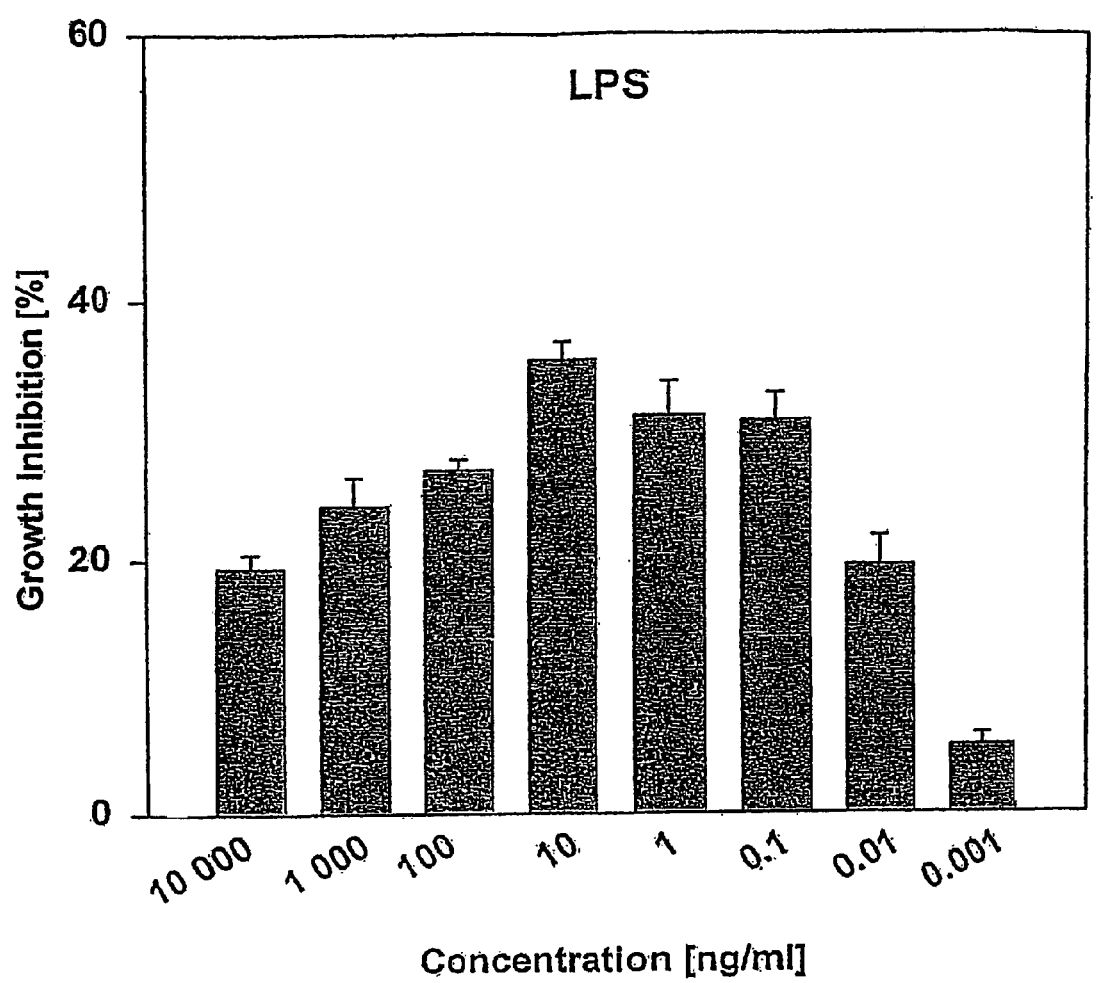

FIG. 55: Cytostatic activity of human monocytes activated by LPS against the tumor cell line LNCaP (E:T=Effector:Target Cell Count.=1:1)

Figure 56:
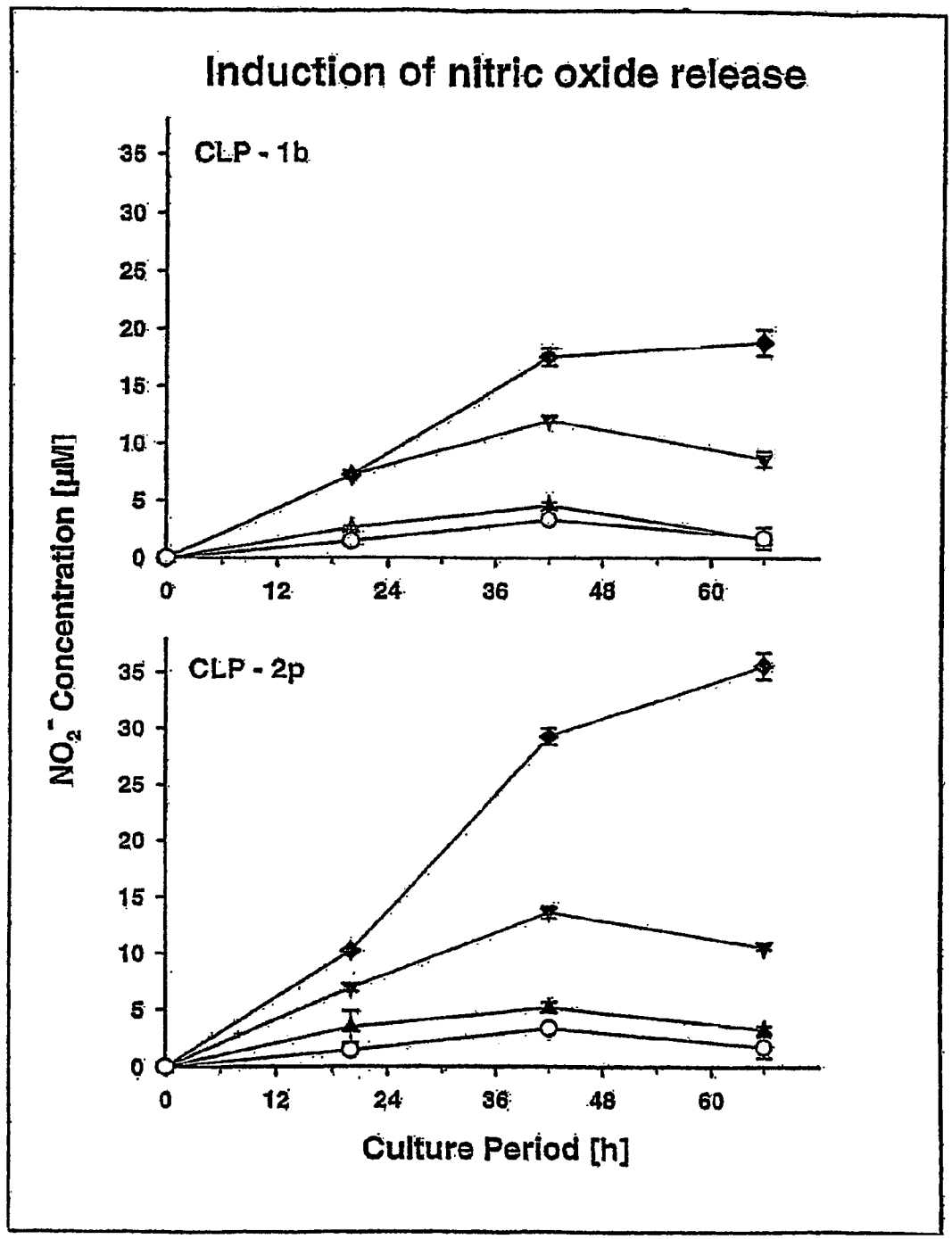

FIG. 56: Kinetics of the induction of nitric oxide release in murine BMDM by CLP1b and CLP2p.

Murine BMDM were stimulated with various dilutions of CLP1b or CLP2p stock solutions (40 mg/ml and 17 mg/ml for CLP1b and CLP2p, respectively). The release of nitric oxide was determined as nitrite concentration in the culture supernatants at the time points indicated. The dilutions used were: 1:100 (diamonds), 1:1000 (triangles, down) and 1:10000 (triangles, up). Macrophages cultured in medium (circles) were used as controls.

Figure 57:
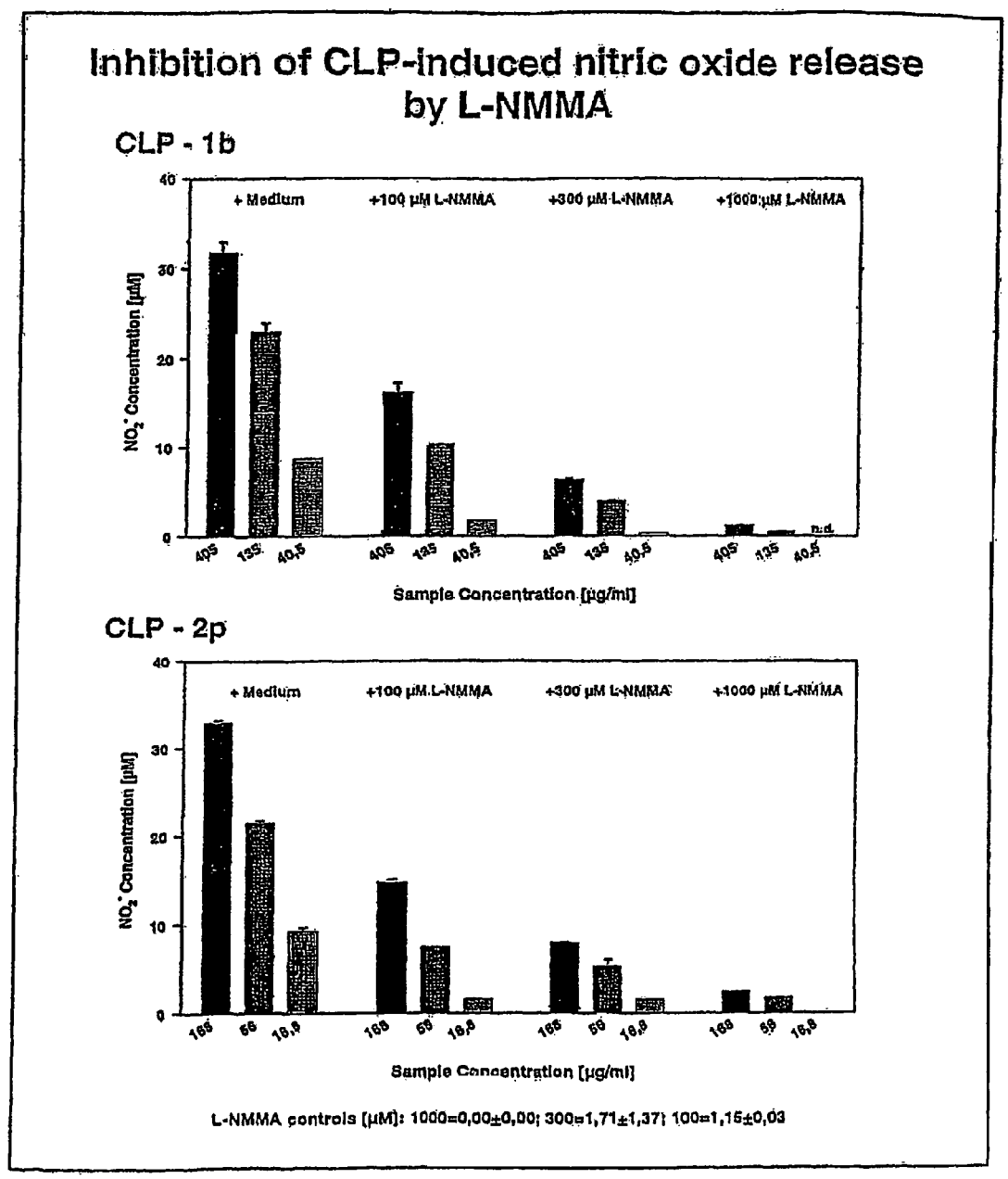

FIG. 57: Inhibition of the nitric oxide release induced by CLP1b or CLP2p by addition of the iNOS inhibitor L-NMMA.

Murine BMDM were stimulated with various concentrations of CLP1b or CLP2p in the absence or presence of the iNOS inhibitor L-NMMA at the concentrations indicated. The release of nitric oxide was determined after 48 h.

Figure 58:
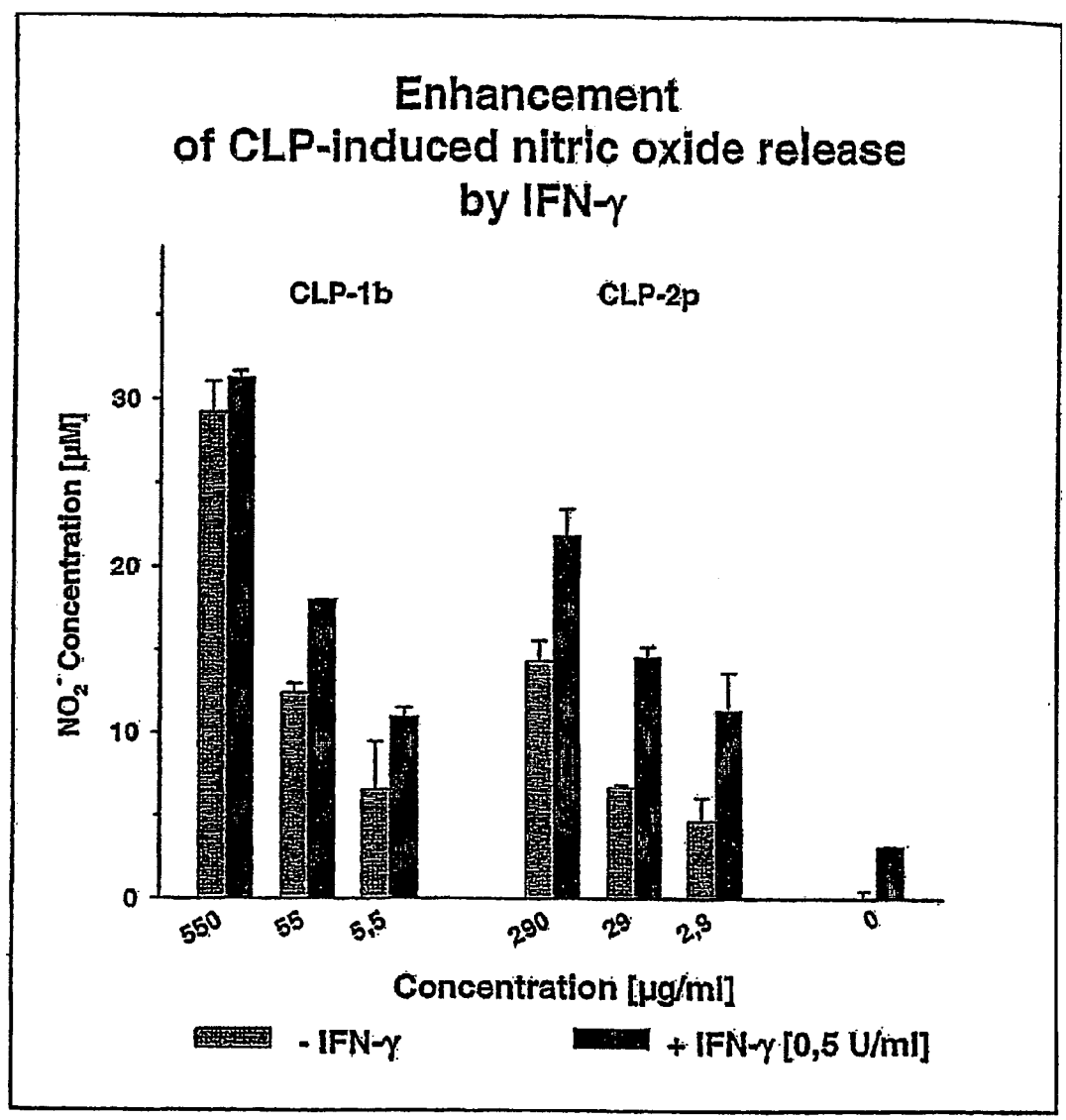

FIG. 58: Enhancement of the nitric oxide release induced by CLP1b or CLP2p in murine BMDM by IFN-γ

Murine BMDM were stimulated with various concentrations of CLP1b (550, 55, 5.5 µg/ml) or CLP2p (290, 29, 2.9 µg/ml) in the absence or presence of 0.5 U/ml recombinant mIFN-γ The release of nitric oxide was determined after 48 h.

Figure 59:
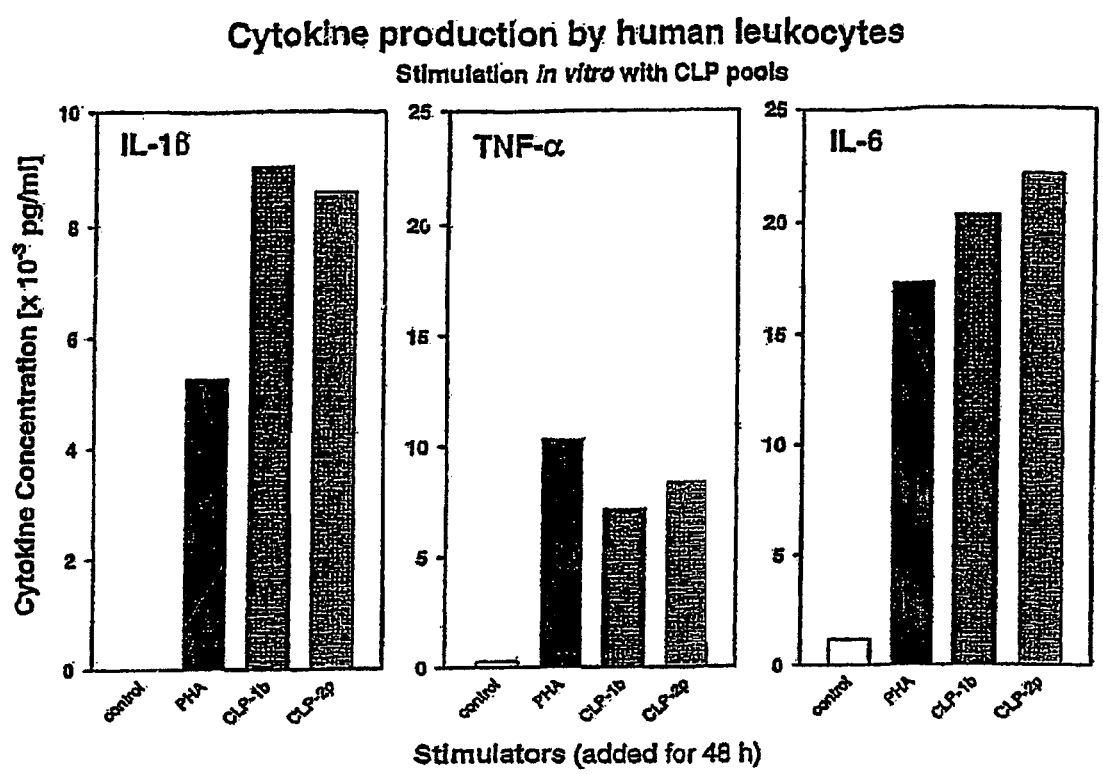

FIG. 59: Release of cytokines by human leukocytes stimulated with CLP1b or CLP2p.

Human whole blood cultures were set up and stimulated with CLP1b [200 µg/ml] or CLP2p [100 µg/ml] for 48 h. PHA [10 µg/ml] was used as positive control. Cytokines released into the supernatants were detected by ELISA.

FIG. 60: Release of cytokines by human peripheral blood monocytes stimulated with CLP1b or CLP2p.

Human monocytes isolated from peripheral blood were stimulated with CLP1b [140 µg/ml] or CLP2p [120 µg/ml]. Cytokines released into the culture supernatants were detected by ELISA at the time points indicated.

The Examples illustrate the invention.

1. EXAMPLE 1

Preparation of Fetal Sheep Liver Extract

FSLE

Pregnant sheep with a fetus of 2-4 weeks before birth were sacrificed in a steam-disinfected room. The fetus in the amnion sack was delivered by caesarian operation as a whole and immediately transferred to the laboratory under conditions of refrigeration. The following steps were performed at temperatures of about +4° C. The amnion sack was disinfected, freed from amnion fluid, and organs of the fetus, especially the liver, were prepared under sterile conditions. The liver was washed with sterile water, the arteries were cleaned with water using sterile syringes. Then it was cut into small pieces of about 1 cm in diameter, the pieces were being immediately transferred into liquid nitrogen and stocked in a freezer at −80° C.

The pieces were lyophilized and powdered in a RETSCH-apparatus (Shieritz & Hauenstein AG, Ariesheim, Switzerland), using a filter of 0.25 mm diameter. The powder was stocked in sterile flasks at −80° C. until used for extraction.

The yield of fetal liver powder (FLP, lyophilized liver homogenate) was 18% of the weight of the starting fresh liver. The liver weight of a single fetus, taken between 2 to 4 weeks before birth was in the order of 100-120 g.

As a quality control, ad hoc samples of FLP can be analyzed chemically (protein profile, see FIG. 12) and/or biologically (antitumoral activity, see FIG. 3).

Continuous health controls were performed, in particular to insure that the sheep-stock is free of known viruses. Ultracentrifugation of liver extract would lead to sedimentation of possibly present viruses. In addition, pasteurization step [Heimburger, H., 1989] inactivates all known viruses without decreasing relevant biological activities. It may be emphasized that prions are not present in FLP because sheep liver neither contains prion protein ($PrP^c$) nor mRNA coding for prions [Horiuchi, M., 1995].

1.1 Extraction

Fetal liver powder (1 kg) was mixed with 6.5 l of sterile NaCl (0.9%) and stirred for 10-15 min with a Magnetic stirrer (Colora) at 4° C. The mixture was centrifuged at 12,500 rpM for 50 min using a Beckman-Coulter centrifuge. The supernatant was then ultracentrifuged at 50,000 rpM (Beckmann-Coulter, Optima L70 Kin) for 1 hr. The supernatant was sterile-filtered using Gelman filters (Super DCF, pharmaceutical grade, sterile 0.8/0.2 nm EFA: 1000 ml (CFS 92-DS)). The yield of FSLE was about 2.5-2.7 l based on 1 kg of liver powder. The protein content of the extract was estimated in an Autoanalyser Integra 400 (Roche Diagnostics) and found to be in the order of 50 µl. Portions containing 300 mg of protein (=1 Unit), i.e. 6 ml extract, were filled into flasks of 25 ml content and lyophilized. One lyophilized Unit is, thus, composed of about 300 mg protein, 60 mg inorganic salt (mainly NaCl), and approximately 320 mg non-protein aqueous organic matter, so that one Unit makes up about 680 mg totally.

Altogether, from 1 kg of FLP about 400 Units (with 300 mg protein each) were being obtained. They contained approximately 250 g of extracted organic matter, or 25% of the total powder weight. The so prepared FSLE contained according to *Limulus*-lysate analysis LPS-equivalents in the order of 10 ng/g extract.

The flasks with lyophilized FSLE were kept in a freezer at −80° C. until redissolved for application.

For clinical use, a lyophilized Unit is taken up in sterile water, isotony of the solution (for injection) being assured using an osmometer (Knauer, Berlin). Under the above experimental conditions 7 ml of water have to be added to 1 lyophilized Unit. The lyophilized material is easily soluble in water yielding a clear solution of slightly yellow-brownish color.

1.2 Protocol of Routine Testing of FSLE by In Vitro Activation of Murine Spleen Cells and Bone Marrow-Derived Macrophages (BMDM) to Macrophage-Mediated Tumor Cytotoxicity On day −4 mice (Balb/c×C57Bl/6) were injected s.c. with a solution of 0.5 ml containing 1 mg of FSLE. On day 0 the animals were sacrificed, spleens were taken and cells are cultivated.

Cells, i.e. $10^6$ spleen cells, $10^5$ BMDM (non-activated) and $10^3$ tumor cells (Abelson 8.1 lymphoma) were incubated. Parallel cultures which serve as controls constituted i) Tumor cells alone, ii) Tumor cells+macrophages, iii) Tumor cells+macrophages+spleen cells from non-FSLE-pretreated animals.

The tumor cells in controls ii) and iii) must show the same or better growth as control i). In this way the non-activated status of the macrophages and spleen cells from non-pretreated mice was controlled.

At various times (48, 72 and 96 h) after the start of cultures, the growth of tumor cells in the various setups was estimated by using the alkaline phosphatase test [Modolell, M., 1994]. The biological potency of FSLE was quantitatively estimated according to the formula:

(Growth of tumor cells in the presence of activated spleen cells+macrophages)/(Growth of tumor cells)×100

In FIG. 3 the results obtained with 12 samples of FSLE are shown. The observed variations reflect to differences of individual mice from which the immune cells were taken.

2. EXAMPLE 2

Fractionation of FSLE

Preparation of Pools CLP1b and CLP2p

Of lyophilized fetal sheep liver extract 1.5 g were dissolved in 8 ml water and dialyzed overnight (dialysis bags with a cut-off of 3.500 Dalton) against 10 volumes of 0.03 M phosphate buffer (pH 7.4) with two changes of dialysis buffer. The dialyzed extract, adjusted to 10 ml buffer was applied to a Sephadex© G-100 column (Pharmacia; volume 600 ml, diameter 24 mm, length 130 cm), equilibrated in the same 0.03 M phosphate buffer. Elution fractions (8 ml) were collected and read for optical density at 280 nm. (See the elution profile in FIG. 4.) Fractions were pooled and the 5 pools termed CLP1, CLP1b, CLP2p, CLP2 and CLP2b. As shown in FIG. 4, CLP1b is contained between the end of the steep decrease of optical density of pool I and the next steep decrease of optical density, corresponding to fractions 53 to 71 (elution volume 424 to 568 ml). CLP2p is contained between the end of pool I-bis and the increase of optical density of pool II corresponding to fractions 72-82 (elution volume 576 to 656 ml).

The pooled fractions were lyophilized, dissolved in one tenth of the original volume in water, dialyzed against phosphate buffer saline (PBS) diluted 1/3 (original PBS=0.14 M NaCl in 0.01 M phosphate, pH 7.4) followed by a second lyophilization.

In biological tests it was found that the bulk of biomedical activities concentrates in pools CLP1b and CLP2p. From 1.5 g of FSLE the yield of CLP1b is ≈40±4 mg and for CLP2p≈10±3 mg. Both pools were, thus, obtained in amounts of ca. 50 mg totally, i.e. approximately 3% of FSLE. The LPS content of pools CLP1b and CLP2p is in the order of 100 ng/mg (i.e. 100 μg/g).

It is important to note that the dialysis step does not lead to any loss of bioactivity of FSLE or CLP-pools to be generated (see below) as shown in FIG. 5 for CLP2p.

3. EXAMPLE 3

Biochemical and Physicochemical Analysis of FSLE and Pools CLP1b and CLP2p 3.1 Methods
3.1.1 Biological Assay Systems
3.1.1.1 Bone Marrow-Derived Macrophages Murine bone marrow-derived macrophages were differentiated in vitro from bone marrow precursor cells as described elsewhere [Hoffmann, P., 1989]. Briefly, bone marrow cells were flushed from femur and tibia of 6- to 8-week-old BALB/c mice (Charles River; Sulzfeld, or MPI for Immunobiology, Freiburg, FRG), washed twice in RPMI 1640 (Gibco BRL, Life Technologies, Eggenstein, FRG) and grown for 11 days in teflon film bags (SLG, Gauting, FRG) at 37° C. and 5% $CO_2$. The culture medium consisted of RPMI 1640, supplemented with 15% L-cell-conditioned medium as source of M-CSF (see below), 10% heat inactivated FCS, 5% heat inactivated horse serum, 1 mM sodium pyruvate, 50 U/ml penicillin, 50 μg/ml streptomycin (all from Seromed Biochrom KG, Berlin, FRG), and $5 \times 10^{-5}$ M 2-mercaptoethanol. Cultures were set up with $6 \times 10^6$ cells/50 ml. After harvesting, the macrophages were washed once, counted and resuspended at $2 \times 10^6$ cells/ml in DMEM with 4.5 g/l glucose (Seromed Biochrom KG), supplemented with 10% FCS, 2 mM L-glutamine, 1% non-essential amino acids (NEAA), 100 U/ml penicillin, and 100 μg/ml streptomycin (cDMEM). To obtain L-cell-conditioned medium, $1 \times 10^5$ L 929 cells/ml were cultured in 100 ml-batches in cell culture flasks (Falcon, Becton Dickinson, Heidelberg) in RPMI 1640 medium with 10% FCS, 4 mM L-glutamine, 1% NEAA, 100 U/ml penicillin, and 100 g/ml streptomycin at 37° C. and 5% $CO_2$. After 7 days, the culture supernatants were harvested, cleared from cell debris by centrifugation (1500×g, 15 min.) and stored at −20° C.

3.1.1.2 Tumor Cell Line

The murine B cell lymphoma cell line Abelson 8-1 was kept in cDMEM in 6-well-plates (Falcon, Becton Dickinson) at 37° C., 10% $CO_2$. Cells were grown until confluency was reached in the culture well, and passaged twice a week.

3.1.1.3 Determination of Cell-Mediated Antitumoral Activity (TCGI Assay)

Macrophage mediated tumor cell growth inhibition [Hoffmann, P., 1989] was determined in the alkaline phosphatase assay [Modolell, M., 1994]. Cultures were set up in flat bottom microtiter plates in a total volume of 200 μl. $5 \times 10^3$ tumor cells together with $1 \times 10^5$ BMDM and CLP pools at various concentrations were cultured in cDMEM at 10% $CO_2$. After 3 days the plates were centrifuged at 660×g for 2 min and the supernatants were decanted. To each well 100 μl of buffer, pH 10.2 containing diethanolamine (200 mM), $MgCl_2$ (2 mM), Triton X-100 (10%) and p-nitrophenylphosphate (10 mM)

were added and the plates were incubated for 60 min at RT in the dark on a horizontal shaker. The enzyme reaction was stopped by adding 100 µl/well of 0.5 M NaOH. O.D. was measured at 405/490 nm in an automated ELISA reader (MRX Dynatech, Denkendorf, FRG). Wells with O.D.>3.000 were diluted accordingly with 0.5 M NaOH into new plates and measured again. O.D. values of cultures containing tumor cells and unstimulated effector cells were set to 100%.

3.1.1.4 Induction of Nitric Oxide (NO) Production in Murine BMDM

Mature BMDM were harvested after incubation on ice for 10 min followed by gentle rolling of the teflon bags. The cells were washed once and resuspended in RPMI 1640 medium supplemented with 10% FCS, 1% NEAA, 100 U/ml penicillin, and 100 µg/ml streptomycin. $1 \times 10^5$ cells/well were seeded into the wells of 96-well flat bottom microtiter plates (Falcon, Becton Dickinson) and stimulated with various concentrations of CLP pools +/−IFN-γ (4-20 U/ml) in a total volume of 150 µl. Culture supernatants were harvested after 24 or 48 h and checked for nitrite concentration as described below. All assays were performed in triplicate.

3.1.1.5 Determination of Nitric Oxide (NO) Release from Murine Macrophages

Production of NO. by macrophages [Stuehr, D. J., 1989] was determined by measuring nitrite, a stable metabolite of NO, in culture supernatants using the Griess reagent [Green, L. C., 1982]: 100 µl culture supernatant were mixed with 100 µl Griess reagent (1% sulfanilamide and 0.1% N-(1-naphthyl) ethylenediamine in 2.5% phosphoric acid) and the absorbancy at 570 nm was measured using a Dynatec MRX ELISA plate reader (Denkendorf, FRG). Nitrite concentrations were calculated from a standard curve prepared with sodium nitrite. The absorbance of the RPMI 1640 medium alone was subtracted from all values.

3.1.1.6 Separation of FSLE and CLP Pools by SDS-PAGE

SDS-PAGE analyses of FSLE and CLP pools were performed according to standard procedures using 12-20% gels [Laemmli, U.K., 1970].

3.2 Results 3.2.1 Heat Stability of the Principal Antitumoral Macrophage Activator in CLP1b and CLP2p For testing the influence of heat pretreatment to the profound stimulation of macrophage-mediated antitumoral activities by CLP1b and CLP2p, 0.25 mg of lyophilized material were solubilized in water at pH 5.8 or in 20 mM sodium acetate buffer, pH 4.7 and incubated for 60 min at 4° C. and 100° C., respectively. Antitumoral activation of macrophages by heat-treated and control samples was determined in the tumor cell growth inhibition (TCGI) assay (see Example 3.1.1.3) according to [Modolell, M., 1994] using cocultures of Abelson 8-1 tumor cells with in vitro differentiated bone marrow-derived macrophages from BALB/c mice [Hoffmann, P., 1989].

Heating of CLP1b and CLP2p at 100° C. for up to 1 h at pH 5.8 and also at pH 4.7—the latter condition is known to favour selective cleavage of acid labile oligosaccharide or polysaccharide side chains from glycoconjugates—did not lead to significant changes in antitumoral activation of macrophages by the CLP preparations as compared to the control samples. The macrophage directed immunostimulatory activity in CLP1b and CLP2p proved to be heat stable (FIG. 6).

3.2.2 Protease Resistance of the Principal Antitumoral Macrophage Activator in CLP1b and CLP2p For further biochemical characterization of the antitumoral macrophage activator, CLP1b and CLP2p pools were subjected to proteolytic digestion. Pyrogen-free preparations of proteinase K, pronase, papain, subtilisin, trypsin and endoprotease Glu-C (V8-protease) were purchased from Boehringer Mannheim (Germany). Then, 0.24 mg of CLP1b and CLP2p were treated with each of the selected proteases at an enzyme to total protein ratio of 1:10 (w/w) in 0.24 ml of pyrogen-free water at 37° C. for 21 h. After withdrawal of probes for analysis by SDS-PAGE on 15% (w/v) acrylamide gels and subsequent silver staining the remaining samples were incubated at 100° C. for 30 min to inactivate the individual proteases. The protease treated samples and nontreated controls of CLP1b and CLP2p were finally tested for antitumoral macrophage activation in the TCGI assay (compare Example 3.1.1.3).

Figure 7A:
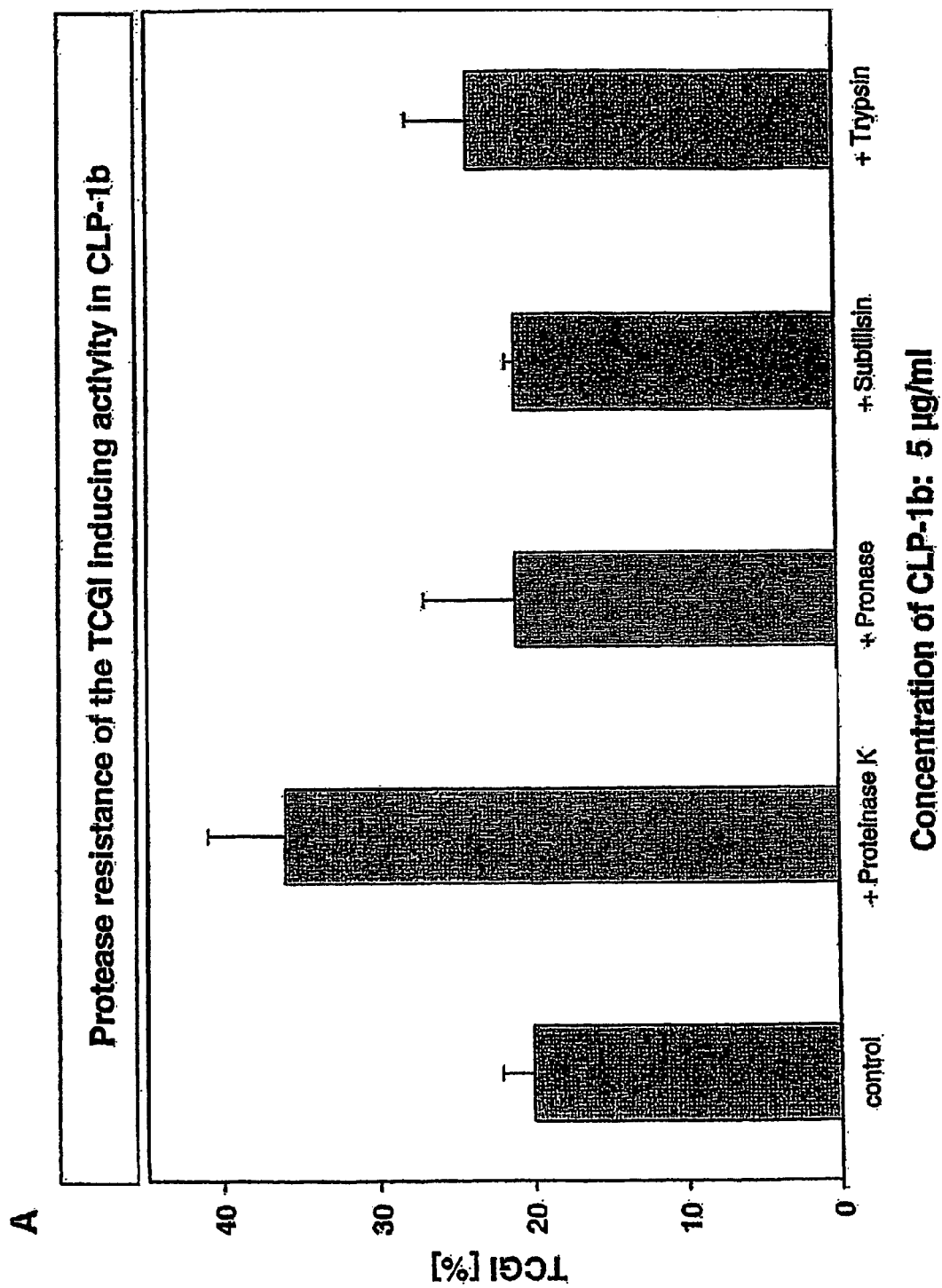
Figure 7B:
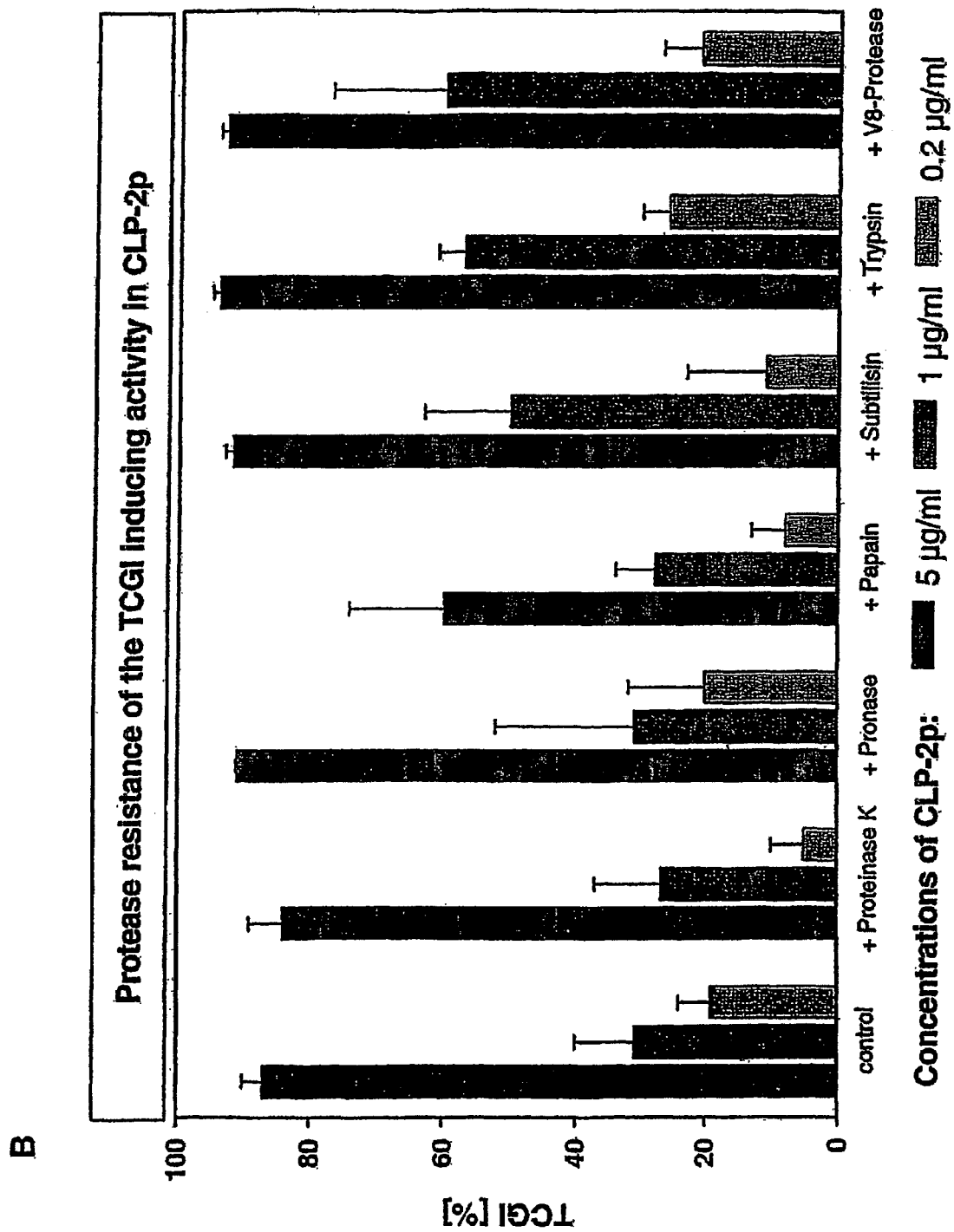

The total or partial degradation of the proteins in CLP1b and CLP2p and the subsequent heat inactivation step did not result in significant alterations in the macrophage mediated antitumoral activities of either CLP preparation as determined in the TCGI assay (FIGS. 7A and 7B). The antitumoral macrophage activator in CLP1b and CLP2p turned out to be strongly protease resistant.

3.2.3 Sensitivity of the Antitumoral Macrophage Activator in CLP2p to Mild Periodate Treatment Consequences of mild oxidation to the antitumoral macrophage activator in CLP2p were analyzed by sodium periodate (NaIO$_4$) treatment at 4° C. Briefly, 2.5 mg portions of lyophilized material were dissolved in 0.9 ml of 100 mM sodium acetate buffer, pH 4.7 in darkened glass vials. Periodate oxidation was performed after addition of 0.1 ml of 2.5 mM sodium periodate at 4° C. for 2 h under constant stirring. The reaction was stopped by addition of 0.01 ml ethylene glycol. Samples were dialysed against pyrogen-free water in Spektra/Por® dialysis tubings (i.d. 11.5 mm; molecular weight cut off: 3500 Da; Serva, Germany) and lyophilized. Samples of 0.25 mg of freeze-dried material were subjected to methanolysis in 0.5 M HCl/methanol at 45° C. for 45 min and peracetylation in acetanhydride/pyridin (85° C., 30 min) and analyzed for monosaccharide compositions by combined gas-liquid chromatography/mass spectrometry. The remaining parts of the sample and corresponding controls were finally tested for antitumoral macrophage activation in the TCGI assay.

Treatment of CLP2p with sodium periodate at mild reaction conditions resulted in a selective reduction of the sialic acid content of the preparation (suggesting the presence of glycoproteins) as revealed by GC/MS analysis and a marked decrease in macrophage-mediated growth inhibition and destruction of tumor cells as detected in the TCGI assay (FIG. 8). Thus, the antitumoral macrophage activator in CLP2p was found to be sensitive to treatment with sodium periodate under mild conditions suggesting the carbohydrate part of the molecule(s) to be involved in TCGI activity. As oxidative inactivation of LPS by sodium periodate has been described by Neter and Godin [Neter, E., 1956; Godin, D. V., 1983]. The data are consistent with the conclusion of LPS being involved in macrophage activation by CLP2p.

3.3 Identification of Components in CLP1b and CLP2p 3.3.1 Lipopolysaccharide (LPS, Endotoxin)

3.3.1.1 *Limulus* Amoebocyte Lysate Assay, LAL Test

For analysis of potential presence of bacterial lipopolysaccharides (LPS) in CLP1b and CLP2p two commercially available chromogenic *Limulus amebocyte* lysate (LAL) assays—the QCL-1000® test (BioWhittaker; Walkersville, Md., U.S.A) and the COATEST®—Endotoxin test (Charles River Endosafe, Charleston, U.S.A.)—were used. Briefly the lyophilized CLP-preparations were dissolved and appropriately diluted in LAL reagent water (<0.005 EU/ml) obtained from BioWhittaker (Walkersville, Md., U.S.A.). For inactivation of potentially interfering proteins the samples were preincubated at 75° C. for 5 min followed by vigorous shaking and sonification for 30 min at 37 C. Subsequently the samples were applied to the LAL tests according to the protocols of the manufacturers using LPS prepared from *E. coli* O111:B4 as calibration standard. In addition to a total of 16 lots of CLP1b and CLP2p 3 different lots of fetal sheep liver extract (were analyzed by the LAL test procedure described above.

By means of both chromogenic LAL assays [Levin, J., 1982] low but significant amounts of endotoxin were detected in the CLP1b/2p preparations. The apparent LPS contents for the individual lots of CLP1b and CLP2p were found to vary with an average of 100 ng (1000 EU) per mg (100 μg/g) as determined in 12 lots of CLP preparations. The LAL results for 3 lots of the fetal sheep liver extract (FSLE) revealed apparent LPS contents of approximately 10 ng of LPS equivalents per g of lyophilized material. Thus, the amounts of apparent LPS in FSLE were found to be substantially lower as compared to CLP1b and CLP2p indicating an average enrichment of about 10.000-fold of the LAL reactive material.

From these results and from the observations of heat and protease resistance it was concluded that the macrophage activator as enriched in CLP1b and CLP2p consists primarily of endogenous LPS having interacted with fetal sheep liver components, (compare Example 4).

3.3.1.2 Affi-Prep® Polymyxin Based Adsorption of LPS

In an attempt to deplete LPS detectable by the LAL tests from CLP1b and CLP2p, treatment of samples with Affi-Prep®—a LPS selective affinity resin purchased from BIO-RAD (Hercules, Calif., U.S.A.)—was performed. The CLP-preparations were incubated at final concentrations of 1 mg/ml in 0.7 ml pyrogen-free water at 4° C. for 14 h under gentle shaking in the presence or absence of 0.05 mg of the affinity sorbent. Subsequently, the affinity resin was sedimented by centrifugation at 5000×g for 5 min, and the supernatants were tested in the TCGI assay.

Figure 9:
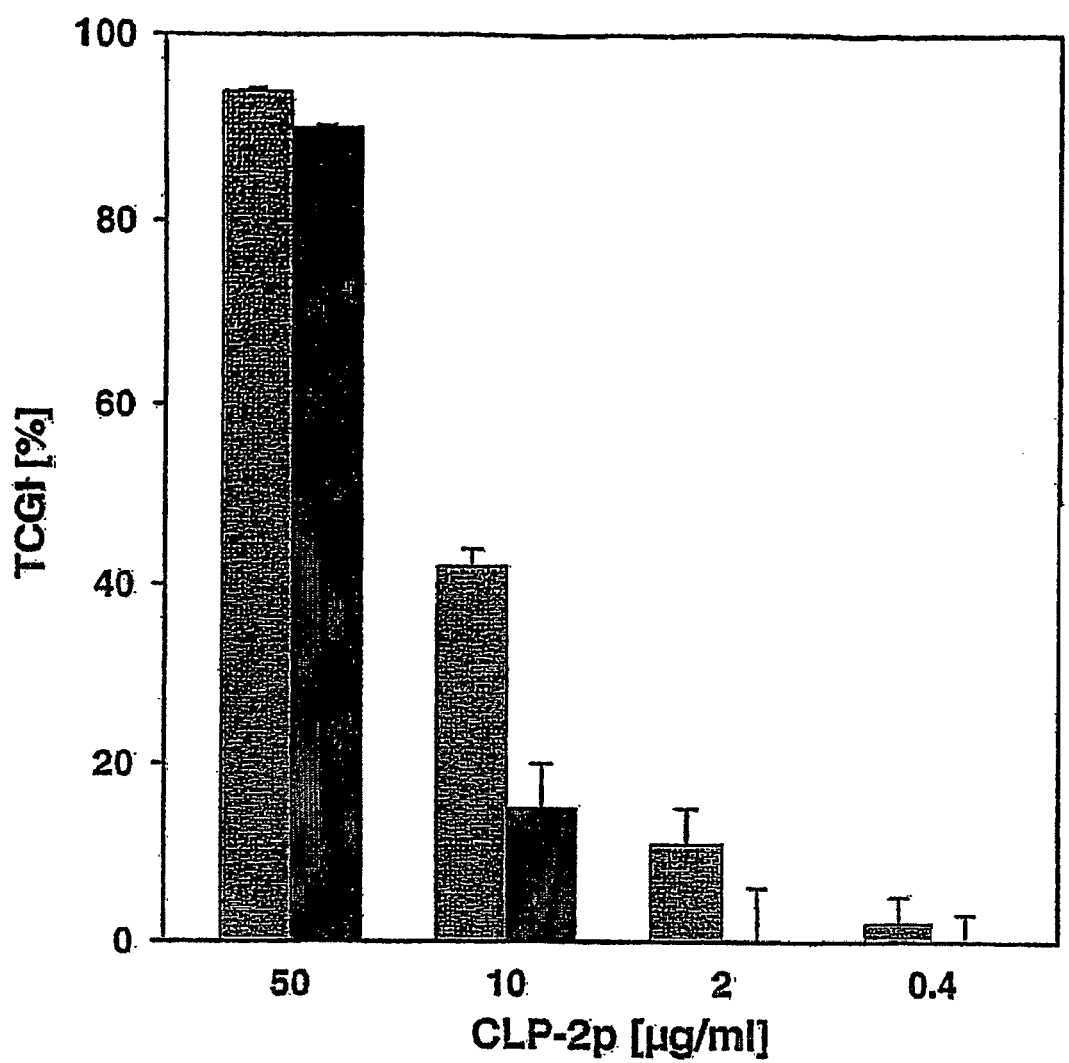

As shown in FIG. 9, Polymyxin B (PxB) treatment of CLP2p significantly reduced its bioactivity (TCGI) [Rifkind, D., 1967]. As LPS is known to be neutralized by PxB this result supports the notion that LPS is a bioactive principle of CLP2p.

3.3.1.3 Induction of nitric oxide Release in BMDM from LPS Non-Responder Mice

The NO-inducing activity of CLP1b and CLP2p was determined in bone marrow-derived macrophages from LPS responder (C57B1/10 ScSn) and LPS non-responder (C57B1/10 ScCr) mice [Freudenberg, M. A., 1991]. As FIG. 10 shows, the NO release in response to the CLP pools is markedly reduced in BMDM from LPS non-responder animals as compared to those from LPS responder mice. However, there is still a low but significant dose-dependent induction of NO release also in BMDM from LPS non-responder mice, which, in contrast, show no or only marginal NO secretion after simulation with isolated LPS from *Salmonella abortus equi* or *Escherichia coli*.

This result shows that the principle inductor of NO in CLP pools is LPS, but that (an) additional fetal liver component(s), possibly of proteinaceous nature, contribute(s) to bioactivity of CLP pools.

3.3.1.4 Costimulation of Macrophages with LPS/CLP2p and Recombinant Cytokines

LPS, as well as many defined cytokines, including IL-1, IL-6, IL-10, IL-12, IL-13 and IFNγ, stimulate macrophages to produce other cytokines in vitro and in vivo. In order to compare the material in pools of CLP with these stimulating agents, the effects of culturing macrophages or dendritic cells with CLP2p or recombinant cytokines alone, or with mixtures of these reagents were compared. In addition, cells were treated with CLP2p, or with cytokines, in the presence of monoclonal antibodies to cytokines. Cytokine production was measured by ELISA (all reagents purchased by Pharmingen, San Diego, USA). It is important to note that FSLE was found to be free of IL-2, IL-6, and IL-10.

IL-12 is a primary physiological stimulus for cytokine production by macrophages during inflammation [Wang, J., 1999], and LPS may mediate its stimulatory effects by inducing IL-12 production. Similarly, IL-13 may be a physiologic counter-regulator of stimulation by IL-12 [Machado, F., 1998]. In order to compare the effects of CLP1b and CLP2p stimulation with these recombinant cytokines, spleen adherent cells were cultured with LPS (1 μg/ml), CLP2p, or with rIL-12, or rIL-13 alone, or in combination, prior to assay for cytokine production. In some cultures a monoclonal antibody to IL-12 was included. (Recombinant cytokines were obtained according to conventional protocols.) Data pooled from 3 such studies are shown in Table 1.

TABLE 1

Co-stimulation of macrophages with CLP2p and recombinant cytokines

| Treatment[a] | Cytokine levels in culture supernatants[b] | | |
|---|---|---|---|
| | TNFα ng/ml | IL-1 | IL-6 pg/ml |
| None | <10 | 2.0 | 24 |
| LPS (1 μg/ml) | 135 | 190 | 362 |
| CLP2p (0.3 μg/ml) | 85 | 135 | 167 |
| rIL-12 (0.1 μg/ml) | 149 | 235 | 359 |
| rIL-13 (0.1 μg/ml) | 40 | 15 | 1040 |
| CLP2p + rIL-12 | 92 | 370 | 152 |
| CLP2p + rIL-13 | 90 | 705 | 1140 |
| CLP2p + anti-IL-12 (10 μg/ml) | 20 | 180 | 1250 |
| LPS + rIL-12 | 166 | 340 | 790 |
| LPS + rIL-13 | 69 | 110 | 1450 |
| LPS + anti-IL-12 | 68 | 80 | 75 |

[a]Fresh adherent spleen cells were obtained from a pool of 4 to 8-week old DBA/2 mice. 500 μl cultures containing 0.5 × 10$^6$ cells/ml were incubated in triplicate under the conditions shown for 18 h, and supernatants pooled from equivalent groups for cytokine assays.
[b]Arithmetic mean (±SD) of 3 independent assays, each performed in triplicate.

LPS and CLP2p stimulation seems to mimic stimulation by rIL-12. There is some synergistic interaction with rIL-12; stimulation of cytokine production by LPS is significantly inhibited by anti-IL-12; and finally rIL-13 significantly antagonizes cytokine production by LPS (with subsequent induction of increased levels of IL-6). Obviously, stimulation by CLP2p replicates many of the effects of LPS (and/or rIL-12) stimulation.

3.3.1.5 Inhibition of LPS or CLP2p-Induced Macrophage Activation by Anti-CD14-Antibodies Given the similarity in stimulation induced in spleen adherent cells by LPS and CLP2p it was tested whether CLP2p might actually stimulate cells following binding (and triggering) to CD14, a macrophage-surface molecule important in LPS-mediated stimulation. Using a commercial anti-CD14 monoclonal antibody (UCHM-1, Sigma), stimulation of TNFα production by spleen adherent cells in the presence/absence of different concentrations of anti-CD14 was compared. Data pooled from 3 such studies are shown in Table 2. The data show that CLP2p is significantly inhibited by anti CD14 antibodies and that there was no discernible difference in inhibition of LPS and CLP2p activity.

TABLE 2

Inhibition of Cell Stimulation with LPS or CLP2p by anti-CD14 antibodies

| Stimulus[a] | Anti-CD14 added[b] | TNF-α[c] ng/ml | Inhibition % |
|---|---|---|---|
| None | None | <10 | |
| None | 10 μg/ml | <10 | |
| LPS (1 μg/ml) | None | 138 ± 24 | — |
| LPS (1 μg/ml) | 10 μg/ml | 26 ± 8 | 81 |
| LPS (1 μg/ml) | 2.5 μg/ml | 58 ± 10 | 58 |
| CLP2p (0.3 μg/ml) | None | 98 ± 21 | — |
| CLP2p (0.3 μg/ml) | 10 μg/ml | 20 ± 5 | 80 |
| CLP2p (0.3 μg/ml) | 2.5 μg/ml | 53 ± 10 | 46 |

[a]Fresh adherent spleen cells were obtained from a pool of 4 to 8-week old DBA/2 mice. 500 μl cultures containing $0.5 \times 10^6$ cells/ml were incubated in triplicate under the conditions shown for 18 h, and supernatants pooled from equivalent groups for cytokine assays.
[b]Where anti-CD14 was added during stimulation with LPS/CLP2p, the concentrations used were as shown. In control tests using a standard quantity of rTNFα, these concentrations of anti-CD14 added in the cytokine assays themselves produced no change in the detected level of TNF-α.
[c]Arithmetic mean (±SD) of 3 independent assays, each performed in triplicate.

3.3.1.6 Tolerance Induction to CLP2p Stimulation by LPS

Recent studies have shown that stimulation of macrophages by LPS can be inhibited by preincubation of the same cells with a suboptimal (1/100 of the optimally activating dose) concentration of LPS [Ziegler-Heitbrock, H.-W., 1992]. In order to examine possible cross-tolerance induced by LPS for optimal stimulation by either LPS or CLP2p, cells were preincubated (24 h) with 10 ng/ml LPS, washed four times in medium, and recultured in optimal concentrations of either LPS or CLP2p. TNF-α production was assayed 18 h later. Data pooled from 3 studies are shown in Table 3.

TABLE 3

Tolerance induction to CLP2p stimulation by LPS

| Pretreatment[a] | Stimulation[b] | TNFα produced[c] ng/ml | Inhibition % |
|---|---|---|---|
| Medium | None | <10 | — |
| Medium | LPS (1 μg/ml) | 155 ± 20 | — |
| Medium | CLP2p(0.3 μg/ml) | 124 ± 18 | — |
| LPS (10 ng/ml) | None | 20 ± 5 | — |
| LPS (10 ng/ml) | LPS (1 μg/ml) | 30 ± 8 | 81 |
| LPS (10 ng/ml) | CLP2p (0.3 μg/ml) | 33 ± 10 | 77 |
| LPS (10 ng/ml) + Wort (0.3 mM) | None | 14 ± 4 | — |
| LPS (10 ng/ml) + Wort (0.3 mM) | LPS (1 μg/ml) | 149 ± 23 | 4 |
| LPS (10 ng/ml) + Wort (0.3 M) | CLP2p (0.3 μg/ml) | 127 ± 21 | 0 |

[a]$6 \times 10^6$ fresh spleen adherent cells isolated from a pool of 4 8-week old DBA/2 mice were incubated for 24 h with medium alone (first three rows) or medium with 10 ng/ml LPS (next six rows) or 3 ng/ml CLP2p (final three rows). Some cells pretreated with LPS were cultured with Wortmannin (0.3 M). Cells were washed four times with 10 mls fresh medium, and recultured as shown (second column).
[b]$5 \times 10^5$ cells were incubated in triplicate for 18 hrs in 500 μl medium, or in medium containing LPS (1 ng/ml) or CLP2p (0.3 μg/ml). Supernatants were pooled from equivalent cultures at 18 h.

Consistent with data from other groups [Zuckermann, S. H., 1991], a preincubation of spleen adherent cells with 10 ng/ml LPS led to an inability to stimulate TNF-α production from these cells with optimal concentrations (1 μg/ml) LPS 24 h later. Notably, LPS preincubation also abolished subsequent simulation by CLP2p. As shown, this tolerance induction was itself inhibited if incubation was performed in the presence of 0.3 μM wortmannin.

Taken together, the data shown in Tables 1-3 suggest that the active principle in CLP2p represents or comprises a novel component whose function in activating macrophages/dendritic cells is not replaceable by the individual cytokines described. Furthermore, while CLP1b/CLP2p stimulation is inhibited by anti-CD14 monoclonal antibody, stimulation by these pools is somewhat different from that produced by isolated LPS itself. In general, however, there are significant parallels with LPS activity, among them the striking correlation of increased biological activity (TCGI and NO production as well as cytokine production) and increased detectable LPS contents (LAL assays) in CLP pools prepared from fetal liver homogenate after controlled incubation at 37° C.

In summary the data are best explained by stating that LPS is present in pools CLP1b and CLP2p, that it plays an important role in the bioactivity of these preparations and that its activity is modified by (an)other molecule(s) interacting with LPS.

3.3.2 Proteins
3.3.2.1 Methods
3.3.2.1.1 Protein Estimation and Pattern (SDS-PAGE)

The total protein content of CLP1b and CLP2p was determined by the bichinchoninic acid (BCA™) assay purchased from PIERCE (Rockford, Ill., U.S.A.) using fatty acid free bovine serum albumin (BSA) as a calibration standard. Overall protein compositions of the CLP-preparations were analyzed by SDS-PAGE on 15% (w/v) acrylamide gels and silver staining according to [Laemmli, U.K., 1970] and [Heukeshoven & Demick (1988)]. Individual proteins were isolated by preparative SDS-PAGE and subsequent electroblotting onto polyvinylidene difluoride (PVDF) Immobilon-P membrane obtained from Millipore (Bedford; U.S.A.). After staining by Coomassie Blue R250 the bands of the proteins were excised and subjected to N-terminal microsequencing employing an Applied Biosystems 473 A protein sequencer [Hunkapiller et al. 1983].

3.3.2.12 Two-Dimensional Electrophoretic Analysis of FSLE, CLP1b and CLP2p

For detailed characterization of the protein composition of the FSLE as well as of CLP1b and CLP2p, high resolution two-dimensional electrophoresis (2-DE) was performed [Jungblut, P., 1992; Jungblut, P., 1994; Otto, A., 1996, Thiede, B., 1996; Müller, E.-C., 1999]. For comparison, the protein composition of a CLP1b preparation derived from adult ovine liver was also analyzed by the 2DE technique. Briefly, CLP1b preparations were solubilized in sample buffer (25 mM Tris-HCl, pH 7.1; 9 M urea; 50 mM KCl; 3 mM EDTA; 70 mM DTT; 2.9 μM benzamidine, 2.1 μM leupeptin; 0.1 μM pepstatin; 1 mM PMSF and a total of 4% (w/w) carrier ampholytes WITAlytes, pH 2-11, WITA, Teltow, Germany) at a concentration of 10 mg CLP1b per mL. Subsequently, 12 μl of the sample solution were applied to the anodic side of the isoelectrophoretic focussing rod gel (first dimension; 3.5% (w/v) acrylamide, 0.3% (w/v) piperazine diacrylamide; Bio-Rad, Munich, Germany) and focused at 8870 V. After focussing, the gels were equilibrated for 10 min. in buffer containing 125 mM Tris/phosphate, pH 6.9, 40% (w/v) glycerol, 70 mM DTT and 3% (w/v) SDS and stored frozen at −70° C. Following thawing, the isoelectric focussing gels were immediately applied to SDS-PAGE gels (23×30 cm; 15% (w/v) acrylamide; 0.2% (w/v) N,N'-methylenebisacrylamide) and electrophoresis in the second dimension was performed using a two-step increase of current starting with 15 min at 120 mA, followed by a run of 7-8 h at 150 mA. For analytical investigations proteins in 0.75 mm gels were detected by silver staining according to the method described by Heukeshoven [Heukeshoven, J., 1985], whereas for micropreparative purposes concerning mass spectrometry techniques the silver staining method of Blum [Blum, H., 1987] was applied. Following in gel-digestion of excised spots by trypsin the peptide mixtures were purified and desalted with a peptide collection device [Otto, A., 1996] and subjected to mass spectrometric analysis. Mass and sequence determination of peptides was performed with a hybrid quadrupole-orthogonal acceleration time of flight (Q-Tof) mass spectrometer (Micromass, Manchester, UK) equipped with an nanoflow Z-spray ion source in the tandem mass spectrometry (MS/MS) mode [Müller, E. C., 1999]. In addition, corresponding 1.5 mm 2-DE gels were subjected to electrotransfer onto Immobilon PVDF membranes (Millipore, Eschbom, Germany) under semi-dry blotting conditions. Following blotting the proteins were visualized by Coomassie Brilliant Blue R-250 and excised protein spots were analyzed by automated Edman sequencing on a 477A pulse-liquid sequencer equipped with an on-line 120A PTH-amino acid analyzer, (Applied Biosystems, Foster City, Calif.; U.S.A.). Following primary identification of individual spots in the silver stained 2-DE gels of CLP1p by mass spectrometry and/or Edman sequencing corresponding proteins were assigned in fetal CLP 1p preparations and an CLP1b sample prepared from adult sheep liver by application of overlay software package. Delta2D (DEC-ODON GmbH; Greifswald).

3.3.2.2 Results 3.3.2.2.1 Protein Pattern of CLP1b and CLP2p (SDS-PAGE)

High contents of protein were determined for CLP1b (>70% w/w) of lyophilized material. In contrast, about a three- to fourfold lower protein content was detected in the corresponding. CLP2p preparations. Analysis by SDS-PAGE and subsequent silver staining revealed the prevalence of low molecular weight proteins in both CLP-pools ranging in molecular weight between about 4 and 30 kDa for CLP1b and about 4 and 10 kDa for CLP2p (FIG. 11). However, by examination of higher amounts of the latter CLP-pool the 10 to 30 kDa protein species present in CLP1b were also detected at minor levels in CLP2p. In total, about 20 to 25 single protein bands were visualized by silver staining in either CLP-pool, which were further subdivided by relative staining intensities into a group of 8 to 10 major bands and a complementary subset of minor bands. Following preparative SDS-PAGE, electroblotting and N-terminal Edman sequencing, five of the major proteins in the one-dimensional electrophoretic patterns of CLP1b and CLP2p were identified as phophatidylethanol binding protein (PEBP or PBP; P23.4), peptidylprolyl-cis-trans-isomerase A (PPlase A; p16.9), cellular retinol protein I (cRBP I; p14.6), thioredoxin (Trx; p9.5) and ubiquitin (Ub; p6.2).

3.3.2.2.2 Two-Dimensional Electrophoretic (2-DE) Analysis of FSLE, CLP1b and CLP2p Analysis by two-dimensional electrophoresis (2-DE) and silver staining proved to be a fast and reproducible technique for the characterization of the overall protein compositions of the original FSLE (FIG. 12) as well as of the extract-derived fractions CLP1b (FIG. 13) and CLP2p (FIG. 14). In the two-dimensional electrophoretic analysis of FSLE an extended pattern of about 2200 single protein spots in the 100 to 2 kDa molecular weight and the 4.0 to 9.0 isoelectric point (I.P.) range was detected (FIG. 12). The 2-DE analysis of CLP1b preparations revealed a highly reproducible pattern of a total of 576 individual spots that were systematically numbered according to decreasing molecular weight and I.P. assignments (FIG. 13). The vast majority of spots in the 2-DE separation pattern was detected in the apparent molecular weight area between 40 and about 6 kDa, ranging in isoelectric point (I.P.) values from 4.0 to 9.0. In addition to the group of proteins described in the previous section 20 further proteins representing spots of major intensity in the 2-DE separation pattern of CLP1b were identified by Edman sequencing or tryptic digestion and MS/MS analysis in combination with database-related sequence homology searches (Table 4). The identified proteins were found to represent cytoplasmic proteins that are evolutionary highly conserved in mammalian species (Table 4). In corroboration of the initial data based on the one-dimensional electrophoretic separation phosphatidylethanolamine binding protein (PBP or PEBP), peptidyl-prolyl-cis-trans-somerase A (PPlase A)/Cylophilin A (Cyp A) and cellular retinol-binding protein I (cRBP I) were assigned to the major spots 321, 403/405 and 454 in the 2-DE pattern of CLP1b.

The pro-inflammatory cytokine and proteohormone—macrophage migration inhibitory factor (MIF)—was identified to be present at a content of about 0.5% (w/w) in the total proteins of CLP1b (spot 536). As the primary structures of MIF from human and bovine sources display an overall sequence identity of about 93% [Weiser, W. Y.; 1989, Galat, A., 1994] the ovine form of the protein is predicted to display an analogous high degree of phylogenetic conservation. MIF has been shown to be stored in intracellular granules in mammalian cells from a wide variety of tissues including monocytes and macrophages [Calandra, T., 1994], T lymphocytes [Bacher, M., 1996], corticotropic cells of the anterior pituitary [Bernhagen, J., 1993], islet β cells of the pancreas [Waeber, G., 1997] as well as hepatocytes and Kupffer cells of rat liver [Bacher, M., 1997]. The factor has been characterized to be a central immuno-neuroendocrine mediator that displays a series of regulatory and enzymatic activities [Bernhagen, J., 1998; Metz, C. N., 2001]. Above all, MIF neutralizes and overrides the immunosuppressive effects of glucocorticoids and reinforces responses of myeloid cells to bacterial LPS [Calandra et al., 1994; Bernhagen, J., 1998; Metz, C. N., 2000]. Thus, MIF may contribute to the antitumoral immunostimulatory effects induced by the LPS component of CLP1b in murine and human test systems.

In an initial analysis high level of sequence identity of tryptic peptides of spot 458 to a partial sequence of 204 amino acids that has been deposited in the TrEMBL database under accession number Q12915 were found. This preliminary database entry had been postulated to represent a fragment of inflammatory bowel disease protein 1 (IBD1). According to genetic linkage analysis the IBD1 locus has been implicated in determining the susceptibility of humans to inflammatory bowel diseases such as Crohn's disease and ulcerative colitis (Mirza et al., 1998; Forabosco et al, 2000). However, according to novel genome sequencing data deposited in the TrEMBL database entries Q9BRA2, Q95M49 and Q921A9 this spot was identified to represent a putative 42-9-9 protein characterized by a predicted thioredoxin type 2 domain as the major structural element.

In confirmation of the fetal origin of the preparation spot 498 was shown to be identical to the ovine form of the fetal hemoglobin gamma (Hbγ) chain, whereas spots 506 and 510 were identified to represent isoforms of the ovine hemoglobin alpha (Hbα) chain. From the relative silver staining intensities of all spots representing hemoglobin alpha and gamma chains the total amount of fetal hemoglobin (HbF) in CLP1b was estimated to be approximately 5.6% (compare Example 4.2).

A larger group of the identified proteins in CLP1b represent 'house-keeping proteins' that are exemplified by aldose 1-epimerase, alcohol dehydrogenase, carbonic anhydrase isoforms II and III, acyl CoA-binding protein, liver fatty acid binding protein (L-FABP) and ubiquitin. In contrast to apoptosis or programmed cell death necrosis of mammalian cells is characterized by the release of multiple intracellular components and has been documented to provide a pro-inflammatory and antitumoral stimulus to myeloid cells in vitro [Reiter et al., 1999]. Thus, the extracellular application of small and phylogenetically conserved intracellular 'house keeping' proteins may also contribute to the immunostimulatory effects of the CLP preparations. By comparison to the results obtained for CLP1b the 2DE-analysis of CLP2p revealed a mostly analogous overall pattern of spots that was characterized by an enrichment of the lower molecular weight proteins in the range between 20 and about 6 kDa (FIG. 14). Individual spots in the silver stained 2-DE gels of CLP 1p could be assigned according to identified proteins in CLP1b by application of the software package Delta2D (DECODON GmbH; Greifswald).

By additional 2DE analysis of a CLP1b sample obtained from adult sheep liver (FIG. 15) and subsequent administration of the Delta2D overlay software a group of spots could be identified that were present in higher quantities in the fetal material as compared to only minor amounts or even the absence of the corresponding proteins in the adult CLP1b preparation (FIG. 16). This particular group of predominant fetal proteins included the spots of the ovine fetal hemoglobin gamma (Hbγ) chain (spot 498 in fetal CLP1b) and also that of the ovine hemoglobin alpha (Hbα) chain (spots 506 and 510 in fetal CLP1b) as well the spot of macrophage migration inhibitory factor (MIF; spot 536 in fetal CLP1b). The significantly higher overall hemoglobin content of the fetal CLP1b samples as compared to the adult preparation is apparently correlated to the specific function of the fetal mammalian liver as a primary hematopoietic organ during fetal development whereas in the period around birth and the following postnatal stages of the mammalian life the predominant site of hematopoiesis shifts to the red matter of the bone marrow.

Most of the identified proteins are evolutionary highly conserved and display a widespread issue distribution in mammalian species [Schoentgen, F., 1987; Seddiqi, N., 1994; Harding, M. W., 1986; Haendler, B., 1987; Colantuoni, V., 1985; Sherman, D. R., 1987; Droogmans, L., 1994; Wollman, E. E., 1988; Schlesinger, D. H., 1975; Ozkaynak, E., 1984]. They are therefore expected to be functionally active when applied to the human organism for medical treatment without having xenogenic side effects. According to the published features of MIF, thioredoxin and ubiquitin, these proteins are considered in accordance with the present invention to contribute to the profound immunostimulatory, antitumoral etc. activities of the CLP-pools in an enhancing or synergistic manner [Bernier, I., 1986; Lotan, R., 1996; Bertini, R., 1999; Nabika, T., 1999].

TABLE 4

Identification of major spots in the 2-DE separation pattern of CLP1b by N-terminal Edman sequencing or MS/MS analysis of tryptic peptides

| Spot Nr. | Identification/Database | Human Protein AA; $MW_{calc.}$ $I.P._{calc./app.}$ | Sequence Identity of Human Protein to ... |
|---|---|---|---|
| 16 | Aldose 1-Epimerase | 342 AA; 37765 Da $I.P._{calc.}$: 6.18 | Porcine: 89% Mouse: 87% |
| 51 | Alcohol Dehydrogenase (ADH) | 374 AA; 39723 Da $I.P._{calc.}$: 8.26 | Mouse: 83% Rat: 80% |
| 52 | Prostaglandin-F Synthase (PGF) | 323 AA; 36826 Da $I.P._{calc.}$: 8.05 | Bovine: 78% |
| 64 | Prostaglandin-F | Bovine | 'Bovine: 75%' |
| 78 | Synthase 2 (PGF2) | 323 AA; 36742 Da $I.P._{calc.}$: 6.80 | [to human PGF(1)] |
| 74 | Regucalcin (RGN)/Senescence | 299 AA; 33253 Da $I.P._{calc.}$: 5.89 | Mouse: 88% |
| 76 | Marker Protein-30 (SMP-30) | | Rat: 88% |
| 81 | Thiosulfate Sulfurtransferase (TST) | 296 AA; 33297 Da $I.P._{calc.}$: 8.09 | Bovine: 89% Mouse: 90 Rat: 90% |
| 125 | Carbonyl Reductase 1 | 276 AA; 30244 Da $I.P._{calc.}$: 8.55 | Rabbit: 83% Mouse: 86% |
| 126 | (CBR1) | | Rat: 85% |
| 145 | 3-Hydroxyanthranilate 3,4-Dioxygenase (3-HAO) | 286 AA; 32542 Da $I.P._{calc.}$: 5.62 | Rat: 87% |
| 158 | Guanidinoacetate-N-Methyltransferase (GAMT) | 236 AA; 26318 Da $I.P._{calc.}$: 5.74 | Mouse: 87% Rat: 86% |
| 168 | Carbonic Anhydrase III (CA-III) | 259 AA; 29440 Da $I.P._{calc.}$: 6.94 | Horse: 87% Mouse: 90% |
| 172 | | | Rat: 91% |
| 180 | Carbonic Anhydrase II (CA-II) | Ovine [Human]: 259 AA; 29080 Da [259 AA; 29115 Da] $I.P._{calc.}$: 6.40 [6.86] | Ovine: 78% Bovine: 78% |
| 292 | Catechol-O-Methyltransferase, Soluble Isoform (S-COMT) | 220 AA; 24318 Da $I.P._{app.}$: 5.15 | Mouse: 80% Rat: 79% |
| 321 | Phosphatidylethanolamine-Binding Protein (PEBP) | 186 AA; 20925 Da $I.P._{app.}$: 7.33 | Bovine: 95% Rat: 85% |
| 403 | Peptidyl-Prolyl-cis-trans-Isomerase A (PPIase A) Cyclophilin A (Cyp A) | 164 AA; 17881 Da $I.P._{app.}$: 6.67; 7.06; 7.59; 8.04 | Bovine: 98% Mouse: 95% |
| 405 | | | |
| 425 | Superoxide Dismutase (SOD) | Ovine [Human]: 151 AA; 15563 Da [153 AA; 15804 Da] $I.P._{calc.}$: 6.16 [5.70] | Ovine: 82% Bovine: 82% Horse: 80% Mouse: 83% Rat: 83% Rabbit: 81% |
| 454 | cellular Retinol-Binding Protein I (cRBP I) | 134 AA; 15719 Da $I.P._{app.}$: 4.70 | Mouse: 96% Rat: 98% |
| 457 | Glycine Cleavage System H Protein (GCSH) | 125 AA; 13813 Da $I.P._{app.}$: 4.36 | Bovine: 96% |

TABLE 4-continued

Identification of major spots in the 2-DE separation pattern of CLP1b by N-terminal Edman sequencing or MS/MS analysis of tryptic peptides

| Spot Nr. | Identification/Database | Human Protein AA; $MW_{calc.}$ $I.P._{calc./app.}$ | Sequence Identity of Human Protein to ... |
|---|---|---|---|
| 458 | Putative 42-9-9 Protein | 123 AA; 13941 Da $I.P._{calc.}$: 5.40 | Mouse: 79% |
| 498 | Hemoglobin Gamma Chain (Hb-gamma) | Ovine [Human]: 145 AA; 15931 Da [146 AA; 16009 Da] $I.P._{calc.}$: 6.59 [6.71] | Ovine: 72% Bovine: 72% Rabbit: 78% |
| 506 510 | Hemoglobin alpha Chain (Hb-alpha) | Ovine [Human]: 141 AA; 15033 Da [141 AA; 15126 Da] $I.P._{calc.}$: 8.73 [8.73] | Ovine: 86% Bovine: 87% Mouse: 85% Rat: 78% |
| 520 | Fatty Acid-Binding Protein, Liver (L-FABP) | 127 AA; 14208 Da $I.P._{calc.}$: 6.60 | Bovine: 81% Porcine: 89% Mouse: 84% Rat: 82% |
| 536 | Macrophage Migration Inhibitory Factor (MIF) | 114 AA; 12345 Da $I.P._{calc.}$: 8.24 | Bovine: 93% Mouse: 89% Rat: 90% |
| 555 | Acyl-CoA-Binding Protein (ACBP) | 86 AA; 9913 Da $I.P._{calc.}$: 6.11 | Bovine: 93% Porcine: 89% Mouse: 77% Rat: 77% |

3.3.2.3 Arginase—a Constituent of FSLE with Bioactive Potential

An important protein present in standard FSLE is arginase, an enzyme with inhibitory effects on in vitro cell cultures mainly due to its arginine-depriving capacity. A direct dose-dependent effect of arginase on the growth of Abelson 8-1 tumor cells could be shown. To analyse to what extent arginase could be responsible for the TCGI seen in cultures set up with CLP1b and CLP2p, its activity was determined in these pools according to [Corraliza, J. M., 1994]. Tab. 5 shows that CLP1b exhibited some minor arginase activity, whereas pool 1 displayed high arginase activity comparable to that found in standard FSLE. In contrast, no arginase activity could be detected in CLP2p despite the fact that this pool was highly active in the TCGI assay. Hence, arginase can be excluded as a major cause of the growth inhibiting effects seen in cultures set up with pools CLP1b and CLP2p.

TABLE 5

Arginase Activity in FSLE and CLP-Pools

| Analayzed Preparation | Arginase Activity U/mg protein |
|---|---|
| CLP 1 | 19.6 |
| CLP1b | 0.8 |
| CLP2p | —* |
| FSLE | 22.0 |

*Arginase content below detection limit of 0.2 U/ml

4. EXAMPLE 4

Interaction of Lipopolysaccharide with Fetal Hemoglobin

The small amounts of endotoxin present in FSLEs did not entirely explain the degree of bioactivity of these preparations. It was, therefore, speculated that an additional component to FSLE, CLP1b and CLP2p was involved, modifying the bioactivity of endotoxin by interacting with it. For the characterization of this component the following experiments were performed.

4.1 Methods

In order to identify the LPS or Lipid A-interacting protein(s) in CLP1b a LPS/Lipid A-specific adsorption assay was developed. In this screening system polyvinylchloride 96-well microtiter plates (Becton Dickinson) were coated for 14 h at 4° C. with S-form LPS from *Salmonella enterica* sv. Minnesota 188233, Re-LPS from *E. coli* F515 or a Lipid A preparation derived from the *E. coli* strain solubilized as triethylamine (TEA) salts in LAL reagent water (BioWhittaker) at concentrations of 5 µg/ml or 2 µg/ml, respectively. As a control a series of wells was similarly treated with LAL reagent water without the addition of LPS or Lipid A. Subsequently, the solutions were decanted and the wells were rinsed four times with Dulbeccos phosphate-buffered saline (D-PBS; Lifetechnologies) without magnesium or calcium salts. For reduction of potential non-LPS- or Lipid A-dependent binding of proteins in CLP1b the LPS- or Lipid A-coated wells and the corresponding control wells were then treated with 0.2% (w/v) gelatine (Aurlon) in D-PBS at 37° C. for 1 h under constant shaking. After an additional rinsing step (four times with D-PBS) the wells were incubated with CLP1b solutions of 1.0 and 0.1 mg/ml in D-PBS at 37° C. for 1 h under constant shaking. The supernatants of the binding incubation were lyophilized for final analysis by SDS-PAGE. Then a series of four washing steps with D-PBS at 37° C. for 20 min. under constant shaking was performed and the corresponding wash solutions were also freeze-dried. Subsequent to this intensive washing procedure, 50 µl of SDS sample buffer was added to each well for resolving of the remaining adsorbed protein and coating materials. In addition, the lyophilized samples from the prior CLP1b incubation and the following sequence of washing steps were resuspended in 50 µl SDS-Sample buffer and the compositions of the collected samples from the adsorption assay were analyzed by SDS-PAGE in 15% (w/v) polyacrylamide gels and silver staining according to the method described by Heukeshoven [Heukeshoven, J., 1986].

4.2 Results

The SDS-PAGE and silver staining analysis consistently revealed the LPS- or Lipid A-dependent adsorption of a single protein band from CLP1b displaying an apparent molecular weight of approximately 12.0 (±1.0) kDa in the wells coated with S-form LPS from *Salmonella enterica* sv. Minnesota (FIG. 17), Re-LPS from *E. coli* F515 (FIG. 18) and the Lipid A preparation derived from the *E. coli* strain (FIG. 19), respectively. By preparative performance of the adsorption assay (coating material: Re-LPS from *E. coli* F515) followed by mass spectrometric analysis of tryptic peptides the major component of this protein band was identified as the ovine hemoglobin alpha chain (Hb-alpha) (FIG. 20). For further confirmation of the observed highly selective adsorption of fetal ovine hemoglobin (HbF) or the corresponding HbF subunits to the LPS- or Lipid A coated microtiter plates an initial hemoglobin-directed depletion step was included in the test system using the acute phase reactant human haptoglobin (1-1) [h-Hp(1-1); Sigma-Aldrich] as a hemoglobin-specific reagent. Preincubation of CLP1b with h-Hp(1-1) in the adsorption assay (coating material: Re-LPS from *E. coli* F515) lead to a marked reduction in the intensity of the 12 kDa-band in the final SDS-PAGE analysis as compared to the non-haptoglobin treated CLP1b sample (FIG. 21). In previous studies, binding of human, bovine and porcine adult hemoglobin (HbA) to LPS or free Lipid A as well as a substantial enhancement of LPS bioactivities in vitro and in vivo by the presence of the purified adult hemoglobin preparations have been described indicating a novel immunomodulatory function of hemolytically released free mammalian hemoglobins in addition to their primary oxygen transport function in intact red blood cells [Roth, R. J., 1994; Roth R. J., 1999; Belanger, M. 1995].

Thus, ovine fetal hemoglobin [sheep HbF; s-HbF] was here identified as the major LPS/Lipid A-interacting component in the CLP1b preparations. Quantitative estimations using protein absorption measurements at 405 nm revealed an apparent HbF content of approximately 10% (w/w) in FSLE of about 3.2% (w/w) in CLP1b and of about 1.2% (w/w) in CLP2p. In corroboration of the 2-DE data (see Example 3.3.2.2.2). Thus, HbF represents a major protein component in the fetal liver-derived extract.

The gestation time of sheep fetuses being five months and the change from fetal hemoglobin, containing α and γ chains (α2γ2) to adult hemoglobin, containing α and β chains (α2β2$^A$ and/or α2β2$^B$) occurring at the time of birth, heparinized blood was taken from fetuses of 4 month gestation. Fifty ml of blood were taken from the umbilical vein. A similar quantity of blood was taken from control adult sheep for comparison. The red blood cells were washed 4 times with 5 volumes of phosphate buffered saline (0.14 M NaCl 0.01 M Phosphate pH 7.4) by 4 centrifugations at 1000×g, to remove plasma proteins.

The washed packed red cells were lysed by adding 5 volumes of distilled $H_2O$. After ultracentrifugation at 10,000×g to remove cell membranes, the supernatant was applied to Sephadex G100 column equilibrated in 0.03 M phosphate buffer pH 7.4 at 4° C. A major central peak eluted with an apparent molecular weight of about 70 kDa was selected.

The proteins from the central Sephadex G100 peak were further purified on a DEAE cellulose ion exchange column (DE52 Whatman) equilibrated in 0.005 M phosphate buffer pH 8.5. The major part of the red proteins were eluted by a stepwise addition of 0.05 M phosphate buffer pH 8.0 (FIG. 23). Almost identical results were obtained for the purification of hemoglobin from adult sheep blood. Fetal and adult purified sheep hemoglobin preparations were dialyzed against $H_2O$ and lyophilized.

Analysis of purified fetal and adult hemoglobin by SDS-PAGE, 15%, gave a major band with an apparent molecular weight of 17 kDa and a smaller band of about 34 kDa under non reducing conditions, suggesting the presence of a small percentage of undissociated dimeric hemoglobin chains. Under reducing conditions (20 mM DL-dithiothreitol Sigma), both fetal and adult hemoglobin preparations gave a single band of 17 kDa, indicating a high degree of purity of the two preparations (FIG. 24). Amino acids sequence analysis of the first 16 positions from purified fetal hemoglobin confirmed that it contains only α-chains and γ-chains/i.e. no β-chains (Table 6). Table 6 discloses SEQ ID NOS: 1-4, respectively, in order of appearance.

TABLE 6

N-terminal sequencing of fetal sheep hemoglobin preparation

| | Position | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Intact fetal hemoglobin | V | M | L | S.T | A | A E | D.E | K. | S.A | N.S | V | K.I | A.S | A.L | W.F | G.A | K |
| Reference Hb α-chain | V | | L | S | A | A | D | K | S | N | V | K | A | A | W | G | K |
| Reference Hb γ-chain | | M | L | T | A | E | E | K | A | S | V | I | S | L | F | A | K |
| Reference Hb β-chain | | M | L | T | A | E | E | K | A | A | V | T | G | F | W | G | K |

The amino acid residues specific for the γ chain in positions 9, 11, 12 and 13 are underlined.

The primary structure of the ovine hemoglobin alpha and gamma chains are shown in FIG. 22.

5. EXAMPLE 5

Purification of Fetal Sheep Hemoglobin and Partial Structures Thereof

5.1 Hemoglobin

5.2 Removal of Heme from Purified Fetal and Adult Sheep Hemoglobin [Winterhalter and Huehns, 1964]

To 50 mg of lyophilized purified fetal or adult hemoglobin dissolved in 2 ml of ice cooled $H_2O$ were added 45 ml of acetone containing 6 mM HCl and maintained at −20° C. After 30 min incubation at −20° C., the pink supernatant was separated from precipitated proteins and discarded. The precipitated proteins were washed 3 times with 45 ml of pure acetone at −20° C. After centrifugation at 2500×g, acetone was removed and the pelleted proteins dissolved in 3 ml of ice cold water and lyophilized. The proteins were perfectly soluble in water at 4° C. and had no more red color. Analysis on SDS-PAGE, 15%, of the acetone-treated proteins gave almost the same pattern as purified intact hemoglobin with a major band at 17 kDa and a minor band at 34 kDa under nonreducing conditions and a single band of 17 kDa under reducing conditions (FIG. 25). Thus they can be considered as globin or heme-free hemoglobin.

5.3 Attempt of Dissociation and Purification of γ-Chain from Fetal Hemoglobin 5.3.1 Conventional Methods

[Bucci and Fronticelli, 1965; Winterhalter and Colosimo, 1971]

To 50 mg of lyophilized purified fetal oxyhemoglobin dissolved in 4 ml of 0.1 M $KH_2PO_4$ solution containing 0.2 M NaCl were added 8 mg of 4-hydroxymercury benzoate (HMB) (Sigma) dissolved first in 1 ml of 0.1M NaOH followed by the addition of 2 ml of 0.1 M $KH_2PO_4$ and by titration to pH 5.8 with about 75 μl of 1 M acetic acid. The molar ratio between HMB and hemoglobin was 7.5 to 1. Following an incubation at 4° C. for 18 hours, the excess HMB was removed by filtration on a Sephadex G25 column (Pharmacia) equilibrated in 10 mM MES buffer at pH 6.0.

The fetal Hb was then applied to an UNO-S cation exchange column (BIO-RAD) equilibrated in the same MES buffer and eluted by a gradient of increased NaCl molarity up to 1 molar. Hemoglobin was eluted in two peaks, as shown in FIG. 26. The first peak contained intact tetrameric hemoglobin, whereas the second one contained monomeric hemoglobin chains, with an apparent molecular weight of about 17 kDa, as demonstrated by its elution on a Superdex S75 (Pharmacia) column (FIG. 27).

The second peak of the UNO-S column was further analyzed on an UNO-Q (BIO-RAD) anion exchange column, equilibrated in a 10 mM Tris-buffer pH 8.0, where it was eluted as a single peak by applying a gradient of increased NaCl molarity up to 1 M (FIG. 28). Thus, a protein was obtained which gave a single peak with an apparent molecular weight of 17 kDa on a molecular sieving column as well as an homogeneous single peak elution pattern on both cation and anion exchange chromatography.

Amino acid sequence analysis of the first N-terminal positions revealed that the protein was a mixture of the α- and γ-chains of fetal sheep hemoglobin (FIG. 22). Adult sheep blood hemoglobin α,β-chain mixtures were purified with the same results.

5.3.2 A New Procedure: the Thiol Agarose Method

A new and more efficient methodology for hemoglobin subunit (α, β and γ globin chains) separation by covalent chromatography is here described.

Human as well as non-human hemoglobins are first immobilized on activated thiol resins through cleavable disulfide bonds linking "exposed" —SH groups of either beta- or gamma-chains to the solid-phases. Then, α-chain is selectively eluted with 50% acetic acid or other strongly solvating agents. After disulfide bonds reduction, beta- as well as gamma-chains are finally recovered by elution with 50% acetic acid or other strongly solvating agents.

The method reported below is not intended to limit the present invention and further modifications deriving from the advancement of the hemoglobin/activated thiol resins, the elution protocols being within the scope of the present invention.

The new methodology includes: 1) the covalent linking of fetal sheep hemoglobin to thiol activated cross-linked agarose (active group: 2-pyridyl disulfide); 2) the selective elution of alfa-chains by 50% acetic acid and 3) the reduction of disulfide bridges with 20 mM dithiothreitol followed by the elution of gamma-chains from the solid-phase by 50% acetic acid. Details of these steps are as follows:

1. The activated thiol agarose resin was prepared starting from Affigel 102 (Biorad) with a nominal free amine substitution of 10-12 micromole/ml of drained gel. 5 g of the commercial resin were first repeatedly rinsed with ammonium acetate buffer, pH 7.5, to eliminate additives and then reacted overnight, at room temperature, with 10 equivalents (calculated over the amine substitution) of Pierce Sulfo-LC-SPDP (Sulfosuccinimidyl 6-[-3-(2-pyridyldithio)propionamido]hexanoate). Excess reagent was eliminated by washing with ammonium acetate buffer, pH 7.5. 1.5 ml of drained activated thiol resin were then reacted with 25 mg of fetal sheep hemoglobin dissolved in 0.2 ml of PBS buffer, pH 7.5, for about 3 h. The total amount of hemoglobin bound to the resin (ca. 15 mg) was obtained by subtracting the amount of hemoglobin eluting during resin loading and final washings.

2. Selective alfa-chain elution was accomplished with about 20 ml of 50% acetic acid. The collected, hemin containing 1.0 ml fractions were evaluated by MALDI/MS (Matrix-assisted Laser Desorption/Ionization Mass Spectrometry) using a Voyager-DE RP time-of-flight instrument (PerSeptive Biosystems, Framingham, Mass., USA). Two separate and independent MALDI measurements were made for each fraction to evaluate the reproducibility of the averaged 50 laser shots. Mass analysis showed a single peak at 15,120 Da corresponding to the expected mass of the α-globin chain. The purified alfa-globin/hemin showed a typical absorption spectrum with peaks at 556, 538, 420, 343 and 270 nm. The product was isolated by freeze-drying. (Yield, 3.2 mg).

3. The resin was incubated with 20 mM dithiothreitol in ammonium acetate buffer, pH 7.5, for about 2 h at room temperature, washed repeatedly with ammonium acetate buffer, pH 7.5, to eliminate the released 2-thiopyridone and excess thiol and then treated with 50% acetic acid to elute γ-chains still adsorbed on the solid-phase. The collected fractions were analyzed by MALDI/MS as described before for alfa-chains. Mass analysis showed a single peak at 15,997 Da, which corresponds to the expected mass of the fetal sheep gamma-globin chain (data not shown). The absorption spectrum was closely similar to that of α-chains. The product was isolated by freeze-drying. Yield, 1.8 mg.

Thus, the methodology for the separation of human and non-human hemoglobin into subunits (α, β and γ globin chains), based on the use of solid phase substrates and characterized by the following steps:

1. reaction of the hemoglobin "exposed" thiol groups with an activated thiol agarose resin;
2. selective elution of alfa globin/hemin with strong solvating agents;
3. disulfide bonds reduction followed by elution of pure beta- or gamma globin chains with strong solvating agents.

5.3.3 Cloning and Expression of Isolated Sheep and Human Hemoglobin Chains

In addition the application of biochemical procedures for isolation of hemoglobin chains molecular cloning was employed. The procedures used for the cloning and expression of sheep and human Hb chains are as follows.

The eukaryotic expression vector, PIRESneo3, was redesigned to include an Ig k-chain leader sequence (atggagacagacacactcctgctatgggtactgctgctctgggttccaggttccactggtgac (SEQ ID NO: 5)) upstream of the globin genes, to allow for secretion of the globin chains in eukaryotic cells (CHO). The following set of primers (with mRNA isolated from human PBL) were used in this strategy:

```
Sense primer:
                                        (SEQ ID NO: 6)
TAA ATG CTA GCG CCA CCA TGG AGA CAG AC Antisense primer:
                                        (SEQ ID NO: 7)
ATT ATA CCG GTG TCA CCA GTG GAA CCT GG
```

Human and sheep α, β and γ-chains of hemoglobin were amplified by RTPCR from mRNA extracts of commercially obtained human bone marrow and sheep fetal liver respectively, using the following primer pairs (the region underlined represents the AgeI restriction site for cloning into the eukaryotic expression vector

```
Human α-chain:
Sense primer:
                                        (SEQ ID NO: 8)
TAA TA A CCG GT A TGG TGC ACC TGA CTC CTG AGG A Antisense primer:
                                        (SEQ ID NO: 9)
ATT TA A CCG GT A GCT TAG TGA TAC TTG TGG GCC A Human β-chain:
Sense primer:
                                        (SEQ ID NO: 10)
TAA TA A CCG GT A TGG TGC ACC TGA CTC CTG AGG A Antisense primer:
                                        (SEQ ID NO: 11)
ATT TA A CCG GT A GCT TAG TGA TAC TTG TGG GCC A Human γ-chain:
Sense primer:
                                        (SEQ ID NO: 12)
TAA TA A CCG GT A TGG GTC ATT TCA CAG AGG AG Antisense primer:
                                        (SEQ ID NO: 13)
ATT TA A CCG GT C TCA GTG GTA TCT GGA GGA CA Sheep α-, β- and γ-chains:
Sense primer:
                                        (SEQ ID NO: 14)
TAA TA A CCG GT A TGC TGA CTG CTG AGG AGA A Antisense primer:
                                        (SEQ ID NO: 15)
ATT TA A CCG GT G GAA GGG GAG CTT AGT GAT A
```

Note that in the case of sheep hemoglobin chains, sequence similarity between the chains necessitated cloning blindly using identical primer pairs, with subsequent RFLP (later) analysis of clones, and individual DNA sequencing, to identify clones unique for individual hemoglobin chains.

The following steps were common to all cloning strategies: AgeI digestion of PCR products and vector, followed by purification of AgeI digested PCR products with phenol chloroform and CIP treatment of vector, using a QIAgen quick Gel Extraction kit. Thereafter we performed ligation with T4 DNA ligase and transformation. A number of independently transformed bacterial colonies were picked and grown in 5 ml of LB cultures. Plasmid DNAs, were isolated from each culture and analyzed by digestion with either EcoRI (for sheep α-, β- and γ-chains) or BamHI (for human α-, β- and γ-chains), followed by gel electrophoresis. This served to identify clones likely to contain unique inserts for the respective hemoglobin chains. The latter was confirmed by DNA sequencing.

Following construction of vectors including the hemoglobin chains linked to Ig k-hemoglobin chain inserts, we designed an independent set of PIRESneo3vectors to include a 6-His tag (SEQ ID NO: 16) with an enterokinase cleavage site inserted between the Ig k-leader sequence and the hemoglobin chain coding sequence, for ease of purification of the cloned proteins. The following primers pairs were used at this stage:

```
6xHis-human hemoglobin α-sense:
                                        (SEQ ID NO: 17)
AGCACCGGTCATCATCATCATCATCATGATCTGTACGACGATGACGATAA

GATGGTGCACCTGACTCCTGAGGA

6xHis-human hemoglobin β-sense:
                                        (SEQ ID NO: 17)
AGCACCGGTCATCATCATCATCATCATGATCTGTACGACGATGACGATAA

GATGGTGCACCTGACTCCTGAGGA

6xHis-human hemoglobin γ-sense:
                                        (SEQ ID NO: 18)
AGCACCGGTCATCATCATCATCATCATGATCTGTACGACGATGACGATAA

GATGGGTCATTTCACAGAGGAGGAC

6xHis-sheep hemoglobin α-, β- and γ-sense:
                                        (SEQ ID NO: 19)
AGCACCGGTCATCATCATCATCATCATGATCTGTACGACGATGACGATAA

GATGCTGACTGCTGAGGAGAAGGC

Anti-sense universal primer:
                                        (SEQ ID NO: 20)
TCCGAATTCGAATCCGGAGAC
```

After AgeI digestion, T4 ligation, and transformation, independent clones containing 6-His (SEQ ID NO: 16) tagged hemoglobin chains were used to transfect CHO cells, followed by selection in G418. Clones were screened for secretion of material reacting in ELISA with the heterologous antibodies described below (section 5.4). High-producing clones were then serially adapted to growth in serum-free conditions, using Sigma 301medium. 10×-concentrated supernatants of these clones were run on Western gels, before and after enterokinase digestion, with individual lanes in the gels developed with either an anti-His or anti-hemoglobin antibody.

5.4 Antibodies to Hb and Hbγ-chain

For the production of monoclonal antibodies to the γ-chain of human Hb, a 25-mer peptide (corresponding to positions 48-72 of the full-length γ-chain), SAIMGNPKVKAH-GKKVLTSLGDAI (SEQ ID NO: 21), was synthesized (American Peptide Co., CA) and coupled to KLH. Rats were immunized with the KLH-coupled protein prior to harvest of spleen cells, fusion with YB2 parent myeloma cells, and selection in ELISA (with plates coated with peptide or γ-chain of hemoglobin) for hybridomas producing mAbs detecting human γ-chain.

A similar strategy was used to produce anti-sheep γ-chain, using the synthesized peptide DAILGNPKVKGHGKKV-LNSFSEGLK (SEQ ID NO: 22), immunizing with BSA-coupled peptide and screening as above. Confirmation that the heterologous and mAbs detected the relevant hemoglobin chains was obtained by Western gels.

Commercial anti-sheep and anti-human hemoglobins were obtained from Sigma.

6. EXAMPLE 6

Preparation and Characterization of LPS, Lipid A and Monophosphoryl Hexaacyl Lipid A 6.1.1 Growth of Bacteria, LPS Extraction and Preparation of Monophosphate Lipid A (MPLA)

Four batches of the *E. coli* Re mutant strain F515 [Schmidt G. et al., 1970] were grown with a 10-L fermenter (Biostate E) in a caseine peptone medium [Schlecht S. et al., 1975] inoculated with 2% of an 1 h culture at 37° C., pH 7.2 for 18 h to stationary phase. Bacteria were killed with 1% phenol and harvested by centrifugation (JLA-8100, Beckman). The cells (wet weight 402 g) were washed with 2 L each distilled water, ethanol, acetone (twice), and once with 1 L diethyl ether, then dried (yield: 101.5 g).

LPS was extracted from freeze-dried cells by the phenol-chloroform-petroleum ether (PCP I) extraction method. [Galanos C. et al., 1969] The last precipitate was washed twice with acetone (100 mL) to remove residual phenol, centrifuged (10,000×g, JA-10, Beckman) and the pellet suspended in distilled water (20 mg/mL); the pH was adjusted to ~8 and the suspension extensively dialyzed against distilled water. The retentate was lyophilized to give purified Re-LPS (3.23 g, 3.2% w/w).

6.1.2 Isolation and Purification of Monophosphoryl Lipid A

Crude monophosphoryl Lipid A (MPLA) was obtained from 1.0 g Re-LPS of *E. coli* F515 by hydrolysis in 100 mL hydrochloric acid (0.1 M HCl) at 100° C. for 30 min. The hydrolysate was cooled on ice, centrifuged (4.000 rpm, 4° C., 10 min, Hettich, Rotixa RP), the sediment resuspended in chloroform:methanol 80:20 (by vol.) and dried to give 731.8 mg of crude MPLA (73% w/w). TLC of this material showed considerable homogeneity of natural MPLA with two major Lipids co-migrating with hexa-acyl ($R_F$ 0.77) and penta-acyl ($R_F$=0.71) MPLA. (FIG. 29).

6.1.3 Analytical Thin Layer (TLC) and Preparative Layer Chromatography (PLC)

Analytical TLC (FIG. 29) was done on aluminum silica gel sheets (0.2 mm, Kieselgel 60 $F_{254}$, Merck) to which 30 μg of each sample were applied per lane. TLC sheets were developed in chloroform:methanol:1% acetic acid 100:50:3 (v/v/v) and stained by dipping in ethanol: conc. sulfuric acid 85:15 (v/v) and heating. Preparative purification of Lipid A fractions was done applying crude Lipid A (total 170 mg) on preparative layer chromatography (PLC) plates loaded with silica gel using the same solvent system as for analytical TLC. Preparative layer chromatography (PLC) was done loading crude MPLA (160 mg) in eight aliquots of 20 mg per PLC plate (2 mm thickness, 20×20 cm, Kieselgel 60, Merck). After PLC, MPLA bands became visible when spraying the plates with bi-distilled water. Fractions were scraped off from the dried plates and eluted with chloroform:methanol 80:20 (v/v) from silica gel by filtration and washed twice with 10 mL of the above solvent. Pure MPLA fractions were concentrated on a rotary evaporator and re-suspended in 2-5 mL water, to which aqueous triethylamine (TEN, 0.36 M) was added drop wise until pH ~8.5 was reached. The Lipid A TEN-salt suspension was dialyzed against water (600 mL, four times) and freeze dried.

6.1.4 Compositional Analysis, Sugar, Phosphate and Fatty Acids

GlcN was determined by the method of Strominger et al., [Strominger J. L., et al., 1959] after hydrolysis with 4 M HCl (100° C., 16 h), and phosphate by the method of Lowry et al. 1954. For the fatty acid analysis freeze-dried Lipid A samples (200 μg) were mixed with 50 μg of internal standard (heptadecanoic acid, 17:0). Total fatty acid analysis was performed after methanolysis with 1.5 mL 2 M HCl/MeOH at 120° C. for 16 h in sealed ampoules. The methanolysed samples were dissolved in water and the resulting fatty acid methyl esters were extracted three times with 3 mL chloroform, concentrated, and analyzed by GLC.

GLC analysis was performed with a Varian model 3700 chromatograph equipped with a capillary column of SPB-5® (Supelco Inc., Bellefonte, USA) using a temperature gradient starting from 120° C. to 260° C. at 5° C./min. Injector and detector temperature was 290° C. Hydrogen was used as carrier gas at a flow rate of 1 mL/min, a column pressure of 2 kg·cm², and the split ratio was 1:10. An external standard of fatty acid methyl esters was used for qualitative and quantitative determination of the liberated fatty acids.

6.1.5 Matrix-Assisted Laser Desorption/Ionization Time-of-Flight (MALDI-TOF) Mass Spectrometry MALDI-TOF MS was performed with a Bruker-Reflex II (Bruker-Franzen, Bremen, Germany) in linear configuration at an acceleration voltage of 20 kV. Lipid A was dissolved in aqueous TEN (0.07 M) at a concentration of 2 μg/μL, treated with a small amount of an Amberlite IR-120 ($H^+$) cation-exchange resin to remove excess of sodium and potassium, and 1 μL solution was mixed with 1 μL 0.5 M 2,4,6-trihydroxyacetophenone (Aldrich, Deisenhofen, Germany) in methanol as matrix solution. Aliquots of 0.5 μL were deposited on a metallic sample holder and analyzed immediately after drying in a stream of air. Mass spectra were recorded in the negative and positive ion mode. The instrument was mass calibrated externally with similar compounds of known chemical structure.

6.1.6 Nuclear Magnetic Resonance (NMR) Spectroscopy

For NMR analysis, the fully protonated Lipid A form had to be prepared which was obtained suspending 13 mg purified MPLA in 2 mL distilled water at 0° C., increasing the pH to ~9 by addition of 0.36 M aqueous TEN and consequent decreasing of the pH to ~2 by adding drop wise 0.1 M HCl in the cold. The precipitated Lipid A was isolated by centrifugation (2500 g, 5 min, 4° C.). The sediment was dissolved in 3 mL 4:1 chloroform/methanol (v/v) and washed three times with 5 mL distilled water. After removal of the solvent the residue was dried over $P_4O_{10}$ in a desiccator. NMR spectra of MPLA were recorded in 0.5 mL chloroform-d/methanol-$d_4$ 4:1 (v/v) in 5 mm high precision NMR sample tubes (Promochem).

Proton ($^1H$) and all proton detected 2D-NMR spectra have been recorded on a Bruker DRX-600 AVANCE spectrometer at 600 MHz. Spectra in 2:1 chloroform-d/methanol-$d_4$ (v/v) have been recorded at 295 K and referenced to internal methanol ($\delta_H$ 3.35 ppm, $\delta_C$ 49.0 ppm) $1H/^1H$—COSY experiments were performed using standard Bruker software (XWIN-NMR 2.6).

6.2 Results 6.2.1 Purification of Lipid A and TLC Analysis by Immunostaining

TLC analysis of the crude Lipid A hydrolysate, as it was obtained by acetic hydrolysis of LPS, revealed surprisingly only two fractions (FIG. 29). The following two MPLA fractions were obtained by preparative layer chromatography (PLC) and tentatively assigned based on their known $R_F$ values [Zähringer U., et al., 2001] and MALDI-TOF mass spectrometry: $MPLA_{hexa}$ ($R_F$ 0.77, 13.1 mg,), (yield 8% w/w). The $MPLA_{penta}$ present in all crude Lipid A was not further investigated.

6.2.2 Compositional Chemical Analysis of LPS: Sugars, Phosphate and Fatty Acids

Fatty acid analysis of the MPLA revealed (R)-3-hydroxytetradecanoate [14:0(3-OH)] (1411 nmol/mg) in a molar ratio of 3.7 mol/2 mol GlcN whereas 12:0 (1.0 mol/2 mol GlcN) and 14:0 (0.8 mol/2 mol GlcN) were found to be in the expected range. Phosphate was estimated as 0.9 mol/2 mol GlcN, compatible with the structure for the MPLA Lipid A backbone [(4'-P-β-D-GlcpN-(1'→6)-D-GlcpN]. Further analysis was necessary in order to assign the positions of the various fatty acids in the purified MPLA$_{hexa}$ by MALDI-TOF mass spectrometry and NMR spectroscopy for the complete structural analysis of the target molecule.

6.2.3 MALDI-TOF Mass Spectrometry of MPLA$_{hexa}$

The negative ion MALDI-TOF mass spectrum of MPLA-$_{hexa}$ revealed a prominent molecular ion peak [M$_{MPLAhexa}$-H]$^-$ at m/z 1716.15 (FIG. 30), being in excellent agreement with a MPLA$_{hexa}$ consisting of the de-1-phospho Lipid A backbone and carrying four 14:0(3-OH) and one of each 12:0 and 14:0 (calculated monoisotopic molecular mass M$_r$ 1717.21 for C$_{94}$H$_{193}$O$_{30}$N$_2$P). The spectrum also showed minor peaks most likely corresponding to fragmentation of 14:0 and [14:0(3-OH)+14:0], respectively.

6.2.4 NMR Spectroscopy of MPLA$_{hexa}$

The primary structure of MPLA$_{hexa}$ was further investigated by proton ($^1$H), carbon ($^{13}$C), and, phosphorus ($^{31}$P) NMR spectroscopy in 2:1 chloroform-d/methanol-d$_4$ (v/v). The 1D and 2D NMR spectra enabled an unambiguous determination of the primary Lipid A structure, including the phosphate and fatty acid substitution pattern (FIG. 31).

The reducing end of GlcN I showed two anomeric protons (H-1α 4.68 ppm and H-1β 4.03 ppm) with J$_{1,2}$-coupling constants of 3.5 Hz and 8.4 Hz, respectively indicating α- and β-configuration in the proportion of 5:1 for the reducing MPLA. The H-1' signal (4.26 ppm) of GlcN II (J$_{1,2}$ 8.1 Hz) indicated a β(1'→6) interglycosidic linkage in the Lipid A backbone. All other protons in GlcN I and GlcN II were assigned by $^1$H/$^1$H—COSY (FIG. 24c) and $^1$H/$^1$H-TOCSY (not shown) by consequent $^3$J$_{H-H}$ connectivities, starting from the H-1 or H-1' signals, respectively. All chemical shifts are in good agreement with previous published NMR data of non-derivatized Lipid A hexa-acyl molecules [Zähringer U., et al., 2001; Ribeiro A. A., et al., 1999].

The acylation pattern of the four primary [14:0(3-OH)] and two secondary fatty acids (14:0 and 12:0) was concluded from a comparison with NMR spectra of Lipid A$_{hexa}$ (Lipid A bisphosphate) [Ribeiro A. A., et al., 1999]. The diagnostic cross peaks of H-3$^c$, and H-3$^d$ in the primary fatty acids possessed the same chemical shift as the analogue nuclei in Lipid A$_{hexa}$, representing the identical acylation pattern (4+2).

Taking together the results of the chemical analysis, MALDI-TOF mass spectrometry, and 1D and 2D homo- and heteronuclear NMR spectroscopy, the structural identity of natural hexa-acyl monophoryl Lipid A (MPLA$_{hexa}$) from *E. coli* mutant strain F515 was unequivocally shown in this study. Its backbone was determined as [4'-P-β-D-GlcpN$^{II}$-(1'→6)-D-GlcpN$^I$] of which both amino groups in position 2 and 2' and both hydroxyl groups in position 3 and 3' were acylated by 3-hydroxytetradecanoic acids. The 14:0(3-OH) in positions 2' and 3' (GlcN II) are further acylated with 12:0 and 14:0, respectively. The hydroxyl groups at positions 4 (GlcN I) and 6' (GlcN II) of the Lipid A backbone are unsubstituted. The complete MPLA$_{hexa}$ structure is shown in FIG. 2.

7. EXAMPLE 7

Biochemical Characterisation of LPS-Disaggregating Activities of Fetal Ovine Hemoglobin and HEME-Free HbF 7.1 Methods Concerning the molecular mechanism of the enhancement of LPS bioactivities by adult mammalian hemoglobin (HbA) preparations, a profound dispersion of the physiologically predominating large LPS aggregates (MW≧10$^6$ Da) by HbA has been described [Roth, R. J., 1994; Kaca, W., 1994; Roth R. J., 1999]. For analysis of potential analogous effects of highly purified fetal ovine hemoglobin (s-HbF) an automated native PAGE assay was established employing the PhastSystem™ apparatus (Amersham Pharmacia Biotech). Briefly, Re-LPS purified from *E. coli* F515 or S-form LPS from *Salmonella enterica* sv. Minnesota 188233 at a final concentration of 0.275 µg/µl was incubated in the presence or absence of the analyzed hemoglobin preparations (0.375 µg/µl) at 37° C. for 30 min. Subsequently, the samples were placed in ice, adjusted to native PAGE conditions by the addition of four-fold concentrated native sample buffer (200 mM Tris HCl, pH=7.6; 40 mM 2-mercaptoethanol; 40% (w/v) glycerol; 0.008% (w/v) bromphenolblue) and sample volumes of 1 µl were automatically applied to the stacking gel zone of a PhastGel™ Homogeneous-20 gel equipped with native PhastGel™ Native buffer strips (Amersham Pharmacia Biotech) in the PhastSystem™ electrophoresis unit. Non-denaturing electrophoresis was performed at 4° C. and a constant voltage of 400 V in a programmed mode. Following native PAGE the gels were silver stained in the PhastSystem™ development unit according to the protocol of Heukeshoven and Demick [Heukeshoven, J., and Demick, R., 1988]. For control of the integrity of the protein components throughout the prior native incubation procedures SDS was added at a final concentration of 2% (w/v) and the samples were heated at 95° C. for 5 min. The denatured samples were finally analyzed by SDS-PAGE in PhastGel™ Homogeneous-20 gels equipped with PhastGel™ SDS buffer strips (Amersham Pharmacia Biotech) according to the standard protocol of the manufacturer and subsequent silver staining. In comparison to ovine HbF preparations of human HbA (SIGMA-Aldrich), adult ovine hemoglobin (s-HbA) and heme-free fetal ovine hemoglobin (s-HbF/hf) were analysed for LPS disaggregation activities in the native Phast™ PAGE assay.

7.2 Results

Native Phast™ PAGE analysis revealed that in the presence of ovine adult and fetal hemoglobin preparations as well as in the presence of human HbA both, R- and S-type LPS, electrophoretically migrated over a broader range of distances into the separating gel zones of the 20% polyacrylamide gels, whereas the non-hemoglobin treated LPS preparations were found to be retarded in the stacking gel zone in accordance with the predominant formation of large aggregates (MW≧10$^6$ Da) under the chosen native conditions (FIG. 32). The native PAGE data obtained for human HbA were analogous to results from a previous report employing a larger scale version of native PAGE [Kaca, W., 1994]. Our data strongly indicate a profound dispersion of LPS aggregates by the highly purified ovine HbA and HbF preparations [Roth, R. J., 1994; Kaca, W., 1994; Roth R. J., 1999]. In particular, the native electrophoresis data provided evidence for stronger LPS disaggregation activities of fetal ovine hemoglobin as compared to the ovine HbA preparation. Surprisingly, in an additional native Phast™ PAGE analysis the LPS disaggregation activities were shown to be preserved also in a heme-iron depleted preparation of fetal ovine hemoglobin (FIG. 33).

The observed profound dispersion of LPS aggregates represents a novel property of fetal ovine hemoglobin that has not been described for mammalian species to date. Moreover, in clear distinction from the well documented oxygen-transport functions of fetal hemoglobins our analysis surprisingly revealed that the observed LPS disaggregation activities are mediated by the protein (globin) chains of fetal ovine hemoglobin in a heme-iron independent fashion.

8. EXAMPLE 8

Synergistic Bioactivities of LPS or MPLA and Fetal Ovine Hemoglobin In Vitro 8.1. Nitric Oxide Induction by LPS or Lipid A and Hemoglobin
8.1.1 Methods
8.1.1.1 Reagents
LPS and free Lipid A from *S. enterica* sv. Minnesota Re-mutant R595 as well as MPLA were employed.
8.1.1.2 Mice
6- to 10-week old female and male BALB/c mice were obtained from the breeding facilities of the Max-Planck-Institut für Immunbiologie, Freiburg.
8.1.1.3 Preparation of Murine Bone Marrow-Derived Macrophages (BMDM)
see Example 3.1.1.1
8.1.1.4 Induction and Determination of Nitric Oxide Release in Murine BMDM
see Example 3.1.1.4
8.1.1.5 Human Cells
8.1.1.5.1 Isolation of Mononuclear Cells from Human Heparinized Blood Human mononuclear cells (MNC) from adult healthy donors were isolated on a ficoll-density gradient [Böyum, 1968]. MNC were washed four times in HBSS and resuspended in RPMI 1640 medium, supplemented with 1% L-glutamine and 1% penicillin-streptomycin, to adjust the concentration to $4 \times 10^6$ cells/ml.

8.1.1.5.2 Stimulation Assay and Detection of TNFα

The freshly isolated human MNC were plated at a density of $1.6 \times 10^6$ cells/400 µl per well in a 48-well dish. SHbF2 (10 µl/ml) and/or CLP2p (10 µl/ml) were preincubated with or without LPS (10 µl/ml) for 30 minutes at 37° C. and added to the MNC. Following incubation for 22-24 hrs, cell-free supernatants were harvested and analysed for TNFα release by ELISA.

8.1.2 Results (Mice)
8.1.2.1 Induction of NO Production by BMDMs Stimulated with LPS or Mono-Phosphoryl-Lipid A and HbF with and without Heme In order to investigate the dependence of synergistic effects between LPS and fetal hemoglobin as well as heme-free HbF, their ability to stimulate NO-production in BMDM was investigated.

In these experiments (FIGS. 34 *a,b*, 35 *a,b* and 36 *a,b*) a clear synergistic effect was visible, independent of the presence of the heme group and with both Re-LPS and mono-phosphorylLipid A. A synergistic effect was clearly visible demonstrating that the heme group is not necessary for the effect shown in these experiments.

8.2 Cytokine (TNFα and Interleukin 6) Induction In Vitro by LPS, Lipid A or Partial Structures and Hemoglobin or Substructures Derived Thereof
8.2.1 Methods Mouse splenocytes or human PBL (Ficoll-Hypaque purified) were incubated for 24 hrs at 37° C. in 1 ml MEM medium (with 10% FCS) at a concentration of $1 \times 10^6$ cells/ml, alone or in the presence of varying concentrations of LPS, with/without added LPS-free (LAL assay) FSLE or with and without Hb or subfractions. Supernatants were assayed for TNFα BY ELISA or bioassay (inhibition of growth of Wehi 1643 tumor cells), using recombinant mouse TNFα as standard.

8.2.2 Results

Two types of studies have been performed to assay the synergistic action between LPS and Hb or subfractions. In the first series of experiments (FIGS. 37 and 38) using murine spleen cells clear evidence for a synergy in the production of TNFα (FIG. 37) or IL-6 (FIG. 38) was seen when ovine fetal Hb (in contrast to ovine adult Hb) was used. In the second series of experiments human PBL's were treated with LPS and Hb. Again a striking synergy was observed for the production of TNFα (FIG. 39) when HbF was used as compared to HbA. Finally, using two independent human PBL donors (panels A and B of FIG. 40) different substructures of HbA or HbF were employed for their ability to produce this synergy. It is obvious that optimal synergy for TNFα production was caused by fetal Hb α,γ-dimers in conjunction with LPS (FIG. 40).

In a further set of experiments, the cloned γ-chain of sheep Hb was assayed in comparison with the cloned β-chain (FIG. 40*a*). As determined by TNFα-production of mouse spleen cells and as FIG. 40*a* shows, an impressive synergistic effect was seen between LPS and the γ-chain substructure which was not obvious in the case of the cloned β-chain. This result proves that the γ-chain is involved in the synergistic activity between LPS and Hb. It is however not excluded that the α,γ-dimer is involved in this synergistic effect.

8.3 Synergism between Monophosphoryl Lipid A (MPLA) and Purified Sheep γ-Chain the Human System In order to analyse whether the biochemically purified fetal sheep γ-chain would exhibit a synergistic activity, its effect on the bioactivity of MPLA was analysed (FIG. 40*b*). As determined by TNFα release by human peripheral monocytes, the purified γ-chain exhibited a dramatic effect in enhancing MPLA bioactivity the α-chain being much less active (FIG. 40*b*). These results support the previous notion that the γ-chain is involved in mediating the Hb effect on LPS bioactivity.

8.4 Synergy between LPS, Hb and CLP In Vitro in the Mouse System

The results obtained demonstrating a synergistic effect between LPS and Hb and an enhancing activity by CLP pools is shown in FIG. 40*c*. As determined by TGFβ release from murine spleen-cells, LPS alone and Hb substructures alone (upper panel) led to low cytokine release (<250 pg/ml). If LPS and Hb substructures were analysed together with CLP1b or CLP2p (lower panel) a clear synergistic effect was seen in the case of the fetal γ-chain. In fact, the addition of CLP1b enhanced the TGFβ production about twofold (middle panel) as compared to controls (upper panel, without CLP1b). These data show that in CLP1b/CLP2p and accordingly in FSLE (a) molecule(s) are (is) present which accentuate(s) the LPS/Hb synergism in the murine spleen cell system.

8.5 Synergy between LPS, Hb and CLP In Vitro in the Human System

In order to test whether FSLE (in the form of CLP2p) exerts a modulatory activity in the synergistic sHbF/LPS system, also in the case of human cells, human peripheral monocytes were treated in combination of LPS, sHbF and CLP2p as described in section 8.1.1.5.1. As determined by TNFα production and shown in FIG. 40*d*, a significant enhancement of the synergistic LPS/sHbf effect was seen if CLP2p was added. This result shows that in FSLE(a) factor(s) are (is)

9. EXAMPLE 9

Modulation of Immune Functions In Vivo Following Administration of LPS, Hb and Subfractions as Well as FSLE and LPS, Particularly by the Oral Route

9.1 Methods

Mice received challenges by gavage (in 100 µl PBS) and/or by the i.p. or i.m. route. Animals were sacrificed after 24 h and serum was assayed for TNFα (see Example 8.2.1) and IFNγ (ELISA). In addition, peritoneal wash fluid was centrifuged to remove cells and similarly assayed for cytokine levels.

9.2. Results

In most of the work described so far, whenever CLP-Pools (1b/2p) were given in vivo, either i.p.-, i.m.- or i.v.-injections were applied. It was investigated whether these fractions would act (locally and systemically) following other routes of administration such as the oral route.

9.2.1 Synergy between CLP, LPS and Hb Including Substructures Thereof In Vivo To investigate evidence for synergy between FSLE, Hb structures and LPS in cytokine induction the indirect stimulation of TNFα and IFNγ cells was studied in vivo. Mice received 10 µg LPS by ip or gavage (in 100 µl of PBS), or FSLE by gavage (300 µg/mouse). Each preparation was given either alone or in combination. Animals were sacrificed at 24 hrs and blood collected by cardiac puncture. 2.0 ml of warm MEM with 10% FCS was injected into the peritoneal cavity, and the cavity wash was collected sterilely. The latter, and serum, were then titrated for estimation of TNFα and IFNγ concentration as in FIG. 41. Again only data from bioassays are shown (equivalent data were obtained in ELISA-bioassay and data for IFNγ using Wehi 279 cells). In addition, only data for one serum concentration and one concentration of wash fluid (in each case 20 µl/200 µl test well) are shown. As shown in the FIG. 41 a synergistic increased production of TNFα (in serum) and IFNγ (in peritoneal wash) was seen following oral gavage with CLP, whether LPS was administered orally or by ip route. Optimal synergy seemed to follow gavage with both FSLE/LPS.

In previous studies [Gorczynski, R. M., 1997; Gorczynski R. M., 1998] we reported that chronic administration of CLP in vivo to aged mice would reverse the polarization in cytokine production seen when spleen cells from those animals were stimulated in vitro with Con A. Thus, cells from young animals (~8 weeks of age) generally produce predominantly type-1 cytokines (IL-2, IFNγ) while in contrast cells from aged mice (>20 months) produce predominantly type-2 cytokines (IL-4, IL-10). However, after chronic administration of FSLE we reported that even cells from aged mice produced predominantly type-1 cytokines after ConA activation in vitro. However, in these systems CLP1b and CLP2p or synergistic activity with LPS had not been analyzed.

Now we investigated whether there was a synergy between LPS and CLP in this reversal of polarization in cytokine production from aged cells. Groups of 5 mice received gavage with LPS (10 µg/mouse) or FSLE (150 µg/mouse) alone or in combination, with gavage performed on days 0 and 10 of study. All mice were sacrificed at 20 days, individual spleen cell preparations made, and cells stimulated for 40 hrs with Con A (5 µg/ml). Supernatants were assayed for IL-2 and IL-4 by ELISA and bioassay (stimulation of growth of CTLL-2 or CT4.S respectively). Only data for ELISA assays are shown in FIG. 42 (arithmetic group means-one of 3 studies).

Cells from young mice produce predominantly the type-1 cytokine IL-2, regardless of pretreatment (data to right of FIG. 42). In contrast, aged mice (untreated) produce predominantly the type-2 cytokine (IL-4) rather than IL-2 (data to far left of FIG. 42). However, following combination treatment with LPS and FSLE, there is a marked shift in cytokine production from aged mice, with predominantly IL-2 production, as in young animals. This is not seen following gavage with either FSLE or LPS alone at the doses used, though at much higher doses (300-500 µg FSLE/mouse), and more frequent exposure (4× at 5 day intervals), FSLE alone produces similar effects.

9.2.2 Analysis of Synergy in Induction of TNFα In Vivo Following Gavage of Mice with CLP and LPS or Lipid A Partial Structures, or Purified Hemoglobin Chains and LPS In order to investigate synergistic interactions in vivo between FSLE (or hemoglobin protein chains) and LPS (or Lipid A fractions), the following studies were performed. Groups of 5 C57BL/6 mice received at least one stimulus by gavage in 100 µl saline. In experiments presented in FIG. 43, the other, stimulus (LPS or Lipid A partial structures) was given intraperitoneally. In experimental data shown in FIG. 44 the additional stimulus (LPS) was included in the gavage solution. All mice were sacrificed 24 hrs later when serum was collected and assayed in triplicate for cytokines by ELISA. Further details are given in the Figure legends.

It is clear that independent of whether synergy between FSLE and LPS (or Lipid A partial structures—see FIG. 43), or between hemoglobin chains and LPS (FIG. 44) was investigated, clear evidence of enhanced TNFα production was observed, when at least one of the stimuli was given by oral gavage. In fact, data presented in FIG. 44 indicate that even if both stimuli are given by gavage synergy exists (see also FIG. 42).

9.2.3 Separate Application of LPS and CLP1b

Mice received the different pools (CLP1b/CLP2p) by i.v.-, i.p.- or i.m.-injection, as well as by gavage (in 0.2 ml sterile PBS). Doses ranged from 0.5-50 µg/mouse. Animals were sacrificed at various times post treatment (from 1 to 48 h). In some cases lymphoid cells from various sources (spleen; Peyer's Patch (PP); axillary LN; mesenteric LN; peritoneal cells) were incubated without further stimulation for 24 h and cytokines in the cell supernatant assayed. Data showing cytokine production from PP cells after gavage of CLP1b are shown in Table 7.

In Table 7 only cytokine data for PP following gavage of CLP1b are shown. However, our combined data indicate that mRNAs and functional production of bioactive cytokines/chemokines is stimulated locally (in the PP and MLN) after gavage with CLP1b and/or CLP2p, while i.m.- i.p.- or i.v.-injection induces similar chemokines/cytokines in a systemic fashion (axillary LN, spleen). Table 7 also shows that quantitatively CLP1b, after oral gavage, is more active than "free" LPS as assayed by cytokine induction. The data also indicate that the active fetal principle is resistant to enzymes of the digestive tract, in accord with the findings about protease resistance of CLP1b and CLP2p (see Example 3.2.2).

TABLE 7

| Treatment of mice[a] | Spontaneous cytokine production from (Peyer's Patch)[b] cells after 24 h in culture | | |
|---|---|---|---|
| (24 h before sacrifice, all doses in µg) | TNFα [ng/ml] | TGFβ | IL-6 [pg/ml] |
| None | <5.0 | <5.0 | 30 |

TABLE 7-continued

| Treatment of mice[a] | | Spontaneous cytokine production from (Peyer's Patch)[b] cells after 24 h in culture | | |
|---|---|---|---|---|
| (24 h before sacrifice, all doses in μg) | | TNFα [ng/ml] | TGFβ | IL-6 [pg/ml] |
| CLP1b | 50 μg | 92 | 61 | 380 |
| CLP1b | 15 μg | 79 | 51 | 325 |
| CLP1b | 5 μg | 34 | 28 | 180 |
| CLP1b | 1.5 μg | 28 | 21 | 155 |
| CLP1b | 0.5 μg | 21 | 18 | 120 |
| LPS | 250 μg | 70 | 41 | 255 |
| LPS | 50 μg | 24 | 19 | 140 |
| LPS | 10 μg | 14 | 14 | 67 |
| LPS | 2.0 μg | 6.2 | n.d. | n.d. |
| LPS | 0.4 μg | n.d. | n.d. | n.d. |

[a]Groups of 5 C57BL/6 mice (8 weeks of age) received LPS or CLP1b by gavage (in 0.2 ml PBS) 24 h before sacrifice. Cell recovery was the same in all groups. Individual cell suspensions from the Peyer's Patch of each individual were cultured (2 × 10$^6$ cells/ml) for 24 h in αMEM with 10% FCS with no further stimulation. Supernatants were assayed for cytokines as before.
[b]Arithmetic mean (SD < 15% in all cases) for different cytokines.
n.d. indicates below limits of detection in assay (not detectable).

10. EXAMPLE 10

Immunomodulating Activities of CLP Pools

Part I

CLP Pool Activities Including TNFα Production, NO Production, and Spleen Cell Proliferation Using TLR4 Gene Deficient Mice
10.1 Methods
10.1.1 Mice C57Bl/10ScSn and Balb/c mice (both LPS responder) and C57Bl/10ScCr mice (LPS non-responder, TLR4 gene deficient mice), were obtained from the Max-Planck-Institut für Immunbiologie, Freiburg, FRG. Mice were housed at 3-5/cage and allowed food and water ad libitum.
10.1.2 Preparation of Splenocytes Mice (6-8 weeks of age) were sacrificed by cervical dislocation. Spleens were removed aseptically and the tissue disrupted using a glass homogenizer (Braun, Melsungen, Germany). The resultant cell suspensions were washed twice using RPMI without supplements and resuspended in RPMI containing 10% FCS, 100 U/ml penicillin, and 100 μg/ml streptomycin (cRPMI).
10.1.3 Determination of Spleen Cell Proliferation Splenocyte proliferation was determined by measuring $^3$H-thymidine incorporation into DNA. Cultures were set up in flat bottom microtiter plates in a total volume of 150 μl/well. 3×10$^5$ splenocytes and CLP1b (100, 20, 4 μg/ml), CLP2p (100, 20, 4 μg/ml), or LPS (1, 0.1 μg/ml) were cultured in cRPMI at 5% $CO_2$. Control cultures received plain medium. After 24 h cells were pulsed for 24 h by the addition of $^3$H-thymidine (23.125 KBq/well). After freezing and thawing the $^3$H-thymidine incorporation into DNA was determined by liquid scintillation counting.
10.1.4 Determination of TNFα Production For stimulation, bone marrow-derived macrophages (BMDM) (4×10$^5$/well) with a total volume of 600 μl/well were set up in 24 well microtiter plates (Fa. Falcon, Becton Dickinson Europe, Le Pont de Claix, France) and stimulated with LPS (10 ng/ml-0.01 ng/ml) and 5 μg/ml FSLE (Lot 072). Control cultures received plain medium. Cultures were incubated at 37° C., 5% $CO_2$. For determination of cytokine production supernatants were collected after 4 or 24 h. Cytokine concentrations in the supernatants were determined by ELISA (all reagents from Pharmingen, BD Biosciences, Heidelberg, Germany) according to the instructions of the manufacturer.
10.1.5 Determination of NO Production The determination of NO production in the supernatants of bone marrow-derived macrophage cultures was performed as described in Example 3.1.1.4.
10.2 Results
10.2.1 Induction of Spleen Cell Proliferation Using TLR4 Gene Deficient Mice The results of the spleen cell proliferation experiments are demonstrated in FIG. 45. Cells from C57Bl/10 ScSn mice showed a normal reaction to LPS, as can be seen by a markedly increased $^3$H-thymidine incorporation after stimulation with 1 and 0.1 μg/ml LPS. The closely related C57Bl/10 ScCr mice bear a null mutation in the LPS gene located on chromosome 4 [Poltorak, A. 1998]. This renders their cells, as shown here for splenocytes, highly refractory to LPS stimulation. In LPS responder mice, CLP1b induced a markedly increased $^3$H-thymidine incorporation at 100, 20 or 4 μg/ml, maximum activity was found around 100 μg/ml. The activity of CLP1b exceeded that of CLP2p. In LPS nonresponder mice CLP1b and CLP2p induced much lower, but significant $^3$H-thymidine incorporation at 100, 20 or 4 μg/ml.
10.2.2 Induction of NO Production Using TLR4 Gene Deficient Mice The results of the experiments on the induction of NO production using bone marrow derived macrophages from TLR4 gene deficient mice are demonstrated in FIG. 46. BMDM from C57Bl/10 SCSn LPS responder mice showed a strongly enhanced nitric oxide release after stimulation with the doses used (0.8-100 μg/ml) CLP1b or CLP2p for 48 h. In C57Bl/10 ScCr LPS nonresponder, TLR4 deficient mice, CLP1b and CLP2p were active to a much lower degree. This experiment proves that the bioactivity of CLP pools is dependent on LPS but that part of the activity is mediated by another factor(s).

11. EXAMPLE 11

Immunomodulating Activities of CLP-Pools

Part II

Reversal of Age-Associated Immune Imbalances
11.1 Biological Systems (Methods)
11.1.1 Murine Systems in Age-Related Experiments Young (8 week) and aged (100-115 week) BALB/cNia, DBA/2Nia and C57BL/6Nia mice were purchased from the National Institute on Aging from Charles River Laboratories (Stony Ridge, N.Y.). Mice were housed 5/cage and allowed food and water ad libitum. All mice were used within 2 weeks of arrival from the supplier. In some cases mice received 800 Rads γ-irradiation ($^{137}$Cs source, dose rate 102 R/min), with spleen cell reconstitution as induced via the lateral tail vein.
11.1.2 Treatment of Mice with Pools of FSLE Animals received intraperitoneal injections with 10-100 μg of CLP1b/CLP2p in 0.25 ml PBS every 3.5 days for either 4 treatments or for 6 treatments (after irradiation and spleen cell reconstitution). Mice were sacrificed 2 days after the last injection and spleen (or Peyer's Patch, lymph node) cells harvested. In some cases mice were immunized in vivo with 4×10$^8$ sheep erythrocytes (SRBC), or received 1×10$^5$ syngeneic bone marrow cells after lethal irradiation (900 Rads). In some experiments some groups also received daily i.v. injections with N$^G$-methyl-L-arginine (L-NMMA), at a dose of 30 mg/kg.

11.1.3. Determination of Cytokines

In cultures used to assess cytokine production $5 \times 10^5$ responder cells were stimulated in triplicate in microtitre plates with either 5 µg/ml ConA or in plates with wells pre-coated with anti-CD3-ε (100 ng/ml). Supernatants were pooled at 40 h from replicate wells and assayed in triplicate for lymphokine production in ELISA assays.

For IFNγ assay flat-bottomed 96-well Nunc plates (Gibco, BRL) were used, coated with 100 ng/ml R4-6A2. Varying volumes of supernatant were bound in triplicate at 4° C., washed 3×, and biotinylated anti-IFNγ (XMG1.2) was added. After washing, plates were incubated with strepavidin-horse radish peroxidase, developed with appropriate substrate and $OD_{405}$ determined using an ELISA plate reader.

IL-10 was assayed using a similar ELISA system with JES5-2A5 as the capture antibody, and biotinylated SXC-1 as developing antibody. ELISA assays for IL-2 and IL-4 used JES6-1A12 and 11B11 as capture antibodies, with biotinylated JES6-5H4 or BVD6-24G2 as developing antibodies. The sensitivity of detection was 10 pg/ml for all cytokines as determined in studies using purified recombinant material.

IL-1 assays used the cytokine-dependent cells D10, while IL-6 assays used the B9 cell line. TGFβ was assayed using inhibition of growth (over 40 hr of incubation) of a mink lung epithelial cell line (ATCC). TNFα was similarly assayed by inhibition of growth of the Wehi 1643 cell line (ATCC). In all cases the sensitivity of detection was 30 pg/ml cytokine, again as determined by standardization using recombinant material.

No differences in cytokine levels have been detected from cultures between 36 and 50 h of culture, and no significant differences have been seen between anti-CD3-ε and ConA stimulated cells. Antibody forming assays for SRBC were standard Jeme PFC assays, as modified by Cunningham [Gorczynski, R. M., 1978]; spleen colony counts were performed at 12-14 days post irradiation and bone marrow reconstitution.

11.2. Biological Systems (Results)
11.2.1. Role of CLP1b and CLP2p as Anti-Aging Principles Profound changes in age-associated immune responsiveness have been documented for all mammalian species studied to date [Wechsler, M. E., 1992; McLachlan, J. A., 1995; Burns, E. A., 1997]. These alterations seem most marked in the T cell compartment of the immune system. A number of studies have addressed possible explanations for this dysregulation of T cell immunity with age, asking whether there is a universal decline in the frequency of responding cells, a functional change in the capacity of cells to respond with age, and/or interruptions in the highly orchestrated network of cytokines, growth factors and hormones which regulate the overall functioning of the immune system [Miller, R. A., 1996]. The following studies clearly demonstrate that CLP1b/2p can reverse age-associated immune changes in mice.

In the experiment shown in Table 8, groups of young or aged DBA/2 or C57BL/6 mice received infusions of CLP2p or saline only (no treatment) prior to immunization with SRBC. Anti-SRBC spleen IgG-PFC were determined at 7 days post immunization. It is clear that the 3-fold decline in IgG-PFC seen in aged mice is reversed in mice receiving CLP2p prior to immunization.

TABLE 8

Restoration of antibody production in aged DBA/2 and C57BL/6 mice after CLP2p injection

| Mouse strain[a] | Treatment[b] | Antibody Production IgG PFC/$10^6$ spleen cells (day 7)[c] |
|---|---|---|
| DBA/2 | | |
| Young | None | 3,255 ± 565 |
| Young | CLP2p | 3,015 ± 635 |
| Aged | None | 1,105 ± 360 |
| Aged | CLP2p | 2,850 ± 510* |
| C57BL/6 | | |
| Young | None | 3,345 ± 610 |
| Young | CLP2p | 3,650 ± 545 |
| Aged | None | 1,240 ± 415 |
| Aged | CLP2p | 3,010 ± 675* |

[a]6 mice were used/group. Young mice were 12 weeks of age, aged from 100-120 weeks. All mice received 4 × $10^8$ sheep erythrocytes (SRBC) i.v. in 0.5 ml PBS.
[b]Mice received 5 i.v. injections of CLP2p (50 µg/mouse) at 3 day intervals before SRBC immunization.
[c]PFC/1 × $10^6$ spleen cells in mice at 7 days post SRBC. Mean cell recovery/spleen was equivalent in all groups (120 × $10^6$ ± 10 × $10^6$)

A second series of studies addressed the question whether CLP2p is able to also enhance spleen colony formation from bone marrow after lethal irradiation, a measure of hematopoietic reconstitution [Worton, R. G., 1969]. Eight mice/group of young or aged DBA/2 mice received saline or CLP2p i.v. (3 injections) prior to lethal irradiation and reconstitution with $1 \times 10^5$ syngeneic bone marrow cells from young (12 week) DBA/2 donors. Animals were sacrificed 12 days after reconstitution and spleen colonies counted (Table 9).

TABLE 9

CLP2p has an effect on hematopoietic reconstitution of irradiated (900Rad) young DBA/2 mice, as assessed by spleen colony assay

| Bone marrow[a] | Treatment of recipients[b] | CFU-S (day 12)/1 × $10^5$ bone marrow[c] |
|---|---|---|
| Young | None | 8.4 ± 2.6 |
| Young | CLP2p | 16 ± 3.3* |
| Aged | None | 8.0 ± 2.9 |
| Aged | CLP2p | 14 ± 3.1* |

[a]Bone marrow was pooled from 3 donors/group. Young mice were 12 weeks of age, aged mice were 24 months of age.
[b]Mice received CLP2p i.v. x3 (50 mg/mouse/injection) at 3 day intervals before irradiation.
[c]Mice were sacrificed at 12 days and spleen colonies counted visually. Data are arithmetic means (+SD) for 8 mice/group.
*p < 0.05 compared with age-matched control.

These data show that CLP2p is able to reverse the decline in PFC (to SRBC) in aged mice, and to increase spleen colony formation (lympho-hematopoietic regeneration) after lethal irradiation and bone marrow reconstitution (Table 9).

11.2.2 Capacity of CLP1b and CLP2p to reverse cytokine Production in Aged Mice As noted above, a most important observation in the immunological literature is the evidence that aging is associated with altered production of cytokines from stimulated lymphocytes [Miller, R. A., 1996; Wechsler, M. E., 1992]. While young animals (and humans) produce mainly IFNγ and IL-2, with age increased amounts of IL-4, IL-6, IL-10 and TGFβ are produced. Accordingly, a series of investigations was designed to assess whether FSLE and, in particular, the CLP pools (CLP1b or CLP2p) injected into mice are able to reverse the altered cytokine production profile in aged mice, and to what degree these effects might be explained by the (known) alteration in the numbers of naïve v.s. memory lymphocytes in aged animals (see [Gorczynski, R. M., 1998] for FSLE).

Groups of young or aged DBA/2 mice received i.m. injections with CLP1b (or CLP2p) prior to sacrifice. Spleen cells were stimulated in vitro with ConA and supernatants harvested to assess cytokine production at 40 h. Data pooled from 2 such studies are shown in Table 10.

TABLE 10

CLP pools reverse age-related cytokine production in leukocytes from aged mice

| Source of Donor cells[a] | Cytokine levels in culture supernatants[b] | | | | | | |
|---|---|---|---|---|---|---|---|
| | IL-2 pg/ml | IL-4 | IL-6 | IL-1 ng/ml | IL-10 | TGFβ | IFNγ |
| Young-NS | 1025 ± 210 | 50 ± 9 | 30 ± 42 | 6.3 ± 1.5 | 13 ± 3 | 50 ± 9 | 85 ± 15 |
| Aged-NS | 340 ± 76* | 200 ± 17* | 930 ± 145* | 16 ± 2.5* | 60 ± 9* | 102 ± 21* | 160 ± 22* |
| CLP1b | 530 ± 60* | 90 ± 14* | 650 ± 110* | 12 ± 2.2* | 49 ± 10* | 85 ± 11* | 114 ± 18* |
| CLP2p | 840 ± 120# | 69 ± 10# | 490 ± 85*# | 8.0 ± 1.8# | 25 ± 5# | 58 ± 10# | 103 ± 19# |

[a]Individual spleen cell samples were tested from 4 donors/group. $5 \times 10^5$ responder cells were incubated in triplicate with 5 μg/ml ConA in microtitre plates, and supernatants harvested at 40 h. Mice received 5 i.m. injections with 50 μg/mouse CLP1b (or CLP2p) at 3 day intervals, prior to sacrifice and use of spleen cells for cytokine production in vitro 3 days after the last injection. Control (untreated) mice received normal saline (NS) only. Tests on CLP pools are shown for aged mice only.
[b]Arithmetic mean (±SD) cytokine levels, averaged over three studies, from triplicate assays using cultures of cells from young (8-weeks) or aged (110 weeks) DBA/2Nia mice.
There was no significant effect of CLP-pool treatment on cytokine production from young recipients (data equivalent to first row).
*p < 0.05, compared with control (first row).
p < 0.05, compared with age-matched control mice injected with PBS alone.

These data clearly indicate that CLP1b/2p, injected at concentrations of 50 μg/mouse, reverse the alteration in cytokine production seen using stimulated lymphocytes from aged individuals.

It has previously been demonstrated that age-associated immune imbalances can be counterregulated by dehydroepiandrosterone (DHEA) and its sulfate-derivative (DHEAS) [Daynes, R. A., 1992; Daynes, R. A., 1993]. CLP1b and CLP2p do not contain DHEA or DHEAS. Whereas CLP pools, efficient in mice, do not cause detrimental or unwanted side effects, there was some warning raised with regard to clinical application of DHEA [Durgan, J., 1997].

12. EXAMPLE 12

Immunomodulating Activities of CLP Pools

Part III

Anti-Tumoral Activity of CLP-Pools
12.1 Further Murine Systems (Methods)
12.1.1 Determination of Macrophage/Splenocyte Mediated Tumor Cytostasis (Proliferation Assay)

Macrophage and spleen cell mediated cytostasis was determined in co-cultures of effector and target cells by reduced incorporation of $^3$H-thymidine (methyl$^3$H-TdR, specific activity 5 Ci=185 GBq/mMol, Amersham Buchler, Braunschweig, FRG) into the tumor cell DNA. Cultures were set up in flat bottom microtiter plates in a total volume of 200 μl. $5 \times 10^3$ tumor cells together with BMDM and/or spleen cells and CLP pools at various concentrations were cultured in cDMEM (Abelson) or cRPMI (Sp2/0) for one to three days at 10% and 5% $CO_2$, respectively. Proliferating cells were labelled for the last 4 h by addition of 25 μl=0.5 Ci$^3$H-TdR/well. Labelled cultures were frozen (−20° C.) and thawed and harvested on glass fiber filter plates with an automatic cell harvester (Pharmacia LKB, Freiburg, FRG). Incorporated radioactivity was determined by liquid scintillation counting (Beta Plate, Pharmacia LKB). Control cultures containing only BMDM and/or spleen cells were treated accordingly and cpm values from these cultures were subtracted from those of the co-cultures to correct for radioactivity incorporated by effector cells.

12.2 Induction of Anti-Tumoral Activities by FSLE/CLP-Pools in the Murine System 12.2.1 Tumor Cell Growth Inhibition by Macrophages and/or Spleen Cells Stimulated with CLP1b/2p CLP1b/2p have been applied to the TCGI assay in a wide concentration range. Both pools induced a strong dose-dependent macrophage activation and, in consequence, a pronounced inhibition of Abelson 8-1 tumor cell growth starting at concentrations around or below 1 μg/ml (FIG. 47A). The addition of spleen cells to the co-cultures of macrophages and tumor cells led to a markedly increased TCGI activity in cultures set up with CLP1b or CLP2p (FIG. 47B).

12.2.2 Anti-Metastatic Activity of FSLE

Since tumor metastasis from a primary tumor is a crucial medical problem, models for studying that phenomenon are of great interest. A system using the Lewis-lung carcinoma, a tumor which once arose spontaneously in C57Bl/6 mice [Seguira, S., 1955], is particularly useful because it metastases into the lungs. Its high malignancy has been related to its low immunogenic properties [De Wys, W. D., 1972].

The model works as follows [Berdel, W. E., 1981]: 1 million viable tumor cells in 0.05 ml of medium are injected subcutaneously into the left hind foot of each mouse. Within 6-10 days the injected foot reaches a diameter of 0.5-0.6 cm, due to tumor growth. 18-21 days after the primary tumor transplantation the animals begin to die from lung metastases.

Imitating the clinical situation, the primary tumor can be surgically removed at any given time after tumor transplantation. With or without further treatment, the lungs of the animals can be examined for the number of micro-metastases which are counted histologically after staining. —Only if surgery is done at an early stage after tumor transplantation, metastases can be prevented.

Using this system, FSLE was injected, starting 1 day after surgery with a subcutaneous dose of 1 mg in 0.1 ml into a group of 10 mice which was repeated twice, after 2 and 4 days. The controls received 0.1 ml of sodium chloride. The animals were observed over the following weeks. As expected, all controls died from lung metastases within day 18 to 39 of the experiment, as shown in FIG. 48. In contrast, until day 39, 8 of the extract-treated group (80%) were still alive, and none of them died within the following 120 days. Histologic controls revealed that the survivors had no lung metastases. Similar results are being obtained with injections of 10 μg/ml of CLP2p.

12.2.3 Macrophage- and Lymphocyte-Activating Potential of Liver Extracts Prepared from Sheep at Different Developmental Stages To determine the level of macrophage- and splenocyte-activating factors in sheep liver extract, or pools at different stages of development, liver extracts from newborn as well as from 3-4 year old animals were prepared, separated on Sephadex G-100®, and the resulting fractions pooled as described in Example 2. These pools were tested in comparison to the corresponding CLP pools for TCGI inducing activity. Major differences became apparent in the CLP2p pools: CLP2p from fetal and newborn animals was 100 to 1000 times more active in macrophage stimulation than CLP2p prepared from adult animals (FIG. 49). When comparing the relative TCGI activities of pools 1b and 2p prepared from extracts at different developmental stages in a way that the activity of the most active pool from each separation (fetal extract, extract from newborn and extract from adult sheep) is arbitrarily set to 100 (see FIG. 50), it becomes apparent, that the relative activities of CLP1b and CLP2p are decreasing after birth. This could be explained either by the disappearance of a stimulator activity in the course of fetal life, or by a modification of a fetal active principle around birth, —such as hemoglobin—resulting in a different behaviour of the compound during separation.

This indicates that the here described bioactive principle(s) may be produced preferably from liver tissue prepared before or at birth (FIGS. 49 and 50).

12.3 Human System (Methods)

12.3.1 Isolation of Human MNC from Peripheral Blood and Enrichment of Monocytes

Blood samples were obtained from healthy human donors (Transfusionmedicine, University Hospital Freiburg). Blood was diluted 1:2 with PBS and mononuclear cells (MNC) were collected using a Ficoll-Paque gradient (density 1.077 g/ml, Pharmacia, Freiburg). Cells were washed four times with PBS and added to Petri dishes ($1-2\times10^8$ MNC/20 ml RPMI 1640 (F1215, Seromed Biochrom KG, Berlin) precoated with human autologous plasma. The cells were incubated for 1-1.5 h allowing monocytes to adhere. Thereafter, non-adherent cells were carefully discarded and the adherent monocytes were gently detached with a cell scraper. Cells were washed once and either resuspended in RPMI 1640 with 10% FCS, 1% non-essential amino acids, 100 U/ml penicillin, 100 μg/ml streptomycin (cRPMI) for the direct use in cytostasis assays or further differentiated in vitro into macrophages (see below).

12.3.2 Assay for Monocyte-Mediated Tumor Cytostasis

Cytostasis assays were performed in flat bottom microtiter plates (Falcon 3075, Becton Dickinson, Heidelberg) in cRPMI (see above). Isolated human monocytes ($5\times10^4$ or $2.5\times10^5$/well) were incubated together with $5\times10^3$ U937 tumor cells and various concentrations of the different stimuli in a total volume of 200 μl/well for 72 h at 37° C., 5% $CO_2$. For the last 4 h of co-culture, the proliferating tumor cells were labelled by the addition of [$^3$H]-thymidine (125 Bq=0.625 Ci/well; specific activity: 185 GBq/mmol; Amersham Buchler, Braunschweig). After freezing and thawing, the cultures were harvested on glass fiber filters with an automatic cell harvester (type 1295-001, Pharmacia LKB, Freiburg) and the radioactivity incorporated into the DNA of the tumor cells was measured in a liquid scintillation counter (Betaplate 1205, Pharmacia LKB). The inhibition of proliferation, i.e. the reduction of incorporated radioactivity was calculated defining U937 cells incubated in the presence of unstimulated monocytes as unaffected controls (0% inhibition).

To measure the tumor cytostatic activity of monocyte-derived soluble factors, $5\times10^5$ monocytes/500 μl/well were stimulated in 24-well-plates for 4-48 h. Supernatants were harvested at different time points, centrifuged at high speed to remove any cell debris and tested for cytostatic activity. To this, 50 μl supernatant were added to $5\times10^3$ U937 cells in flat bottom microtiter plates; total culture volume was 200 μl. Cultures were kept for 48 h, for the last 4 h proliferating cells were labelled with [$^3$H]-thymidine. Incorporated radioactivity was determined and calculations were done as described above.

12.3.3 Induction of LAK Cell Activity by CLP1b and CLP2p

Human PBMC were obtained by density gradient centrifugation on Ficoll for 20 min at 1400×g (density 1.077 g/ml, Pharmacia LKB, Freiburg, FRG). To remove contaminating platelets, the collected cells were washed up to six times with phosphate-buffered saline (PBS). Monocytes and B lymphocytes were reduced by adherence to plastic for 1 h at 37° C. and 5% $CO_2$. Nonadherent cells were cultured in RPMI 1640 supplemented with 25 mM HEPES, 2 mM L-glutamine, 1% NEAA 10% heat-inactivated fetal calf serum, 100 U/ml penicillin, 50 μg/ml streptomycin (all Seromed Biochrom KG, Berlin). The cells were cultured at a concentration of $1\times10^6$/ml for 3-4 days at 37° C. and 5% $CO_2$. For LAK cell generation, rhuIL-2 (100 U/ml; Becton Dickinson, Heidelberg, FRG) or a 1:1 mixture of CLP1b and -2p was added to the corresponding cultures.

12.3.4 Determination of CLP Pool-Induced LAK Cell Activity 3,3'-dioctadecyloxacarbocyanine perchlorate ($DIOC_{18}(3)$/ "DIO"; 2.5 mg/ml in DMSO; Molecular Probes, Eugene, Oreg., USA) was added directly to Raji cells ($5\times10^5$/ml) in a final concentration of 10 μg/ml. Labeling was performed overnight under standard culture conditions. Before onset of the cytotoxicity assay, cells were washed in culture medium to remove free label.

$1\times10^5$/ml prelabelled target cells were resuspended in medium and dispensed in 96 well microtiter plates (3077, Becton Dickinson, Heidelberg, FRG; 100 μl/well). Effector cells were also resuspended in medium at a cell density of $1\times10^6$/ml; 100 μl, 20 μl or 3.3 μl of the effector cell suspensions were added to the target cell cultures to yield the final effector-target ratios (E:T) of 10:1, 1:1 and 0.3:1. As control, only medium was added to the target cell cultures. Incubation of the cells was performed in a final culture volume of 200 μl for 4 hours at 37° C. and 5% $CO_2$. For flow cytometric analysis, cells of each well were resuspended and transferred into round bottom tubes (2058, Becton Dickinson). FACS data acquisition and analysis were performed on an EPICS XL-MCL flow cytometer (Coulter) equipped with an argon ion laser at an excitation wavelength of 488 nm. Before measurement, propidium iodide (PI, final concentration: 20 μg/ml) was added to the samples. The DIO fluorescence was recorded in the green channel (FL1) using a 530×20 nm bandpass filter, while PI fluorescence was measured in the red channel (FL3; 630 nm longpass filter). Fluorescence was recorded on a logarithmic scale without compensation of inter-channel crosstalk, while forward and right angle scatter characteristics were recorded on a linear scale. Calculation of specific lysis (in %) was performed by subtracting the non-specific cell death in control samples (in %) from % lysis of target cells in experimental samples, whereby analysis included only FL1-FL3 double positive events:

$$\% \text{ specific lysis} = \% [FL1^+/FL3^+]_{exp.} - \% [FL1^+/FL3^+]_{control}$$

12.4 Induction of Anti-Tumoral Activity in Human Leukocytes (Results)

Human monocytes enriched from peripheral blood could be rendered tumor cytostatic in a dose-dependent way by CLP1b or CLP2p. Cytostasis was determined after co-culture for 3 days by incorporation of $^3$H-thymidine into the DNA of U 937 tumor target cells: both pools induced a rather strong cytostatic activity (FIG. 51).

Human monocytes stimulated with CLP1b or CLP2p released significant amounts of soluble cytostatic factors already after 4 h of incubation. Factor-induced tumor cytostasis was determined after 2 days of culture by incorporation of 3H-thymidine into the DNA of U 937 tumor target cells. Again, both pools were active (FIG. 52).

In other experiments an induction of LAK (lymphokine activated killer) cell activity by CLP pools could be demonstrated. Human monocyte-depleted lymphocytes from peripheral blood were stimulated in vitro for 3 days with 1:1 mixtures of CLP1b and 2p prepared from fetal, newborn or adult (3-4 year-old) animals (50-80 µg/ml). At the end of the incubation time, cells were tested for LAK cell activity in a 4 h cytolysis assay with Raji tumor cells (human B cell lymphoma) as targets. Pools of fetal and newborn origin were nearly as effective as IL-2 in inducing LAK-cell activity, whereas those prepared from adult animals showed only 55% activity, as compared to the positive control (FIG. 53). These data are in accordance with the results obtained in the mouse system, indicating a much higher leukocyte stimulating activity in CLP2p of fetal or newborn origin as compared to pools obtained from adult animals.

12.5 Induction of Antitumoral Activity Against Prostate Carcinoma Cells by Human Monocytes

12.5.1 Tumor Cells

The human metastatic prostate adenocarcinoma cell line LNCaP was kept in RPMI-1640 medium (Gibco BRL, Eggenstein, FRG), supplemented with 10% heat inactivated FCS, 1% non-essential amino acids (NEAA), 100 U/ml penicillin, and 100 µg/ml streptomycin (all from Seromed Biochrom KG, Berlin, FRG).

12.5.2 Isolation of Human Mononuclear Cells (MNC) from Peripheral Blood and Enrichment of Monocytes Blood samples were obtained from healthy human donors (Transfusionmedicine, University Hospital Freiburg). Blood was diluted 1:2 with PBS and mononuclear cells (MNC) were collected using a Ficoll-Paque gradient (density 1.077 g/ml, Pharmacia, Freiburg). Cells were washed four times with PBS and added to Petri dishes (1-2×10$^8$ MNC/20 ml RPMI 1640 (F1215, Seromed Biochrom KG, Berlin) precoated with human autologous plasma. The cells were incubated for 1-1.5 h allowing monocytes to adhere. Thereafter, non-adherent cells were carefully discarded and the adherent monocytes were gently detached with a cell scraper. Cells were washed once and either resuspended in RPMI 1640 with 10% FCS, 1% non-essential amino acids, 100 U/ml penicillin, 100 µg/ml streptomycin (cRPMI) for the direct use in cytostasis assays.

12.5.3 Assay for Monocyte—Mediated Tumor Cytostasis

Cytostasis assays were performed in flat bottom microtiter plates (Falcon 3072, Becton Dickinson, Heidelberg) in cRPMI (see above). Isolated human monocytes (5×10$^5$, 2.5×10$^5$ or 5×10$^4$/well) were incubated overnight. Thereafter, 5×10$^4$ LNCaP tumor cells and various concentrations of the different stimuli in a total volume of 200 µl/well were added and incubated for 72 h at 37° C., 5% $CO_2$. For the last 24 h of co-culture, the proliferating tumor cells were labelled by the addition of [$^3$H]-thymidine (23 125 Bq=0.625 µCi/well; specific activity: 185 GBq/mmol; Amersham Buchler, Braunschweig).

After freezing and thawing, the cultures were harvested on glass fibre filters with an automatic cell harvester (type 1295-001, Pharmacia LKB, Freiburg) and the radioactivity incorporated into the DNA of the tumor cells was measured in a liquid scintillation counter (Betaplate 1205, Pharmacia LKB). The inhibition of proliferation, i.e. the reduction of incorporated radioactivity was calculated defining LNCaP cells incubated in the presence of unstimulated monocytes as unaffected controls (0% inhibition).

The experiments show that pools CLP1b and CLP2p can induce human enriched monocytes to anti-tumoral activity against human prostate adenocarcinoma cells in threshold doses of about 1-5 µg/ml (FIG. 54) and with maximal activity at 50-100 µg/ml. In the same system, pure LPS is maximally active at 10 ng/ml (FIG. 55).

13. EXAMPLE 13

Induction of Cytokine and Nitric Oxide Production in Cells of the Myeloid Lineage by FSLE/CLP-Pools

13.1 Murine System (Methods)

13.1.1 Preparation of Dendritic Cells/Macrophages

Spleen cell suspensions were prepared aseptically from individual mice of the different groups in each experiment as described above. Where cells were used for preparation of dendritic cells/macrophages, the tissues were first digested at 37° C. for 45 min with a mixture of collagenase/dispase, prior to separation over mouse lymphopaque (Cedarlane Labs, Hornby, Ontario, Canada) and adherence to tissue culture plates for 90 min at 37° C. in α-Minimal Essential Medium supplemented with 2-mercaptoethanol and 10% fetal calf serum (αF10). Non-adherent cells were discarded after washing 3× with 25 ml of pre-warmed medium. Dendritic cells were subsequently isolated as non-adherent cells obtained by washing the culture plates after overnight incubation, while a crude macrophage pool was represented by the cells obtained by scraping these plates. In our hands routine staining of splenocytes with FITC-NLDC-145 (anti DC) or FITC-MAC-1 (anti macrophages) after this separation procedure produced the following staining pattern in crude dendritic cells/macrophages: 85%±14%, 12%±5% and 5%±3%, 82%±16% respectively.

13.1.2 Measurement of Serum Nitrite/Nitrate

Compare Example 3.1.1.5

13.2 Murine System (Results)

13.2.1 Induction of Cytokine Production in Murine Macrophages/Dendritic Cells by CLP1b/2p In Vitro First, cytokine production from spelling macrophages or dendritic cells, isolated as described above from young or aged mice, and incubated in vitro with CLP1b (CLP2p) for 24 h was assayed. These data are shown in Tables 11 and 12. For comparison cells from the same animals were stimulated with 100 ng/ml LPS.

TABLE 11

CLP1b and CLP2p induce cytokine production from murine spleen tissue macrophages

| Treatment[a] of cells | Cytokine levels in culture supernatants[b] | | | | |
|---|---|---|---|---|---|
| | IL-1 ng/ml | TNFα | TGFβ | IFNγ | IL-6 pg/ml |
| Young donors | | | | | |
| None | 17 ± 5 | 10 ± 4 | 18 ± 6 | 24 ± 7 | 45 ± 9 |
| LPS (100 ng/ml) | 128 ± 20* | 16 ± 15* | 72 ± 13* | 108 ± 20* | 290 ± 41* |
| CLP1b (50 ng/ml) | 26 ± 8 | 44 ± 7* | 32 ± 6 | 37 ± 9 | 80 ± 23 |
| CLP2p (15 ng/ml) | 81 ± 14* | 99 ± 15* | 70 ± 9 | 72 ± 12* | 315 ± 48* |
| Aged donors | | | | | |
| None | 30 ± 7 | 28 ± 5 | 69 ± 12 | 48 ± 8 | 160 ± 34 |
| LPS (100 ng/ml) | 81 ± 12* | 66 ± 12* | 130 ± 22* | 153 ± 22* | 740 ± 130* |
| CLP1b (50 ng/ml) | 39 ± 9 | 30 ± 8 | 55 ± 10 | 53 ± 9 | 210 ± 54 |
| CLP2p (15 ng/ml) | 57 ± 10* | 49 ± 7* | 99 ± 15* | 109 ± 13* | 440 ± 70* |

[a]4 DBA/2Nia mice/group were used, with subsequent assay of individual spleen samples in each group. Tissue macrophages were obtained for each spleen preparation as described above. Cells were incubated for 24 h with CLP pools as shown, and supernatants tested for different cytokines. Control cultures were incubated in medium only or with 100 ng/ml LPS.
[b]Data (arithmetic mean ± SD) shown are pooled from 4 identical studies, using triplicate cultures for assay of each cytokine. Cytokine levels are shown as ng/ml, except for IL-6 (pg/ml).
*$p < 0.05$, compared with age-matched control cells incubated with medium only (first row of each donor group).

TABLE 12

CLP1b and CLP2p induce cytokine production from spleen dendritic cells

| Treatment[a] of cells | Cytokine levels in culture supernatants[b] | | | | |
|---|---|---|---|---|---|
| | IL-1 ng/ml | TNFα | TGFβ | IFNγ | IL-6 pg/ml |
| Young donors | | | | | |
| None | 4 ± 2 | 4 ± 2 | 6 ± 2 | 9 ± 2 | 15 ± 5 |
| LPS (100 ng/ml) | 156 ± 25* | 37 ± 9* | 36 ± 9* | 65 ± 10* | 330 ± 55* |
| CLP1b (50 ng/ml) | 46 ± 8* | 10 ± 3 | 14 ± 4 | 24 ± 6* | 137 ± 13* |
| CLP2p (15 ng/ml) | 96 ± 13* | 22 ± 6* | 24 ± 5* | 35 ± 6* | 152 ± 28 |
| Aged donors | | | | | |
| None | 12 ± 4 | 5 ± 2 | 7 ± 2 | 4 ± 4 | 44 ± 8 |
| LPS (100 ng/ml) | 196 ± 35* | 25 ± 6* | 63 ± 7* | 88 ± 12* | 1230 ± 230* |
| CLP1b (50 ng/ml) | 59 ± 18* | 8 ± 3 | 28 ± 6* | 39 ± 8* | 470 ± 76* |
| CLP2p (15 ng/ml) | 139 ± 16* | 12 ± 4 | 46 ± 9* | 64 ± 9* | 740 ± 120 |

[a],[b]as for Table 4. Dendritic cells were obtained for each spleen preparation as described earlier [see Expl. 13.1.1]. Data (arithmetic mean ± SD) shown are pooled from 5 experiments, using triplicate cultures for assay of each cytokine.
*$p < 0.05$, compared with age-matched control cells incubated with medium only (first row of each donor group).

These data suggest that regulation of monokine/cytokine production by macrophages is an important variable in the aging process, and that the manipulation of this function by fractions CLP1b (CLP2p) might contribute to altered immunocompetence in aged individuals. The effect of CLP pools on IL-6 production is particularly interesting since it was found that IL-6 itself might contribute to changes in type-1 (IL-2, IFNγ) and type-2 (IL-4, IL-10, TGFβ) cytokine production from activated T cells [Gorczynski, R. M., 1997; Rincon, M., 1997].

13.2.2 Macrophage Derived Nitric Oxide as a Mediator of CLP-Induced Effects In Vivo and In Vitro Production of NO by macrophages has been implicated in the immunoregulation performed by those cells [Stuehr, D. J., 1989; Nathan, C., 1992]. To check whether CLP pools may induce some of its effects by perturbing NO production (by influencing the induction/activity of iNOS), the effect of simultaneous administration of CLP2p and L-NMMA, an inhibitor of iNOS, on the in vivo modulation of cytokine production in aged vs young mice was examined. Data from such studies is shown in Table 13. Serum nitrite/nitrate as well as ConA induced cytokine production from stimulated spleen cells was measured as described above.

TABLE 13

Effect of L-NMMA on reversal of age-related changes in cytokine production by CLP2p

| Source of[a] Cells/serum | Serum[b] nitrate/nitrite (μM) | Cytokine levels in culture supernatants[c] | | | | |
|---|---|---|---|---|---|---|
| | | IL-2 ng/ml | IL-4 | IL-10 | IFNγ | IL-6 pg/ml |
| Young (S) | 52 ± 13 | 1120 ± 220 | 55 ± 9 | 16 ± 5 | 115 ± 22 | 220 ± 35 |
| Young (E) | 94 ± 22* | 1260 ± 180 | 52 ± 8 | 16 ± 4 | 107 ± 24 | 254 ± 32 |
| Young (E + N) | 12 ± 3.0* | 1280 ± 240 | 49 ± 9 | 18 ± 5 | 119 ± 19 | 228 ± 39 |
| Aged (S) | 43 ± 10 | 385 ± 70* | 139 ± 25* | 55 ± 9* | 179 ± 30* | 1146 ± 110* |
| Aged (E) | 136 ± 26# | 910 ± 130# | 54 ± 13# | 16 ± 3# | 105 ± 22# | 575 ± 63# |
| Aged (E + N) | 22 ± 5.0* | 480 ± 88* | 146 ± 26* | 63 ± 8* | 162 ± 28 | 1095 ± 153* |

TABLE 13-continued

Effect of L-NMMA on reversal of age-related changes in cytokine production by CLP2p

| | Serum[b] | Cytokine levels in culture supernatants[c] | | | | |
|---|---|---|---|---|---|---|
| Source of[a] Cells/serum | nitrate/nitrite (μM) | IL-2 ng/ml | IL-4 | IL-10 | IFNγ | IL-6 pg/ml |

[a]Young or aged (120 weeks) C57BL/6Nia were used (4/group). N refers to daily injections with L-NMMA (30 mg/Kg) throughout the experiment. E indicates injection with CLP2p (100 μg/mouse i.m.; 4 doses at 3 day intervals). Mice were sacrificed 3 days after the last injection of CLP2p or saline (S).
[b]Mean serum (nitrate + nitrite) (±SD) at time of sacrifice in μM.
[c]As for Tables 11 and 12.
*p < 0.05, compared with first row.
p < 0.05, compared with rows 4 or 6.

Inhibition of iNOS in vivo (with L-NMMA) inhibited the reversal of age-associated alterations in cytokine production as induced by in vivo injection of CLP2p, along with inhibition of serum nitrate/nitrite induction produced by CLP2p. In separate studies in which tissue macrophages were stimulated directly in vitro with CLP1b/2p, the dose required for stimulation of cytokine or NO production was in the range 0.02-0.05 μg/ml.

13.2.3 Induction of Nitric Oxide Release in Murine BMDM

Stimulation of murine BMDM in vitro with CLP1b or 2p for 42-48 h induced the release of NO. in a dose-dependent manner, with both pools being potent inducers (FIG. 56). For both, CLP1b and -2p the kinetics of this process were determined (FIG. 56). The involvement of the inducible isoform of the NO synthase (iNOS) could be demonstrated by the addition of L-NMMA (FIG. 57). Furthermore, CLP1b/2p synergize with IFN-γ in iNOS activation (FIG. 58), an effect also seen with LPS. The ability of the CLP pools to induce NO release was not restricted to the BALB/c inbred strain, but was also detectable with BMDM from other mouse inbred strains (e.g. C57Bl/6, C57Bl/10, 129Sv).

13.3 Human System In Vitro (Methods)

13.3.1 Cytokine Induction and Determination

Whole blood cultures from freshly drawn peripheral blood of healthy donors were set up in 5 ml tubes (Falcon, Becton Dickinson) in a total volume of 500 μl. They consisted of 50 μl whole blood, 50 μl stimulator (PHA at 100 μg/ml or CLP1b/2p at 1:10 dilutions) and 400 μl RPMI 1640 medium, supplemented with L-glutamine (2 mM) and antibiotics. After 48 h the cultures were centrifuged, supernatants were harvested and tested for their cytokine contents by ELISA.

Cultures of human peripheral blood monocytes ($5 \times 10^5$ cells/500 μl/well) were stimulated with CLP1b or -2p in 24-well-plates for 18-72 h. Supernatants were harvested at different time points, centrifuged at high speed to remove any cell debris and tested for their TNF-α and Interleukin 6 (IL-6) content by ELISA (R & D Systems, Wiesbaden). ELISA's were performed following the manufacturer's instructions.

13.4 Human System In Vitro (Results)

13.4.1 Induction of Cytokines in Cultures of Human Leukocytes and Isolated Monocytes by CLP1b/2p Whole blood cultures were set up and the cells were stimulated for 48 h with CLP1b and CLP2p. The release of IL-1β, TNF-α and IL-6 was determined by ELISA. Both pools induced a similar release of all three cytokines (FIG. 59).

Cultures of peripheral blood monocytes were set up as described above and stimulated with CLP1b and CLP2p for various periods of time. The release of the cytokines TNF-α and IL-6 into the culture supernatants was determined by ELISA after 18, 48 and 72 h (FIG. 60). The results confirmed those obtained with whole blood cultures. The release of TNF-α showed a maximum at 18 h. In contrast, IL-6 reached its maximum between 48 and 72 h of stimulation.

14. EXAMPLE 14

Antiviral Effect of CLP-Pools in Mouse Macrophages

Bone marrow derived macrophages ($10^6$/well in 200 μl culture buffer (DMEM)) were treated with CLP-Pools in different concentrations (Table 14). Cells were washed and kept at 37° C. for 24 h. Supernatants (100 μl) were added to L929-cells, which were subsequently infected with vesicular stomatitis virus (VSV). Treated L929-cells were kept at 48 h and destruction of cells determined microscopically. As Table 14 shows, CLP-Pools were capable of inhibiting the cytostatic effects of the virus, most likely by inducing (antiviral) interferons. This antiviral effect is corroborated by clinical observations which show that herpes Infections are susceptible to treatment with FSLE. Yokochi [Yokochi, S. (1977)] reported that a phenol extract of hog liver together with IFNα exhibits an antiviral effect. As completely different methods of extract preparation, ways of biological analysis and test systems were employed, these findings are not relevant for the present invention.

TABLE 14

| CLP-Pools | Inhibition of virus-induced cytopathogenicity by CLP-Pools in doses of μg/culture*) | | | | | | | | |
|---|---|---|---|---|---|---|---|---|---|
| | 100 | 50 | 25 | 12.5 | 6.3 | 3.2 | 1.6 | 0.8 | 0 |
| CLP1b | + | + | + | + | + | + | + | − | − |
| CLP2p | + | + | + | + | + | + | − | − | − |
| Medium | − | − | − | − | − | − | − | − | − |

*)
+= Virus inhibition due to the presence of Interferon
−= Cell destruction (cytopathic effect) by active virus.

15. EXAMPLE 15

Clinical Aspects of FSLE and CLP-Pools 15.1. Immuno-Modulation

In co-operation with healthy volunteers of both sexes and different ages (45-85 years) and with informed consent orienting trials were performed with regard to the dynamics of cytokine production by whole blood after intramuscular injections of FSLE (300 mg proteins per unit injection).

In every experiment groups of 6-8 volunteers were involved, and the individual data were used to calculate average figures. The number of voluntary participants per experiment (6-8) is, of course, too small for reliable statistic analyses; i.e., only tendencies in the change of cytokine production can be recognized. In addition, it is well known that individual human immune parameters may vary, so that final conclusions would need much larger numbers of participants per experiment.

The effect of a single injection and of two injections given in a distance of either two or seven days was measured. For that purpose whole blood samples, taken before and at various times (weeks, months) after FSLE-injections, were analyzed for cytokine production without any further activation, at 24, 48, 72 and 96 h of culture.

15.2 Results

From these first trials it is obvious that (i.m.) injections of FSLE induce a wave of changes in the production of several relevant cytokines within days to weeks, levels in single cases remaining changed over months.

After i.m. FSLE the production of Interferon-$\gamma$ (IFN-$\gamma$), a T-cell product and powerful macrophage-activating factor [Robert, W. R., 1982; Vitteta, E. S., 1990] increases about 5-fold with a maximum after 14-21 days. The increased IFN-$\gamma$ may explain the observed antiviral effects of FSLE and Pools CLP1b/2p (see Example 14).

Interleukin-2 (IL-2) is a potent T-cell growth stimulator inducing naïve T-cells to T-effector cells [Janeway, Ch. A., 1995]. Also B-cell growth and differentiation has been demonstrated. IL-2, furthermore, can function as a growth inhibitor in neoplastic cells [Rosenberg, S. A., 1987; Hatakeyama, M., 1991]. Synergistic co-operation of IL-2 and IFN-$\gamma$ in antitumoral activity have been described [see Vitteta, E. s., 1990]. After FSLE (i.m.), IL-2 production increases with a maximum two-fold the average control figure, after 2-3 weeks, remaining elevated over several months.

Interleukin-6 (IL-6), however, shows a tendency of decreasing after FSLE injections. Most figures measured, especially after two injections (2 or 7 days distance), are below those of the non-treated controls. This effect may be in accord with the here described finding that FSLE-injections in mice reverse age-associated cytokine imbalances, with a decrease of elevated IL-6 production (Example 11.2.2 and Table 10)—an effect which can also be induced by giving anti-IL-6 antibodies [Gorczynski, R. M., 1997]. It is known that aging humans have elevated IL-6 serum levels.

Of interest is the dynamics of Interleukin-10 (IL-10), known as pleiotropic antiinflammatory regulator of macrophage activities [Marchant, A., 1999; Moore, K. W., 1993]. After two FSLE injections in one week distance, IL-10 production increases about 4-5 fold with a maximum after 14-21 days, slowly returning to normal values over 1-2 months.

From these experiments it appears that FSLE stimulates the production of inflammatory up- and down-regulators in a "natural" equilibrium, a fact which might also explain the good tolerability of injections and the prevention of any undesired longer-lasting (over-)activation of macrophages [see D'Andrea, A., 1993]. It should be mentioned that two consecutive injections of FSLE in 2 days distance may lead to a partial state of short-lasting "tolerance" in vivo. (in vitro: compare Example 8.9); its induction, or prevention, might be of clinical importance.

15.3. Summary

In summary, FSLE in vivo and CLP1b and CLP2p induce a cascade of immune up- and down-regulators of clinical significance in an orchestrated manner. Further, the clinical results with foetal liver extract in human volunteers clearly confirm the observations made in vitro and in vivo in the Examples demonstrated before, mainly the ones using human adeno-carcinoma cells of the prostate gland and human monocytes and also the experiments describing reverting of cytokine pattern of ageing mice. About 100 patients were treated in recent years, either for oncologic purposes or in chronic relapsing or chronic viral diseases (herpes and hepatitis B and C). Many patients undergoing radiation treatment for adeno-carcinoma of prostate gland were showing immediate response to FSLE by lowering PSA (prostate specific antigen) values down to normal long before usually radiation starts to develop its effects. Many patients suffering from relapsing herpes virus experience immediately that they either don't relapse or do so much less frequently. Several cases of non-responders of hepatitis B and C have been kept under control with a viral load which is below the level of disease activity and is probably related to the stimulation of interferon production.

In summary, constituents of FSLE contained in CLP1b and CLP2p are presently under further clinical experimentation and clinical observation of a large number of volunteers and patients confirms its good tolerance and effects which last about 18-24 months and may be monitored by clinical well-being and immune responses.

REFERENCES

Alexander, C. and Rietschel E. Th.: J. Endotoxin Res. 7, 167-202 (2001).
Aliprantis, A. O. et al.: Science 285, 736-739 (1999)
Ausubel et al.: Current Protocols in Molecular Biology, Green Publishing Associates and Wiley Interscience, N.Y. (1989)
Bacher, M. et al.: Proc. Natl. Acad. Sci. U.S.A 93, 7849-7854 (1996).
Bacher, M. et al.: Am. J. Pathol. 150, 235-246 (1997).
Belanger, M. et al: Infect Immun. 63, 656-662 (1995).
Berdel, W. E. and P. G. Munder: Anticancer Res. 1, 397-402 (1981).
Bernhagen, J. et al.: Nature 365, 756-9 (1993).
Bernhagen, J. et al.: J. Mol. Med. 76, 151-161 (1998).
Bertok, L.: Microbiology—1980 (D. Schlesinger, edit) (1980), 91-93.
Bernier, I. et al.: Biochim. Biophys. Acta 871, 19-23 (1986).
Bertini, R. et al.: J. Exp. Med. 189, 1783-89 (1999).
Blum, H. et al.: Electrophoresis 8, 93-99 (1987).
Böyum, A.: Scand. J. Clin. Lab. Invest. 21, 77-89 (1968)
Brabetz, W. et al.: Symp. In Immunology VIII, 89-121 (1999). Eibl. et al. edit. Springer Berlin, Heidelberg.
Brade, H. et al. (edit): Endotoxin in Health and Disease, 950 pages. Marcel DEKKER; New York, Basel (1999).
Brandenburg, K. et al.: J. Endotoxin Res. 3, 173-78 (1996).
Bucci and Fronticelli: J. Biol. Chem. 248, 551-556 (1965)
Burns, E. A. and J. S. Goodwin: Immunodeficiency and Aging (Review) Drugs and Aging 11 (5), 374-397 (1997).
Calandra, T. et al.: J. Exp. Med. 179, 1895-1902 (1994).
Carrillo E. H. et al.: J. Trauma 52, 449-452 (2002)
Coggin, J. H. et al.: J. Immunol. 107, 526-331 (1971).
Colantuoni, V. et al.: Biochem. Biophys. Res. Commun. 130, 431-39 (1985).
Coley, W. B.: Am. J. Med. Sci 105, 487-511 (1893)
Corraliza, J. M. et al.: J. Immunol. Methods 174, 231-35 (1994).
D'Andrea, A. et al.: J. Exp. Med. 178, 1041-48 (1993).
David, S. A.: See Brade, H., 413-423 (1999).
Daynes, R. A. and B. A. Araneo: Aging, Immunol. Infect. Dis. 3, 135-53 (1992).
Daynes, R. A. et al.: J. Immunol. 150, 5219-30 (1993).
DeWys, W. D.: Cancer Res. 32, 374-79 (1972).
Droogmans, L et al.: DNA Seq. 4, 277-279 (1994).

Dunn, D. L. et al.: Surgery 93, 653-659 (1983)
Durgan, J.: J. Natl. Cancer Just. 89, 681-83 (1997).
Elin, R. J.: J. Infect. Dis. 144, 329-36 (1981).
Engelhardt, R. et al.: J. Biol. Resp. Med. 9, 480-491 (1990)
Forabosco, P. et al.: Eur. J. Hum. Genet. 8, 846-852 (2000).
Freudenberg, M. A. and Ch. Galanos: Int. Rev. Immunol. 6, (4), 207-21 (1990).
Freudenberg, M. A. et al.: Infect. Immun. 59, 3487-91 (1991).
Freudenberg, M. A. et al.: Infect. Immun. 51, 891-895 (1986).
Galanos, Ch. et al.: Eur. J. Biochem. 9, 245-249 (1969)
Galanos, Ch. and O. Lüderitz: Europ. J. Biochem. 54, 601-10 (1975).
Galat A. et al.: Eur. J. Biochem. 224, 417-421 (1994).
Godin, D. V. and J. M. Tuchek: Brit. J. Pharmacol. 79, 421-28 (1983).
Gorczynski, R. M. and Cunningham A. J.: Eur. J. Immunol. 8, 753-755 (1978)
Gorczynski, R. M. et al.: Eur. J. Immunol. 10, 781-787 (1980).
Gorczynski, R. M. et al.: Immunology 92, 20-25 (1997).
Gorczynski, R. M. et al.: Immunol. Letters 60, 154-64 (1998).
Gorczynski, R. M. et al.: Clin. Immunol. 101, 328-334 (2001)
Gorczynski, R. M. et al.: Europ. J. Immunol. 31, 2331-2337 (2001)
Goto, S. et al.: Cancer Immunol. Immunotherap. 42, 255-61 (1996).
Green, L. C. et al.: Analyt. Biochem. 126, 5241-44 (1982).
Hammerberg et al. Ann N.Y. Acad. Sci. 241, 672-682 (1974)
Harding, M. W. et al.: J. Biol. Chem. 261, 8547-8555 (1986).
Haendler, B. et al.: EMBO J. 6, 947-50 (1987).
Hateyama, M. and T. Toniguchi: In: Peptide Growth Factors and their Receptorsl., M. B. Sporn and A. B. Roberts (edit.), 523-540 (1991), Springer New York.
Heimburger, N. and H. E. Karges: In Current Studies in Hematol. and Blood. Transfusion No. 56, A. Hässigetol. edit. Karger, Beseldo. (1989).
Heukeshoven, J. and Dernick, R.: Electrophoresis 6, 103-112 (1985)
Heukeshoven, J. and Demick, R.: Electrophoresis 9, 28-32 (1988).
Hoffmann, P. et al.: Biol. Chem. Hoppe-Seyler 370, 575-82 (1989).
Horiuchi, M. et al.: J. Gen. Virology 76, 2583-87 (1995).
Hunkapiller, M. W. and L. E. Hood: Science 219, 650-59 (1983).
Inagawa, H., et al.: Anticancer Res. 17, 2153-58 (1997).
Janeway, Ch. A. and P. Travers: Immunologie (Textbook, German version), 297 (1995), Spektrum-Verlag, Berlin, Oxford.
Jeanin, J. F. et al.: Gastroenterology 101, 726-33 (1991).
Jungblut, P et al.: Electrophoresis 13, 739-741 (1992).
Jungblut, P. et al.: Electrophoresis 15, 685-707 (1994).
Kaca, W. et al.: J. Biol. Chem. 269, 25078-25084 (1994)
Kaca W. et al.: Biochim. Biophys. Acta 17, 49-56 (1995)
Katayama, Y. et al.: Japan J. Med. Sci. 28, 304-307 (1975).
Kusama, T. et al.: Chem. Pharm. Bull. 39, 3244-53 (1991)
Laemmli, U. K.: Nature 227, 680-85 (1970).
Lambert, G.: Conquest of Life—The extraordonary story of Dr. Paul Niehans. Rinehart & Co. Inc., New York, Toronto (1959).
Levin, J.: Progr. Clin. Biol. Res. 93, 7-24 (1982).
Lotan, R. et al.: FASEB J. 10, 1031-39 (1996).
Lowry O. H. et al.: J. Biol. Chem. 207, 1-17 (1954)
Lüderitz, O. et al.: Biochem. Z. 330, 34-46 (1958).
Machado, P. et al.: Europ. J. Dermatol. 8, 98-103 (1998).
Malmgren, R. A. and W. Mills: J. Natl. Cancer Inst. 26, 525-31 (1961).
Marchant, A. et al.: In: Endotoxin in Health and Disease, H, Brade et al, (edit.), 581-590 (1999), Marcel Dekker, Inc., New York.
McLachlan, J. A. et al.: J. Immunol. 154, 832-43 (1995).
Metz, C. N. and Bucala, R.: Cytokine Reference: 703-716 (2001); Academic Press; CA, USA (ed. Oppenheim, J. J., Feldmann, M., Durum, S. K., Hirano, T., Vilcek, J., Nicoal, N. A.).
Miller, R. A.: Science 273, 70-74 (1996).
Mirza, M. M. et al.: J. Med. Genet. 35, 218-221 (1998).
Modolell, M. and P. G. Munder: J. Immunol. Methods 174, 203-208 (1994).
Moore, K. W. et al.: Ann. Rev. Immunol. 11, 165-190 (1993).
Müller, E C. et al.: Electrophoresis 20, 320-330 (1999).
Munford, R. S. and C. L. Hall: Science 234, 203-205 (1986).
Nabika, T. et al.: Biochim. Biophys. Acta 1450, 25-34 (1999).
Nathan, C.: FASEB Journal 6, 3051-3056 (1992).
Neter, E., et al.: Proc. Soc. Exp. Biol. Med. 88, 339-341 (1955).
Neter, E. et al.: Can. J. Microbiol. 4, 371-383 (1958).
Nishizawa, T. et al.: Chem. Pharm. Bull. 40, 479-483 (1992).
Opal, S. M. and R. L. Yu: Drugs Apr. 55, 497-508 (1998).
Otto, A. et al.: Electrophoresis 17, 1643-1650 (1996).
Ozkaynak, E. et al.: Nature 312, 663-66 (1984).
Pfannes, S. D. C. et al.: J. Leukoc. Biol. 69, 590-597 (2001)
Poltorak, A., et al.: Science 282, 2085-2088 (1998)
Porro, M.: See Brade, H. et al., 1999, 403-412.
Poelstra, K. et al.: Am. J. Pathol. 151, 1163-1169 (1997).
Reiter, I. et al.: J. Immunol. 15; 163, 1730-1732 (1999).
Renner, H.: Fortsch. Med. 92, 175-178 (1974).
Ribeiro, A. A. et al.: Magn. Reson. Chem. 37, 620-630 (1999).
Rietschel, E. Th. et al.: FASEB J. 8, 217-225 (1994)
Rincon, M. et al.: J. Exp. Med. 185, 461-467 (1997).
Rifkind, D.: J. Bacteriol. 93, 1463-1464 (1967).
Robert, W. K. and A. Vasil: J. Interferon Res. 2, 519-532 (1982).
Röhrer, H.: Krebs-Medizin 8, 3-10 (1987).
Roger, T. et al.: Nature 414, 920-924 (2001)
Rosenberg, S. A. et al.: New Engl. J. Med. 316, 889-897 (1987).
Rosenberg, S. A. et al.: Ann. Surg. 208, 121-135 (1988).
Roth, R. J. et al.: Prog. Clin. Biol. Res. 388, 161-172 (1994)
Roth, R. J. and Levin, J.: Endotoxin in Health and Disease,: see Brade et al. (1999) 389-402
Sambrook et al., "Molecular Cloning, A Laboratory Manual", CSH Press, Cold Spring Harbor (1989).
Scopes, "Protein Purification", Springer-Verlag, N.Y. (1982).
Schlecht, S. Zbl. Bakt. Hyg. I Abt. Orig. A232, 61-72 (1975)
Schlesinger, D. H. et al.: Biochemistry 14, 2214-18 (1975).
Schmid, F. and J. Stein (edit): Zellforschung und Zelltherapie (Cellular Research and Cell Therapy). H. Huber, Bern, Stuttgart (1963).
Schmidt, G. et al.: Eur. J. Biochem. 16, 382-392 (1970)
Schoentgen, F. et al.: Eur. J. Biochem. 166, 333-38 (1987).
Schreck, R. et al.: EMBO Journal 10, 2247-2258 (1991).
Seddiqi, N. et al.: J. Mol. Evol. 39, 655-60 (1994).
Seguira, I. and Ch. C. Stock: Cancer Res. 15, 38-51 (1955).
Sherman, D. R. et al.: Proc. Natl. Acad. Sci. USA 84, 3209-13 (1987).
Strominger, J. L. et al.: J. Biol. Chem. 234, 3263-3267 (1959)
Stuehr, D. J. and C. F. Nathan: J. Exp. Med. 169, 1543-1555 (1989).
Su D. et al.: Infect. Immun. 65, 1258-1266 (1997)
Takeuchi, O., et al.: Immunity 11, 443-451 (1999)
Thiede, B. et al.: Electrophoresis 17, 588-599 (1996).

Ulrich, J. T. and Myers K. R.: Pharm. Biotechnol. 6, 495-524 (1995)
Van Bossuyt, H., et al.: J. Hepathology 7, 325-337 (1988).
Vitteta, E. S. and W. E. Paul: In: Peptide Growth Factor and their Receptors, II., 412, (1990).
Waeber, G. et al.: Proc. Natl. Acad. Sci. U.S.A, 94, 4782-4787 (1997).
Wang, J. et al.: J. Clin. Invest. 103, 1023-1029 (1999).
Wechsler, M. E., and R. Schwab: Exp. Clin. Immunogenetics 9, 182-187 (1992).
Weiser, W Y. et al.: Proc. Natl. Acad. Sci. U.S.A 86, 7522-7526 (1989).
White C. T. et al.: J. Lab. Clin. Med. 108, 132-137 (1986)
Winterhalter and Colosimo: Biochem. 10, 621-628 (1971)
Winterhalter and Huehns: J. Biol. Chem. 239, 3699-3705 (1964)
Wollman, E. E. et al.: J. Biol. Chem. 263, 15506-12 (1988).
Worton, R. G. et al.: J. Cell. Physiol. 74, 171-179 (1969).
Yokochi, S. et al.: Arzneimittel-Forsch./Drug-Research 47, 968-974 (1997).
Zähringer, U. et al.: Adv. Carbohydr. Chem. Biochem. 50, 211-276 (1994).
Zähringer, U. et al.: J. Endotoxin Res. 7, 133-146 (2001)
Zhang, M. and K. J. Tracey: see H. Brade et al. (edit.), pgs. 915-926. (1999).
Ziegler-Heitbrock, H. W. et al.: Immunology 75, 264-270, (1992).
Zuckermann, S. H. et al.: Infect. Immun. 59, 2774-2781, (1991).

The invention claimed is:

1. A composition comprising:
   (a) endotoxin or an endotoxically active portion thereof,
   (b) fetal hemoglobin, one or more single chains thereof, or one or more combinations of chains thereof, and
   (c) a pharmaceutically acceptable carrier, diluent or excipient, wherein the endotoxin or endotoxically active portion thereof; and the fetal hemoglobin, one or more single chains thereof, or one or more combinations of chains thereof; are present in amounts that synergistically enhance at least one endotoxin bioactivity, and wherein the composition is suitable for pharmaceutical administration.

2. The composition of claim 1, wherein said fetal hemoglobin, one or more single chains thereof or one or more combinations of chains thereof, is obtained from non-human fetal tissue.

3. The composition of claim 2, wherein said non-human fetal tissue is obtained from sheep, goat, horse or cow.

4. The composition of claim 1, further comprising a fetal liver peptide or glycopeptide.

5. The composition of claim 4, wherein said fetal liver peptide or glycopeptide is thioredoxin, ubiquitin, aldose 1-epimerase, alcohol dehydrogenase, prostaglandin-F synthase, prostaglandin-F synthase 2, regucalcin/senescence marker protein-30, thiosulfate sulfurtransferase, carbonyl reductase 1,3-hydroxyanthranilate 3,4-dioxygenase, guanidinoacetate-N-methyltransferase, carbonic anhydrase III, carbonic anhydrase II, catechol-O-methyltransferase (soluble isoform), phosphatidylethanolamine-binding protein, peptidyl-prolyl-cis-trans-isomerase A, cyclophilin A, superoxide dismutase, cellular retinol-binding protein I, glycine cleavage system H protein, putative 42-9-9 protein, hemoglobin gamma chain, hemoglobin alpha chain, fatty acid-binding protein (liver), macrophage migration inhibitory factor or acyl-CoA-binding protein.

6. The composition of claim 1, wherein said combination of chains is an $\alpha$, $\gamma$-dimer of fetal hemoglobin.

7. The composition of claim 1, wherein said single chain is a $\gamma$-chain of fetal hemoglobin.

8. The composition of claim 1, wherein said one or more combinations of chains are free of heme.

9. The composition of claim 1, wherein said endotoxin is bacterial S- or R-form lipopolysaccharide (LPS).

10. The composition of claim 1, wherein said endotoxically active portion of endotoxin is the polysaccharide-free lipid A component obtained from LPS.

11. The composition of claim 1, wherein said endotoxin is natural or synthetic pentaacyl-lipid A, natural or synthetic hexaacyl-lipid A, or a combination thereof.

12. The composition of claim 11, wherein said natural or synthetic pentaacyl- or hexaacyl-lipid A is a monophosphate.

13. The composition of claim 1, wherein the ratio by weight of the fetal hemoglobin, single chains thereof or combinations of chains thereof component to the endotoxin or the endotoxically active portion thereof component ranges from 1:1 to 1000:1.

14. The composition of claim 1 confectioned for oral administration.

15. A method for enhancing at least one endotoxin bioactivity in a subject, comprising the step of administering to the subject the composition of claim 1.

16. A composition comprising:
  (a) endotoxin or an endotoxically active portion thereof,
  (b) fetal hemoglobin, one or more single chains thereof, or one or more combinations of chains thereof, and
  (c) a pharmaceutically acceptable carrier, diluent or excipient, wherein the ratio by weight of the fetal hemoglobin, single chains thereof or combinations of chains thereof component to the endotoxin or the endotoxically active portion thereof component ranges from 1:1 to 1000:1, and wherein the composition is suitable for pharmaceutical administration.

17. The composition of claim 13 or 16 comprising between 0.001 and 10 mg of fetal hemoglobin, single chains thereof or combinations of chains thereof, and between 0.01 and 1000 µg of endotoxin or an endotoxically active portion thereof.

* * * * *